(12) United States Patent
Buchstaller et al.

(10) Patent No.: US 7,589,112 B2
(45) Date of Patent: Sep. 15, 2009

(54) METHYLENE UREA DERIVATIVES

(75) Inventors: Hans-Peter Buchstaller, Weiterstadt (DE); Matthias Wiesner, Seeheim-Jugenheim (DE); Oliver Schadt, Rodenbach (DE); Christiane Amendt, Darmstadt (DE); Frank Zenke, Darmstadt (DE); Christian Sirrenberg, Darmstadt (DE); Matthias Grell, Darmstadt (DE); Dirk Finsinger, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 607 days.

(21) Appl. No.: 10/532,574

(22) PCT Filed: Oct. 8, 2003

(86) PCT No.: PCT/EP03/11134

§ 371 (c)(1),
(2), (4) Date: Apr. 25, 2005

(87) PCT Pub. No.: WO2004/037789

PCT Pub. Date: May 6, 2004

(65) Prior Publication Data

US 2006/0199844 A1    Sep. 7, 2006

Related U.S. Application Data

(60) Provisional application No. 60/490,285, filed on Jul. 28, 2003.

(30) Foreign Application Priority Data

Oct. 24, 2002    (EP)    .................... 02023906

(51) Int. Cl.
*A61K 31/4412*    (2006.01)
*C07D 213/68*    (2006.01)

(52) U.S. Cl. ........................ 514/350; 514/345; 546/290; 546/298

(58) Field of Classification Search .................. 546/290, 546/298; 514/345, 350
See application file for complete search history.

(56) References Cited

U.S. PATENT DOCUMENTS

| 4,057,636 | A | 11/1977 | Petersen |
| 5,441,984 | A | 8/1995 | Heath, Jr. et al. |
| 2003/0171351 | A1 | 9/2003 | Brendel et al. |
| 2004/0039038 | A1 | 2/2004 | Bernardon et al. |

FOREIGN PATENT DOCUMENTS

| DE | 199 47 457 A1 | 4/2001 |
| EP | 0 839 803 A1 | 5/1998 |
| WO | WO 95/18126 A1 | 7/1995 |
| WO | WO 00/61559 A1 | 10/2000 |
| WO | WO 00/61561 A1 | 10/2000 |
| WO | WO 01/38324 A2 | 5/2001 |
| WO | WO 01/57008 A1 | 8/2001 |
| WO | WO 02/02534 A1 | 1/2002 |
| WO | WO 02/12210 A1 | 2/2002 |
| WO | WOX 02/24679 A1 | 3/2002 |
| WO | WO 02/062750 A1 | 8/2002 |
| WO | WO 02/062763 A2 | 8/2002 |

OTHER PUBLICATIONS

Vippagunta et al., "Crystalline Solid", Advanced Drug Delivery Reviews 48 (2001) 3-26.*
Guillory (In Brittain ed), "Polymorphism, etc.," NY: Marcel Dekker, Inc., 1999, 1-2. 183-226.*
Yu et al., "Physical characterization of, etc.," PSTT, vol. 1 (3), 118-127 (1998).*
Roger A. Smith et al., "Discovery of Heterocyclic Ureas as a New Class of Raf Kinase Inhibitors: Identification of a Second Generation Lead by a Combinatorial Chemistry Approach", Bioorganic & Medicinal Chemistry Letters, 2001, pp. 2775-2778, vol. 11.
Thutam P. Hopkins et al., "Solid-Phase Synthesis of Trisubstituted Guanidines", J. Comb. Chem., 2002, pp. 167-174, vol. 4.

* cited by examiner

*Primary Examiner*—Patricia L Morris
(74) *Attorney, Agent, or Firm*—Arent Fox LLP

(57) ABSTRACT

The present invention relates to methylene urea derivatives of formula (I), the use of the compounds of formula (I) as inhibitors of raf-kinase, the use of the compounds of formula (I) for the manufacture of a pharmaceutical composition and a method of treatment, comprising administering said pharmaceutical composition to a patient.

4 Claims, No Drawings

METHYLENE UREA DERIVATIVES

The present application claims priority to International Application No. PCT/EP03/11134 filed Oct. 8, 2003, which claims priority to both European Patent Application No. 02023906.7 filed Oct. 24, 2002 and U.S. Provisional application No. 60/490,285 filed Jul. 28, 2003. The contents of each of the three priority applications are expressly incorporated herein by reference in their entireties.

The present invention relates to methylene urea derivatives, methylene urea derivatives as medicaments, methylene urea derivatives as inhibitors of raf-kinase, the use of methylene urea derivatives for the manufacture of a pharmaceutical, a method for producing a pharmaceutical composition containing said methylene urea derivatives, the pharmaceutical composition obtainable by said method and a method of treatment, comprising administering said pharmaceutical composition.

Protein phosphorylation is a fundamental process for the regulation of cellular functions. The coordinated action of both protein kinases and phosphatases controls the levels of phosphorylation and, hence, the activity of specific target proteins. One of the predominant roles of protein phosphorylation is in signal transduction, where extracellular signals are amplified and propagated by a cascade of protein phosphorylation and dephosphorylation events, e.g. in the $p21^{ras}$/raf pathway.

The $p21^{ras}$ gene was discovered as an oncogene of the Harvey (rasH) and Kirsten (rasK) rat sarcoma viruses. In humans, characteristic mutations in the cellular ras gene (c-ras) have been associated with many different types of cancers. These mutant alleles, which render Ras constitutively active, have been shown to transform cells, such as the murine cell line NIH 3T3, in culture.

The $p21^{ras}$ oncogene is a major contributor to the development and progression of human solid cancers and is mutated in 30% of all human cancers (Bolton et al. (1994) Ann. Rep. Med. Chem., 29, 165-74; Bos. (1989) Cancer Res., 49, 4682-9). Oncogenic Ras mutations have been identified for example in lung cancer, colorectal cancer, pancreas, thyroid cancer, melanoma, bladder tumors, liver tumor, kidney tumor, dermatological tumors and haematological tumors (Ddjei et al. (2001), J. Natl. Cancer Inst. 93(14), 1062-74; Midgley, R. S. and Kerr, D. J. (2002) Critical Rev. Onc/hematol 44, 109-120; Downward, J. (2003), Nature reviews 3, 11-22). In its normal, unmutated form, the ras protein is a key element of the signal transduction cascade directed by growth factor receptors in almost all tissues (Avruch et al. (1994) Trends Biochem. Sci., 19, 279-83).

Biochemically, ras is a guanine nucleotide binding protein, and cycling between a GTP-bound activated and a GDP-bound resting form is strictly controlled by ras endogenous GTPase activity and other regulatory proteins. The ras gene product binds to guanine triphosphate (GTP) and guanine diphosphate (GDP) and hydrolyzes GTP to GDP. It is the GTP-bound state of Ras that is active. In the ras mutants in cancer cells, the endogenous GTPase activity is alleviated and, therefore, the protein delivers constitutive growth signals to downstream effectors such as the enzyme raf kinase. This leads to the cancerous growth of the cells which carry these mutants (Magnuson et al. (1994) Semin. Cancer Biol., 5, 247-53). The ras proto-oncogene requires a functionally intact c-raf1 proto-oncogene in order to transduce growth and differentiation signals initiated by receptor and non-receptor tyrosine kinases in higher eukaryotes.

Activated Ras is necessary for the activation of the c-raf-1 proto-oncogene, but the biochemical steps through which Ras activates the Raf-1 protein (Ser/Thr) kinase are now well characterized. It has been shown that inhibiting the effect of active ras by inhibiting the raf kinase signaling pathway by administration of deactivating antibodies to raf kinase or by co-expression of dominant negative raf kinase or dominant negative MEK also called ERK, the substrate of raf kinase, leads to the reversion of transformed cells to the normal growth phenotype see: Daum et al. (1994) Trends Biochem. Sci., 19, 474-80; Fridman et al. (1994) J. Biol. Chem., 269, 30105-8. Kolch et al. (1991) Nature, 349, 426-28) and for review Weinstein-Oppenheimer et al. Pharm. & Therap. (2000), 88, 229-279.

Similarly, inhibition of raf kinase (by antisense oligodeoxynucleotides) has been correlated in vitro and in vivo with inhibition of the growth of a variety of human tumor types (Monia et al., Nat. Med. 1996, 2, 668-75; Geiger et al. (1997), Clin. Cancer Res. 3(7): 1179-85; Lau et al. (2002), Antisense Nucl. Acid. Drug Dev. 12(1): 11-20; McPhillips et al. (2001), Br. J. Cancer 85(11): 1753-8).

Raf serine- and threonine-specific protein kin ases are cytosolic enzymes that stimulate cell growth in a variety of cell systems (Rapp, U. R., et al. (1988) in The oncogene handbook; T. Curran, E. P. Reddy, and A. Skalka (ed.) Elsevier Science Publishers; The Netherlands, pp. 213-253; Rapp, U. R., et al. (1988) Cold Spring Harbor Sym. Quant. Biol. 53:173-184; Rapp, U. R., et al. (1990) Inv Curr. Top. Microbiol. Amunol. Potter and Melchers (eds), Berlin, Springer-Verlag 166:129-139).

Three isozymes have been characterized:
c-Raf (also named Raf-1, c-raf-1 or c-raf1) (Bonner, T. I., et al. (1986) Nucleic Acids Res. 14:1009-1015). A-Raf (Beck, T. W., et al. (1987) Nucleic Acids Res. 15:595-609), and B-Raf (Qkawa, S., et al. (1998) Mol. Cell. Biol. 8:2651-2654; Sithanandam, G. et a. (1990) Oncogene:1775). These enzymes differ in their expression in various tissues. Raf-1 is expressed in all organs and in all cell lines that have been examined, and A- and B-Raf are expressed in urogenital and brain tissues, respectively (Storm, S. M. (1990) Oncogene 5:345-351).

Raf genes are proto-oncogenes: they can initiate malignant transformation of cells when expressed in specifically altered forms. Genetic changes that lead to oncogenic activation generate a constitutively active protein kinase by removal or interference with an N-terminal negative regulatory domain of the protein (Heidecker, G., et al. (1990) Mol. Cell. Biol. 10:2503-2512; Rapp, U. R., et al. (1987) in Oncogenes and cancer S. A. Aaronson, J. Bishop, T. Sugimura, M. Terada, K. Toyoshima, and P. K. Vogt (ed). Japan Scientific Press, Tokyo). Microinjection into NIH 3T3 cells of oncogenically activated but not wild-type versions of the Raf-protein prepared with *Escherichia coli* expression vectors results in morphological transformation and stimulates DNA synthesis (Rapp, U. R., et al. (1987) in Oncogenes and cancer, S. A. Aaronson, J. Bishop, T. Sugimura, M. Terada, K. Toyoshima, and P. K. Vogt (ed.) Japan Scientific Press, Tokyo; Smith, M. R., et al (1990) Mol. Cell. Biol. 10:3828-3833). Activating mutants of B-Raf have been identified in a wide range of human cancers e.g. colon, ovarien, melanomas and sarcomas (Davies, H., et al. (2002), Nature 417 949-945. Published online Jun. 9, 2002, 10.1038/nature00766). The preponderant mutation is a single phosphomimetic substitution in the kinase activation domain (V599E), leading to constitutive kinase activity and transformation of NIH3T3 cells.

Thus, activated Raf-1 is an intracellular activator of cell growth. Raf-1 protein serine kinase in a candidate downstream effector of mitogen signal transduction, since Raf oncogenes overcome growth arrest resulting from a block of cellular ras activity due either to a cellular mutation (ras revertant cells) or microinjection of anti-ras antibodies (Rapp, U. R., et al. (1988) in The Oncogene Handbook, T. Curran, E. P. Reddy, and A. Skalka (ed.), Elsevier Science Publishers; The Netherlands, pp. 213-253; Smith, M. R., et al. (1986) Nature (London) 320:540-543).

c-Raf function is required for transformation by a variety of membrane-bound oncogenes and for growth stimulation by mitogens contained in serums (Smith, M. R., et al. (1986) Nature (London) 320:540-543). Raf-1 protein serine kinase activity is regulated by mitogens via phosphorylation (Morrison, D. K., et al. (1989) Cell 58:648-657), which also effects sub cellular distribution (Olah, Z., et al. (1991) Exp. Brain Res. 84:403; Rapp, U. R., et al. (1988) Cold Spring Harbor Sym. Quant. Biol. 53:173-184. Raf-1 activating growth factors include platelet-derived growth factor (PDGF) (Morrison, D. K., et al. (1988) Proc. Natl. Acad. Sci. USA 85:8855-8859), colony-stimulating factor (Baccarini, M., et al. (1990) EMBO J. 9:3649-3657), insulin (Blackshear, P. J., et al. (1990) J. Biol. Chem. 265:12115-12118), epidermal growth factor (EGF) (Morrison, R. K., et al. (1988) Proc. Natl. Acad. Sci. USA 85:8855-8859), interleukin 2 (Turner, B. C., et al (1991) Proc. Natl. Acad. Sci. USA 88:1227), and interleukin 3 and granulocytemacrophage colony-stimulating factor (Carroll, M. P., et al (1990) J. Biol. Chem. 265:19812-19817).

Upon mitogen treatment of cells, the transiently activated Raf-1 protein serine kinase translocates to the perinuclear area and the nucleus (Olah, Z, et al. (1991) Exp. Brain Res. 84:403; Rapp, U. R., et al. (1988) Cold Spring Habor Syrn. Quant. Biol. 53:173-184). Cells containing activated Raf are altered in their pattern of gene expression (Heidecker, G., et al. (1989) in Genes and signal transduction in multistage carcinogenesis, N. Colburn (ed.), Marcel Dekker, Inc., New York, pp. 339-374), and Raf oncogenes activate transcription from Ap-I/PEA3-dependent promoters in transient transfection assays (Jamal, S., et al (1990) Science 344:463-466; Kaibuchi, K., et al (1989) J. Biol. Chem. 264:20855-20858; Wasylyk, C., et al. (1989) Mol. Cell. Biol. 9:2247-2250).

There are at least two independent pathways for Raf-1 activation by extracellular mitogens: one involving protein kinase C (KC) and a second initiated by protein tyrosine kinases (Blackshear, P. J., et al. (1990) J. Biol. Chem. 265: 12131-12134; Kovacina, K. S., et al (1990) J. Biol. Chem. 265:12115-12118; Morrison, D. K., et al. (1988) Proc. Natl. Acad. Sci. USA 85:8855-8859; Siegel, J. N., et al (1990) J. Biol. Chem. 265:18472-18480; Turner, B. C., et al (1991) Proc. Natl. Acad. Sci. USA 88:1227). In either case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233:305-312).

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels.

Normal angiogenesis is activated during tissue growth, from embryonic development through maturity and then enters a period of relative quiescence during adulthood.

Normal angiogensesis is also activated during wound healing, and at certain stages of the female reproductive cycle. Inappropriate or pathological angiogenesis has been associated with several disease states including various retinopathies; ischemic disease; atherosclerosis; chronic inflammatory disorders; rheumatoid arthritis, and cancer. The role of angiogenesis in disease states is discussed, for instance, in Fan et al, Trends in Pharmacol Sci. 16:54 66; Shawver et al, DOT Vol. 2, No. 2 Feb. 1997; Folkmann, 1995, Nature Medicine 1:27-31.

In cancer the growth of solid tumors has been shown to be angiogenesis dependent. (See Folkmann, J., J. Nat'l. Cancer Inst., 1990, 82, 4-6.) Consequently, the targeting of pro-angiogenic pathways is a strategy being widely pursued in order to provide new therapeutics in these areas of great, unmet medical need.

Raf is involved in angiogenic processes. Endothelial growth factors (e.g. vascular endothelial growth factor VEGF or basic fibroblast growth factor bFGF) activates receptor tyrosine kinases (e.g. VEGFR-2) and signal through the Ras/Raf/Mek/Erk kinase cascade and protects endothelial cells from apoptosis (Alavi et al. (2003), Science 301, 94-96; Hood, J. D. et al. (2002), Science 296, 2404; Mikula, M. et al. (2001), EMBO J. 20, 1952; Hauser, M. et al. (2001), EMBO J. 20, 1940; Wojnowski et al. (1997), Nature Genet. 16, 293). Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, April 2000).

Mice with a targeted disruption in the Braf gene die of vascular defects during development (Wojnowski, L. et al. 1997, Nature genetics 16, page 293-296). These mice show defects in the formation of the vascular system and in angiogenesis e.g. enlarged blood vessels and increased apoptotic death of differentiated endothelial cells.

For the identification of a signal transduction pathway and the detection of cross talks with other signaling pathways suitable models or model systems have been generated by various scientists, for example cell culture models (e.g. Khwaja et al., EMBO, 1997, 16, 2783-93) and transgenic animal models (e.g. White et al., Oncogene, 2001, 20, 7064-7072). For the examintion of particular steps in the signal transduction cascade, interfering compounds can be used for signal modulation (e.g. Stephens et al., Biochemical J., 2000, 351, 95-105). The compounds according to the invention may also be useful as reagents for the examination of kinase dependent signal transduction pathways in animal and/or cell culture models or any of the clinical disorders listed throughout this application.

The measurement of kinase activity is a well known technique feasible for each person skilled in the art. Generic test systems for kinase activity detection with substrates, for example histone (e.g. Alessi et al., FEBS Lett. 1996, 399, 3, page 333-8) or myelin basic protein are well described in the literature (e.g. Campos-González, R. and Glenney, Jr., J. R. 1992 J. Biol. Chem. 267, Page 14535).

For the identification of kinase inhibitors various assay systems are available (see for example Walters et al., Nature Drug Discovery 2003, 2; page 259-266). For example, in scintillation proximity assays (e.g. Sorg et al., J. of Biomolecular Screening, 2002, 7, 11-19) or flashplate assays the radioactive phosphorylation of a protein or peptide as substrate with □ATP can be measured. In the presence of an inhibitory compound no signal or a decreased radioactive signal is detectable. Furthermore homogeneous time-resolved fluorescence resonance energy transfer (HTR-FRET), and fluorescence polarization (FP) technologies are useful for assay methods (for example Sills et al., J. of Biomolecular Screening, 2002, 191-214).

Other non-radioactive ELISA based assay methods use specific phospho-antibodies (AB). The phospho-AB binds only the phosphorylated substrate. This binding is detectable with a secondary peroxidase conjugated antibody, measured for example by chemiluminescence (for exaple Ross et al., Biochem. J., 2002, 366, 977-981).

The present invention provides compounds generally described as methylene urea derivatives, including both aryl and/or heteroaryl derivatives which are preferably kinase inhibitors and more preferably inhibitors of the enzyme raf kinase. Since the enzyme is a downstream effector of p21$^{ras}$, the inhibitors are useful in pharmaceutical compositions for human or veterinary use where inhibition of the raf kinase pathway is indicated, e.g., in the treatment of tumors and/or cancerous cell growth mediated by raf kinase. In particular, the compounds are useful in the treatment of human or animal solid cancers, e.g. murine cancer, since the progression of these cancers is dependent upon the ras protein signal transduction cascade and therefore susceptible to treatment by interruption of the cascade, i.e., by inhibiting raf kinase. Accordingly, the compound of Formula I or a pharmaceutically acceptable salt thereof is administered for the treatment of diseases mediated by the raf kinase pathway especially cancers, including solid cancers, such as, for example, carcinomas (e.g., of the lungs, pancreas, thyroid, bladder or colon), myeloid disorders (e.g., myeloid leukemia) or adenomas (e.g., villous colon adenoma), pathological angiogenesis and metastatic cell migration. Furthermore the compounds are useful in the treatment of complement activation dependent chronic inflammation (Niculescu et al. (2002) Immunol. Res., 24:191-199) and HIV-1 (human immunodeficiency virus type1) induced immunodeficiency (Popik et al. (1998) J Virol, 72: 6406-6413) and infection disease, Influenza A virus (Pleschka, S. et al. (2001), Nat. Cell. Biol, 3(3):301-5) and *Helicobacter pylori* infection (Wessler, S. et al. (2002), FASEB J., 16(3): 417-9).

Therefore, subject of the present invention are methylene urea derivatives of formula I

A-D-B    (I)

wherein

D is a bivalent methylene urea moiety which is directly bonded to A and B, preferably to one bonding partner via the carbon atom of the N-methylene moiety and to the other bonding partner via the N'-nitrogen atom, wherein the carbon atom of the N-methylene moiety is unsubstituted or substituted with one or more substituents, wherein said substituents are preferably selected from the group consisting of alkyl, alkylene, halogen, haloalkyl, $C_3$-$C_7$-cycloalkyl, $C_3$-$C_7$-cycloalkylene, heterocyclyl, aryl, aralkyl, heteroaryl, hydroxy, alkoxy, haloalkoxy, aralkoxy, aryloxy, mercapto, alkylsulfanyl, haloalkylsulfanyl, arylsulfanyl, heteroarylsulfanyl, alkylsulfenyl, haloalkylsulfenyl, arylsulfenyl, heteroarylsulfenyl, alkylsulfonyl, haloalkylsulfonyl, arylsulfonyl, heteroarylsulfonyl, carboxy, cyano, cyanoalkyl, aminosulfonyl, acyl, acyloxy, carbamoyl, aroyl, heteroaryl, heteroaroyloxy, unsubstituted amino groups and substituted amino groups, and wherein the carbonyl group of said methylene urea moiety can be derivatized, preferably to a C=S, C=NR$^5$, C=C(R$^5$)—NO$_2$, C=C(R$^5$)—CN or C=C(CN)$_2$ group A is a unsubstituted or preferably substituted moiety of up to 40 carbon atoms of the formula: -L-(M-L')$_\alpha$, where L is a 5, 6 or 7 membered cyclic structure, preferably selected from the group consisting of aryl, heteroaryl, arylene and heteroarylene, bound directly to D,L' comprises an optionally substituted cyclic moiety having at least 5 members, preferably selected from the group consisting of aryl, heteroaryl, aralkyl, cycloalkyl and heterocyclyl, M is a bond or a bridging group having at least to one atom, α is an integer of from 1-4; and each cyclic structure of L and L' contains 0-4 members of the group consisting of nitrogen, oxygen and sulfur, wherein L' is preferably substituted by at least one substituent selected from the group consisting of —SO$_\beta$R$_x$, —C(O)R$_x$ and —C(NR$_y$)R$_z$, B is a substituted or unsubstituted, up to tricyclic aryl or heteroaryl moiety of up to 30 carbon atoms, preferably of up to 20 carbon atoms, comprising at least one 5-, 6-, or 7-membered cyclic structure, preferably a 5- or 6-membered cyclic structure, bound directly to D containing 0-4 members of the group consisting of nitrogen, oxygen and sulfur, wherein said cyclic structure directly bound to D is preferably selected from the group consisting of aryl, heteroaryl and heterocyclyl, R$_y$ is hydrogen or a carbon based moiety of up to 24 carbon atoms optionally containing heteroatoms selected from N, S and O and optionally halosubstituted, up to per halo, R$_z$ is hydrogen or a carbon based moiety of up to 30 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen;

R$_x$ is R$_z$ or NR$_a$R$_b$, where R$_a$ and R$_b$ are a) independently hydrogen, a carbon based moiety of up to 30 carbon atoms optionally containing heteroatoms selected from N, S and O and optionally substituted by halogen, hydroxy and carbon, based substituents of up to 24 carbon atoms, which optionally contain heteroatoms, selected from N, S and O, and are optionally substituted by halogen, or —OSi(R$_f$)$_3$ where R$_f$ is hydrogen or a carbon based moiety of up to 24 carbon atoms optionally containing heteroatoms selected from N, S and O and optionally substituted by halogen, hydroxy and carbon based substituents of up to 24 carbon atoms, which optionally contain heteroatoms selected from N, S and O, and are optionally substituted by halogen; or b) R$_a$ and R$_b$ together from a 5-7 member heterocyclic structure of 1-3 heteroatoms selected from N, S and O, or a substituted 5-7 member heterocyclic structure of 1-3 heteroatoms selected from N, S and O substituted by halogen, hydroxy or carbon based substituents of up to 24 carbon atoms, which optionally contain heteroatoms selected from N, S and O and are optionally substituted by halogen; or c) one of $R_a$ or $R_b$ is —C(O)—, a $C_1$-$C_5$ divalent alkylene group or a substituted $C_1$-$C_5$ divalent alkylene group bound to the moiety L to form a cyclic structure with at least 5 members, wherein the substituents of the substituted $C_1$-$C_5$ divalent alkylene group are selected from the group consisting of halogen, hydroxy, and carbon based substituents of up to 24 carbon atoms, which optionally contain heteroatoms selected from N, S and O and are optionally substituted by halogen; where B is substituted, L is substituted or L' is additionally substituted, the substituents are selected from the group consisting of halogen, up to per-halo and W$\gamma$, where $\gamma$ is 0-3; wherein each W is independently selected from the group consisting of —CN, —CO$_2$R, —C(O)NR$^5$R$^5$, —C(O)—R$^5$, —NO$_2$, —OR$^5$, —SR$^5$, —NR$^5$R$^5$, —NR$^5$C(O)OR$^5$, —NR$^5$C(O)R$^5$, -Q-Ar, and carbon based moieties of up to 24 carbon atoms, optionally containing heteroatoms selected from N, S and O and optionally substituted by one or more substituents independently selected from the group consisting of —CN, —CO$_2$R, —C(O)NR$^5$R$^5$, —C(O)—R$^5$, —NO$_2$, —OR$^5$, —SR$^5$, —NR$^5$R$^5$, —NR$^5$C(O)OR$^5$, —NR$^5$C(O)R$^5$ and halogen up to per-halo; with each R$^5$ independently selected from H or a carbon based moiety of up to 24 carbon atoms, optionally containing heteroatoms selected from N, S d) and O and optionally substituted by halogen;
wherein Q is —O—, —S—, —N(R$^5$)—, —(CH$_2$)$_\beta$-, —C(O)—, —CH(OH)—, —(CH$_2$)$_\beta$—, —(CH$_2$)$_\beta$S—, —(CH$_2$)$_\beta$N(R$^5$)—, —O(CH$_2$)$_\beta$—CHHal-, —CHal$_2$-, —S—(CH$_2$)— and —N(R$^5$)(CH$_2$)$_\beta$— where $\beta$=1-3, and Hal is halogen; and
Ar is a 5- or 6-member aromatic structure containing 0-2 members selected from the group consisting of nitrogen, oxygen and sulfur, which is optionally substituted by halogen, up to per-halo, and optionally substituted by Z$_{\delta 1}$ wherein $\delta 1$ is 0 to 3 and each Z is independently selected from the group consisting —CN, —CO$_2$R$^5$, —C(O)NR$^5$R$^5$, —C(O)—R$^5$, —NO$_2$, —OR$^5$, —SR$^5$, —NR$^5$R$^5$, —NR$^5$C(O)OR$^5$, —NR$^5$C(O)R$^5$, and a carbon based moiety of up to 24 carbon atoms, optionally containing heteroatoms selected from N, A and O and optionally substituted by one or more substituents selected from the group consisting of —CN, —CO$_2$R$^5$, —C(O)NR$^5$R$^5$, —C(O)—R$^5$, —NO$_2$, —OR$^5$, —SR$^5$, —NR$^5$R$^5$, —NR$^5$C(O)OR$^5$, —NR$^5$C(O)R$^5$, and with R$^5$ as defined above,
and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

More preferred, in the compound of formula I,
$R_y$ is hydrogen, $C_{1-10}$ alkyl, $C_{1-10}$ alkoxy, $C_{3-10}$ cycloalkyl having 0-3 heteroatoms, $C_{2-10}$ alkenyl, $C_{1-10}$ alkenoyl, $C_{6-12}$ arly, $C_{3-12}$ hetaryl having 1-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl having 0-3 heteroatoms selected from N, S and O, substituted $C_6$-$C_{14}$ aryl, substituted $C_{3-12}$ hetaryl having 1-3 heteroatoms selected from N, S and O, substituted $C_{7-24}$ alkaryl or substituted $C_{7-24}$ aralkyl, where Ry is a substituted group, it is substituted by halogen up to per halo, $R_z$ is hydrogen, $C_{1-10}$ alkyl, $C_{1-10}$ alkoxy, $C_{3-10}$ cycloalkyl having 0-3 heteroatoms, $C_{2-10}$ alkenyl, $C_{1-10}$ alkenoyl, $C_{6-12}$ aryl, $C_{3-12}$ hetaryl having 1-3 heteroatoms selected form S, N and O, $C_{7-24}$ alkaryl, $C_{7-24}$ aralkyl, substituted $C_3$-$C_{10}$ cycloalkyl having 0-3 heteroatoms selected from S, N and O, substituted $C_{3-12}$ hetaryl having 1-3 heteroatoms selected from S, N and O, substituted $C_{7-24}$ alkaryl or substituted $C_7$-$C_{24}$ aralkyl, where $R_z$ is a substituted group, it is substituted by halogen up to per halo, hydroxy, $C_{1-10}$ alkyl, $C_{3-12}$ cycloalkyl having 0-3 heteroatoms selected from N, S and O, substituted $C_3$-$C_{12}$ hetaryl having 1-3 heteroatoms selected from N, S and O, $C_{1-10}$ alkoxy, $C_{6-12}$ aryl, $C_{1-6}$ halo substituted alkyl up to per halo alkyl, $C_6$-$C_{12}$ halo substituted aryl up to per halo aryl, $C_3$-$C_{12}$ halo substituted cycloalkyl up to per halo cycloalkyl having 0-3 heteroatoms selected from N, S and O, halo substituted $C_3$-$C_{12}$ hetaryl up to per halo, hetaryl having 1-3 heteroatoms selected from O, N and S, halo substituted $C_7$-$C_{24}$ aralkyl up to per halo aralkyl, halo substituted $C_7$-$C_{24}$ alkaryl up to per halo alkaryl, and —C(O)R$_g$, $R_a$ and $R_b$ are,
a) independently hydrogen, a carbon based moiety selected from the group consisting of $C_1$-$C_{10}$ alkyl, $C_1$-$C_{10}$ alkoxy, $C_{3-10}$ cycloalkyl, $C_{2-10}$ alkenyl, $C_{1-10}$ alkenoyl, $C_{6-12}$ aryl, $C_{3-12}$ hetaryl having 1-3 heteroatoms selected from O, N and S, $C_{3-12}$ cycloalkyl having 0-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl, having 0-3 heteroatoms selected from N, S and O, substituted $C_{6-12}$ aryl, substituted $C_{3-12}$ hetaryl having 1-3 heteroatoms selected from N, S and O, substituted $C_{7-24}$ aralkyl, substituted $C_{7-24}$ alkaryl, where $R_a$ and $R_b$ are a substituted group, they are substituted by halogen up to per halo, hydroxy, $C_{1-10}$ alkyl, $C_{3-12}$ cycloalkyl having 0-3 heteroatoms selected from O, S and N, $C_{3-12}$ hetaryl having 1-3 heteroatoms selected from N, S and O, $C_{1-10}$ alkoxy, $C_{6-12}$ aryl, $C_{1-6}$ halo substituted alkyl up to per halo alkyl, $C_6$-$C_{12}$ halo substituted aryl up to per halo aryl, $C_3$-$C_{12}$ halo substituted cycloalkyl having 0-3 heteroatoms selected from N, S and O, up to per halo cycloalkyl, halo substituted $C_3$-$C_{12}$ hetaryl up to per halo heteraryl, halo substituted $C_7$-$C_{24}$ aralkyl up to per halo aralkyl, halo substituted $C_7$-$C_{24}$ alkaryl up to per halo alkaryl, and —C(O)R$_g$; or —OSi(R$_f$)$_3$ where R$_f$ is hydrogen, $C_1$-$C_{10}$ alkyl, $C_1$-$C_{10}$ alkoxy, $C_{3-10}$ cycloalkyl, $C_{2-10}$ alkenyl, $C_{1-10}$ alkenoyl, $C_{6-12}$ aryl, $C_{3-12}$ hetaryl having 1-3 heteroatoms selected from O, N and S, $C_{3-12}$ cycloalkyl having 0-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl, having 0-3 heteroatoms selected from N, S and O, substituted $C_{6-12}$ aryl, substituted $C_{3-12}$ hetaryl having 1-3 heteroatoms selected from N, S and O, substituted $C_{7-24}$ aralkyl, substituted $C_{7-24}$ alkaryl, where $R_a$ and $R_b$ are a substituted group, they are substituted by halogen up to per halo, hydroxy, $C_{1-10}$ alkyl, $C_{3-12}$ cycloalkyl having 0-3 heteroatoms selected from O, S and N, $C_{3-12}$ hetaryl having 1-3 heteroatoms selected from N, S and O, $C_{1-10}$ alkoxy, $C_{6-12}$ aryl, $C_{1-6}$ halo substituted alkyl up to per halo alkyl, $C_6$-$C_{12}$ halo substituted aryl up to per halo aryl, $C_6$-$C_{12}$ halo substituted cycloalkyl having 0-3 heteroatoms selected from N, S and O, up to per halo cycloalkyl, halo substituted $C_3$-$C_{12}$ hetaryl up to per halo heteraryl, halo substituted $C_7$-$C_{24}$ aralkyl up to per halo aralkyl, halo substituted $C_7$-$C_{24}$ alkaryl up to per halo alkaryl, and —C(O)R$_g$, or
b) $R_a$ and $R_b$ together form a 5-7 member heterocyclic structure of 1-3 heteroatoms selected from N, S and O, or a substituted 5-7 member heterocyclic structure of 1-3 heteroatoms selected from N, S and O with substituents selected from the group consisting of halogen up to per halo, hydroxy, $C_1$-$C_{10}$ alkyl, $C_1$-$C_{10}$ alkoxy, $C_{3\text{-}10}$ cycloalkyl, $C_{2\text{-}10}$ alkenyl, $C_{1\text{-}10}$ alkenoyl, $C_{6\text{-}12}$ aryl, $C_{3\text{-}12}$ hetaryl having 1-3 heteroatoms selected from O, N and S, $C_{3\text{-}12}$ cycloalkyl having 0-3 heteroatoms selected from N, S and O, $C_{7\text{-}24}$ aralkyl, $C_{7\text{-}24}$ alkaryl, substituted $C_{1\text{-}10}$ alkyl, substituted $C_{1\text{-}10}$ alkoxy, substituted $C_{3\text{-}10}$ cycloalkyl, having 0-3 heteroatoms selected from N, S and O, substituted $C_{6\text{-}12}$ aryl, substituted $C_{3\text{-}12}$ hetaryl having 1-3 heteroatoms selected from N, S and O, substituted $C_{7\text{-}24}$ aralkyl, substituted $C_{7\text{-}24}$ alkaryl, where $R_a$ and $R_b$ are a substituted group, they are substituted by halogen up c) to per halo, hydroxy, $C_{1\text{-}10}$ alkyl, $C_{3\text{-}12}$ cycloalkyl having 0-3 heteroatoms selected from O, S and N, $C_{3\text{-}12}$ hetaryl having 1-3 heteroatoms selected from N, S and O, $C_{1\text{-}10}$ alkoxy, $C_{6\text{-}12}$ aryl, $C_{1\text{-}6}$ halo substituted alkyl up to per halo alkyl, $C_6$-$C_{12}$ halo substituted aryl up to per halo aryl, $C_3$-$C_{12}$ halo substituted cycloalkyl having 0-3 heteroatoms selected from N, S and O, up to per halo cycloalkyl, halo substituted $C_3$-$C_{12}$ hetaryl up to per halo heteraryl, halo substituted $C_7$-$C_{24}$ aralkyl up to per halo aralkyl, halo substituted $C_7$-$C_{24}$ alkaryl up to per halo alkaryl, and —C(O)$R_g$, or d) one of $R_a$ or $R_b$ is —C(O)—, a $C_1$-$C_5$ divalent alkylene group or a substituted $C_1$-$C_5$ divalent alkylene group bound to the moiety L to form a cyclic structure with at least 5 members, wherein the substituents of the substituted $C_1$-$C_5$ divalent alkylene group are selected from the group consisting of halogen, hydroxy, $C_{1\text{-}10}$ alky, $C_{3\text{-}12}$ cycloalkyl having 0-3 heteroatoms selected from, S and N, $C_{3\text{-}12}$ hetaryl having 1-3 heteroatoms selected from N, S and O, $C_{1\text{-}10}$ alkoxy, $C_{6\text{-}12}$ aryl, $C_7$-$C_{24}$ alkaryl, $C_7$-$C_{24}$ aralkyl, $C_{1\text{-}6}$ halo substituted alkyl up to per halo alkyl, $C_6$-$C_{12}$ halo substituted aryl up to per halo aryl, $C_3$-$C_{12}$ halo substituted cycloalkyl having 0-3 heteroatoms selected from N, S and O, up to per halo cycloalkyl, halo substituted $C_3$-$C_{12}$ hetaryl up to per halo heteraryl, halo substituted $C_7$-$C_{24}$ aralkyl up to per halo aralkyl, halo substituted $C_7$-$C_{24}$ alkaryl up to per halo alkaryl, and —C(O)$R_g$, where $R_g$ is $C_{1\text{-}10}$ alkyl; —CN, —$CO_2R_d$, —$OR_d$, —$SR_d$, —$NO_2$, —C(O)$R_e$, —$NR_dR_e$, —$NR_dC(O)OR_e$ and —$NR_d(CO)R_e$ and $R_d$ and $R_e$ are independently selected from the group consisting of hydrogen, $C_{1\text{-}10}$ alkyl, $C_{1\text{-}10}$ alkoxy, $C_{3\text{-}10}$ cycloalkyl having 0-3 heteroatoms selected from O, N and S, $C_{6\text{-}12}$ aryl, $C_3$-$C_{12}$ hetaryl with 1-3 heteroatoms selected from O, N and S and $C_7$-$C_{24}$ aralkyl, $C_7$-$C_{24}$ alkaryl, up to per halo substituted $C_1$-$C_{10}$ alkyl, up to per halo substituted $C_3$-$C_{10}$ cycloalkyl having 0-3 heteroatoms selected from O, N and S, up to per halo substituted $C_6$-$C_{14}$ aryl, up to per halo substituted $C_3$-$C_{12}$ hetaryl having 1-3 heteroatoms selected from O, N and S, halo substituted $C_7$-$C_{24}$ alkaryl up to per halo alkaryl, and up to per halo substituted $C_7$-$C_{24}$ aralkyl, W is independently selected from the group consisting —CN, —$CO_2R^5$, —C(O)$NR^5R^5$, —C(O)—$R^5$, —$NO_2$, —$OR^5$, —$SR^5$, —$NR^5R^5$, —$NR^5C(O)OR^5$, —$NR^5C(O)R^5$, $C_1$-$C_{10}$ alkyl, $C_1$-$C_{10}$ alkoxy, $C_2$-$C_{10}$ alkenyl, $C_1$-$C_{10}$ alkenoyl, $C_3$-$C_{10}$ cycloalkyl having 0-3 heteroatoms selected from O, S and N, $C_6$-$C_{14}$ aryl, $C_7$-$C_{24}$ aralkyl, $C_7$-$C_{24}$ alkaryl, $C_3$-$C_{12}$ heteroaryl having 1-3 heteroatoms selected form O, N and S, $C_4$-$C_{23}$ alkheteroaryl having 1-3 heteroatoms selected from O, N and S, substituted $C_1$-$C_{10}$ alkyl, substituted $C_1$-$C_{10}$ alkoxy, substituted $C_2$-$C_{10}$ alkenyl, substituted $C_1$-$C_{10}$ alkenoyl, substituted $C_3$-$C_{10}$ cycloalkyl having 0-3 heteroatoms selected from O, N and S, substituted $C_6$-$C_{12}$ aryl, substituted $C_3$-$C_{12}$ hetaryl having 1-3 heteroatoms selected from O, N and S, substituted $C_7$-$C_{24}$ aralkyl, substituted $C_7$-$C_{24}$ alkaryl, substituted $C_4$-$C_{23}$ alkheteroaryl having 1-3 heteroatoms selected from O, N and S, and -Q-Ar;

$R^5$ is independently selected from H, $C_1$-$C_{10}$ alkyl, $C_1$-$C_{10}$ alkoxy, $C_2$-$C_{10}$ alkenyl, $C_1$-$C_{10}$ alkenoyl, $C_3$-$C_{10}$ cycloalkyl having 0-3 heteroatoms selected from O, C and N, $C_6$-$C_{14}$ aryl, $C_3$-$C_{13}$ hetaryl having 1-3 heteroatoms selected from O, N and S, $C_7$-$C_{14}$ alkaryl, $C_7$-$C_{24}$ aralkyl, $C_4$-$C_{23}$ alkheteroaryl having 1-3 heteroatoms selected from O, N and S, up to per-halosubstituted $C_1$-$C_{10}$ alkyl, up to per-halosubstituted $C_3$-$C_{10}$ cycloalkyl having 0-3 heteroatoms selected from O, N and S, up to per-halosubstituted $C_6$-$C_{14}$ aryl, up to per-halosubstituted $C_3$-$C_{13}$ hetaryl having 1-3 heteroatoms selected from O, N and S, up to per-halosubstituted $C_7$-$C_{24}$ aralkyl, up to per-halosubstituted $C_7$-$C_{24}$ alkaryl, and up to per-halosubstituted $C_4$-$C_{23}$ alkheteroaryl; and each Z is independently selected from the group consisting —CN, —$CO_2R^5$, —C(O)$NR^5R^5$, —C(O)—$R^5$, —$NO_2$, —$OR^5$, —$SR^5$, —$NR^5R^5$, —$NR^5C(O)OR^5$, —$NR^5C(O)R^5$, $C_1$-$C_{10}$ alkyl, $C_1$-$C_{10}$ alkoxy, $C_2$-$C_{10}$ alkenyl, $C_1$-$C_{10}$ alkenoyl, $C_3$-$C_{10}$ cycloalkyl having 0-3 heteroatoms selected from O, S and N, $C_6$-$C_{14}$ aryl, $C_7$-$C_{24}$ alkaryl, $C_7$-$C_{24}$ aralkyl, $C_3$-$C_{12}$ heteroaryl having 1-3 heteroatoms selected from O, N and S, $C_4$-$C_{23}$ alkheteroaryl having 1-3 heteroatoms selected from O, N and S, substituted $C_1$-$C_{10}$ alkyl, substituted $C_1$-$C_{10}$ alkoxy, substituted $C_2$-$C_{10}$ alkenyl, substituted $C_1$-$C_{10}$ alkenoyl, substituted $C_3$-$C_{10}$ cycloalkyl having 0-3 heteroatoms selected from O, N and S, substituted $C_6$-$C_{12}$ aryl, substituted $C_3$-$C_{12}$ hetaryl having 1-3 heteroatoms selected from O, N and S; wherein if Z is a substituted group, the one or more substituents are selected from the group consisting of —CN, —$CO_2R^5$, —C(O)$NR^5R^5$, —C(O)—$R^5$, —$NO_2$, —$OR^5$, —$SR^5$, —$NR^5R^5$, —$NR^5C(O)OR^5$, —$NR^5C(O)R^5$.

According to the invention, each M independently from one another represents a bond OR is a bridging group, selected from the group consisting of $(CR^5R^5)_h$, or $(CHR^5)_h$-Q-$(CHR^5)_i$, wherein Q is selected from a group consisting of O, S, N—$R^5$, $(CHal_2)_j$, (O—$CHR^5)_j$, ($CHR^5$—O)$_j$, $CR^5$=$CR^5$, (O—$CHR^5CHR^5)_j$, ($CHR^5CHR^5$—O)$_j$, C=O, C=S, C=$NR^5$, CH(O$R^5$), C(O$R^5$)(O$R^5$), C(=O)O, OC(=O), OC(=O)O, C(=O)N($R^5$), N($R^5$)C(=O), OC(=O)N($R^5$), N($R^5$)C(=O)O, CH=N—O, CH=N—$NR^5$, OC(O)$NR^5$, $NR^5$C(O)O, S=O, $SO_2$, $SO_2NR^5$ and $NR^5SO_2$, wherein $R^5$ is in each case independently selected from the meanings given above, preferably from hydrogen, halogen, alkyl, aryl, aralkyl, h, i are independently from each other 0, 1, 2, 3, 4, 5 or 6, preferably 0, 1, 2, or 3, and j is 1, 2, 3, 4, 5 or 6, preferably 0, 1, 2 or 3.

More preferred, each M independently from one another represents a bond or is a bridging group, selected from the group consisting of —O—, —S—, —N($R^5$)—, —($CH_2$)$_\beta$—, —C(O)—, —CH(OH)—, —($CH_2$)$_\beta$O—, —($CH_2$)$_\beta$S—, —($CH_2$)$_\beta$N($R^5$)—, —O($CH_2$)$_\beta$, —CHHal-, —CHal$_2$-, —S—($CH_2$)$_\beta$— and —N($R^5$)($CH_2$)$_\beta$, where $\beta$ is 1 to 6 and especially preferred 1 to 3, Hal is halogen and $R^5$ is as defined above. More preferred, the group B of Formula I is a substituted or unsubstituted six member aryl moiety or six member hetaryl moiety, said hetaryl moiety having 1 to 4 members selected from the group of hetaryl atoms consisting of nitrogen, oxygen and sulfur with the balance of the hetaryl moiety being carbon.

Even more preferred, the group B of Formula I is a) an unsubstituted phenyl group, an unsubstituted pyridyl group, an unsubstituted pyrimidinyl, a phenyl group substituted by a substituent selected from the group consisting of halogen and Wγ wherein W and γ are as defined in claim 1, a pyrimidinyl group substituted by a substituent selected from the group constituting of halogen and Wγ, whereas W and γ are as defined above, or a substituted pyridyl group, substituted by a substituent selected from the group consisting of halogen and Wγ wherein W and γ are as defined above; or a substituted phenyl group, a substituted pyrimidinyl group, or substituted pyridyl group substituted 1 to 3 times by 1 or more substituents selected from the group consisting of —CN, halogen, $C_1$-$C_{10}$ alkyl, $C_1$-$C_{10}$ alkyl alkoxy, —OH, up to per halo substituted $C_1$-$C_{10}$ alkyl, up to per halo substituted $C_1$-$C_{10}$ alkoxy or phenyl substituted by halogen up to per halo; or b) a substituted phenyl group, a substituted pyrimidinyl group, or substituted pyridyl group substituted 1 to 3 times b 1 or more substituents selected from the group consisting of —CN, halogen, alkyl, especially $C_1$-$C_4$ alkyl, alkoxy, especially $C_1$-$C_4$ alkoxy, —OH, up to per halo substituted alkyl, especially up to per halo substituted $C_1$-$C_4$ alkyl, up to per halo substituted alkoxy, especially up to per halo substituted $C_1$-$C_4$ alkoxy or phenyl substituted by halogen up to per halo.

In the formula I, the group L which is directly bound to D is preferably a substituted or unsubstituted 6 member aryl moiety or a substituted or unsubstituted 6 member hetaryl moiety, wherein said hetaryl moiety has 1 to 4 members selected from the group of heteroatoms consisting of nitrogen, oxygen and sulfur with the balance of said hetaryl moiety being carbon, wherein the one or more substituents are selected from the group consisting of halogen and Wγ wherein W and γ are as defined above.

More preferred, the group L is a substituted phenyl, unsubstituted phenyl, substituted pyrimidinyl, unsubstituted pyrimidinyl, substituted pyridyl or unsubstituted pyridyl group.

In the formula I, the group L' preferably comprises a 5 to 6 membered aryl moiety or hetaryl moiety, wherein said hetaryl moiety comprises 1 to 4 members selected from the group of heteroatoms consisting of nitrogen, oxygen and sulfur.

More preferred, the group L' is phenyl, pyridinyl or pyrimidinyl.

According to the invention, a methylene moiety is a bivalent radical of formula —CRR—, where R and R are selected independently from one another from hydrogen or suitable substituents other than hydrogen. Suitable substituents are preferably selected from the group consisting of alkyl, alkylene, halogen, haloalkyl, $C_3$-$C_7$-cycloalkyl, $C_3$-$C_7$-cycloalkylene, heterocyclyl, aryl, aralkyl, heteroaryl, hydroxy, alkoxy, haloalkoxy, aralkoxy, aryloxy, mercapto, alkylsulfanyl, haloalkylsulfanyl, arylsulfanyl, heteroarylsulfanyl, alkylsulfenyl, haloalkylsulfenyl, arylsulfenyl, heteroarylsulfenyl, alkylsulfonyl, haloalkylsulfonyl, arylsulfonyl, heteroarylsulfonyl, carboxy, cyano, cyanoalkyl, aminosulfonyl, acyl, acyloxy, carbamoyl, aroyl, heteroaryl, heteroaroyloxy, unsubstituted amino groups and substituted amino groups. A methylene moiety wherein R and R both are hydrogen is also referred to as an unsubstituted methylene moiety. A methylene moiety wherein R and/or R are other than hydrogen is referred to as a substituted methylene moiety.

Thus, a methylene urea moiety according to the invention is a bivalent radical wherein one of the nitrogen atoms of the urea moiety is substituted by a methylene moiety. Preferably, A and B are bonded to the resulting methylene urea moiety via the nitrogen atom of the urea moiety that is not substituted by the methylene moiety, and to the carbon atom of the methylene moiety, respectively.

The hydrogen atoms of one or both nitrogen atoms of the methylene urea moiety can be substituted by suitable substituents, preferably selected from the group consisting of alkyl, alkylene, haloalkyl, $C_3$-$C_7$-cycloalkyl, $C_3$-$C_7$-cycloalkylene, heterocyclyl, aryl, aralkyl, heteroaryl, carboxy, cyanoalkyl, acyl and heteroaryl. Preferably, both nitrogen atoms of the methylene urea moiety are unsubstituted. In this respect, one or both of the nitrogen atoms of D can, independently from one another, optionally be deprotonated, protonated and/or quarternized. The resulting ions or salts are also subject of the present invention.

Accordingly, preferred compounds of formula I are of formula Ia

A—NH—CO—NH—B      Ia wherein A and B are as defined above/below, and wherein the carbonyl moiety in formula Ia can be derivatized as described above/below, and the salts or solvates thereof. Especially preferred are compounds of formula Ia, wherein the carbonyl moiety is not derivatized.

Preferably, A or B is substituted by one or more substituents as described above/below. More preferably, A and B each are substituted by one or more substituents as described above/below. Even more preferably, A is substituted by two or more substituents as described above/below.

Preferably, subject of the present invention are the optically active forms or stereo isomers of the compounds according to the invention, such as the enantiomers, the diastereomers and/or mixtures thereof in all ratios, such as, for example, stereochemically uniform compounds or racemates. Preferably, further subject of the present invention are the solvates and hydrates of the compounds according to the invention. Preferably, further subject of the present invention are the pharmaceutically acceptable derivatives or physiologically functional derivatives of the compounds according to the invention. More preferably, further subject of the present invention are the salts of the compounds according to the invention, especially the pharmaceutically and/or physiologically acceptable salts of compounds according to the invention.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" preferably refers to a straight or branched chain hydrocarbon having from one to twelve carbon atoms, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$-$C_6$ alkyl" preferably refers to an alkyl group as defined above containing at least 1, and at most 6, carbon atoms. Examples of branched or straight chained "$C_1$-$C_6$ alkyl" groups useful in the present invention include, but are not limited to, methyl, ethyl, n-propyl, isopropyl, isobutyl, n-butyl, t-butyl, n-pentyl and isopentyl.

As used herein, the term "alkylene" preferably refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto; amino optionally substituted by alkyl, carboxy, carbamoyl optionally substituted by alkyl, aminosulfonyl, optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene and the like.

As used herein, the term "$C_1$-$C_6$ alkylene" preferably refers to an alkylene group, as defined above, which contains at least 1, and at most 6, carbon atoms respectively. Examples of "$C_1$-$C_6$ alkylene" groups useful in the present invention include, but are not limited to, methylene, ethylene and n-Propylene.

As used herein, the term "halogen" or "hal" preferably refers to fluorine (F), chlorine (Cl), bromine (Br) or iodine (I).

As used herein, the term "$C_1$-$C_6$ haloalkyl" preferably refers to an alkyl group as defined above containing at least 1, and at most 6, carbon atoms substituted with at least one halogen, halogen being as defined herein. Examples of branched or straight chained "$C_1$-$C_6$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "$C_3$-$C_7$ cycloalkyl" preferably refers to a non-aromatic cyclic hydrocarbon ring having from three to seven carbon atoms and which optionally includes a $C_1$-$C_6$ alkyl linker through which it may be attached. The $C_1$-$C_6$ alkyl group is as defined above. Exemplary "$C_3$-$C_7$ cycloalkyl" groups include, but are not limited to, cyclopropyl, cyclobutyl, cyclopentyl, cyclohexyl and cycloheptyl. The term "cycloalkyl", as used herein preferably also includes saturated heterocyclic groups, which are preferably selected from the cycloalkyl-groups as defined above, wherein one or two carbon atoms are replaced by hetero atoms, selected from the group consisting of O, N and S.

As used herein, the term "$C_3$-$C_7$ cycloalkylene" preferably refers to a non-aromatic alicyclic divalent hydrocarbon radical having from three to seven carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" preferably refers to a three to twelve-membered heterocyclic ring having one or more degrees of unsaturation containing one or more heteroatomic substitutions selected from S, SO, $SO_2$, O or N, optionally substituted with substituents selected from the group consisting of $C_1$-$C_6$alkyl, $C_1$-$C_6$ haloalkyl, $C_1$-$C_6$ alkoxy, $C_1$-$C_6$ alkylsulfanyl, $C_1$-$C_6$ haloalkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, pyrrolidine, piperidine, morpholine, tetrahydrothiopyran, tetrahydrothiophene, and the like.

As used herein, the term "heterocyclylene" preferably refers to a three to twelve-membered heterocyclic ring diradical having one or more degrees of unsaturation containing one or more heteroatoms selected from S, SO, $SO_2$, O or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" preferably refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. Examples of "aryl" groups include, but are not limited to Phenyl, 2-naphthyl, 1-naphthyl, biphenyl, as well as substituted derivatives thereof. As used herein, the term "arylene" preferably refers to a benzene ring diradical or to a benzene ring system diradical fused to one or more optionally substituted benzene rings, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of "arylene" include, but are not limited to benzene-1,4-diyl, naphthalene-1,8-diyl, anthracene-1,4-diyl, and the like.

As used herein, the term "aralkyl" preferably refers to an aryl or heteroaryl group, as defined herein, attached through a $C_1$-$C_6$ alkyl linker, wherein $C_1$-$C_6$ alkyl is as defined herein. Examples of "aralkyl" include, but are not limited to, benzyl, phenylpropyl, 2-pyridylmethyl, 3 isoxazolylmethyl, 5-methyl-3-isoxazolylmethyl and 2-imidazolylethyl.

As used herein, the term "heteroaryl" preferably refers to a monocyclic five to seven-membered aromatic ring, or to a fused bicyclic aromatic ring system comprising two of such monocyclic five to seven-membered aromatic rings. These hetroaryl rings contain one or more nitrogen, sulfur and/or oxygen heteroatoms, where N-Oxides and sulfur Oxides and dioxides are permissible heteroatom substitutions and may be optionally substituted with up to three members selected from a group consisting of $C_1$-$C_6$ alkyl, $C_1$-$C_6$ haloalkyl, $C_1$-$C_6$ alkoxy, $C_1$-$C_6$ alkylsulfanyl, $C_1$-$C_6$ haloalkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "heteroarylene" preferably refers to a five- to seven-membered aromatic ring diradical, or to a polycyclic heterocylic aromatic ring diradical, containing one or more nitrogen, oxygen, or sulfur heteroatoms, where N-Oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,5-diyl, pyridine-2,4-diyl, pyridine-2,3-diyl, pyridine-2,5-diyl, pyrimidine-2,4-diyl quinoline-2,3-diyl, and the like.

As used herein, the term "alkoxy" preferably refers to the group $R_aO$—, where $R_a$ is alkyl as defined above and the term "$C_1$-$C_6$ alkoxy" preferably refers to an alkoxy group as defined herein wherein the alkyl moiety contains at least 1 and at most 6 carbon atoms. Exemplary $C_1$-$C_6$ alkoxy groups useful in the present invention include, but are not limited to methoxy, ethoxy, n-propoxy, isopropoxy, n-butoxy and t-butoxy.

As used herein, the term "haloalkoxy" preferably refers to the group $R_aO$—, where $R_a$ is haloalkyl as defined above and the term "$C_1$-$C_6$ haloalkoxy" preferably refers to an haloalkoxy group as defined herein wherein the haloalkyl moiety contains at least 1 and at most 6 carbon atoms. Exemplary $C_1$-$C_6$ haloalkoxy groups useful in the present invention include, but are not limited to, methoxy, ethoxy, n-propoxy, isopropoxy, n-butoxy and t-butoxy substituted with one or more halo groups, for instance trifluoromethoxy.

As used herein the term "aralkoxy" preferably refers to the group $R_CR_BO$—, where $R_B$ is alkyl and $R_C$ is aryl as defined above.

As used herein the term "aryloxy" preferably refers to the group $R_CO$—, where $R_C$ is aryl as defined above.

As used herein, the term "alkylsulfanyl" preferably refers to the group $R_AS$—, where $R_A$ is alkyl as defined above and the term "$C_1$-$C_6$ alkylsulfanyl" preferably refers to an alkylsulfanyl group as defined herein wherein the alkyl moiety contains at least 1 and at most 6-carbon atoms.

As used herein, the term "haloalkylsulfanyl" preferably refers to the group $R_DS$—, where $R_D$ is haloalkyl as defined above and the term "$C_1$-$C_6$ haloalkylsulfanyl" preferably refers to a haloalkylsulfanyl group as defined herein wherein the alkyl moiety contains at least 1 and at most 6 carbon atoms.

As used herein, the term "alkylsulfenyl" preferably refers to the group $R_AS(O)$—, where $R_A$ is alkyl as defined above and the term "$C_1$-$C_6$ alkylsulfenyl" preferably refers to an alkylsulfenyl group as defined herein wherein the alkyl moiety contains at least 1 and at most 6 carbon atoms.

As used herein, the term "alkylsulfonyl" preferably refers to the group $R_ASO_2$, where $R_A$ is alkyl as defined above and the term "$C_1$-$C_6$ alkylsulfonyl" preferably refers to an alkylsulfonyl group as defined herein wherein the alkyl moiety contains at least 1 and at most 6 carbon atoms.

As used herein, the term "oxo" preferably refers to the group =O.

As used herein, the term "mercapto" preferably refers to the group —SH.

As used herein, the term "carboxy" preferably refers to the group —COOH.

As used herein, the term "cyano" preferably refers to the group —CN.

As used herein, the term "cyanoalkyl" preferably refers to the group —$R_B$CN, wherein $R_B$ is alkylen as defined above. Exemplary "cyanoalkyl" groups useful in the present invention include, but are not limited to, cyanomethyl, cyanoethyl and cyanoisopropyl.

As used herein, the term "aminosulfonyl" preferably refers to the group —$SO_2NH_2$.

As used herein, the term "carbamoyl" preferably refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$— or —$SO_2$—.

As used herein, the term "acyl" preferably refers to the group $R_FC(O)$—, where $R_F$ is alkyl, cycloalkyl or heterocyclyl as defined herein.

As used herein, the term "aroyl" preferably refers to the group $R_CC(O)$—, where $R_C$ is aryl as defined herein.

As used herein, the term "heteroaroyl" preferably refers to the group $R_EC(O)$—, where $R_E$ is heteroaryl as defined herein.

As used herein, the term "alkoxycarbonyl" preferably refers to the group $R_AOC(O)$—, where $R_A$ is alkyl as defined herein.

As used herein, the term "acyloxy" preferably refers to the group $R_FC(O)O$—, where $R_F$ is alkyl, cycloalkyl, or heterocyclyl as defined herein.

As used herein, the term "aroyloxy" preferably refers to the group $R_CC(O)O\text{—}$, where $R_C$ is aryl as defined herein.

As used herein, the term "heteroaroyloxy" preferably refers to the group $R_EC(O)O\text{—}$, where $R_E$ is heteroaryl as defined herein.

As used herein, the term "carbonyl" or "carbonyl moiety" preferably refers to the group C=O.

As used herein, the term "thiocarbonyl" or "thiocarbonyl moiety" preferably refers to the group C=S.

As used herein, the term "amino", "amino group" or "imino moiety" preferably refers to the group $NR_GR_{G'}$, wherein $R_G$ and $R_{G'}$ are preferably selected, independently from one another, from the group consisting of hydrogen, halogen, alkyl, haloalkyl, alkenyl, cycloalkyl, alkylenecycloalkyl, cyanoalkyl, aryl, aralkyl, heteroaryl, acyl and aroyl. If both $R_G$ and $R_{G'}$ are hydrogen, $NR_GR_{G'}$ is also referred to as "unsubstituted amino moiety" or "unsubstituted amino group". If $R_G$ and/or $R_{G'}$ are other than hydrogen, $NR_GR_{G'}$ is also referred to as "substituted amino moiety" or "substituted amino group".

As used herein, the term "imino" or "imino moiety" preferably refers to the group $C=NR_G$, wherein $R_G$ is preferably selected from the group consisting of hydrogen, halogen, alkyl, haloalkyl, alkenyl, cycloalkyl, alkylenecycloalkyl, cyanoalkyl, aryl, aralkyl, heteroaryl, acyl and aroyl. If $R_G$ is hydrogen, $C=NR_G$ is also referred to as "unsubstituted imino moiety". If $R_G$ is a residue other than hydrogen, $C=NR_G$ is also referred to as "substituted imino moiety".

As used herein, the term "ethene-1,1-diyl moiety" preferably refers to the group $C=CR_KR_L$, wherein $R_K$ and $R_L$ are preferably selected, independently from one another, from the group consisting of hydrogen, halogen, alkyl, haloalkyl, alkenyl, cycloalkyl, nitro, alkylenecycloalkyl, cyanoalkyl, aryl, aralkyl, heteroaryl, acyl and aroyl. If both hydrogen $R_K$ and $R_L$ are hydrogen, $C=CR_KR_L$ is also referred to as "unsubstituted ethene-1,1-diyl moiety". If one of $R_K$ and $R_L$ or both are a residue other than hydrogen, $C=CR_KR_L$ is also referred to as "substituted ethene-1,1-diyl moiety".

As used herein, the terms "group", "residue" and "radical" or "groups", "residues" and "radicals" are usually used as synonyms, respectively, as it is common practice in the art.

As used herein, the term "optionally" means that the subsequently described event(s) may or may not occur, and includes both event(s), which occur, and events that do not occur.

As used herein, the term "pharmaceutically acceptable derivative" preferably refers to any physiologically functional derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives. Such derivatives preferably include so-called prodrug-compounds, for example compounds according to the invention that are derivatized with alkyl groups, acyl groups, sugars or peptides, such as oligopeptides, and that are easily degraded or metabolized to the active compounds according to the invention. Such derivatives preferably include biodegradable polymer derivatives of the compounds according to the invention. Suitable polymers and methods for producing biodegradable polymeric derivatives are known in the art, for example from Int. J. Pharm. 115, 61-67 (1995).

As used herein, the term "solvate" preferably refers to a complex of variable stoichiometry formed by a solute (in this invention, a compound of formula I or formula II or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Examples for suitable solvates are the mono- or dihydrates or alcoholates of the compounds according to the invention.

As used herein, the term "substituted" preferably refers to substitution with the named substituent or substituents, multiple degrees of substitution being allowed unless otherwise stated.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, especially mixtures of enantiomers, as well as purified stereoisomers, especially purified enantiomers, or stereoisomerically enriched mixtures, especially enantiomerically enriched mixtures. Also included within the scope of the invention are the individual isomers of the compounds represented by formulae I and II above as well as any wholly or partially equilibrated mixtures thereof. The present invention also covers the individual isomers of the compounds represented by the formulas above as mixtures with isomers thereof in which one or more chiral Centers are inverted. Also, it is understood that all tautomers and mixtures of tautomers of the compounds of formulae (I) or (II) are included within the scope of the compounds of formulae (I) and (II) and preferably the formulae and subformulae corresponding thereto.

Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture.

The diastereomer resolution can also be carried out by standard purification processes, such as, for example, chromatography or fractional crystallization.

It is of course also possible to obtain optically active compounds of the formula I or II by the methods described above by using starting materials which are already optically active.

Unless indicated otherwise, it is to be understood that reference to compounds of formula I preferably includes the reference to the compounds of formula II. Unless indicated otherwise, it is to be understood that reference to the compounds of formula II preferably includes the reference to the sub formulae corresponding thereto, for example the sub formulae II.1 to II.20 and preferably formulae IIa to IIx. It is also understood that the following embodiments, including uses and compositions, although recited with respect to formula I are preferably also applicable to formulae II, sub formulae II.1 to II.20 and preferably formulae IIa to IIx.

Especially preferred compounds according to the invention are compounds of formula II

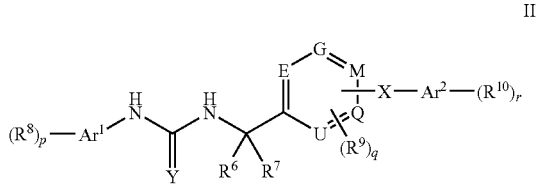

wherein
$Ar^1$, $Ar^2$ are selected independently from one another from aromatic hydrocarbons containing 6 to 14 carbon atoms and ethylenical unsaturated or aromatic heterocyclic residues containing 3 to 10 carbon atoms and one or two heteroatoms, independently selected from N, O and S,
$R^6$, $R^7$ are independently selected from the meanings given for $R^8$, $R^9$ and $R^{10}$,
or $R^6$ and $R^7$ together form a carbocyclic residue comprising 3 to 7 carbon atoms or a heterocyclic residue comprising 1, 2 or 3 hetero atoms, selected from the group consisting of O, N and S, and 2 to 6 carbon atoms, said carbocyclic or heterocyclic residue being unsubstituted or comprising 1, 2 or 3 substituents, selected from the meanings given for $R^8$, $R^9$ and $R^{10}$,
E, G, M, Q and U are selected, independently from one another, from carbon atoms and nitrogen atoms, with the proviso that one or more of E, G, M, Q and U are carbon atoms and that X is bonded to a carbon atom,
$R^8$, $R^9$ and $R^{10}$ are independently selected from a group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_nNR^{11}R^{12}$, $(CH_2)_nO(CH_2)_kNR^{11}R^{12}$ $(CH_2)_nNR^{11}$ $(CH_2)_kNR^{11}R^{12}$, $(CH_2)_nO(CH_2)_kOR^{11}$, $(CH_2)_nNR^{11}$ $(CH_2)_kOR^{12}$, $(CH_2)_nCOOR^{13}$, $(CH_2)_nCOR^{13}$, $(CH_2)_n$ $CONR^{11}R^{12}$, $(CH_2)_nNR^{11}COR^{13}$, $(CH_2)_n$ $NR^{11}CONR^{11}R^{12}$, $(CH_2)_nNR^{11}SO_2A$, $(CH_2)_n$ $SO_2NR^{11}R^{12}$, $(CH_2)_nS(O)_uR^{13}$, $(CH_2)_nOC(O)R^{13}$, $(CH_2)_n$ $COR^{13}$, $(CH_2)_nSR^{11}$, $CH=N-OA$, $CH_2CH=N-OA$, $(CH_2)_nNHOA$, $(CH_2)_nCH=N-R^{11}$, $(CH_2)_nOC(O)$ $NR^{11}R^{12}$, $(CH_2)_nNR^{11}COOR^{13}$, $(CH_2)_nN(R^{11})$ $CH_2CH_2OR^{13}$, $(CH_2)_nN(R^{11})CH_2CH_2OCF_3$, $(CH_2)_nN$ $(R^{11})C(R^{13})HCOOR^{12}$, $(CH_2)_nN(R^{11})C(R^{13})HCOR^{11}$, $(CH_2)_nN(R^{11})CH_2CH_2N(R^{12})CH_2COOR^{11}$, $(CH_2)_nN$ $(R^{11})CH_2CH_2NR^{11}R^{12}$, $CH=CHCOOR^{13}$, $CH=CHCH_2NR^{11}R^{12}$, $CH=CHCH_2NR^{11}R^{12}$, $CH=CHCH_2OR^{13}$, $(CH_2)_nN(COOR^{13})COOR^{14}$, $(CH_2)_n$ $N(CONH_2)COOR^{13}$, $(CH_2)_nN(CONH_2)CONH_2$, $(CH_2)_n$ $N(CH_2COOR^{13})COOR^{14}$, $(CH_2)_nN(CH_2CONH_2)$ $COOR^{13}$, $(CH_2)_nN(CH_2CONH_2)CONH_2$, $(CH_2)_n$ $CHR^{13}COR^{14}$, $(CH_2)_nCHR^{13}COOR^{14}$, $(CH_2)$ $CHR^{13}CH_2OR^{14}$, $(CH_2)_nOCN$ and $(CH_2)_nNCO$, wherein
$R^{11}$, $R^{12}$ are independently selected from a group consisting of H, A, $(CH_2)_mAr^3$ and $(CH_2)_mHet$, or in $NR^{11}R^{12}$,
$R^{11}$ and $R^{12}$ form, together with the N-atom they are bound to, a 5-, 6- or 7-membered heterocyclus which optionally contains 1 or 2 additional hetero atoms, selected from N, O and S,
$R^{13}$, $R^{14}$ are independently selected from a group consisting of H, Hal, A, $(CH_2)_mAr^4$ and $(CH_2)_mHet$,
A is selected from the group consisting of alkyl, alkenyl, cycloalkyl, alkylenecycloalkyl, alkoxy, alkoxyalkyl and saturated heterocyclyl, preferably from the group consisting of alkyl, alkenyl, cycloalkyl, alkylenecycloalkyl, alkoxy and alkoxyalkyl,
$Ar^3$, $Ar^4$ are independently from one another aromatic hydrocarbon residues comprising 5 to 12 and preferably 5 to 10 carbon atoms which are optionally substituted by one or more substituents, selected from a group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2R^{15}R^{16}$, $S(O)_uA$ and $OOCR^{15}$,
Het is a saturated, unsaturated or aromatic heterocyclic residue which is optionally substituted by one ore more substituents, selected from a group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2R^{15}R^{16}$, $S(O)_uA$ and $OOCR^{15}$,
$R^{15}$, $R^{16}$ are independently selected from a group consisting of H, A, and $(CH_2)_mAr^6$, wherein
$Ar^6$ is a 5- or 6-membered aromatic hydrocarbon which is optionally substituted by one or more substituents selected from a group consisting of methyl, ethyl, propyl, 2-propyl, tert-butyl, Hal, CN, OH, $NH_2$ and $CF_3$,
k, n and m are independently of one another 0, 1, 2, 3, 4, or 5,
X represents a bond or is $(CR^{11}R^{12})_h$, or $(CHR^{11})_h$-Q-$(CHR^{12})_i$, wherein
Q is selected from a group consisting of O, S, $N-R^{15}$, $(CHal_2)_j$, $(O-CHR^{18})_j$, $(CHR^{18}-O)_j$, $CR^{18}=CR^{19}$, $(O-CHR^{18}CHR^{19})_j$, $(CHR^{18}CHR^{19}-O)_j$, C=O, C=S, $C=NR^{15}$, $CH(OR^{15})$, $C(OR^{15})(OR^{20})$, $C(=O)O$, $OC(=O)$, $OC(=O)O$, $C(=O)N(R^{15})$, $N(R^{15})C(=O)$, $OC(=O)N(R^{15})$, $N(R^{15})C(=O)O$, $CH=N-O$, $CH=N-NR^{15}$, $OC(O)NR^{15}$, $NR^{15}C(O)O$, S=O, $SO_2$, $SO_2NR^{15}$ and $NR^{15}SO_2$, wherein
h, i are independently from each other 0, 1, 2, 3, 4, 5, or 6, and
j is 1, 2, 3, 4, 5, or 6,
Y is selected from O, S, $NR^{21}$, $C(R^{22})-NO_2$, $C(R^{22})-CN$ and $C(CN)_2$, wherein
$R^{21}$ is independently selected from the meanings given for $R^{13}$, $R^{14}$ and
$R^{22}$ is independently selected from the meanings given for $R^{11}$, $R^{12}$,
p, r are independently from one another 0, 1, 2, 3, 4 or 5,
q is 0, 1, 2, 3 or 4, preferably 0, 1 or 2,
u is 0, 1, 2 or 3, preferably 0, 1 or 2,
and
Hal is independently selected from a group consisting of F, Cl, Br and I;

and the pharmaceutically acceptable derivatives, solvates, salts and stereoisomers thereof, including mixtures thereof in all ratios, and, more preferred the salts and/or solvates thereof, and especially preferred the physiologically acceptable salts and/or solvates thereof.

Even more preferred are compounds of formula II wherein
$Ar^1$, $Ar^2$ are selected independently from one another from aromatic hydrocarbons containing 6 to 10 and especially 6 carbon atoms and ethylenical unsaturated or aromatic heterocyclic residues containing 3 to 8 and especially 4 to 6 carbon atoms and one or two heteroatoms, independently selected from N, O and S and especially selected from N and O,
$R^8$, $R^9$ and $R^{10}$ are independently selected from a group consisting of H, A, cycloalkyl comprising 3 to 7 carbon atoms, Hal, $CH_2Hal$, $CH(Hal)$, $C(Hal)_3$, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}(CH_2)_k$ $NR^{11}R^{12}$, $(CH_2)O(CH_2)_kOR^{11}$, $(CH_2)_nNR^{11}(CH_2)_kOR^{12}$, (CH$_2$)COR$^{13}$, (CH$_2$)$_n$COOR$^{13}$, (CH$_2$)$_n$CONR$^{11}$R$^{12}$, (CH$_2$)NR$^{11}$COR$^{13}$, (CH$_2$)$_n$NR$^{11}$CONR$^{11}$R$^{12}$, (CH$_2$)$_n$NR$^{11}$SO$_2$A, (CH$_2$)$_n$SO$_2$NR$^{11}$R$^{12}$, (CH$_2$)$_n$S(O)$_u$R$^{13}$, (CH$_2$)$_n$OC(O)R$^{13}$, (CH$_2$)$_n$COR$^{13}$, (CH$_2$)$_n$SR$^{11}$, (CH$_2$)$_n$NHOA, (CH$_2$)$_n$NR$^{11}$COOR$^{13}$, (CH$_2$)$_n$N(R$^{11}$) CH$_2$CH$_2$OR$^{13}$, (CH$_2$)$_n$N(R$^{11}$)CH$_2$CH$_2$OCF$_3$, (CH$_2$)$_n$N (R$^{11}$)C(R$^{13}$)HCOOR$^{8}$, (CH$_2$)$_n$N(R$^{11}$), C(R$^{13}$)HCOR$^{8}$, (CH$_2$)$_n$N(COOR$^{13}$)COOR$^{14}$, (CH$_2$)$_n$N(CONH$_2$)COOR$^{13}$, (CH$_2$)$_n$N(CONH$_2$)CONH$_2$, (CH$_2$)$_n$N(CH$_2$COOR$^{13}$) COOR$^{14}$, (CH$_2$)$_n$N(CH$_2$CONH$_2$)COOR$^{13}$, (CH$_2$)$_n$N (CH$_2$CONH$_2$)CONH$_2$, (CH$_2$)$_n$CHR$^{13}$COR$^{14}$, (CH$_2$)$_n$ CHR$^{13}$COOR$^{14}$ and (CH$_2$)$_n$CHR$^{13}$CH$_2$OR$^{14}$, R$^{6}$, R$^{7}$ are independently selected from a the meanings given for R$^{8}$, R$^{9}$ and R$^{10}$, more preferred independently selected from the group consisting of H, A, Hal, CH$_2$Hal, CH(Hal)$_2$, C(Hal)$_3$, NO$_2$, (CH$_2$)$_n$CN, (CH$_2$)$_n$NR$^{11}$R$^{12}$, (CH$_2$)$_n$O (CH$_2$)$_k$NR$^{11}$R$^{12}$, (CH$_2$)$_n$NR$^{11}$(CH$_2$)$_k$NR$^{11}$R$^{12}$, (CH$_2$)$_n$O (CH$_2$)$_k$OR$^{11}$, (CH$_2$)$_n$NR$^{11}$(CH$_2$)$_k$OR$^{12}$, (CH$_2$)$_n$COR$^{13}$, (CH$_2$)$_n$COOR$^{13}$, (CH$_2$)$_n$CONR$^{11}$R$^{12}$, (CH$_2$)$_n$ NR$^{11}$COR$^{13}$, (CH$_2$)$_n$NR$^{11}$CONR$^{11}$R$^{12}$, (CH$_2$)$_n$ NR$^{11}$SO$_2$A, (CH$_2$)$_n$SO$_2$NR$^{11}$R$^{12}$, (CH$_2$)$_n$S(O)$_u$R$^{13}$, (CH$_2$)$_n$COR$^{13}$, (CH$_2$)$_n$SR$^{11}$, (CH$_2$)$_n$NHOA and (CH$_2$)$_n$ NR$^{11}$COOR$^{13}$, or R$^{6}$ and R$^{7}$ together form a carbocyclic residue comprising 3 to 7 carbon atoms or a heterocyclic residue comprising 1, 2 or 3 hetero atoms, selected from the group consisting of O, N and S, and 2 to 6 carbon atoms, said carbocyclic or heterocyclic residue being unsubstituted or comprising 1, 2 or 3 substituents, selected from the meanings given for R$^{8}$, R$^{9}$ and R$^{10}$, more preferred selected from the group consisting of H, A, Hal, CH$_2$Hal, CH(Hal)$_2$, C(Hal)$_3$, NO$_2$, (CH$_2$)$_n$CN, (CH$_2$)$_n$NR$^{11}$R$^{12}$, (CH$_2$)$_n$O(CH$_2$)$_n$NR$^{11}$R$^{12}$, (CH$_2$)$_n$NR$^{11}$(CH$_2$)$_n$NR$^{11}$R$^{12}$, (CH$_2$)$_n$O(CH$_2$)$_k$OR$^{11}$, (CH$_2$)$_n$NR$^{11}$(CH$_2$)$_k$OR$^{12}$, (CH$_2$)$_n$COR$^{13}$, (CH$_2$)$_n$ COOR$^{13}$, (CH$_2$)$_n$CONR$^{11}$R$^{12}$, (CH$_2$)$_n$NR$^{11}$COR$^{13}$, (CH$_2$)$_n$NR$^{11}$CONR$^{12}$, (CH$_2$)$_n$ NR$^{11}$SO$_2$A, (CH$_2$)$_n$ SO$_2$NR$^{11}$R$^{12}$, (CH$_2$)$_n$S(O)$_u$R$^{13}$, (CH$_2$)$_n$COR$^{13}$, (CH$_2$)$_n$ SR$^{11}$, (CH$_2$)$_n$NHOA and (CH$_2$)$_n$NR$^{11}$CORR$^{13}$, X represents a bond or is (CR$^{11}$R$^{12}$)$_h$, or (CHR$^{11}$)$_h$-Q-(CHR$^{12}$)$_i$, wherein Q is selected from a group consisting of O, S, N—R$^{15}$, (CHal$_2$)$_j$, (O—CHR$^{18}$)$_j$, (CHR$^{18}$—O)$_j$, CR$^{18}$=CR$^{19}$, (O—CHR$^{18}$CHR$^{19}$)$_j$, (CHR$^{18}$CHR$^{19}$—O)$_j$, C=O, C=NR$^{15}$, CH(OR$^{15}$), C(OR$^{15}$)(OR$^{20}$), C(=O)N(R$^{15}$), N(R$^{15}$)C(=O), CH=N—NR$^{15}$, S=O, SO$_2$, SO$_2$NR$^{15}$ and NR$^{15}$SO$_2$, wherein h, i and k are independently from each other 0, 1, 2, 3, 4, 5 or 6, preferably 0, 1, 2 or 3 and j is 1, 2, 3, 4, 5 or 6, preferably 1, 2, 3 or 4, p is 1, 2, 3 or 4, preferably 1, 2 or 3, and r is 0, 1, 2, or 3, preferably 0, 1 or 2;

and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Subject of the present invention are especially compounds of formula I and II, in which one or more substituents or groups, preferably the major part of the substituents or groups has a meaning which is indicated as preferred, more preferred, even more preferred or especially preferred.

In compounds of formula II, E, G, M, Q and U constitute, together with the carbon atom that E and U are bound to, a bivalent 6-membered aromatic or nitrogen containing heteroaromatic ring. Preferably, one or more of E, G, M, Q and U, more preferably two or more of E, G, M, Q and U and especially three or more of E, G, M, Q and U are carbon atoms. Especially preferred, none or one of E, G, M, Q and U is a nitrogen atom. Especially preferred, E, G, M, Q and U constitute, together with the carbon atom that E and U are bound to, a 6-membered aromatic or nitrogen containing heteroaromatic ring, selected from the group consisting of phenylen, pyridinylen and pyrimydylen, wherein X is preferably bonded to a carbon atom. The substituents R$^{9}$ are preferably bound to a carbon atom.

Especially preferred as compounds of formula II are compounds of formula II',

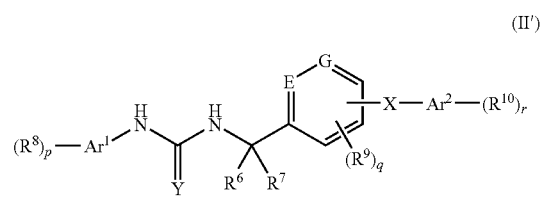

(II')

wherein E and G are as defined above, preferably E and G are both nitrogen atoms; more preferably one of E and G is a nitrogen atom or both E and G are carbon atoms. If E and/or G are carbon atoms, they can be unsubstituted or substituted by R$^{9}$, i.e E and/or G are either CH or CR$^{9}$.

In compounds of formula II, the term alkyl preferably refers to an unbranched or branched alkyl residue, preferably an unbranched alkyl residue comprising 1, 2, 3, 4, 5, 6, 7, 8, 9 or 10, preferably 1, 2, 3, 4, 5 or 6, more preferred 1, 2, 3 or 4 and especially 1 or 2 carbon atoms, or a branched alkyl residue comprising 3, 4, 5, 6, 7, 8, 9 or 10, preferably 3, 4, 5 or 6 more preferred 3 or 4 carbon atoms. The alkyl residues can be optionally substituted, especially by one or more halogen atoms, for example up to perhaloalkyl, by one or more hydroxy groups or by one or more amino groups, all of which can optionally be substituted by alkyl. If an alkyl residue is substituted by halogen, it usually comprises 1, 2, 3, 4 or 5 halogen atoms, depending on the number of carbon atoms of the alkyl residue. For example, a methyl group can comprise, 1, 2 or 3 halogen atoms, an ethyl group (an alkyl residue comprising 2 carbon atoms) can comprise 1, 2, 3, 4 or 5 halogen atoms. If an alkyl residue is substituted by hydroxy groups, it usually comprises one or two, preferably one hydroxy groups. If the hydroxy group is substituted by alkyl, the alkyl substituent comprises preferably 1 to 4 carbon atoms and is preferably unsubstituted or substituted by halogen and more preferred unsubstituted. If an alkyl residue is substituted by amino groups, it usually comprises one or two, preferably one amino groups. If the amino group is substituted by alkyl, the alkyl substituent comprises preferably 1 to 4 carbon atoms and is preferably unsubstituted or substituted by halogen and more preferred unsubstituted. According to compounds of formula II, alkyl is preferably selected from the group consisting of methyl, ethyl, trifluoro methyl, pentafluoro ethyl, isopropyl, tert-butyl, 2-amino ethyl, N-methyl-2-amino ethyl, N,N-dimethyl-2-amino ethyl, N-ethyl-2-amino ethyl, N,N-diethyl-2-amino ethyl, 2-hydroxy ethyl, 2-methoxy ethyl and 2-ethoxy ethyl, further preferred of the group consisting of 2-butyl, n-pentyl, neo-nentyl, isopentyl, hexyl and n-decyl, more preferred of methyl, ethyl, trifluoro methyl, isoproply and tert-butyl.

In compounds of formula II, alkenyl is preferably selected from the group consisting of allyl, 2- or 3-butenyl, isobutenyl, sec-butenyl, furthermore preferably 4-pentenyl, isopentenyl and 5-hexenyl.

In compounds of formula II, alkylene is preferably unbranched and is more preferably methylene or ethylene, furthermore preferably propylene or butylene.

In compounds of formula II, alkylenecycloalkyl preferably has 5 to 10 carbon atoms and is preferably methylenecyclopropyl, methylenencyclobutyl, furthermore preferably methylenecyclopentyl, methylenecyclohexyl or methylenecycloheptyl, furthermore alternatively ethylenecyclopropyl, ethylenecyclobutyl, ethylenecyclopentyl, ethylenecyclohexyl or ethylenencycloheptyl, propylenecyclopentyl, propylenecyclohexyl, butylenecyclopentyl or butylenecyclohexyl.

In compounds of formula II, the term "alkoxy" preferably comprises groups of formula O-alkyl, where alkyl is an alkyl group as defined above. More preferred, alkoxy is selected from group consisting of methoxy, ethoxy, n-propoxy, iso-propoxy, 2-butoxy, tert-butoxy and halogenated, especially perhalogenated, derivatives thereof. Preferred perhalogenated derivatives are selected from the group consisting of O—$CCl_3$, O—$CF_3$, O—$C_2Cl_5$, O—$C_2F_5$, O—$C(CCl_3)_3$ and O—$C(CF_3)_3$.

In compounds of formula II, the term "alkoxyalkyl" preferably comprises branched and unbranched residues, more preferred unbranched residues, of formula $C_uH_{2u+1}$—O—$(CH_2)_v$, wherein u and v are independently from each other 1 to 6. Especially preferred is u=1 and v 1 to 4.

In compounds of formula II the term "alkoxyalkyl" includes alkoxyalkyl groups as defined above, wherein one or more of the hydrogen atoms are substituted by halogen, for example up to perhalo alkoxyalkyl.

In compounds of formula II, cycloalkyl preferably has 3-7 carbon atoms and is preferably cyclopropyl or cyclobutyl, furthermore preferably cyclopentyl or cyclohexyl, furthermore also cycloheptyl, particularly preferably cyclopentyl. The term "cycloalkyl", as used herein preferably also includes saturated heterocyclic groups, wherein one or two carbon atoms are substituted by hetero atoms, selected from the group consisting of O, NH, NA and S, wherein A is as defined as above/below.

In compounds of formula II, $Ar^3$ to $Ar^6$ are preferably selected independently from one another from phenyl, naphthyl and biphenyl which is optionally substituted by one or more substituents, selected from the group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2R^{15}R^{16}$, $S(O)_uA$ and $OOCR^{15}$.

In compounds of formula II, het is preferably an optionally substituted aromatic heterocyclic residue and even more preferred and optionally substituted saturated heterocyclic residue, wherein the substituents are preferably selected from A, CN and hal. Even more preferred, het is selected from the group consisting of 1-piperidyl, 1-piperazyl, 1-(4-methyl)-piperazyl, 4-methylpiperazin-1-yl amine, 4-morpholinyl, 1-pyrrolidinyl, 2-pyrrolidinyl, 3-pyrrolidinyl, 1-pyrazolidinyl 1-(2-methyl)-pyrazolidinyl, 1-imidazolidinyl or 1-(3-methyl)imidazolidinyl, thiophen-2-yl, thiophen-3-yl, 2-pyridyl, 3-pyridyl, 4-pyridyl, 2-oxazolyl, 4-oxazolyl, 5-oxazolyl, 2-thiazolyl, 4-thiazolyl, 5-thiazolyl, chinolinyl, isochinolinyl, 2-pyridazyl, 4-pyridazyl, 2-pyrimidyl, 4-pyrimidyl, 5-pyrimidyl, 2-pyrazinyl and 3-pyrazinyl. Especially the thiophenyl and the pyridyl residues can optionally be substituted by one or more cyano groups.

In compounds of formula II, saturated heterocyclyl is preferably a substituted or unsubstituted saturated heterocyclic residue, more preferred an unsubstituted saturated heterocyclic residue, preferably selected from the saturated groups given above in the definition of het.

In compounds of formula II, aromatic hydrocarbons containing 6 to 14 carbon atoms and ethylenical unsaturated or aromatic heterocyclic residues containing 3 to 10 carbon atoms and one or two heteroatoms, independently selected from N, O and S, are preferably selected from the definitions given herein for aryl, heteroaryl and/or het. Heteroaryl is more preferably furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl and even more preferably pyridinyl, pyrimidyl, chinolinyl, isochinolinyl, thiophenyl, thiadiazolyl, benzothiadiazolyl, oxazolyl, isoxazolyl, pyrazolyl and/or imidazolyl. Aryl more preferably refers to an optionally substituted benzene ring or to an optionally substituted benzene ring system fused to one or more optionally substituted benzene rings to form, for example, anthracene, phenanthrene, or napthalene ring systems. Even more preferably, aryl is selected from the group consisting of phenyl, 2-naphthyl, 1-naphthyl, biphenyl.

In compounds of formula II, $Ar^1$ is preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, and especially from phenyl, pyridinyl, chinolinyl, isochinolinyl, thiophenyl, benzothiadiazolyl, oxazolyl, isoxazolyl and oxazolyl.

In compounds of formula II, $Ar^2$ is preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, even more preferably from phenyl, pyridinyl and pyrimidyl and especially preferred from phenyl and pyridinyl.

Preferably, the sum of h and l exceeds 0.

A preferred aspect of the instant invention relates to compounds of formula II, wherein n is 0 or 1 and especially 0.

Another preferred aspect of the instant invention relates to compounds of formula II, wherein n is 0 in the residues $R^8$, $R^9$ and/or $R^{10}$ and especially in $R^{10}$.

Another preferred aspect of the instant invention relates to compounds of formula II, wherein n is 0 in the residues $R^6$ and/or $R^7$.

Another preferred aspect of the instant invention relates to compounds of formula II, wherein X represents a bridging group, selected from $(CR^{11}R^{12})_h$ or $(CHR^{11})_h$-Q-$(CHR^{12})_l$.

The invention relates in particular to compounds of the formula II in which at least one of said radicals has one of the preferred meanings given above.

Some more preferred groups of compounds may be expressed by the following sub-formulae II.1) to II.20), which correspond to the formula II and in which radicals not denoted in greater detail are as defined in the formula II, but in which II.1) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl;

II.2) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, and p is 1, 2 or 3;

II.3) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, and $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$ $(CH_2)_nCONR^{11}R^{12}$, $(CH_2)_nSO_2NR^{11}R^{12}$ and $(CH_2)_nS(O)_uR^{13}$;

II.4) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl; isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$;

II.5) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, wherein n is 0 or 1;

II.6) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, wherein n is 0 or 1, and u is 0;

II.7) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S;

II.8) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4-carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl;

II.9) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$ wherein n is 0 or 1, u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2NR^{11}R^{12}$, $(CH_2)_nNR^{11}$ $(CH_2)_kNR^{11}R^{12}$, $(CH_2)_nO(CH_2)_kOR^{11}$, $(CH_2)_nNR^{11}$ $(CH_2)_kOR^{12}$, $(CH_2)_nCOR^{13}$, $(CH_2)_nCOOR^{13}$ $(CH_2)_n$ $CONR^{11}R^{12}$, $(CH_2)_nSO_2NR^{11}R^{12}$ and $(CH_2)_nS(O)_u$ $R^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_n$ $COR^{13}$, $(CH_2)_nCOOR^{13}$, $(CH_2)_nCONR^{11}R^{12}$ and especially $(CH_2)_nCONR^{11}R^{12}$;

II.10) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_n$ $COOR^{13}$, $(CH_2)_nCONR^{11}R^{12}$, $(CH_2)SO_2NR^{11}R^{12}$ and $(CH_2)_nS(O)_uR^{13}$, wherein n is 0 or 1, u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, wherein n is 0, 1 or 2, preferably 0 or 1;

II.11) $Ar^1$ is phenyl, pyridinyl, pyrimidyl, chinolinyl, isochinolinyl, thiophenyl, thiadiazolyl, benzothiadiazolyl, oxazolyl, isoxazolyl, pyrazolyl or imidazolyl, preferably phenyl, pyridinyl, chinolinyl, isochinolinyl, thiophenyl, benzothiadiazolyl, oxazolyl, isoxazolyl or oxazolyl, p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}$ $(CH_2)_kNR^{11}R^{12}$, $(CH_2)_nO(CH_2)_kOR^{11}$, $(CH_2)_nNR^{11}$ $(CH_2)_kOR^{12}$, $(CH_2)_nCOR^{13}$, $(CH_2)_nCOOR^{13}$, $(CH_2)_n$ $CONR^{11}R^{12}$, $(CH_2)_nSO_2NR^{11}R^{12}$ and $(CH_2)_nS(O)_u$ $R^{13}$, wherein n is 0 or 1, u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, wherein n is 0, 1 or 2, preferably 0 or 1 and r is 0, 1 or 2, preferably 0 or 1;

II.12) p is 1, 2 or 3, $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}$ $(CH_2)_kNR^{11}R^{12}$, $(CH_2)_nO(CH_2)_kOR^{11}$, $(CH_2)_nNR^{11}$ $(CH_2)_kOR^{12}$, $(CH_2)_nCOR^{13}$, $(CH_2)_nCOOR^{13}$, $(CH_2)_n$ $CONR^{11}R^{12}$, $(CH_2)_nSO_2NR^{11}R^{12}$ and $(CH_2)_nS(O)_u$ $R^{13}$, wherein n is 0 or 1, u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_n$ $NR^{11}(CH_2)_kNR^{11}R^{12}$, $(CH_2)_nO(CH_2)_kOR^{11}$, $(CH_2)_n$ $NR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, wherein n is 0, 1 or 2, preferably 0 or 1 and r is 0, 1 or 2, preferably 0 or 1;

II.13) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}(CH_2)_k$ $NR^{11}R^{12}$, $(CH_2)_nO(CH_2)_kOR^{11}$, $(CH_2)_nNR^{11}(CH_2)_k$ $OR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, wherein n is 0 or 1, u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)COR^{13}$, $(CH_2)_nCOOR^{13}$, $(CH_2)_nCONR^{11}R^{12}$ and especially $(CH_2)_nCONR^{11}R^{12}$ wherein n is 0, 1 or 2, preferably 0 or 1 and r is 0, 1 or 2, preferably 0 or 1;

II.14) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, wherein u is 0, and q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, wherein n is 0, 1 or 2, preferably 0 or 1 and r is 0, 1 or 2, preferably 0 or 1;

II.15) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, wherein q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)COR^{13}$, $(CH_2)_nCOOR^{13}$, $(CH_2)_nCONR^{11}R^{12}$ and especially $(CH_2)_nCONR^{11}R^{12}$, wherein n is 0, 1 or 2, preferably 0 or 1 and r is 0, 1 or 2, preferably 0 or 1;

II.16) q is 0 or 1, and

X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)NR^{11}N(CH_2)_kNR^{11}R^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, wherein n is 0, 1 or 2, preferably 0 or 1 and r is 0, 1 or 2, preferably 0 or 1;

II.17) X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl; and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{12}$, $(CH_2)_nO(CH_2)_kOR^{11}$, $(CH_2)_nNR^{11}(CH_2)_kOR^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)COOR^{13}$, $(CH_2)_nCONR^{11}R^{12}$ and especially $(CH_2)_nCONR^{11}R^{12}$, wherein n is 0, 1 or 2, preferably 0 or 1 and r is 0, 1 or 2, preferably 0 or 1;

II.18) $Ar^2$ is phenyl, pyridinyl or pyrimidyl, and especially is phenyl or pyridinyl; and $R^{10}$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}$ $(CH_2)_kNR^{11}R^{12}$, $(CH_2)_nO(CH_2)_kOR^{11}$, $(CH_2)_nNR^{11}$ $(CH_2)_kOR^{12}$, $(CH_2)_nCOR^{13}$, $(CH_2)_nCOOR^{13}$, $(CH_2)_n$ $CONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, n is 0, 1 or 2, preferably 0 or 1 and r is 0, 1 or 2, preferably 0 or 1;

II.19) $R^{10}$ is selected from the group consisting of H, alkyl comprising 1 to 4 carbon atoms, alkoxy comprising 1 to 4 carbon atoms, Hal, $CH_2$Hal, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}(CH_2)_k$ $NR^{11}R^{12}$, $(CH_2)_nO(CH_2)_kOR^{11}$, $(CH_2)_nNR^{11}(CH_2)_k$ $OR^{12}$, $(CH_2)_nCOR^{13}$, $(CH_2)_nCOOR^{13}$, $(CH_2)_n$ $CONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_n$ $NR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, n is 0, 1 or 2, preferably 0 or 1 and r is 0, 1 or 2, preferably 0 or 1;

II.20) $R^{10}$ is selected from the group consisting of H, alkyl comprising 1 to 4 carbon atoms, alkoxy comprising 1 to 4 carbon atoms, Hal, $CH_2$Hal, $CH(Hal)_2$, perhaloalkyl comprising 1 to 4 carbon atoms, $NO_2$, $(CH_2)_nCN$, $(CH_2)_n$ $NR^{11}R^{12}$, $(CH_2)_nO(CH_2)_kNR^{11}R^{12}$, $(CH_2)_nNR^{11}(CH_2)_k$ $NR^{11}R^{12}$, $(CH_2)_nO(CH_2)_kOR^{11}$, $(CH_2)_nNR^{11}(CH_2)_k$ $OR^{12}$, $(CH_2)COR^{13}$, $(CH_2)_nCOOR^{13}$, $(CH_2)_n$ $CONR^{11}R^{12}$, $(CH_2)_nSO_2NR^{11}R^{12}$ and $(CH_2)_nS(O)_uR^{13}$, preferably alkyl comprising 1 to 4 carbon atoms, $(CH_2)_n$ $NR^{11}R^{12}$, $(CH_2)_nO(CH_2)_kNR^{11}R^{12}$, $(CH_2)_nCOR^{13}$, $(CH_2)$ $COOR^{13}$, $(CH_2)_nCONR^{11}R^{12}$ and especially $(CH_2)_n$ $CONR^{11}R^{12}$ and r is 0, 1 or 2, preferably 0 or 1.

One preferred embodiment of the instant invention relates to compounds of formula II and preferably one or more of sub formulae II.1) to II.20), wherein p is 1, 2 or 3 and $R^8$ is independently selected from the group consisting of methyl, ethyl, isopropyl, tert.-butyl, F, Cl, Br, $CF_3$, $C(CF_3)_3$, $SO_2CF_3$, methoxy, ethoxy, tert-butoxy, perfluoro tert-butoxy (OC $(CF_3)_3$), methyl sulfanyl ($SCH_3$), ethyl sulfanyl ($SCH_2CH_3$), acetyl ($COCH_3$), propionyl ($COCH_2CH_3$), butyryl ($COCH_2CH_2CH_3$). If p is 2 or 3, all substituents can be the same or different.

Another preferred embodiment of the instant invention relates to compounds of formula II and preferably one or more of sub formulae II.1) to II.20), wherein X is selected from the group consisting of S, N—$R^{21}$, $CH_2$, $CH_2CH_2$, $OCH_2$ and $CH_2O$.

Another preferred embodiment of the instant invention relates to compounds of formula II and preferably one or more of sub formulae II.1) to II.20), wherein X is selected from the group consisting of S, $CH_2$.

Another even more preferred embodiment of the instant invention relates to compounds of formula II and preferably one or more of sub formulae II.1) to II.20), wherein X is O.

Another preferred embodiment of the instant invention relates to compounds of formula II and preferably one or more of sub formulae II.1) to II.20), wherein Y is selected from the group consisting of $C(R^{22})$—$NO_2$. $C(R^{22})$—CN and $C(CN)_2$.

Another more preferred embodiment of the instant invention relates to compounds of formula II and preferably one or more of sub formulae II.1) to II.20), wherein Y is selected from the group consisting of O, S and $NR^{21}$.

Another even more preferred embodiment of the instant invention relates to compounds of formula II and preferably one or more of sub formulae II.1) to II.20), wherein Y is selected from the group consisting of O and S.

Another even more preferred embodiment of the instant invention relates to compounds of formula II and preferably one or more of sub formulae II.1) to II.20), wherein Y is O.

Another preferred embodiment of the instant invention relates to compounds of formula II and preferably one or more of sub formulae II.1) to II.20), wherein $R^6$ and $R^7$ both are hydrogen.

Another preferred embodiment of the instant invention relates to compounds of formula II and preferably one or more of sub formulae II.1) to II.20), wherein $R^6$ or $R^7$ is a residue other than hydrogen. In this embodiment, the residue other than hydrogen is preferably selected from the meanings given for $R^8$, $R^9$ and $R^{10}$, more preferably from A, and especially preferred from substituted or preferably unsubstituted alkyl, substituted or preferably unsubstituted alkenyl, substituted or preferably unsubstituted cycloalkyl and substituted or preferably unsubstituted alkylenecycloalkyl, even more preferred substituted or unsubstituted alkyl with 1 to 6 carbon atoms, for example methyl, ethyl, n-propyl, isopropyl, n-butyl, 2-butyl, tert-butyl, optionally substituted by one or more hydroxy groups, preferably one or two hydroxy groups and/or one or more halogen atoms, up to perhalo. Examples for preferred substituted alkyl groups are $CH_2$Hal, especially $CH_2F$, $CH_2Cl$ and $CH_2Br$, $CHal_3$, especially $CF_3$, $CCl_3$ and $CBr_3$, and $(CH_2)OH$, wherein Z is 1 to 6, especially $CH_2OH$ and $CH_2CH_2OH$.

Another preferred embodiment of the instant invention relates to compounds of formula II and preferably one or more of sub formulae II.1) to II.20), wherein $R^6$ or $R^7$ is a residue other than hydrogen. In this embodiment, the residue other than hydrogen is preferably selected from $(CH_2)_n$ $COOR^{13}$, $(CH_2)_nCONR^{11}R^{12}$, $(CH_2)_nNR^{11}COR^{13}$, $(CH_2)_n$ $NR^{11}CONR^{11}R^{12}$, $(CH_2)_nO(CH_2)_kNR^{11}R^{12}$ and $(CH_2)_n$ $NR^{11}(CH_2)_kNR^{11}R^{12}$, more preferred $(CH_2)_nCOOR^{13}$ even more preferred $(CH_2)_nCOOA$ and $(CH_2)_nCOOH$ and especially preferred $(CH_2)_nCOOA$, wherein A is $C_1$-$C_4$-alkyl and $(CH_2)_nCOOH$. In this embodiment, n is as defined above/below and especially is 0.

Another preferred embodiment of the instant invention relates to compounds of formula II and preferably one or more of sub formulae II.1) to II.20), wherein $R^6$ is hydrogen and $R^7$ is methyl, or $R^6$ is methyl and $R^7$ is hydrogen.

Another preferred embodiment of the instant invention relates to compounds of formula II and preferably one or more of sub formulae II.1) to II.20), wherein $R^6$ and $R^7$ are residues other than hydrogen. In this embodiment, $R^6$ and $R^7$ are preferably selected, independently from one another, from the meanings given for $R^8$, $R^9$ and $R^{10}$, more preferably from the meanings given for A, and especially preferred from substituted or preferably unsubstituted alkyl, substituted or preferably unsubstituted alkenyl, substituted or preferably unsubstituted cycloalkyl and substituted or preferably unsubstituted alkylenecycloalkyl, even more preferred substituted or unsubstituted alkyl with 1 to 6 carbon atoms, for example methyl, ethyl, n-propyl, isopropyl, n-butyl, 2-butyl, tert-butyl, optionally substituted by one or more hydroxy groups, preferably one or two hydroxy groups and/or one or more halogen atoms, up to perhalo. Examples for preferred substituted alkyl groups are $CH_2$Hal, especially $CH_2F$, $CH_2C_1$ and $CH_2Br$, $CHal_3$, especially $CF_3$, $CCl_3$ and $CBr_3$, and $(CH_2)_z$ OH, wherein Z is 1 to 6, especially $CH_2OH$ and $CH_2CH_2OH$. In this embodiment, $R^6$ and $R^7$ even more preferred form, together with the carbon atom they are bound to (i.e. the carbon atom of the methylene moiety of the methylene urea moiety), a carbocyclic residue comprising 3 to 6 carbon atoms or a heterocyclic residue comprising one or two heteroatoms, selected from the group consisting of O, N and S, and 2 to 5 carbon atoms, wherein the carbocyclic residue respectively the heterocyclic residue can be substituted by one or more substituents, preferably one or two substituents, selected, independently from one another, from the meanings given for $R^8$, $R^9$ and $R^{10}$. If $R^6$ and $R^7$ form a cyclic residue together with the carbon atom they are bound to, carbocyclic residues are preferred. Even more preferred are carbocyclic residues comprising 3, 4 or 5 carbon atoms, especially 3 carbon atoms which can be substituted once or twice as given above and preferably are unsubstituted. In this respect, one preferred embodiment of the instant invention relates to compounds, wherein $R^6$ and $R^7$ form, together with the carbon atom they are bound to, a cyclopropane moiety.

Another preferred embodiment of the instant invention relates to compounds of formula II and preferably one or more of sub formulae II.1) to II.20), wherein one of the residues $R^6$ or $R^7$ or both residues $R^6$ and $R^7$ are other than hydrogen and are preferably as defined in the preferred embodiments relating to $R^6$ and $R^7$ given above.

Another preferred embodiment of the instant invention relates to compounds of formula II and preferably one or more of sub formulae II.1) to II.20), wherein $Ar^2$ is pyridinyl.

Another preferred embodiment of the instant invention relates to compounds of formula II and preferably one or more of sub formulae II.1) to II.20), wherein r is either 0 or 1. If r is 1, $R^{10}$ is preferably $(CH_2)_n CONR^{11}R^{12}$ and especially $(CH_2)_n CONR^{11}R^{12}$, wherein n in 0. In this embodiment, $R^{11}$ is preferably selected from the group consisting of H and A and more preferred from H and alkyl, and $R^{12}$ is preferably selected from the group consisting of H and A and more preferred from H and alkyl. Especially preferred as residue $R^{10}$ are carbamoyl, more preferred alkyl carbamoyl or dialkyl carbamoyl, even more preferred methyl carbamoyl or dimethyl carbamoyl, ethyl carbamoyl or diethyl carbamoyl and especially preferred methyl carbamoyl (—$CONHCH_3$). This embodiment is especially preferred when $Ar^2$ is pyridinyl. When $Ar^2$ is pyridinyl, $R^{10}$ is preferably bonded in a vicinal position to the nitrogen atom of the pyrindiyl residue, i.e. in 2- and/or 6-position of the pyridinyl residue.

Another preferred embodiment of the instant invention relates to compounds of formula II and preferably one or more of sub formulae II.1) to II.20), wherein $Ar^1$ comprises two or more substituents $R^8$, wherein one or more, preferably one substituent $R^8$ is selected from the group consisting of $(CH_2)_n NR^{11}R^{12}$, $(CH_2)_n O(CH_2)_k NR^{11}R^{12}$, $(CH_2)_n NR^{11}$ $(CH_2)_k OR^{12}$, $(CH_2)_n NR^{11}(CH_2)_k NR^{12}R^{12}$, $(CH_2)_n COOR^{13}$ and $(CH_2)_n S(O)_u R^{13}$ wherein $R^{11}$, $R^{12}$ and $R^{13}$ are defined as above and n is as defined above, preferably n is 0, 1 or 2 and especially is 0, k is 1 to 4 and preferably 1 or 2, and u is preferably 2. In this embodiment $R^{11}$, $R^{12}$ and $R^{13}$ are more preferably selected independently from each other from the group consisting of H, methyl and ethyl. In this embodiment, one or two substituents $R^8$ and preferably one substituent $R^8$ is especially preferably selected from the group consisting of $NH_2$, $N(CH_3)_2$, $N(C_2H_5)_2$, $NHCH_2CH_2NH_2$, $N(CH_3)$ $CH_2CH_2NH_2$, $N(CH_3)CH_2CH_2N(CH_3)_2$, $N(CH_3)CH_2CH_2N$ $(CH_3)_2$, $N(CH_3)CH_2CH_2OCH_3$, $OCH_2CH_2N(CH_3)_2$, $SCH_3$, $SC_2H_5$, $SO_2CH_3$, $COOCH_3$ and $COOH$. Accordingly, in this embodiment $Ar^1$ especially preferably comprises at least one substituent $R^8$ other than $(CH_2)_n NR^{11}NR^{12}$, $(CH_2)_n O(CH_2)_k$ $NR^{11}R^{12}$, $(CH_2)_n NR^{11}(CH_2)_k OR^{12}$, $(CH_2)_n NR^{11}(CH_2)_k NR^{12}R^{12}$, $(CH_2)_n COOR^{13}$ and $(CH_2)_n S(O)_u R^{13}$ as defined in this paragraph and especially other than $NH_2$, $N(CH_3)_2$, $N(C_2H_5)_2$, $NHCH_2CH_2NH_2$, $N(CH_3)CH_2CH_2NH_2$, $N(CH_3)$ $CH_2CH_2N(CH_3)_2$, $N(CH_3)CH_2CH_2N(CH_3)_2$, $N(CH_3)$ $CH_2CH_2OCH_3$, $OCH_2CH_2N(CH_3)_2$, $SCH_3$, $SC_2H_5$, $SO_2CH_3$, $COOCH_3$ and $COOH$.

Another preferred embodiment of the instant invention relates to compounds of formula II and preferably one or more of sub formulae II.1) to II.20), wherein q is 0, i.e. the phenyl group bound to the methylene group of the methylene urea moiety is unsubstituted.

Another preferred embodiment of the instant invention relates to compounds of formula II and preferably one or more of sub formulae II.1) to II.20), wherein q is 1, i.e. the phenyl group bound to the methylene group of the methylene urea moiety is substituted by one substituent, preferably a substituent as defined above and more preferably a substituent selected from alkyl and hal, and especially selected from $CH_3$, $CH_2CH_3$ and hal.

Another preferred embodiment of the instant invention relates to compounds of formula II and preferably one or more of formulae II.1) to II.20), wherein $(R^8)_p$—$Ar^1$ is selected from the group consisting of 3-acetyl-phenyl, 4-acetyl-phenyl, 2-bromo-phenyl, 3-bromo-phenyl, 4-bromo-phenyl, 4-bromo-2-chloro-phenyl, 4-bromo-3-methyl-phenyl, 4-bromo-trifluoromethyl-phenyl, 2-chloro-phenyl, 2-chloro-4-trifluoromethyl-phenyl, 2-chloro-5-trifluoromethyl-phenyl, 3-chloro-phenyl, 3-chloro-4-methyl-phenyl, 3-chloro-4-methoxy-phenyl, 3-chloromethoxy-phenyl, 4-chloro-phenyl, 4-chloro-2-trifluoromethyl-phenyl, 4-chloro-3-trifluoromethyl-phenyl, 4-chloro-2-methyl-phenyl, 5-chloro-2-methyl-phenyl, 5-chloro-2-methoxy-phenyl, 2,3-dichloro-phenyl, 2,4-dichloro-phenyl, 2,5-dichloro-phenyl, 3,4-dichloro-phenyl, 3,5-dichloro-phenyl, 2,4,5-trichloro-phenyl, 4-fluoro-phenyl, 4-fluoro-3-trifluoromethyl-phenyl, 4-ethoxy-phenyl, 2-methoxy-phenyl, 2-methoxy-5-trifluoromethyl-phenyl, 4-methoxy-phenyl, 2,5-dimethoxy-phenyl, 2-trifluoromethyl-phenyl, 3-trifluoromethyl-phenyl, 3-trifluoromethoxy-phenyl, 4-trifluoromethyl-phenyl, 4-trifluoromethoxy-phenyl, 3,5-bis-trifluoromethyl-phenyl, 3-methoxy-phenyl, 3-methylsulfanyl-phenyl, 4-methylsulfanyl-phenyl, o-tolyl (2-methyl-phenyl), m-tolyl (3-methyl-phenyl), p-tolyl (4-methyl-phenyl), 2,3-dimethyl-phenyl, 2,3-dimethyl-phenyl, 2,5-dimethyl-phenyl, 3,4-dimethyl-phenyl, 3,5-dimethyl-phenyl, 2-ethyl-phenyl, 3-ethyl-phenyl, 4-ethyl-phenyl, 4 isopropyl-phenyl, 4-tert-butyl-phenyl and 5-tert-butyl-isoxazol-3-yl.

Another preferred embodiment of the instant invention relates to compounds of formula II and the subformulae related thereto and preferably one or more of formulae II.1) to II.20), wherein the residues $(R^8)_p$—$Ar^1$ are selected from the group consisting of componds of the following formulae:

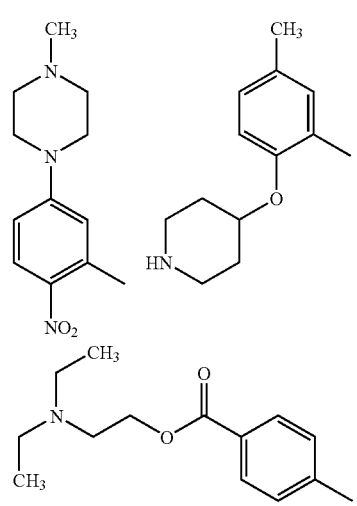

a)

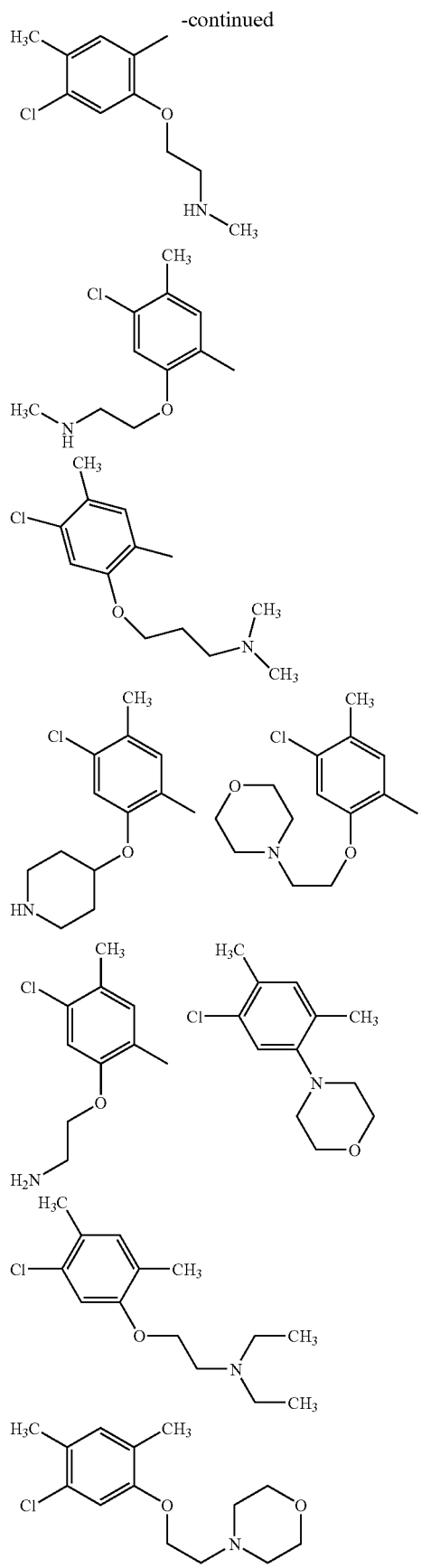
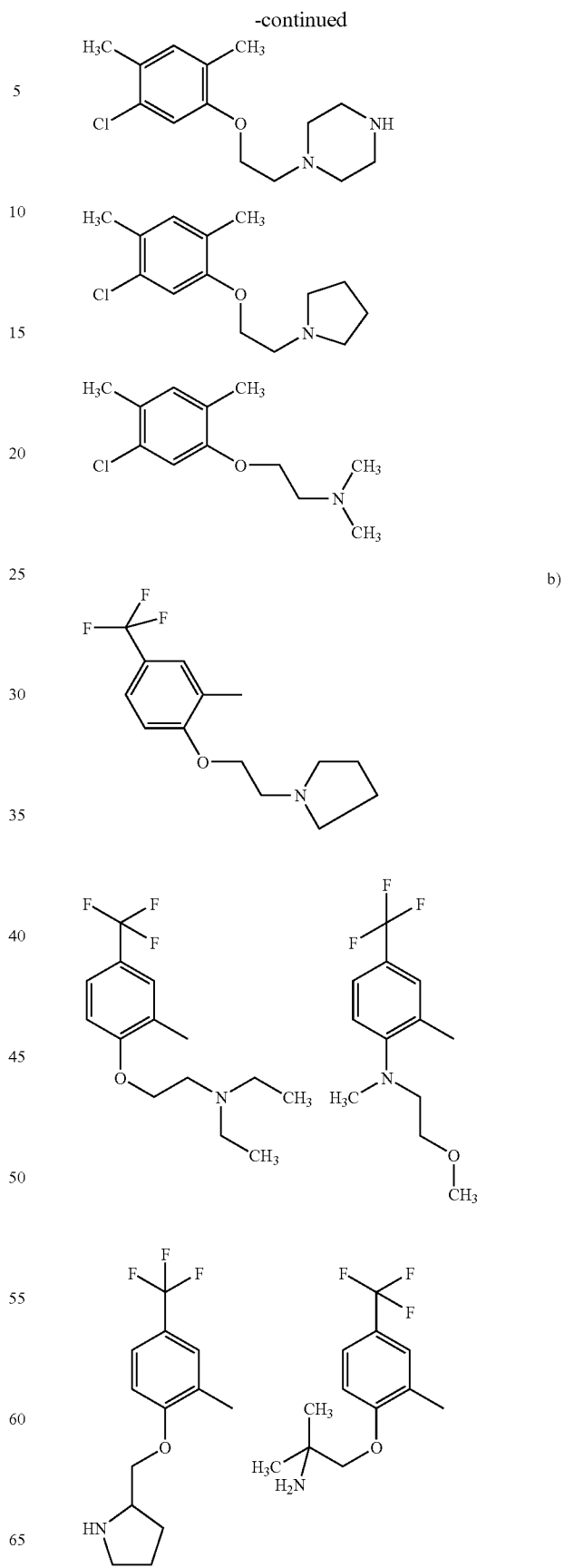

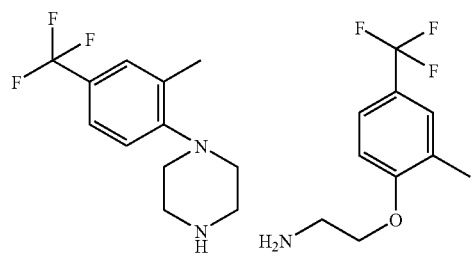
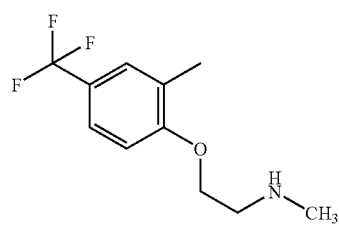
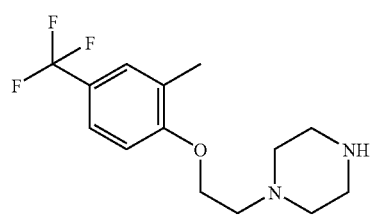
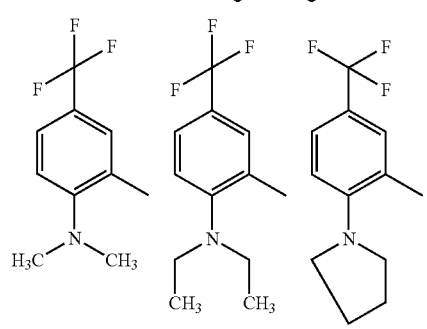
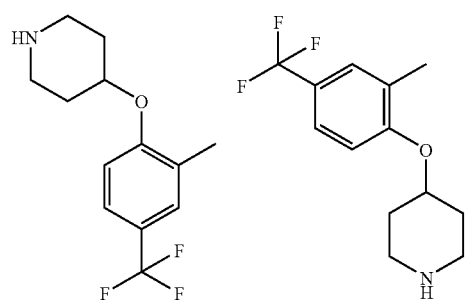
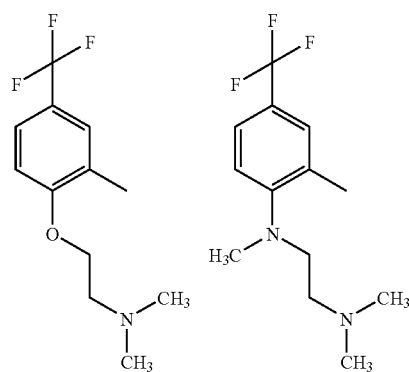
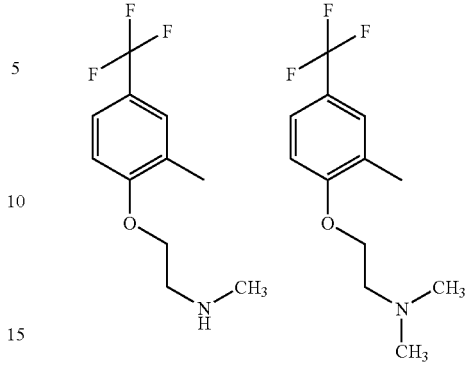
c)
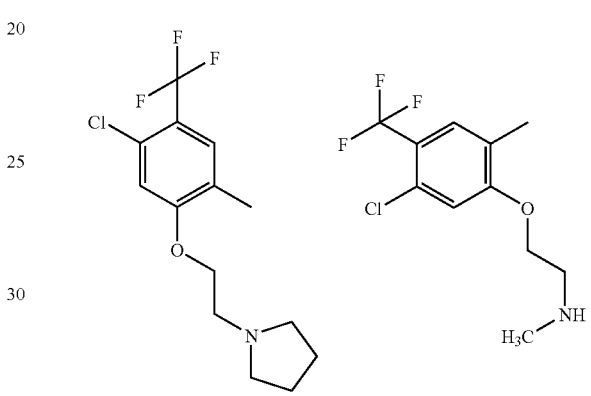
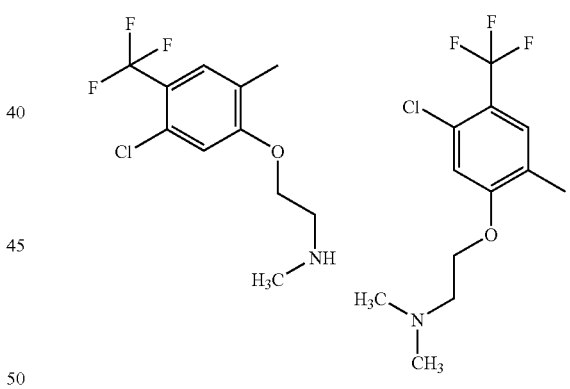
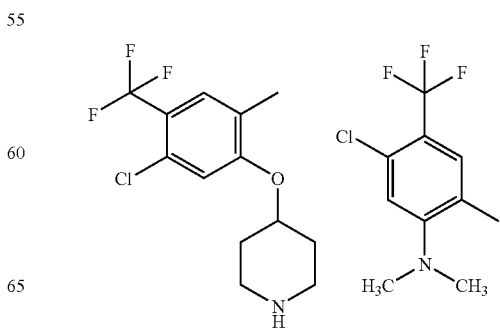

-continued
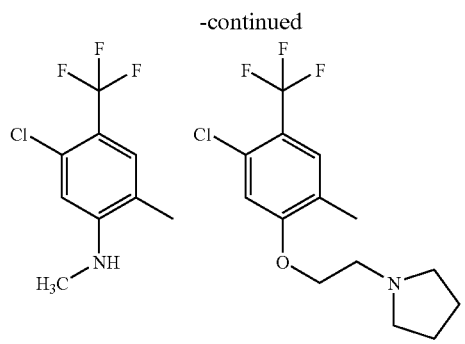
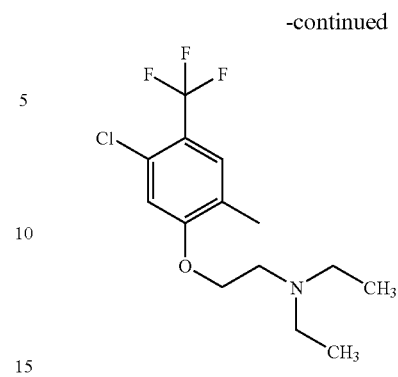
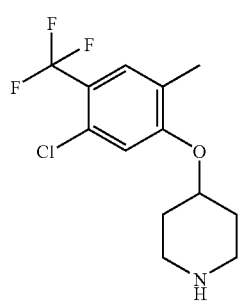
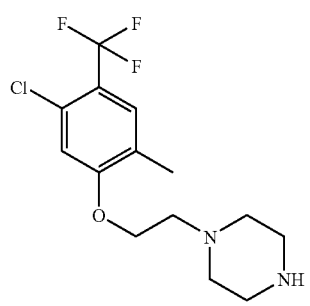
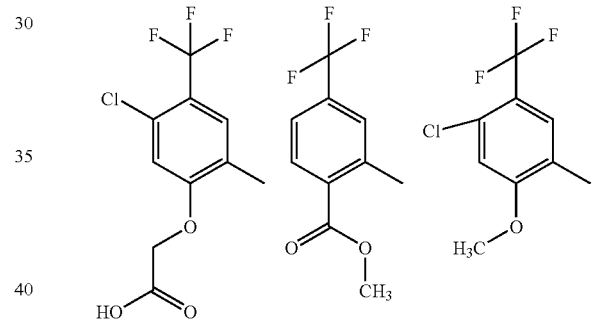
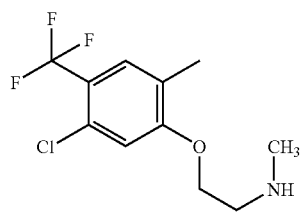
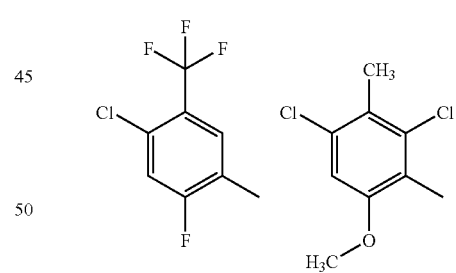
d)
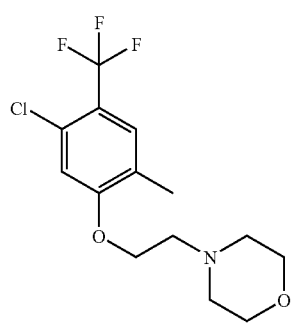
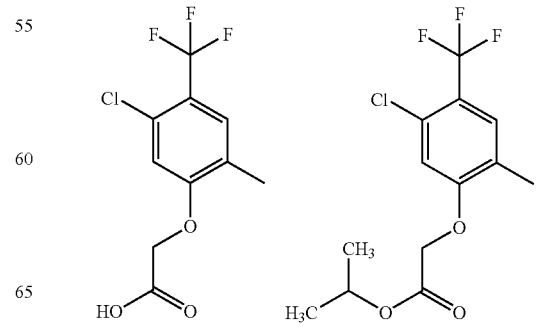

e)
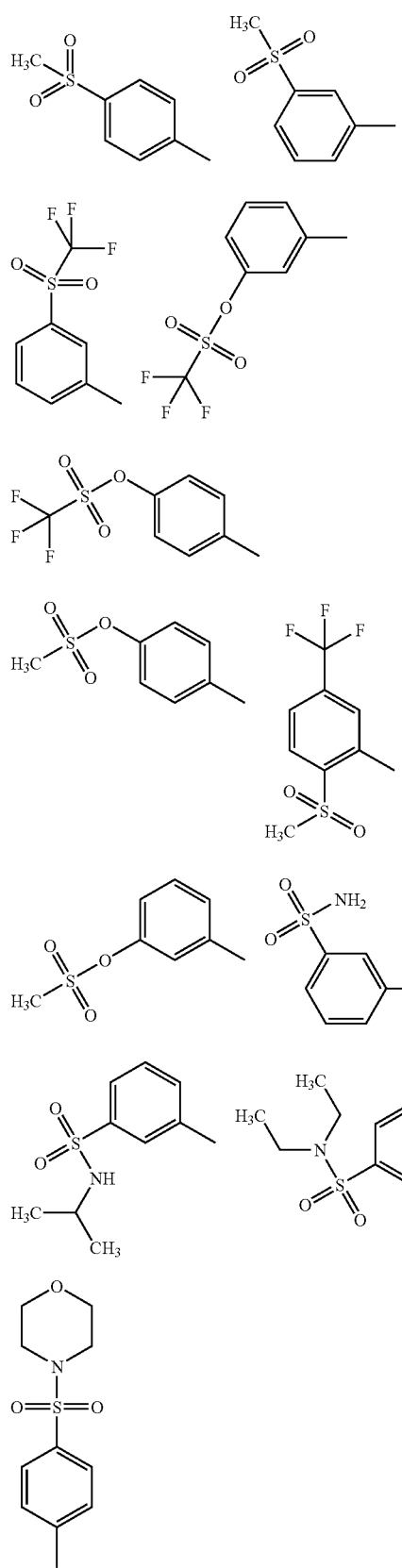
f)
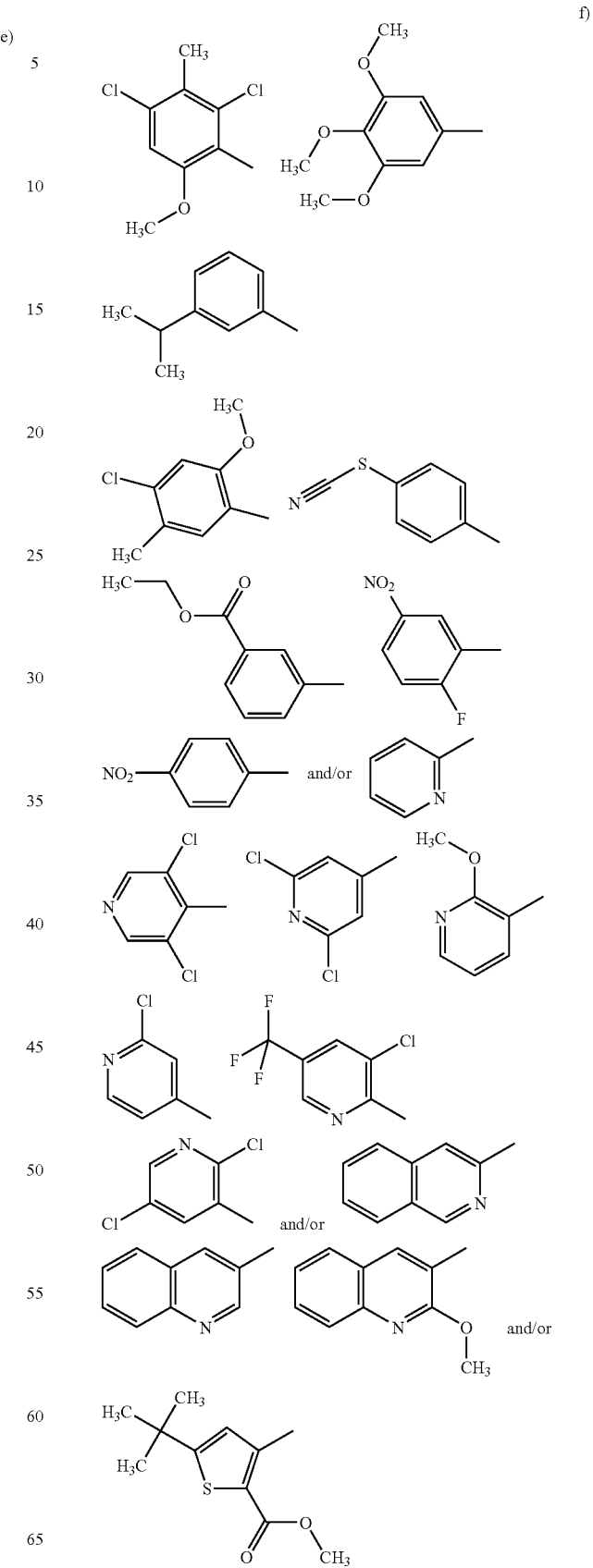

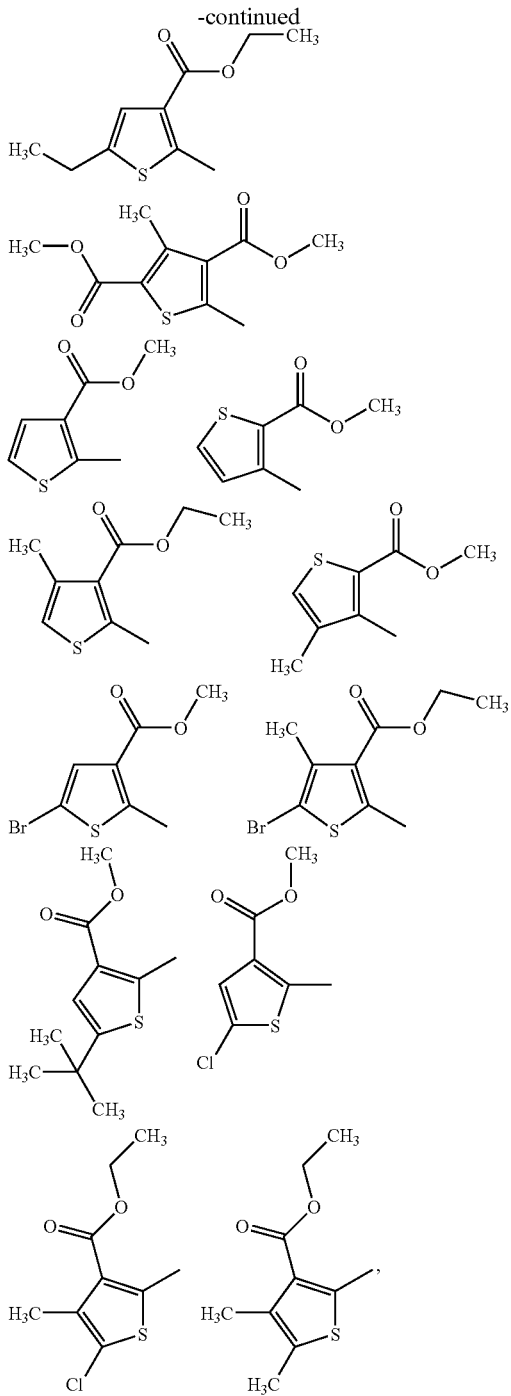

and/or residues of the structures given above that comprise one or two, preferable one additional substituent, independently selected from the meanings given for $R^8$.

Another preferred embodiment of the instant invention relates to compounds of formula II and preferaby one or more of sub formulae II.1) to II.20), wherein $(R^8)_p$—$Ar^1$ is as defined above, but comprises one or more additional residues, preferably one additional residue. The additional residues are preferably selected from the meanings given for $R^8$ and more preferably selected from the group consisting of $(CH_2)_n$ $NR^{11}R^{12}$, $(CH_2)_nO(CH_2)_kNR^{11}R^{12}$, $(CH_2)_nNR^{11}(CH_2)_k$ $OR^{12}$, $(CH_2)_nNR^{11}(CH_2)_kNR^{11}R^{12}$, $(CH_2)_3COOR^{13}$, $(CH_2)_n$ $S(O)_uNR^{11}R^{12}$ and $(CH_2)_nS(O)_uR^{13}$ wherein $R^{11}$, $R^{12}$ and $R^{13}$ are defined as above and n is as defined above, preferably n is 0, 1 or 2 and especially is 0, k is 1 to 4 and preferably 1 or 2, and u is preferably 2. In this embodiment $R^{11}$, $R^{12}$ and $R^{13}$ are more preferably selected independently from each other from the group consisting of H, methyl and ethyl. Even more preferred, the additional residue(s) is/are selected from the group consisting of $NH_2$, $N(CH_3)_2$, $N(C_2H_5)_2$, $NHCH_2CH_2NH_2$, $N(CH_3)CH_2CH_2NH_2$, $N(CH_3)CH_2CH_2N$ $(CH_3)_2$, $N(CH_3)CH_2CH_2N(CH_3)$, $N(CH_3)CH_2CH_2OCH_3$, $OCH_2CH_2N(CH_3)_2$, $SCH_3$, $SC_2H_5$, $SO_2CH_3$, $SO_2CF_3$, $OSO_2CH_3$, $OSO_2CF_3$, $SO_2NH_2$, $SO_2NHCH(CH_3)_2$, $SO_2N$ $(CH_3)_2$, $SO_2N(CH_2CH_3)$, 4-Morpholino-sulfonyl, $COOCH_3$ and $COOH$.

Another preferred embodiment of the instant invention relates to compounds of formula II and the subformulae related thereto and preferably one or more of formulae II.1) to II.20), wherein the residues $Ar^2$—$(R^{10})_r$ are selected from the group consisting of compunds of the following formulae:

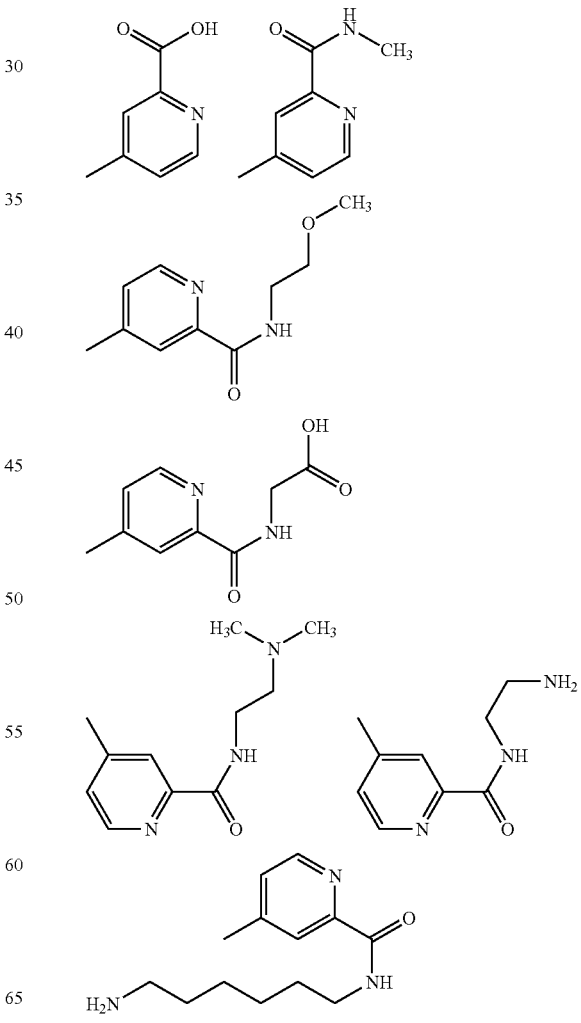

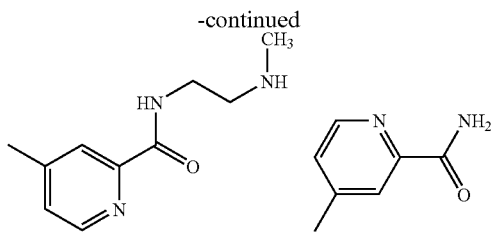 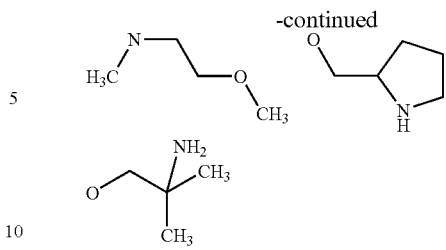

and/or residues of the structures given above that comprise one or two, preferably one additional substituent, independently selected from the meanings given for $R^{10}$.

Another preferred embodiment of the instant invention relates to compounds of formula II and preferably one or more of sub formulae II.1) to II.20), wherein X is bonded in the para- (p-) or metha- (m-)position to the phenyl residue that is bonded directly to the methylene group of the methylene urea moiety.

Another preferred embodiment of the instant invention relates to compounds of formula II and preferably one or more of sub formulae II.1) to II.20), wherein $Ar^2$ is a pyridinyl residue and wherein said pyridinyl residue is bonded to X in the 3- or 4-position, preferably the 4-position, relative to the nitrogen atom of the pyridinyl residue.

Another preferred embodiment of the instant invention relates to compounds of formula II and preferably one or more of sub formulae II.1) to II.20), wherein $Ar^1$ comprises one or more substituents $R^8$ and wherein one or two, preferably one substituent $R^8$ is selected from the group consisting of $NH_2$, $N(CH_3)_2$, $N(C_2H_5)_2$, $NHCH_2CH_2NH_2$, $N(CH_3)CH_2CH_2NH_2$, $N(CH_3)CH_2CH_2N(CH_3)_2$, $N(CH_3)CH_2CH_2N(CH_3)_2$, $N(CH_3)CH_2CH_2OCH_3$, $OCH_2CH_2N(CH_3)_2$, $SCH_3$, $SC_2H_5$, $SO_2CH_3$, $SO_2CF_3$, $OSO_2CH_3$, $OSO_2CF_3$, $SO_2NH_2$, $SO_2NHCH(CH_3)_2$, $SO_2N(CH_3)_2$, $SO_2N(CH_2CH_3)_2$, 4-Morpholino-sulfonyl, $COOCH_3$ and $COOH$, more preferably $NH_2$, $N(CH_3)_2$, $NHCH_3$, $N(C_2H_5)_2$, $HNCH_2CH_2NH_2$, $OCH_2CH_2NH_2$, $HOCH_2CH_2NH$, $OCH_2CH_2NHCH_3$, $N(CH_3)CH_2CH_2NH_2$, $HN(CH_3)CH_2CH_2NH$, $N(CH_3)CH_2CH_2N(CH_3)_2$, $N(CH_3)CH_2CH_2N(CH_3)_2$, $N(CH_3)CH_2CH_2OCH_3$, $OCH_2CH_2N(CH_3)_2$, $OCH_2CH_2N(CH_2CH_3)_2$, $SCH_3$, $SC_2H_5$, and/or compounds of the formulae

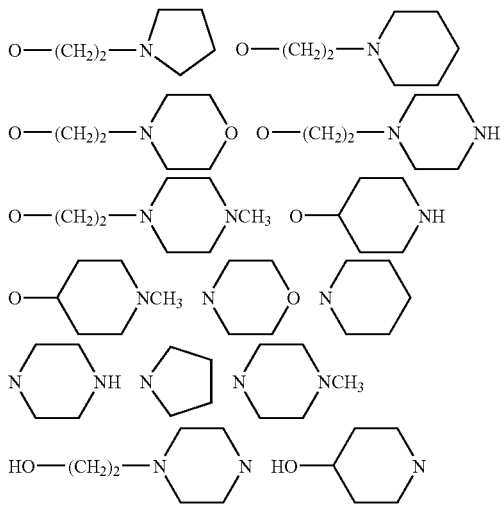

and/or $Ar^2$ comprises one or more substituents $R^{10}$ and wherein one or two, preferably one substituent $R^{10}$ is independently selected from the meanings given for $R^8$ in this paragraph.

Another preferred embodiment of the instant invention relates to compounds of formula II and preferably one or more of sub formulae II.1) to II.20), wherein $Ar^1$ comprises one or more substituents $R^8$ and wherein one or two, preferably one substituent $R^8$ is selected from the group consisting of

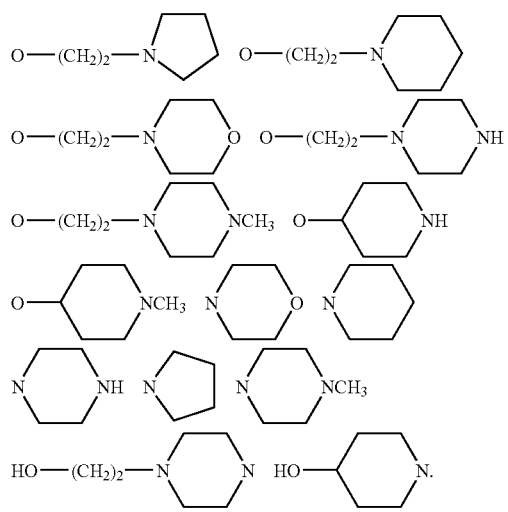

Another preferred embodiment of the instant invention relates to compounds of formula II and preferably one or more of sub formulae II.1) to II.20), wherein $Ar^1$ comprises one or more substituents $R^8$ and wherein one or two, preferably one substituent $R^8$ is selected from the group consisting of $SO_2CH_3$, $SO_2CF_3$, $OSO_2CH_3$, $OSO_2CF_3$, $SO_2NH_2$, $SO_2NHCH(CH_3)_2$, $SO_2N(CH_3)_2$, $SO_2N(CH_2CH_3)_2$ and 4-Morpholine-4-sulfonyl.

Another preferred embodiment of the instant invention relates to compounds of formula II and preferably one or more of sub formulae II.1) to II.20), wherein $Ar^2$ comprises one or more substituents $R^{10}$ and wherein one or two, preferably one substituent $R^{10}$ is selected from unsubstituted or substituted carbamoyl moieties. Substituted carbamoyl moieties are preferably selected from $CONHR^{23}$ or $CONR^{23}R^{24}$, preferably $CONHR^{23}$, wherein $R^{23}$ and $R^{24}$ are independently selected from the definitions given for $R^8$, more preferably selected from alkyl, preferably methyl, ethyl, propyl and butyl, $(CH_2)_nNR^{11}R^{12}$ and $(CH_2)_nOR^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of methyl, ethyl, CH$_2$CH$_2$NH$_2$, CH$_2$CH$_2$N(CH$_3$), CH$_2$CH$_2$N(CH$_2$CH$_3$)$_2$, CH$_2$CH$_2$OH, CH$_2$CH$_2$OCH$_3$ and CH$_2$CH$_2$OCH$_2$CH$_3$.

Another preferred embodiment of the instant invention relates to compounds of formula If and preferably one or more of sub formulae II.1) to II.20), wherein Ar$^2$ comprises one or more substituents R$^{10}$ and wherein one or two, preferably one substituent R$^{10}$ is selected from substituted carbamoyl moieties. Substituted carbamoyl moieties are preferably selected from CONHR$^{23}$, wherein R$^{23}$ is preferably unsubstituted C$_1$-C$_4$-alkyl and especially methyl.

Another preferred embodiment of the instant invention relates to compounds of formula II and preferably one or more of sub formulae II.1) to II.20), wherein Ar$^2$ comprises one or more substituents R$^{10}$ and wherein one or two, preferably one substituent R$^{10}$ is selected from substituted carbamoyl moieties. Substituted carbamoyl moieties are preferably selected from CONHR$^{23}$, wherein R$^{23}$ is selected from (CH$_2$)$_n$NR$^{11}$R$^{12}$ and (CH$_2$)$_n$OR$^{12}$, wherein R$^{11}$, R$^{12}$ and n are as defined above. In this embodiment, n is preferably not 0 and more preferred 1 to 3 and especially 1 or 2. Preferred examples for R$^{23}$ are selected from the group consisting of CH$_2$CH$_2$NH$_2$, CH$_2$CH$_2$N(CH$_3$)$_2$, CH$_2$CH$_2$N(CH$_2$CH$_3$), CH$_2$CH$_2$OH, CH$_2$CH$_2$OCH$_3$ and CH$_2$CH$_2$OCH$_2$CH$_3$.

Another preferred embodiment of the instant invention relates to compounds of formula II and preferably one or more of sub formulae II.1) to II.20), wherein —Ar$^2$—(R$^{10}$) is selected from the formulae

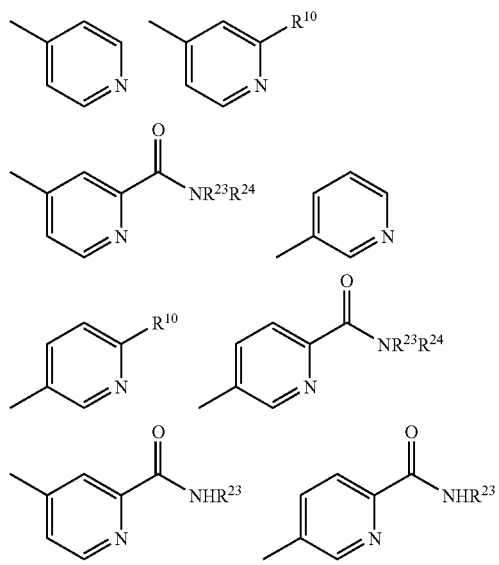

wherein R$^{10}$, R$^{23}$ and R$^{24}$ are as defined above and below.

Another especially preferred embodiment of the instant invention relates to compounds of formula If and preferably one or more of sub formulae II.1) to II.20), wherein one or more features of the above and below mentioned embodiments are combined in one compound.

Subject of the present invention are therefore preferably compounds of formula If according to one or both of the formulae IIa and IIb,

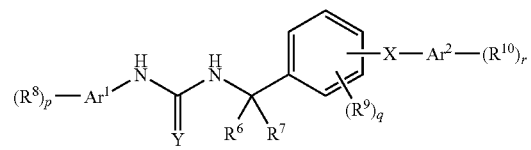

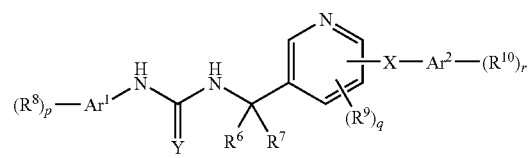

wherein Ar$^1$, R$^8$, p, Y, R$^6$, R$^7$, X, R$^9$, q, Ar$^2$, R$^{10}$ and r are as defined above and below, and preferably as defined in sub formulae II.1) to II.20) and/or the embodiments related thereto.

Subject of the present invention are therefore especially preferred compounds of formula II according to one or both of the formulae IIc and IId,

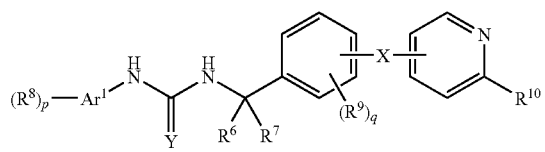

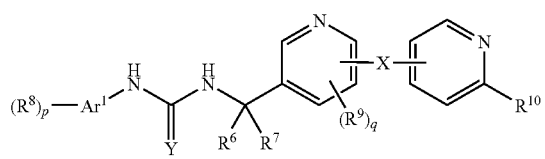

wherein Ar$^1$, R$^8$, p, Y, R$^6$, R$^7$, X, R$^9$ and q are as defined above and below, R$^{10}$ is H or as defined above/below, and preferably as defined in sub formulae II.1) to II.20) and/or the embodiments related thereto;

and/or compounds of formula II according to one or more of the formulae IIe to IIx,

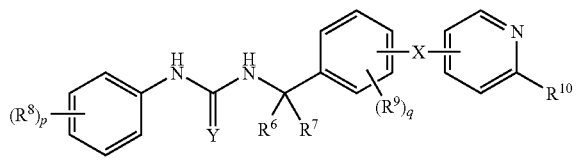

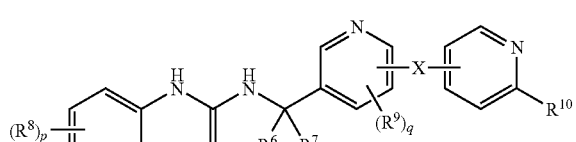

-continued

-continued

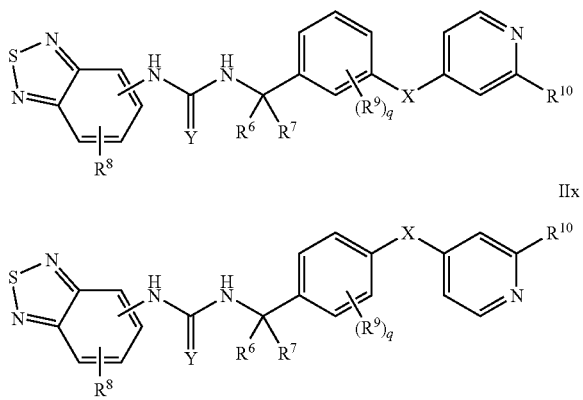

IIw

IIx wherein $R^6$, $R^7$, $R^8$, p, Y, X, $R^9$ and q are as defined above and below, $R^{10}$ is H or as defined above/below, and preferably as defined in sub formulae II.1) to II.20) and/or the embodiments related thereto.

One preferred aspect of the invention relates to compounds of formula II and especially to compounds of one or more of formulae IIa to IIx, wherein both $R^6$ and $R^7$ are hydrogen.

Another preferred aspect of the invention relates to compounds of formula II and especially to compounds of one or more of formulae IIa to IIx, wherein $R^6$ and/or $R^7$ are residues other than hydrogen.

Another preferred embodiment of the instant invention relates to compounds of formula II and preferably one or more of sub formulae II.1) to II.20) and IIa to IIx, wherein $R^{10}$ is a substituted carbamoyl moiety $CONHR^{23}$ or $CONR^{23}R^{24}$, preferably $CONHR^{23}$, wherein $R^{23}$ and $R^{24}$ are independently selected from the definitions given for $R^8$, more preferably selected from $(CH_2)_nNR^{11}R^{12}$ and $(CH_2)_nOR^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of $CH_2CH_2NH_2$, $CH_2CH_2N(CH_3)_2$, $CH_2CH_2N(CH_2CH_3)_2$, $CH_2CH_2OH$, $CH_2CH_2OCH_3$ and $CH_2CH_2OCH_2CH_3$.

It is understood that when a residue, for example $R^8$, $R^9$, $R^{10}$ or $R^{14}$ or $R^{23}$, is comprised twice or more times in one or more of the formulae I, II and the sub formulae corresponding thereto, it is in each case independently from one another selected from the meanings given for the respective residue. For example, $R^{11}$ and $R^{12}$ are defined to be independently selected from a group consisting of H, A, $(CH_2)_mAr^3$ and $(CH_2)_mHet$. Then $(CH_2)_nNR^{11}(CH_2)_mNR^{12}R^{12}$ can be $(CH_2)_nNA(CH_2)_mNA_2$ (if $R^{11}=A$, $R^{12}=A$ and $R^{12}=H$) as well as $(CH_2)_nNA(CH_2)_mNHA$ (if $R^{11}=A$, $R^{12}=H$ and $R^{12}=A$ or $(CH_2)_nNA(CH_2)_mNH(CH_{2m}Het$ (if $R^{11}=A$, $R^{12}=H$ and $R^{12}=(CH_2)_mHet$). Accordingly, if a compound of formula II comprises one residue $R^8$, $R^9$ and $R^{10}$, then for example $R^8$, $R^9$ and $R^{10}$ can all be $(CH_2)_nCOOR^{13}$, wherein all residues $R^{13}$ are the same (for example $CH_2Hal$, wherein Hal is Cl; then all residues $R^8$, $R^9$ and $R^{10}$ are the same) or different (for example $CH_2Hal$, wherein in $R^8$ Hal is Cl; in $R^9$ Hal is F; and in $R^{10}$ Hal is Br, then all residues $R^8$, $R^9$ and $R^{10}$ are different); or for example $R^8$ is $(CH_2)_nCOOR^{13}$, $R^9$ is $NO_2$ and $R^{10}$ is $(CH_2)_nSR^{11}$, wherein $R^{11}$ and $R^{13}$ can be the same (for example both can be H or both can be A which is methyl) of different (for example $R^{11}$ can be H and $R^{13}$ can be A which is methyl).

If not stated otherwise, reference to compounds of formula I and formula II also includes the sub formulae related thereto, especially sub formulae II.1) to II.20) and IIa to IIx.

Subject of the instant invention are especially those compounds of formula I and/or formula II, in which at least one of the residues mentioned in said formulae has one of the preferred or especially preferred meanings given above and below.

The present invention further relates to compounds (1) to (224) of formula A—NH—CO—NH—CH$_2$—B, wherein A and B are as given in the table below:

| | A | B | Rt |
|---|---|---|---|
| (1) | F,F,F-Cl-substituted phenyl | phenyl-O-pyridine (para) | 2.12 |
| (2) | F,F,F-Cl-substituted phenyl | phenyl-O-pyridine (meta) | 4.67$^a$ |
| (3) | dimethyl isoxazole | phenyl-O-pyridine (meta) | 4.10$^a$ |

-continued
| | A | B | Rt |
|---|---|---|---|
| (4) | 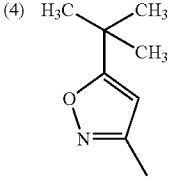 | 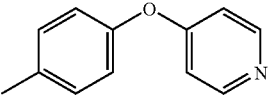 | 3.87 |
| (5) | 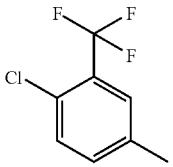 | 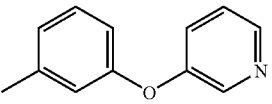 | 2.43 |
| (6) | 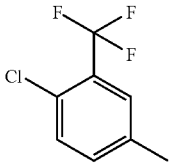 | 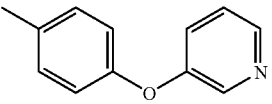 | 2.46 |
| (7) | 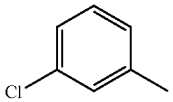 | 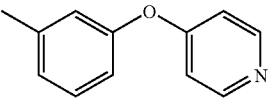 | 1.77 |
| (8) | 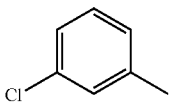 | 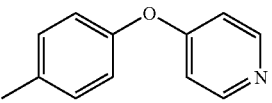 | 1.80 |
| (9) | 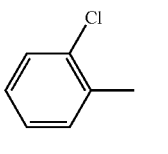 | 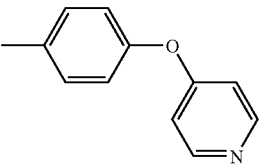 | 1.66 |
| (10) | 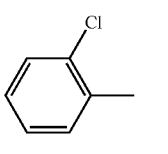 | 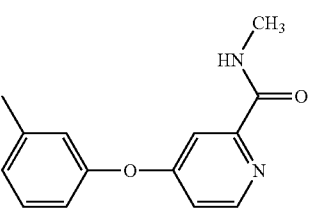 | 2.43 |
| (11) | 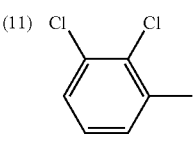 | 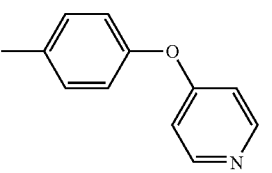 | 1.93 |
| (12) | 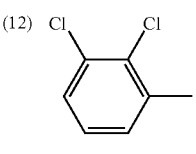 | 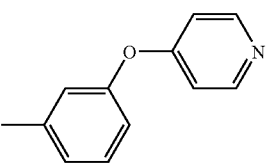 | 1.95 |

-continued
| | A | B | Rt |
|---|---|---|---|
| (13) | 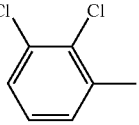 | 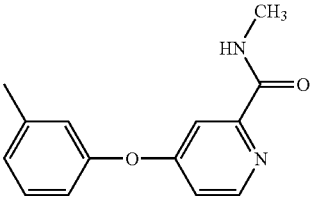 | 2.65 |
| (14) | 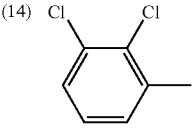 | 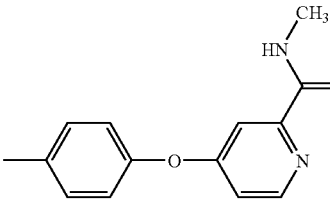 | 2.65 |
| (15) | 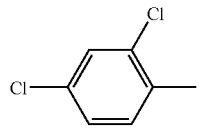 | 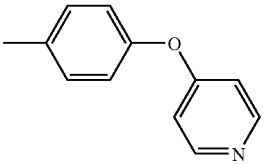 | 1.94 |
| (16) | 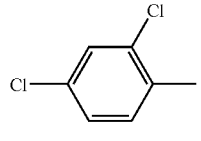 | 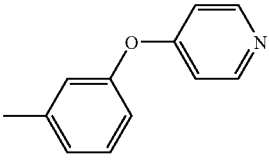 | 1.95 |
| (17) | 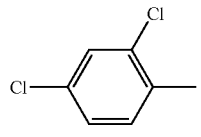 | 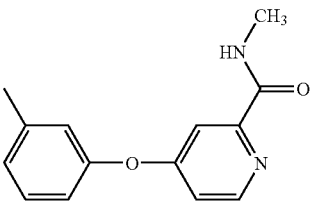 | 2.70 |
| (18) | 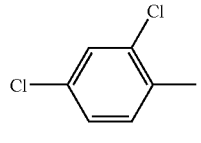 | 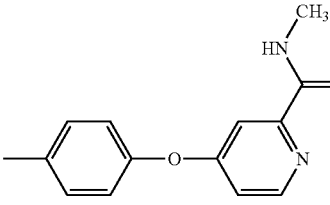 | 2.68 |
| (19) | 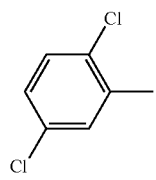 | 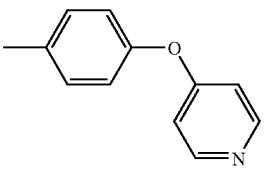 | 2.02 |

-continued
| | A | B | Rt |
|---|---|---|---|
| (20) | 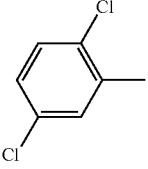 | 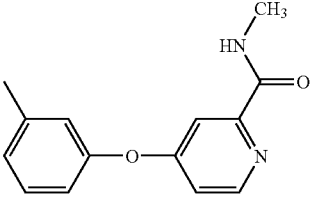 | 2.72 |
| (21) | 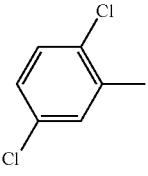 | 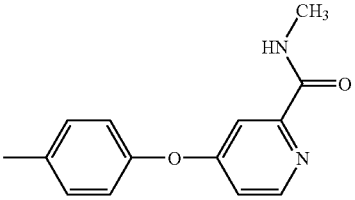 | 2.75 |
| (22) | 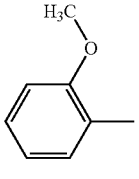 | 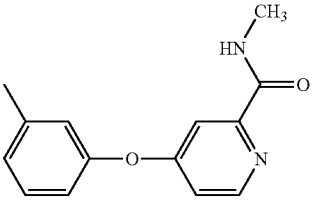 | 2.29 |
| (23) | 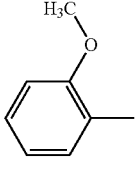 | 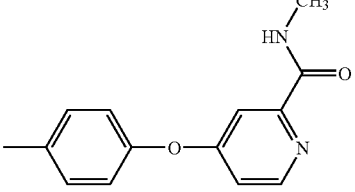 | 2.30 |
| (24) | 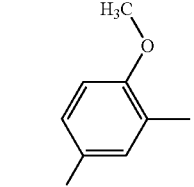 | 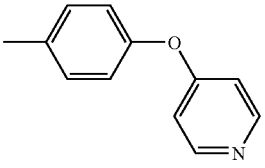 | 1.59 |
| (25) | 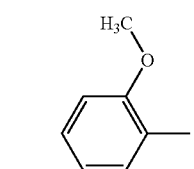 | 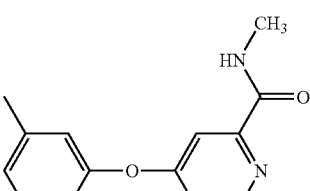 | 2.30 |
| (26) | 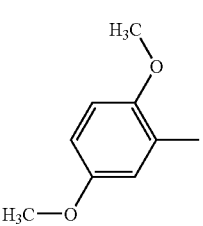 | 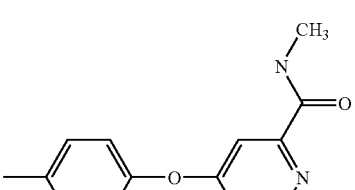 | 2.30 |

-continued
| | A | B | Rt |
|---|---|---|---|
| (27) | 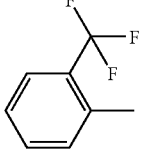 | 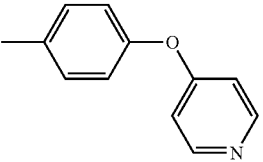 | 2.71 |
| (28) | 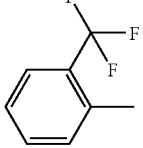 | 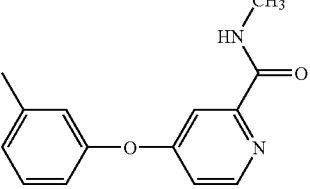 | 2.40 |
| (29) | 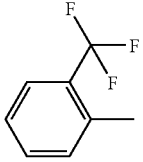 | 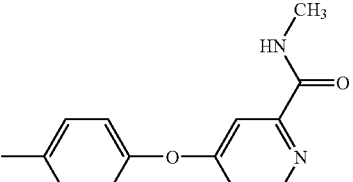 | 2.43 |
| (30) | 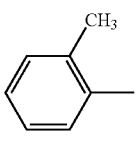 | 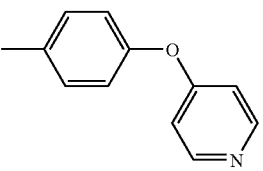 | 1.45 |
| (31) | 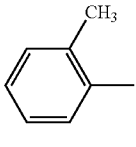 | 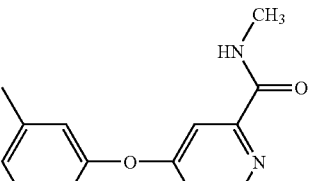 | 2.23 |
| (32) | 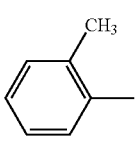 | 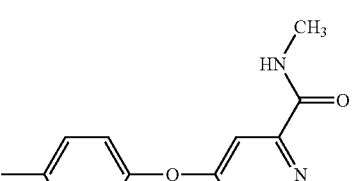 | 2.21 |
| (33) | 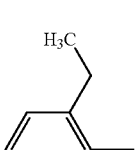 | 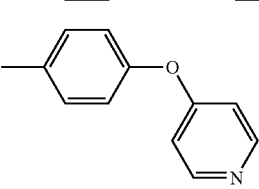 | 1.56 |
| (34) | 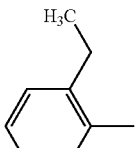 | 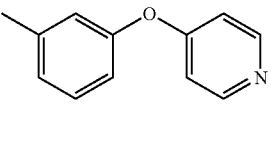 | 1.55 |

-continued
| | A | B | Rt |
|---|---|---|---|
| (35) | 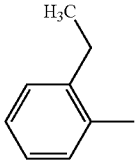 | 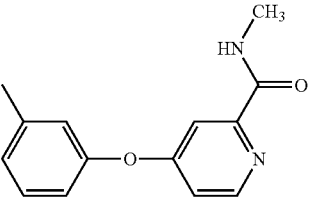 | 2.31 |
| (36) | 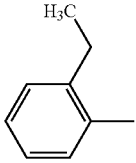 | 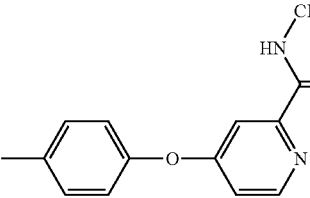 | 2.32 |
| (37) | 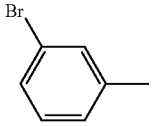 | 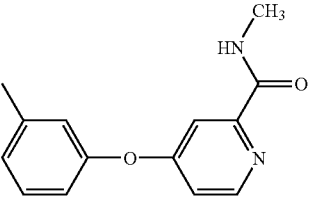 | 2.49 |
| (38) | 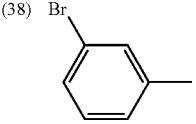 | 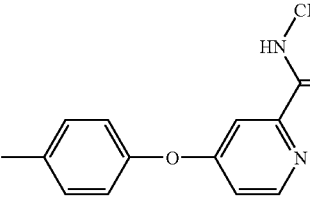 | 2.49 |
| (39) | 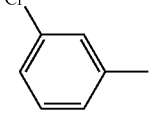 | 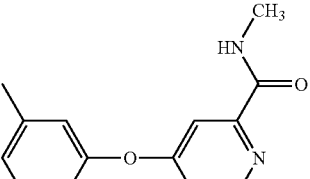 | 2.46 |
| (40) | 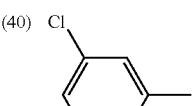 | 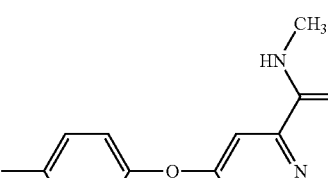 | 2.43 |
| (41) | 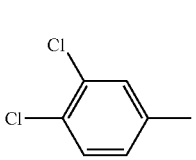 | 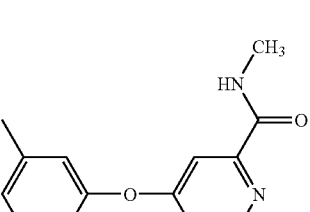 | 2.66 |

-continued
| | A | B | Rt |
|---|---|---|---|
| (42) | 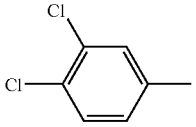 | 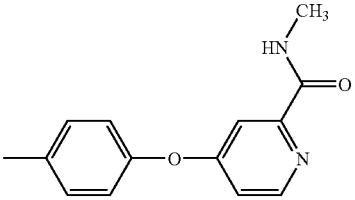 | 2.65 |
| (43) | 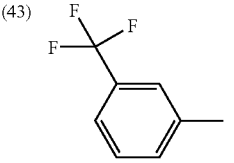 | 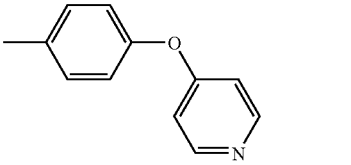 | 1.88 |
| (44) | 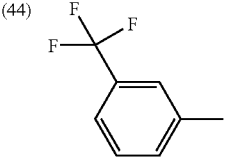 | 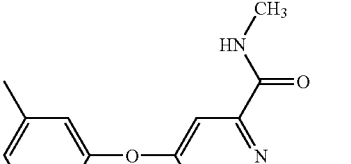 | 2.55 |
| (45) | 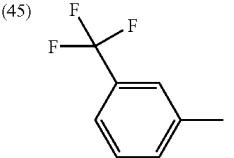 | 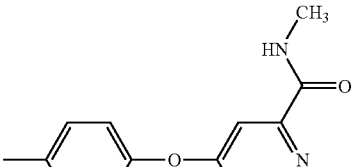 | 2.55 |
| (46) | 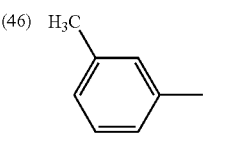 | 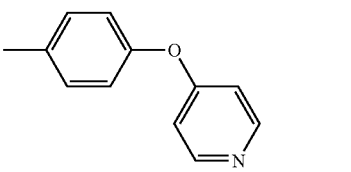 | 1.57 |
| (47) | 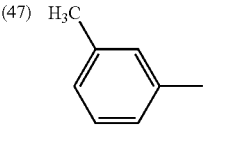 | 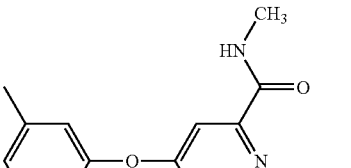 | 2.29 |
| (48) | 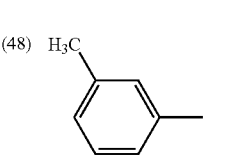 |  | 2.29 |

|     | A | B | Rt |
|-----|---|---|----|
| (49) | 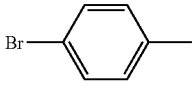 | 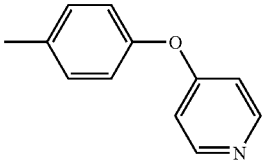 | 1.82 |
| (50) | 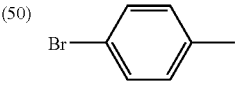 | 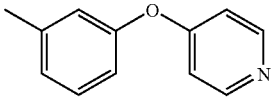 | 1.81 |
| (51) | 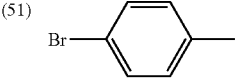 | 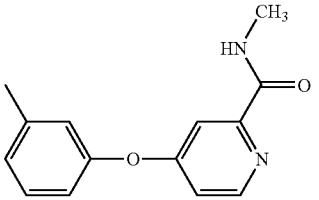 | 2.48 |
| (52) | 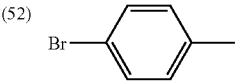 | 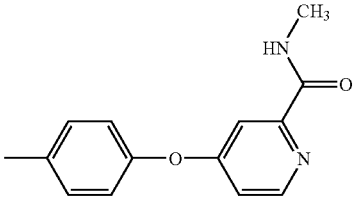 | 2.47 |
| (53) |  | 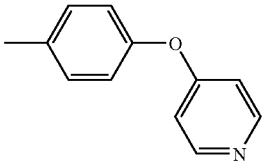 | 1.47 |
| (54) |  | 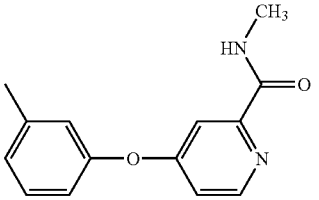 | 2.25 |
| (55) |  | 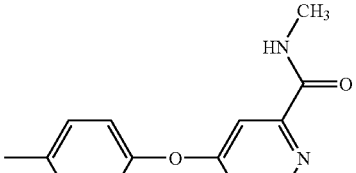 | 2.25 |
| (56) | 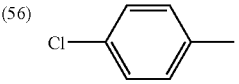 | 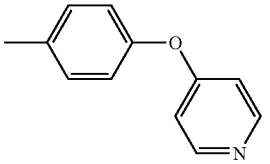 | 1.74 |

-continued

| | A | B | Rt |
|---|---|---|---|
| (57) | 4-chlorophenyl | 3-methylphenoxy-4-pyridyl | 1.71 |
| (58) | 4-chlorophenyl | N-methyl 4-(3-methylphenoxy)pyridine-2-carboxamide | 2.43 |
| (59) | 4-chlorophenyl | N-methyl 4-(4-methylphenoxy)pyridine-2-carboxamide | 2.42 |
| (60) | 4-methoxyphenyl | 4-methylphenoxy-4-pyridyl | 1.39 |
| (61) | 4-methoxyphenyl | N-methyl 4-(3-methylphenoxy)pyridine-2-carboxamide | 2.13 |
| (62) | 4-trifluoromethylphenyl | 4-methylphenoxy-4-pyridyl | 1.95 |
| (63) | 4-trifluoromethylphenyl | N-methyl 4-(3-methylphenoxy)pyridine-2-carboxamide | 2.61 |
| (64) | 4-trifluoromethylphenyl | N-methyl 4-(4-methylphenoxy)pyridine-2-carboxamide | 2.59 |

-continued
| | A | B | Rt |
|---|---|---|---|
| (65) | 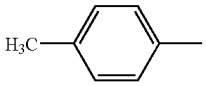 | 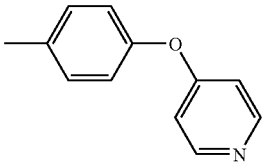 | 1.59 |
| (66) | 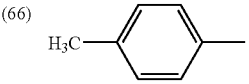 | 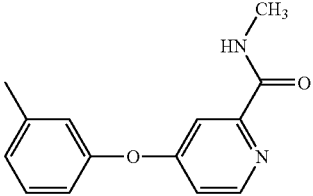 | 2.31 |
| (67) | 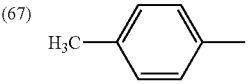 | 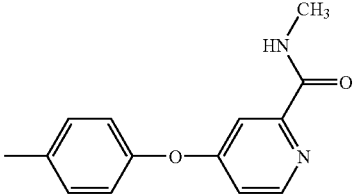 | 2.29 |
| (68) | 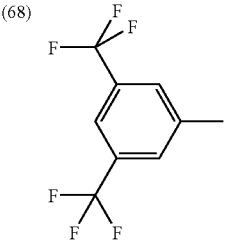 | 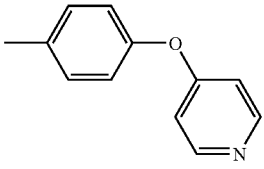 | 2.21 |
| (69) | 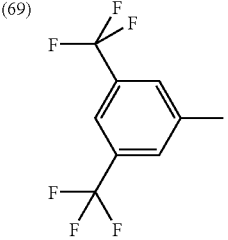 | 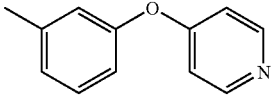 | 2.20 |
| (70) | 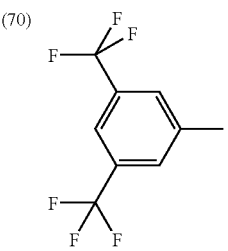 | 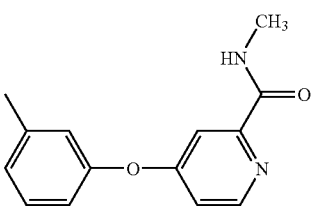 | 2.94 |

-continued
| A | B | Rt |
|---|---|---|
| (71) 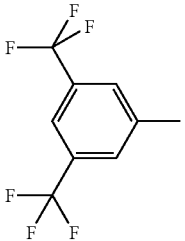 | 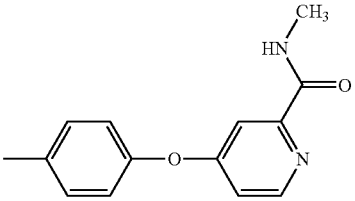 | 2.93 |
| (72) 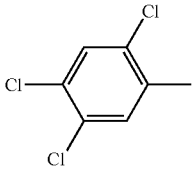 | 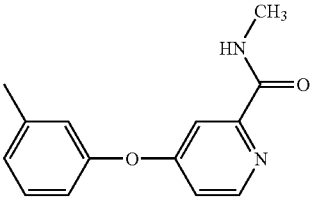 | 2.96 |
| (73) 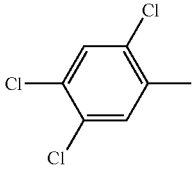 | 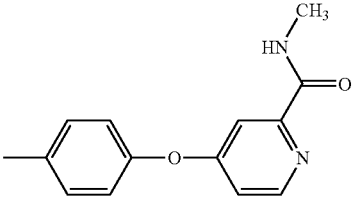 | 2.97 |
| (74) 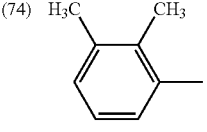 | 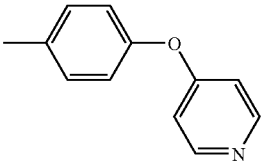 | 1.61 |
| (75) 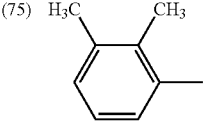 | 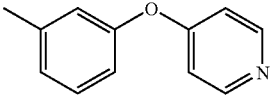 | 1.63 |
| (76) 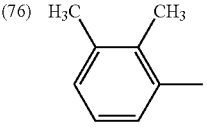 | 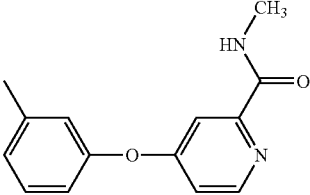 | 2.28 |
| (77) 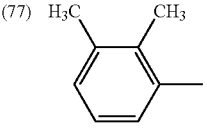 | 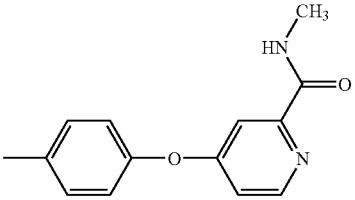 | 2.30 |

-continued
| | A | B | Rt |
|---|---|---|---|
| (78) | 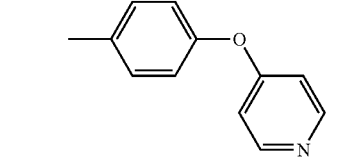 | 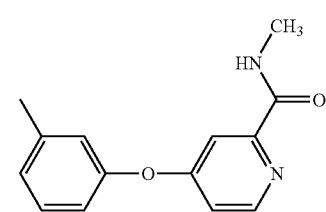 | 1.66 |
| (79) | 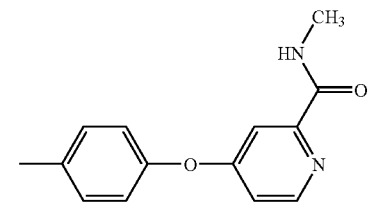 | 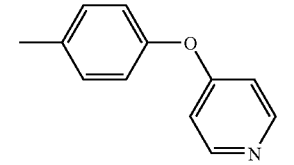 | 2.32 |
| (80) | 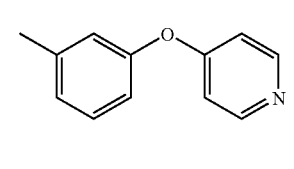 | 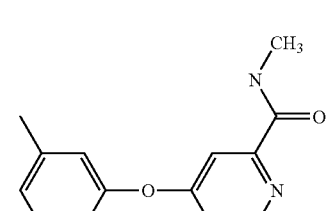 | 2.34 |
| (81) | 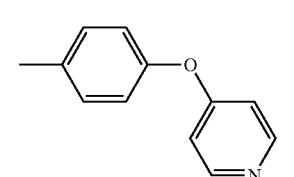 | 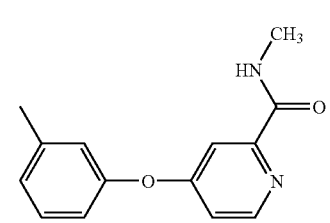 | 1.67 |
| (82) | | | 1.67 |
| (83) | | | 2.35 |
| (84) | | | 1.90 |
| (85) | | | 2.56 |

-continued
| | A | B | Rt |
|---|---|---|---|
| (86) | 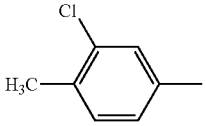 | 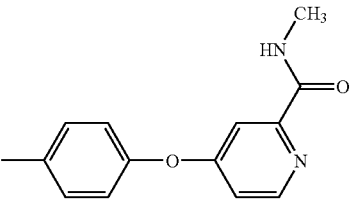 | 2.58 |
| (87) | 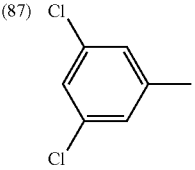 | 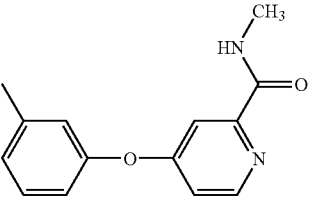 | 2.76 |
| (88) | 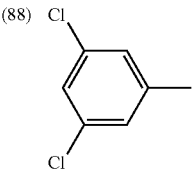 | 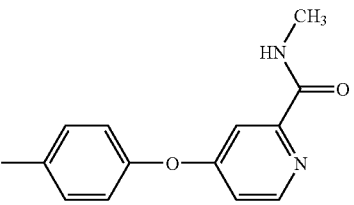 | 2.77 |
| (89) | 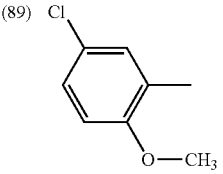 | 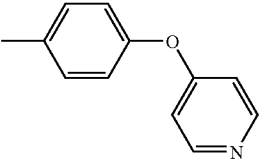 | 1.88 |
| (90) | 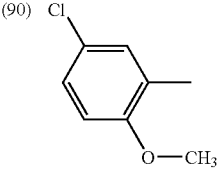 | 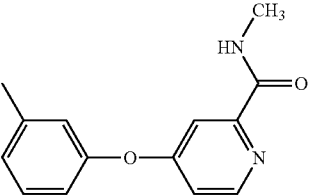 | 2.55 |
| (91) | 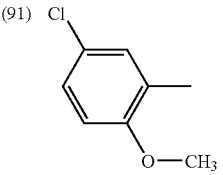 | 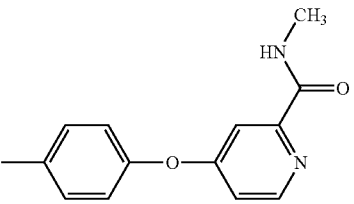 | 2.57 |
| (92) | 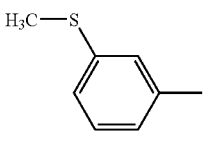 | 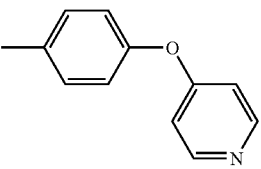 | 1.74 |

-continued
| | A | B | Rt |
|---|---|---|---|
| (93) | 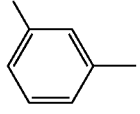 | 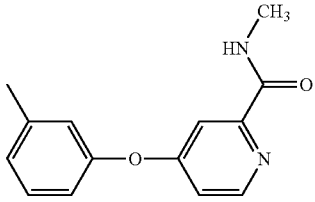 | 2.39 |
| (94) | 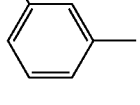 | 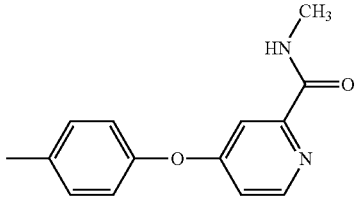 | 2.39 |
| (95) | 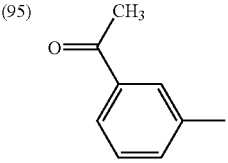 | 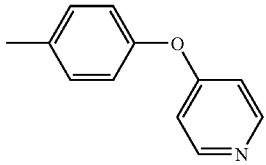 | 1.39 |
| (96) | 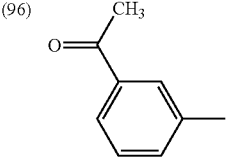 | 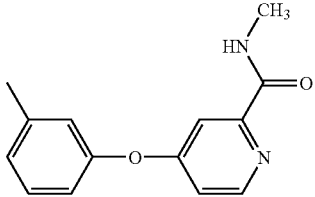 | 2.11 |
| (97) | 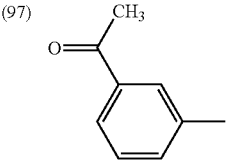 | 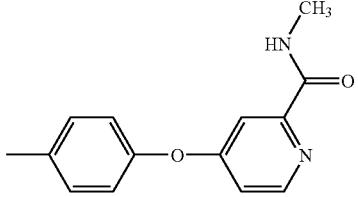 | 2.11 |
| (98) | 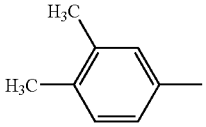 | 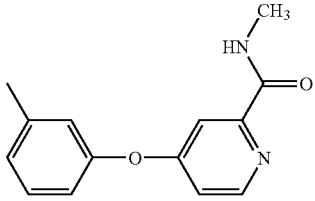 | 2.44 |
| (99) | 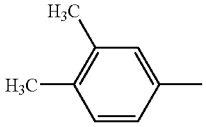 | 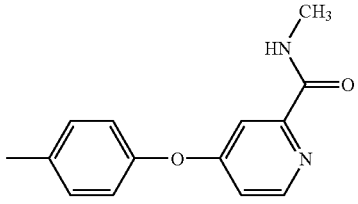 | 2.41 |

-continued

| | A | B | Rt |
|---|---|---|---|
| (100) | 3,5-dimethylphenyl | 4-(3-methylphenoxy)-N-methylpyridine-2-carboxamide | 2.47 |
| (101) | 3,5-dimethylphenyl | 4-(4-methylphenoxy)-N-methylpyridine-2-carboxamide | 2.44 |
| (102) | 3-methylbenzyl (ethyl) | 4-(4-methylphenoxy)-N-methylpyridine-2-carboxamide | 2.46 |
| (103) | 2-chloro-5-methyl-(trifluoromethyl)phenyl | 4-(3-methylphenoxy)-N-methylpyridine-2-carboxamide | 2.77 |
| (104) | 2-chloro-5-methyl-(trifluoromethyl)phenyl | 4-(4-methylphenoxy)-N-methylpyridine-2-carboxamide | 2.75 |
| (105) | 2,4,5-trichlorophenyl | 4-(4-methylphenoxy)pyridine | 2.17 |
| (106) | 2,5-dichlorophenyl | 4-(3-methylphenoxy)pyridine | 1.95 |

-continued
| | A | B | Rt |
|---|---|---|---|
| (107) | 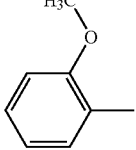 | 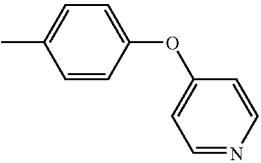 | 1.55 |
| (108) | 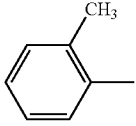 | 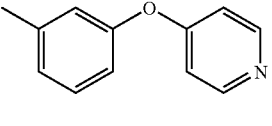 | 1.47 |
| (109) | 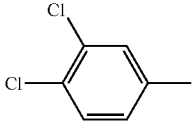 | 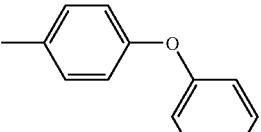 | 1.96 |
| (110) | 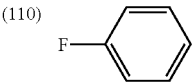 | 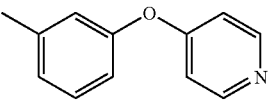 | 1.51 |
| (111) | 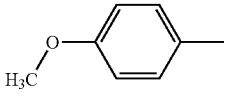 | 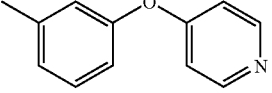 | 1.43 |
| (112) | 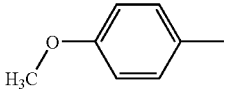 | 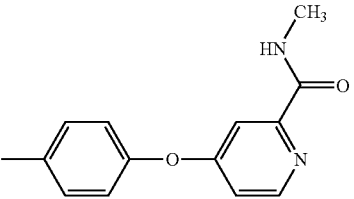 | 2.14 |
| (113) | 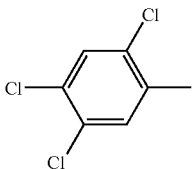 | 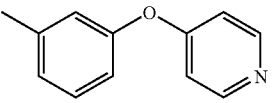 | 2.17 |
| (114) | 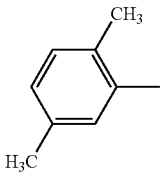 | 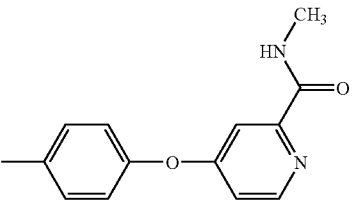 | 2.37 |
| (115) | 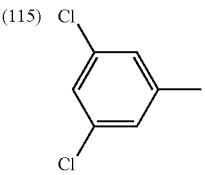 | 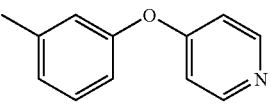 | 2.05 |

-continued
| | A | B | Rt |
|---|---|---|---|
| (116) | 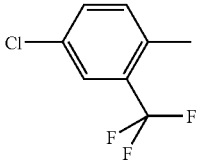 | 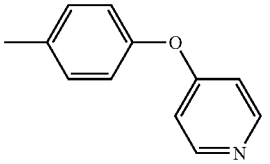 | 2.03 |
| (117) | 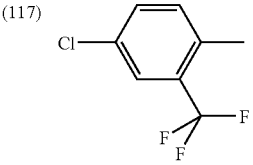 | 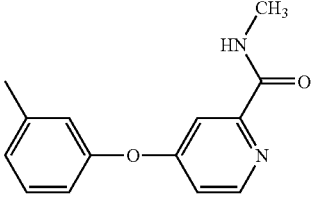 | 2.67 |
| (118) | 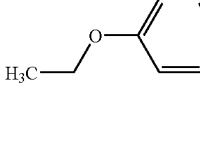 | 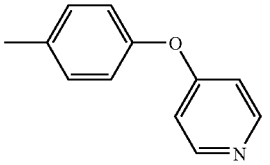 | 1.60 |
| (119) | 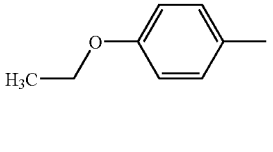 | 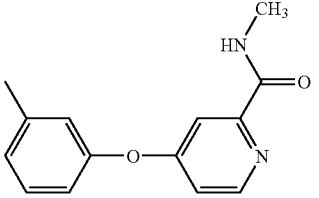 | 2.29 |
| (120) | 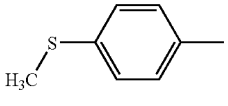 | 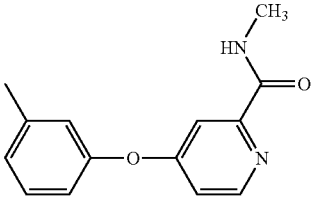 | 2.39 |
| (121) | 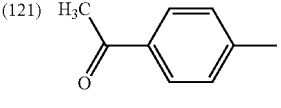 | 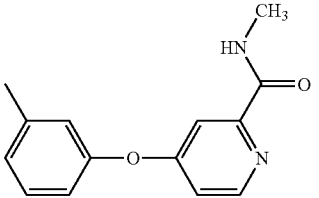 | 2.11 |
| (122) | 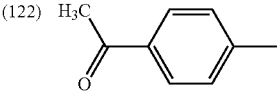 | 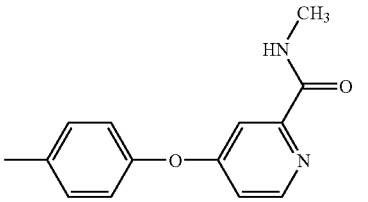 | 2.11 |

-continued

| | A | B | Rt |
|---|---|---|---|
| (123) | 4-isopropylphenyl | 4-(3-methylphenoxy)-N-methylpyridine-2-carboxamide | 2.62 |
| (124) | 4-isopropylphenyl | 4-(4-methylphenoxy)-N-methylpyridine-2-carboxamide | 2.61 |
| (125) | 4-ethylphenyl | 4-(3-methylphenoxy)-N-methylpyridine-2-carboxamide | 2.47 |
| (126) | 4-ethylphenyl | 4-(4-methylphenoxy)-N-methylpyridine-2-carboxamide | 2.49 |
| (127) | 4-chloro-2,3-dimethylphenyl | 4-(3-methylphenoxy)-N-methylpyridine-2-carboxamide | 2.52 |
| (128) | 4-chloro-2,3-dimethylphenyl | 4-(4-methylphenoxy)-N-methylpyridine-2-carboxamide | 2.52 |
| (129) | 4-chloro-2-methylphenyl (with CH3) | 4-(3-methylphenoxy)-N-methylpyridine-2-carboxamide | 2.47 |

-continued

| | A | B | Rt |
|---|---|---|---|
| (130) | 4-chloro-2-methylphenyl (with additional CH3) | N-methyl 4-(4-methylphenoxy)pyridine-2-carboxamide | 2.48 |
| (131) | 4-(trifluoromethoxy)phenyl | N-methyl 4-(3-methylphenoxy)pyridine-2-carboxamide | 2.62 |
| (132) | 4-(trifluoromethoxy)phenyl | N-methyl 4-(4-methylphenoxy)pyridine-2-carboxamide | 2.62 |
| (133) | 4-chloro-3-methyl-5-(trifluoromethyl)phenyl | 4-(4-methylphenoxy)pyridine | 2.09 |
| (134) | 4-chloro-3-methyl-5-(trifluoromethyl)phenyl | N-methyl 4-(3-methylphenoxy)pyridine-2-carboxamide | 2.81 |
| (135) | 4-chloro-3-methyl-5-(trifluoromethyl)phenyl | N-methyl 4-(4-methylphenoxy)pyridine-2-carboxamide | 2.79 |
| (136) | 4-tert-butylphenyl | N-methyl 4-(3-methylphenoxy)pyridine-2-carboxamide | 2.71 |

| | | -continued | |
|---|---|---|---|
| | A | B | Rt |
| (137) | 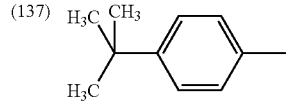 | 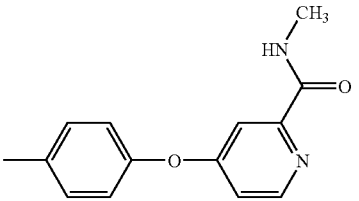 | 2.71 |
| (138) | 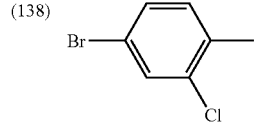 | 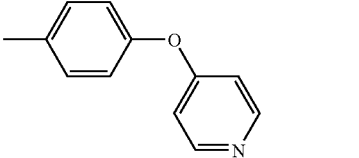 | 2.01 |
| (139) | 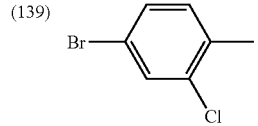 | 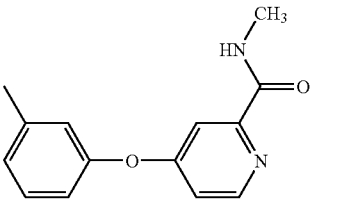 | 2.74 |
| (140) | 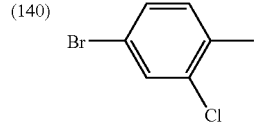 | 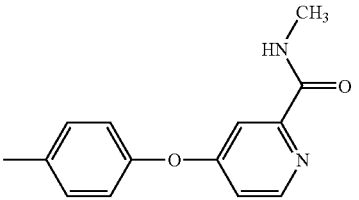 | 2.73 |
| (141) | 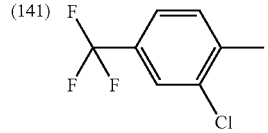 | 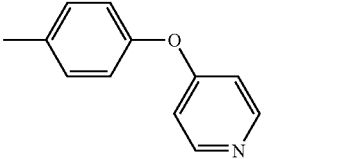 | 2.13 |
| (142) | 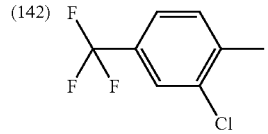 | 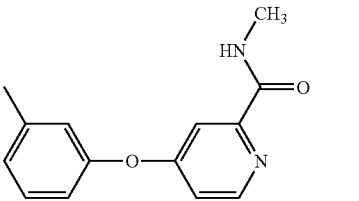 | 2.84 |
| (143) | 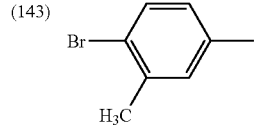 | 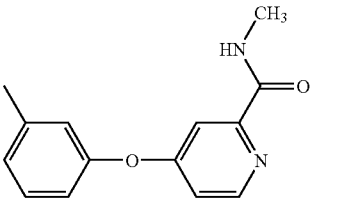 | 2.62 |

-continued
| | A | B | Rt |
|---|---|---|---|
| (144) | 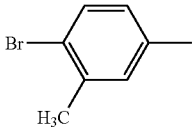 | 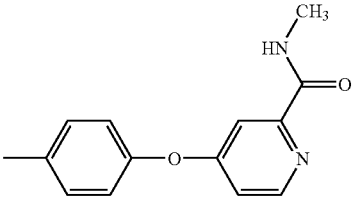 | 2.61 |
| (145) | 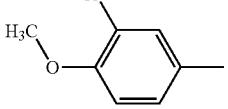 | 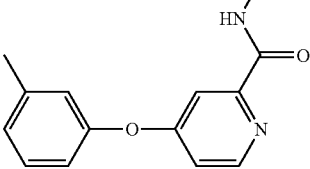 | 2.32 |
| (146) | 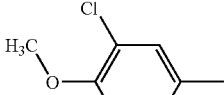 | 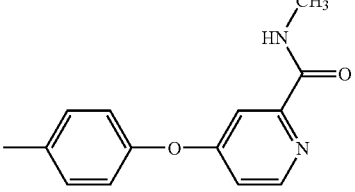 | 2.31 |
| (147) | 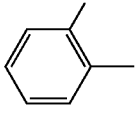 | 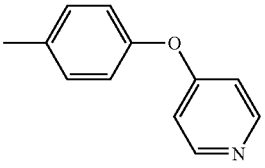 | 1.69 |
| (148) | 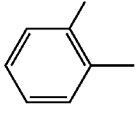 | 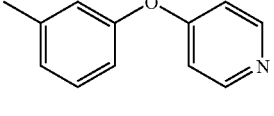 | 1.69 |
| (149) | 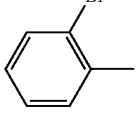 | 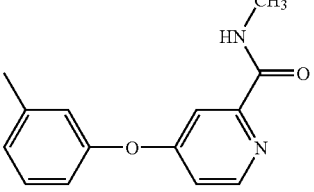 | 2.40 |
| (150) | 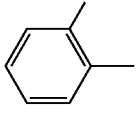 | 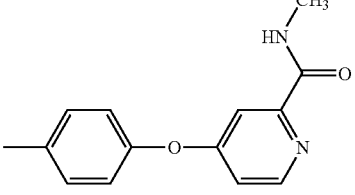 | 2.43 |
| (151) | 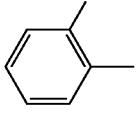 | 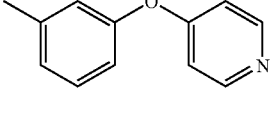 | 1.67 |

-continued

| | A | B | Rt |
|---|---|---|---|
| (152) | 2-chloro-methylphenyl | 4-(4-methylphenoxy)-N-methylpyridine-2-carboxamide | 2.37 |
| (153) | 2-methoxy-methylphenyl | 4-(3-methylphenoxy)pyridine | 1.57 |
| (154) | 2,4-dimethoxy-methylphenyl | 4-(3-methylphenoxy)pyridine | 1.57 |
| (155) | 2-(trifluoromethyl)-methylphenyl | 4-(3-methylphenoxy)pyridine | 1.70 |
| (156) | 3-bromo-methylphenyl | 4-(4-methylphenoxy)pyridine | 1.81 |
| (157) | 3-bromo-methylphenyl | 4-(3-methylphenoxy)pyridine | 1.78 |
| (158) | 3,4-dichloro-methylphenyl | 4-(3-methylphenoxy)pyridine | 1.97 |
| (159) | 3-(trifluoromethyl)-methylphenyl | 4-(3-methylphenoxy)pyridine | 1.94 |
| (160) | 3-methyl-methylphenyl | 4-(3-methylphenoxy)pyridine | 1.57 |

| | A | B | Rt |
|---|---|---|---|
| (161) | 4-(trifluoromethyl)phenyl | 3-(pyridin-4-yloxy)phenyl | 1.91 |
| (162) | 4-methylphenyl | 3-(pyridin-4-yloxy)phenyl | 1.63 |
| (163) | 3,4-dimethylphenyl | 3-(pyridin-4-yloxy)phenyl | 1.62 |
| (164) | 3-chloro-4-methylphenyl | 3-(pyridin-4-yloxy)phenyl | 1.93 |
| (165) | 3,5-dichlorophenyl | 4-(pyridin-4-yloxy)phenyl | 2.05 |
| (166) | 4-chloro-2-methyl-phenyl (with OCH₃) | 3-(pyridin-4-yloxy)phenyl | 1.87 |
| (167) | 3-(methylthio)phenyl | 3-(pyridin-4-yloxy)phenyl | 1.72 |
| (168) | 3-acetylphenyl | 3-(pyridin-4-yloxy)phenyl | 1.45 |
| (169) | 2,4-dimethylphenyl | 4-(pyridin-4-yloxy)phenyl | 1.74 |
| (170) | 2,4-dimethylphenyl | 3-(pyridin-4-yloxy)phenyl | 1.74 |

-continued
| | A | B | Rt |
|---|---|---|---|
| (171) | 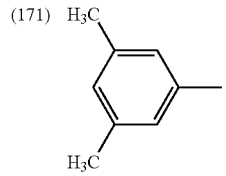 | 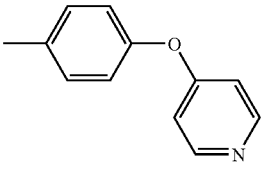 | 1.79 |
| (172) | 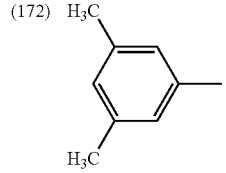 | 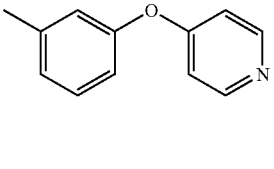 | 1.81 |
| (173) | 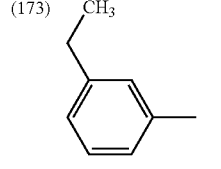 | 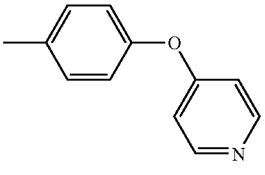 | 1.79 |
| (174) | 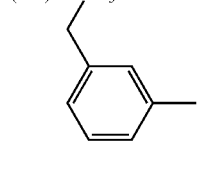 | 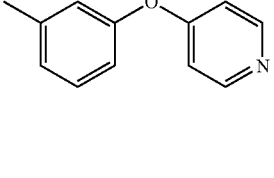 | 1.81 |
| (175) | 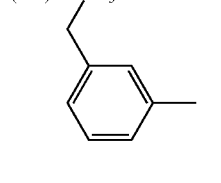 | 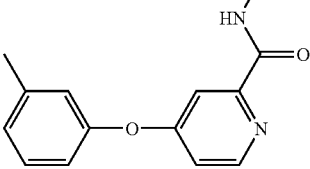 | 2.45 |
| (176) | 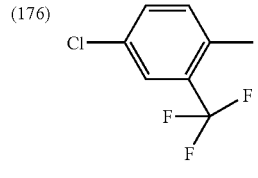 | 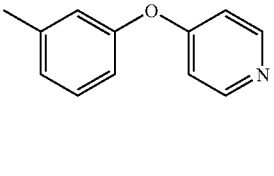 | 1.95 |
| (177) | 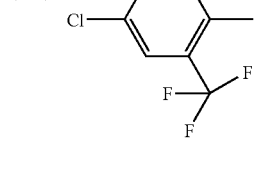 | 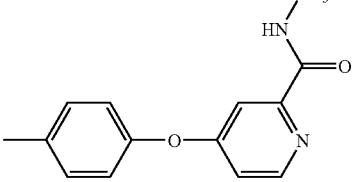 | 2.69 |
| (178) | 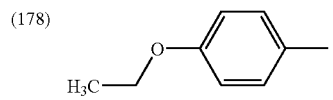 | 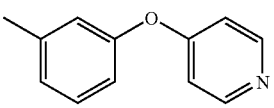 | 1.57 |

-continued
| | A | B | Rt |
|---|---|---|---|
| (179) | 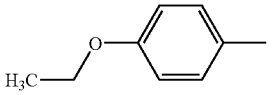 | 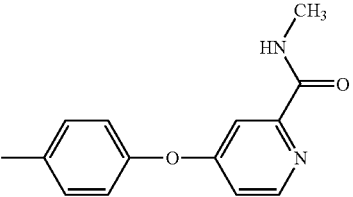 | 2.30 |
| (180) | 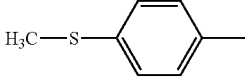 | 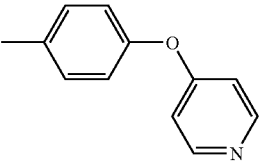 | 1.72 |
| (181) | 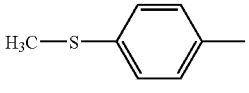 | 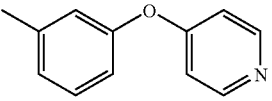 | 1.71 |
| (182) | 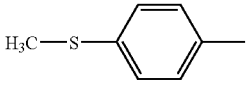 | 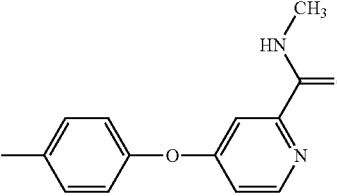 | 2.37 |
| (183) | 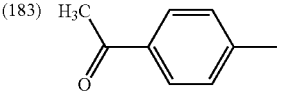 | 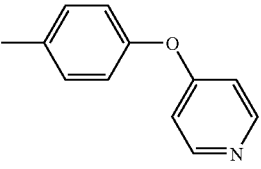 | 1.45 |
| (184) | 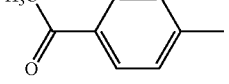 | 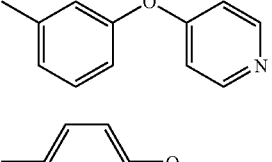 | 1.43 |
| (185) | 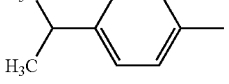 | 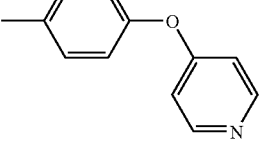 | 1.94 |
| (186) | 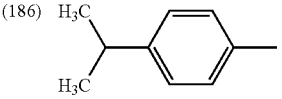 | 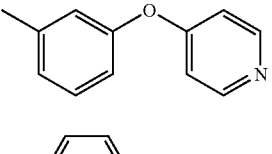 | 1.97 |
| (187) | 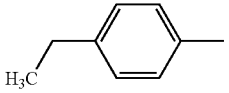 | 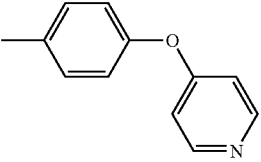 | 1.82 |

-continued
| | A | B | Rt |
|---|---|---|---|
| (188) | 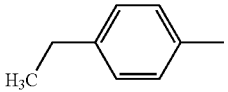 | 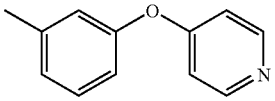 | 1.81 |
| (189) | 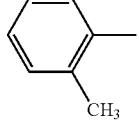 | 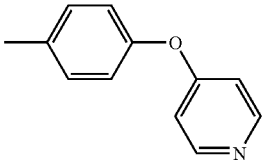 | 1.79 |
| (190) | 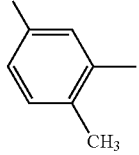 | 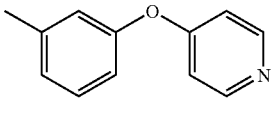 | 1.81 |
| (191) | 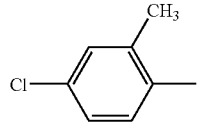 | 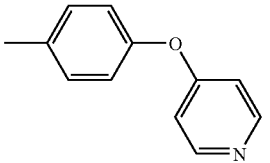 | 1.83 |
| (192) | 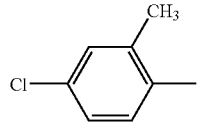 | 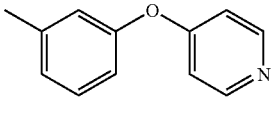 | 1.79 |
| (193) | 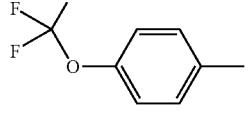 | 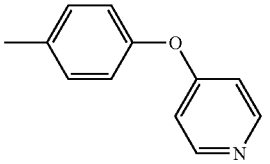 | 1.98 |
| (194) | 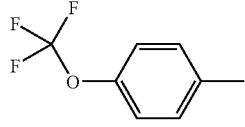 | 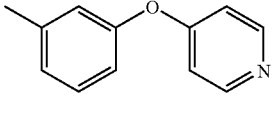 | 1.97 |
| (195) | 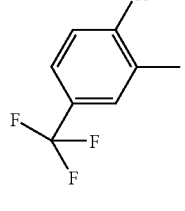 | 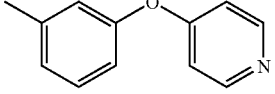 | 2.09 |
| (196) | 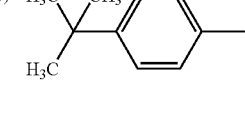 | 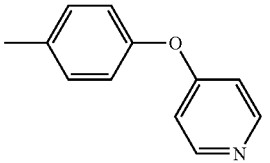 | 2.05 |

-continued

| | A | B | Rt |
|---|---|---|---|
| (197) | 4-tert-butylphenyl | 3-(pyridin-4-yloxy)phenyl | 2.06 |
| (198) | 4-bromo-2-chlorophenyl | 3-(pyridin-4-yloxy)phenyl | 1.96 |
| (199) | 3-chloro-4-(trifluoromethyl)phenyl | 3-(pyridin-4-yloxy)phenyl | 2.11 |
| (200) | 3-chloro-4-(trifluoromethyl)phenyl | 4-{[2-(methylcarbamoyl)pyridin-4-yl]oxy}phenyl | 2.85 |
| (201) | 4-bromo-3-methylphenyl | 4-(pyridin-4-yloxy)phenyl | 1.97 |
| (202) | 4-bromo-3-methylphenyl | 3-(pyridin-4-yloxy)phenyl | 1.95 |
| (203) | 3-chloro-4-methoxyphenyl | 4-(pyridin-4-yloxy)phenyl | 1.64 |
| (204) | 3-chloro-4-methoxyphenyl | 3-(pyridin-4-yloxy)phenyl | 1.67 |
| (205) | 3-methoxyphenyl | 4-(pyridin-4-yloxy)phenyl | 1.43 |

-continued

| | A | B | Rt |
|---|---|---|---|
| (206) | 3-methoxy-methylphenyl | 3-methylphenoxy-pyridine | 1.49 |
| (207) | 3-methoxy-methylphenyl | 3-methylphenoxy-pyridine-2-carboxylic acid methylamide | 2.19 |
| (208) | 3-methoxy-methylphenyl | 4-methylphenoxy-pyridine-2-carboxylic acid methylamide | 2.20 |
| (209) | 2-fluoro-5-methyl-trifluoromethylphenyl | 4-methylphenoxy-pyridine | 1.93 |
| (210) | 2-fluoro-5-methyl-trifluoromethylphenyl | 3-methylphenoxy-pyridine | 1.93 |
| (211) | 2-fluoro-5-methyl-trifluoromethylphenyl | 3-methylphenoxy-pyridine-2-carboxylic acid methylamide | 2.61 |
| (212) | 2-fluoro-5-methyl-trifluoromethylphenyl | 4-methylphenoxy-pyridine-2-carboxylic acid methylamide | 2.63 |

| | A | B | Rt |
|---|---|---|---|
| (213) | 4-methoxy-3-methyl-(trifluoromethyl)benzene | 4-(p-tolyloxy)pyridine | 2.01 |
| (214) | 4-methoxy-3-methyl-(trifluoromethyl)benzene | 4-(m-tolyloxy)pyridine | 1.99 |
| (215) | 4-methoxy-3-methyl-(trifluoromethyl)benzene | N-methyl-4-(p-tolyloxy)pyridine-2-carboxamide | 2.63 |
| (216) | 4-methoxy-3-methyl-(trifluoromethyl)benzene | N-methyl-4-(m-tolyloxy)pyridine-2-carboxamide | 2.65 |
| (217) | 1-bromo-4-methyl-2-(trifluoromethyl)benzene | 4-(p-tolyloxy)pyridine | 2.15 |
| (218) | 1-bromo-4-methyl-2-(trifluoromethyl)benzene | 4-(m-tolyloxy)pyridine | 2.12 |

-continued
| | A | B | Rt |
|---|---|---|---|
| (219) | 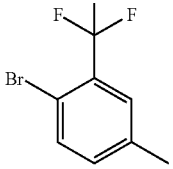 | 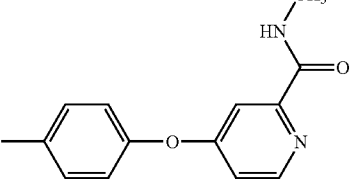 | 2.76 |
| (220) | 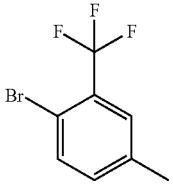 | 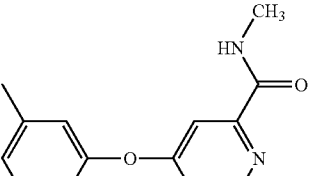 | 2.80 |
| (221) | 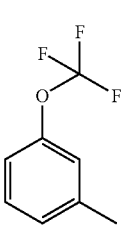 | 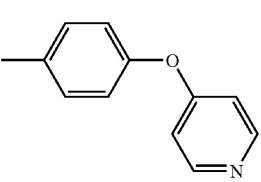 | 1.99 |
| (222) | 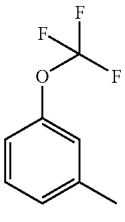 | 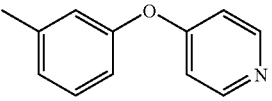 | 1.96 |
| (223) | 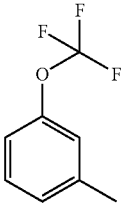 | 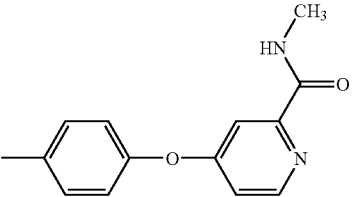 | 2.65 |
| (224) | 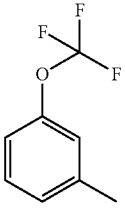 | 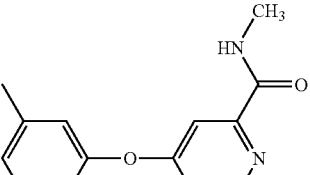 | 2.64 |

The present invention further relates to compounds (225) to (449) of formula A-NH—CO—NH—(CHMe)-B, wherein Me is a methyl group and A and B are as given in the table below:

-continued

| A | B | Rt |
| --- | --- | --- |
| (234) 2-chlorophenyl | 3-methylphenoxy-pyridine-2-carboxylic acid methylamide | |
| (235) 2,3-dichlorophenyl | 4-methylphenoxy-pyridine | |
| (236) 2,3-dichlorophenyl | 3-methylphenoxy-pyridine | |
| (237) 2,3-dichlorophenyl | 3-methylphenoxy-pyridine-2-carboxylic acid methylamide | |
| (238) 2,3-dichlorophenyl | 4-methylphenoxy-pyridine-2-carboxylic acid methylamide | |
| (239) 2,4-dichlorophenyl | 4-methylphenoxy-pyridine | |
| (240) 2,4-dichlorophenyl | 3-methylphenoxy-pyridine | |
| (241) 2,4-dichlorophenyl | 3-methylphenoxy-pyridine-2-carboxylic acid methylamide | |

| A | B | Rt |
|---|---|---|
| (242) 2,4-dichloro-methylphenyl | 4-(4-methylphenoxy)-N-methylpyridine-2-carboxamide | |
| (243) 2,5-dichloro-methylphenyl | 4-(4-methylphenoxy)pyridine | |
| (244) 2,5-dichloro-methylphenyl | 4-(3-methylphenoxy)-N-methylpyridine-2-carboxamide | |
| (245) 2,5-dichloro-methylphenyl | 4-(4-methylphenoxy)-N-methylpyridine-2-carboxamide | |
| (246) 2-methoxy-methylphenyl | 4-(3-methylphenoxy)-N-methylpyridine-2-carboxamide | |
| (247) 2-methoxy-methylphenyl | 4-(4-methylphenoxy)-N-methylpyridine-2-carboxamide | |
| (248) 2,5-dimethoxy-methylphenyl | 4-(4-methylphenoxy)pyridine | |

-continued

| A | B | Rt |
|---|---|---|
| (249) 2,5-dimethoxy-methylphenyl | N-methyl 4-(3-methylphenoxy)pyridine-2-carboxamide | |
| (250) 2,5-dimethoxy-methylphenyl | N-methyl 4-(4-methylphenoxy)pyridine-2-carboxamide | |
| (251) 2-(trifluoromethyl)methylphenyl | 4-(4-methylphenoxy)pyridine | |
| (252) 2-(trifluoromethyl)methylphenyl | N-methyl 4-(3-methylphenoxy)pyridine-2-carboxamide | |
| (253) 2-(trifluoromethyl)methylphenyl | N-methyl 4-(4-methylphenoxy)pyridine-2-carboxamide | |
| (254) 2-methylmethylphenyl | 4-(4-methylphenoxy)pyridine | |
| (255) 2-methylmethylphenyl | N-methyl 4-(3-methylphenoxy)pyridine-2-carboxamide | |

-continued

| | A | B | Rt |
|---|---|---|---|
| (256) | 2-methylphenyl | 4-(pyridin-2-yl-N-methylcarboxamide-4-yloxy)phenyl | |
| (257) | 2-ethylphenyl | 4-(pyridin-4-yloxy)phenyl | |
| (258) | 2-ethylphenyl | 3-(pyridin-4-yloxy)phenyl | |
| (259) | 2-ethylphenyl | 3-(pyridin-2-yl-N-methylcarboxamide-4-yloxy)phenyl | |
| (260) | 2-ethylphenyl | 4-(pyridin-2-yl-N-methylcarboxamide-4-yloxy)phenyl | |
| (261) | 3-bromophenyl | 3-(pyridin-2-yl-N-methylcarboxamide-4-yloxy)phenyl | |
| (262) | 3-bromophenyl | 4-(pyridin-2-yl-N-methylcarboxamide-4-yloxy)phenyl | |

-continued
| A | B | Rt |
|---|---|---|
| (263) 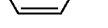 |  | |
| (264) 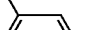 |  | |
| (265)  |  | |
| (266)  |  | 2.70 |
| (267)  | 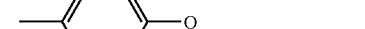 | |
| (268)  |  | |
| (269)  |  | 2.64 |

-continued

| | A | B | Rt |
|---|---|---|---|
| (270) | 3-methylphenyl | 4-(pyridin-4-yloxy)phenyl | |
| (271) | 3-methylphenyl | 4-(3-methylphenoxy)-N-methylpyridine-2-carboxamide | |
| (272) | 3-methylphenyl | 4-(4-methylphenoxy)-N-methylpyridine-2-carboxamide | |
| (273) | 4-bromophenyl | 4-(pyridin-4-yloxy)phenyl | |
| (274) | 4-bromophenyl | 3-(pyridin-4-yloxy)phenyl | |
| (275) | 4-bromophenyl | 4-(3-methylphenoxy)-N-methylpyridine-2-carboxamide | |
| (276) | 4-bromophenyl | 4-(4-methylphenoxy)-N-methylpyridine-2-carboxamide | |
| (277) | 4-fluorophenyl | 4-(pyridin-4-yloxy)phenyl | |

-continued
| | A | B | Rt |
|---|---|---|---|
| (278) |  | 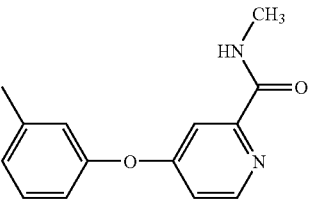 | |
| (279) |  | 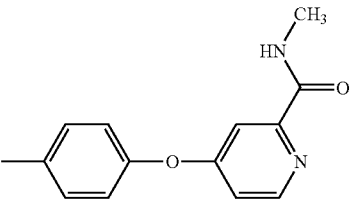 | |
| (280) | 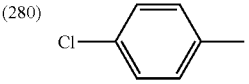 | 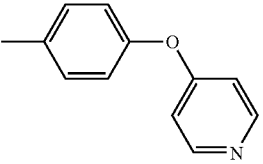 | |
| (281) | 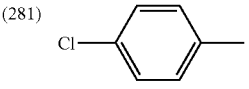 | 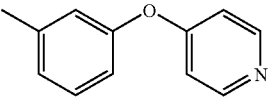 | |
| (282) | 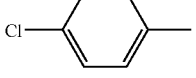 | 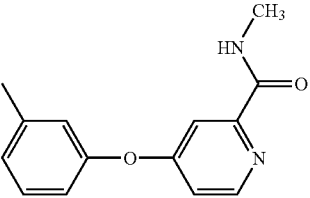 | |
| (283) | 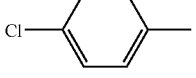 | 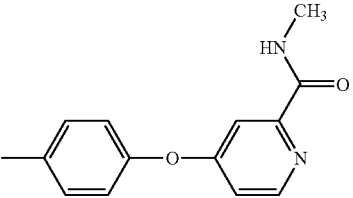 | |
| (284) | 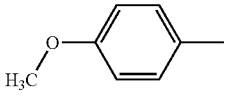 | 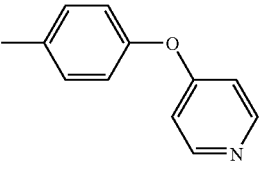 | |
| (285) | 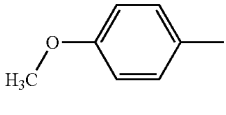 | 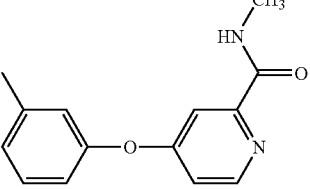 | |

-continued
| A | B | Rt |
|---|---|---|
| (286) 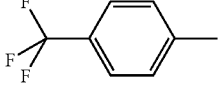 | 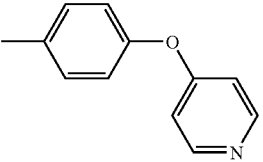 | |
| (287) 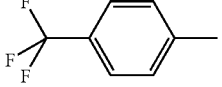 | 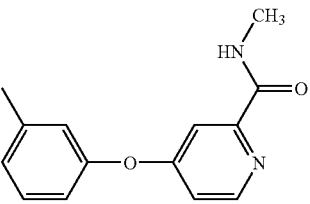 | |
| (288) 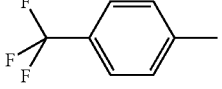 | 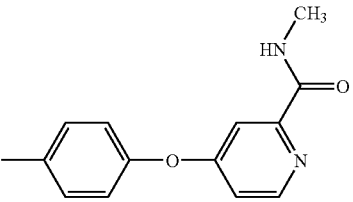 | 2.65 |
| (289) 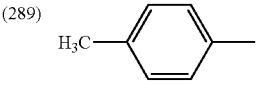 | 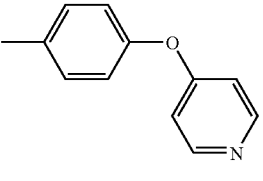 | |
| (290) 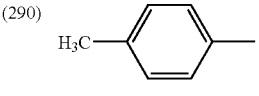 | 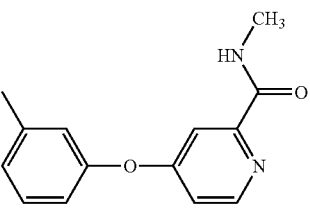 | |
| (291) 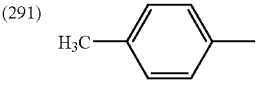 | 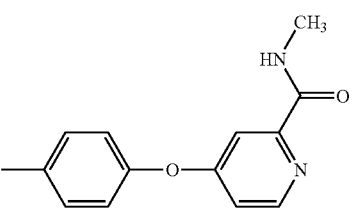 | |
| (292) 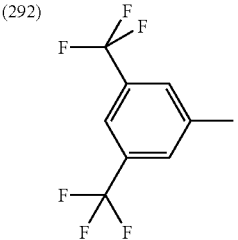 | 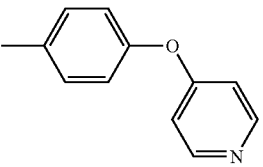 | |

-continued

| A | B | Rt |
|---|---|---|
| (293) 3,5-bis(trifluoromethyl)phenyl | 3-methylphenoxy-4-pyridine | |
| (294) 3,5-bis(trifluoromethyl)phenyl | N-methyl 4-(3-methylphenoxy)pyridine-2-carboxamide | |
| (295) 3,5-bis(trifluoromethyl)phenyl | N-methyl 4-(4-methylphenoxy)pyridine-2-carboxamide | |
| (296) 2,4,5-trichlorophenyl | N-methyl 4-(3-methylphenoxy)pyridine-2-carboxamide | |
| (297) 2,4,5-trichlorophenyl | N-methyl 4-(4-methylphenoxy)pyridine-2-carboxamide | 2.99 |
| (298) 2,3-dimethylphenyl | 4-(4-methylphenoxy)pyridine | |
| (299) 2,3-dimethylphenyl | 4-(3-methylphenoxy)pyridine | |

-continued
| A | B | Rt |
|---|---|---|
| (300) 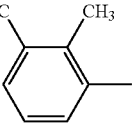 | 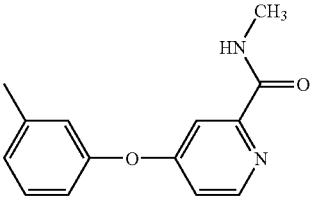 | |
| (301) 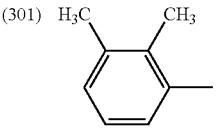 | 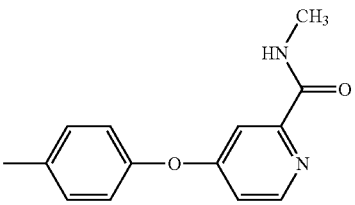 | |
| (302) 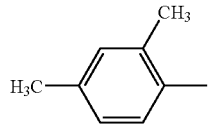 | 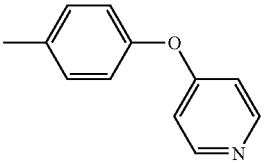 | |
| (303) 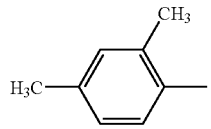 | 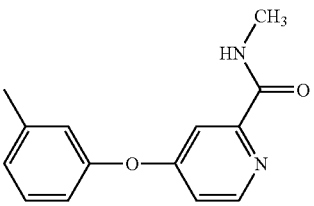 | |
| (304) 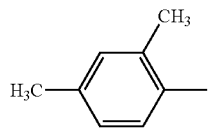 | 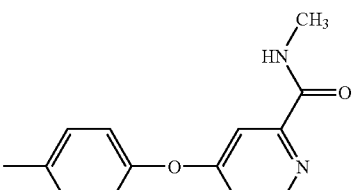 | |
| (305) 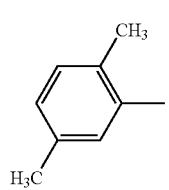 | 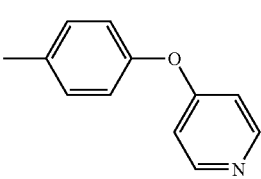 | |
| (306) 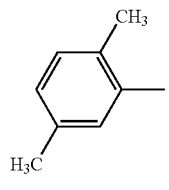 | 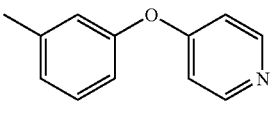 | |

-continued
| A | B | Rt |
|---|---|---|
| (307) 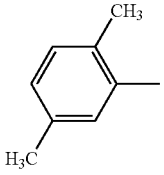 | 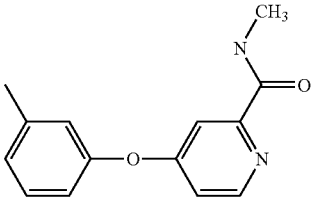 | |
| (308) 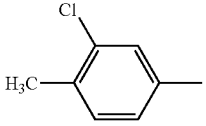 | 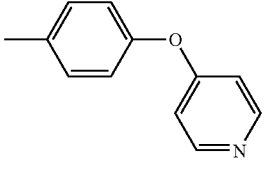 | |
| (309) 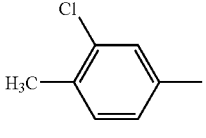 | 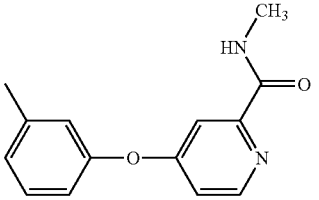 | |
| (310) 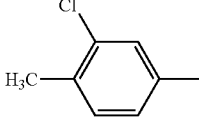 | 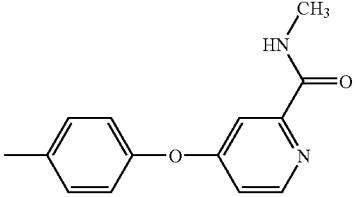 | 2.61 |
| (311) 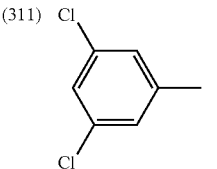 | 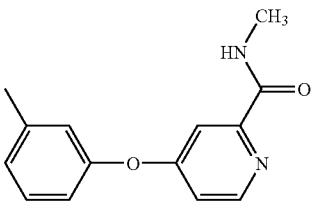 | |
| (312) 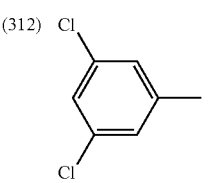 | 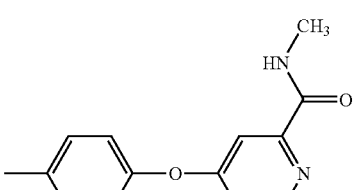 | |
| (313) 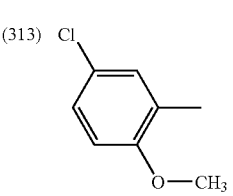 | 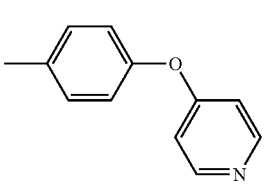 | |

-continued
| | A | B | Rt |
|---|---|---|---|
| (314) | 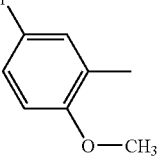 | 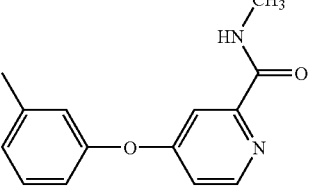 | |
| (315) | 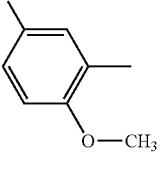 | 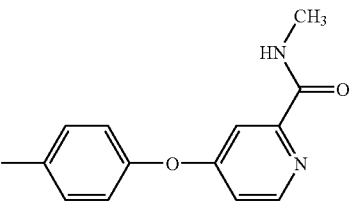 | 2.61 |
| (316) | 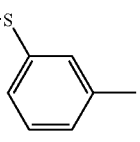 | 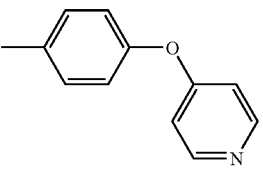 | |
| (317) | 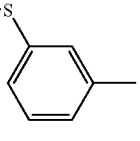 | 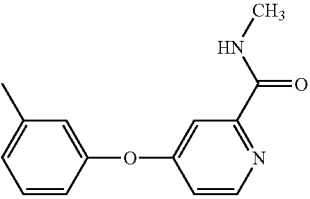 | |
| (318) | 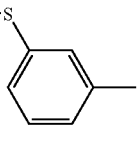 | 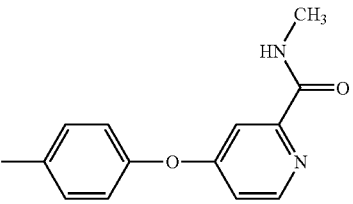 | |
| (319) | 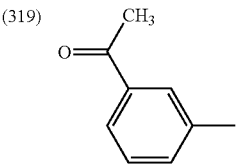 | 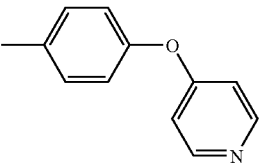 | |
| (320) | 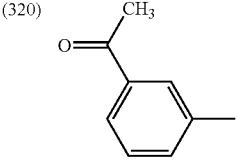 | 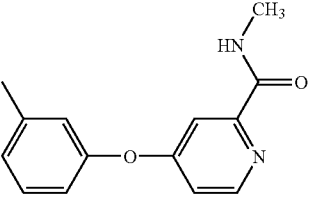 | |

-continued

| A | B | Rt |
|---|---|---|
| (321) 3-acetyl-methylphenyl group | 4-(4-methylphenoxy)-N-methylpyridine-2-carboxamide | |
| (322) 2,3,5-trimethylphenyl group | 4-(3-methylphenoxy)-N-methylpyridine-2-carboxamide | |
| (323) 2,4-dimethylphenyl group | 4-(4-methylphenoxy)-N-methylpyridine-2-carboxamide | |
| (324) 3,5-dimethylphenyl group | 4-(3-methylphenoxy)-N-methylpyridine-2-carboxamide | |
| (325) 3,5-dimethylphenyl group | 4-(4-methylphenoxy)-N-methylpyridine-2-carboxamide | |
| (326) 3-ethylphenyl group | 4-(4-methylphenoxy)-N-methylpyridine-2-carboxamide | |
| (327) 2-chloro-5-methyl-(trifluoromethyl)phenyl group | 4-(3-methylphenoxy)-N-methylpyridine-2-carboxamide | |

| | A | B | Rt |
|---|---|---|---|
| (328) | 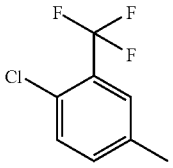 | 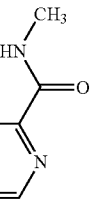 | 2.83 |
| (329) | 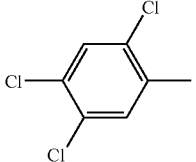 | 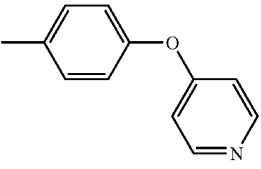 | |
| (330) | 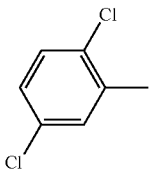 | 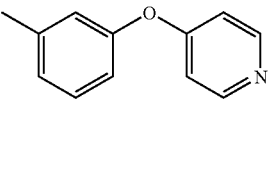 | |
| (331) | 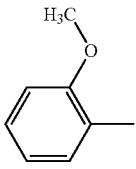 | 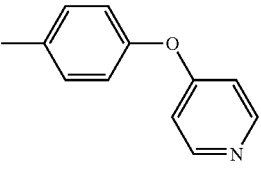 | |
| (332) | 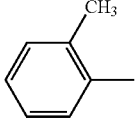 | 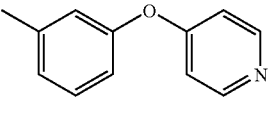 | |
| (333) | 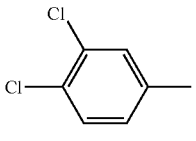 | 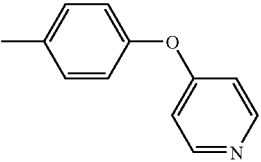 | |
| (334) | 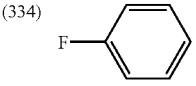 | 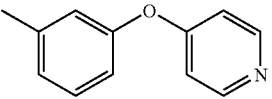 | |
| (335) | 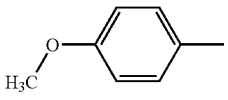 | 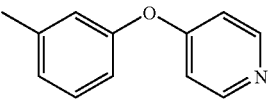 | |
| (336) | 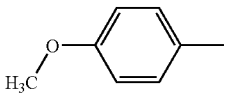 | 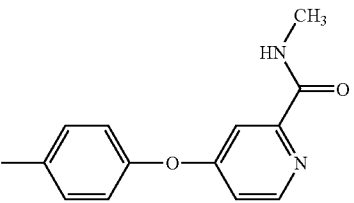 | |

| | -continued | |
|---|---|---|
| A | B | Rt |
(337) 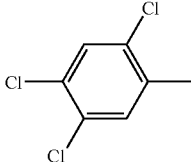 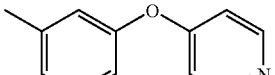
(338) 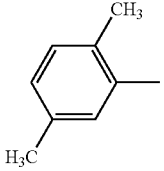 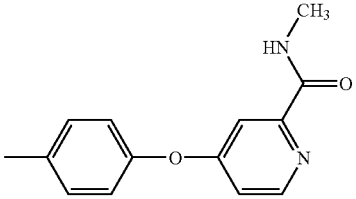
(339) 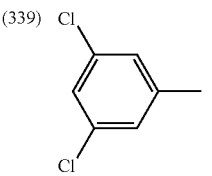 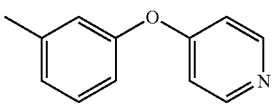
(340) 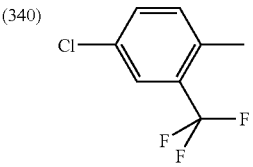 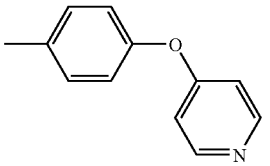
(341) 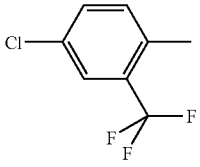 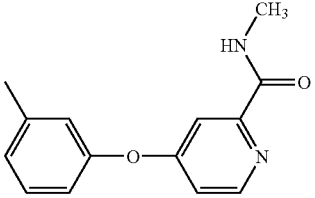
(342) 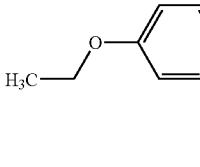 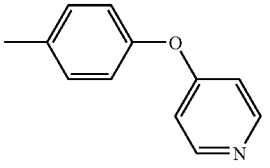
(343) 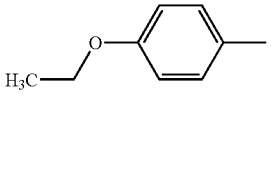 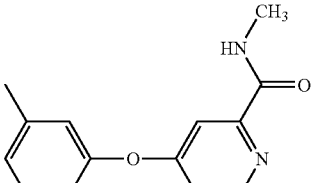
(344) 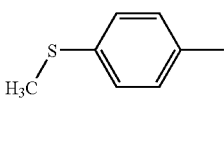 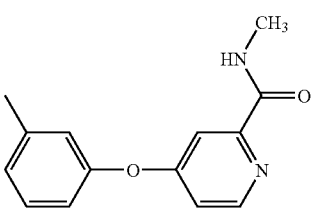

| | -continued | |
|---|---|---|
| A | B | Rt |

(345) 4-acetylphenyl (A); N-methyl 4-(3-methylphenoxy)pyridine-2-carboxamide (B)

(346) 4-acetylphenyl (A); N-methyl 4-(4-methylphenoxy)pyridine-2-carboxamide (B)

(347) 4-isopropylphenyl (A); N-methyl 4-(3-methylphenoxy)pyridine-2-carboxamide (B)

(348) 4-isopropylphenyl (A); N-methyl 4-(4-methylphenoxy)pyridine-2-carboxamide (B)

(349) 4-ethylphenyl (A); N-methyl 4-(3-methylphenoxy)pyridine-2-carboxamide (B)

(350) 4-ethylphenyl (A); N-methyl 4-(4-methylphenoxy)pyridine-2-carboxamide (B)

(351) 4-chloro-2,3-dimethylphenyl (A); N-methyl 4-(3-methylphenoxy)pyridine-2-carboxamide (B)

-continued
| A | B | Rt |
|---|---|---|
| (352) 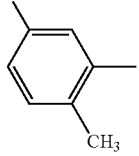 | 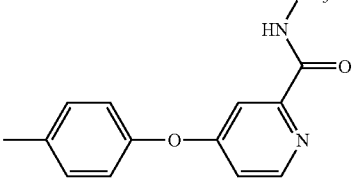 | |
| (353) 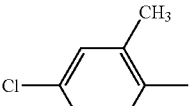 | 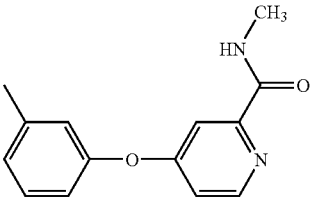 | |
| (354) 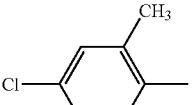 | 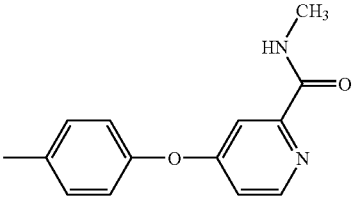 | |
| (355) 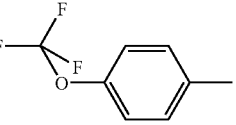 | 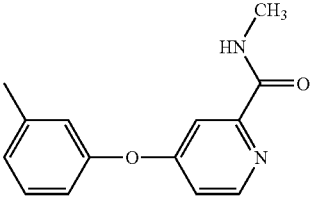 | 2.62 |
| (356) 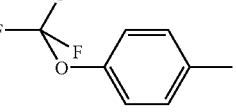 | 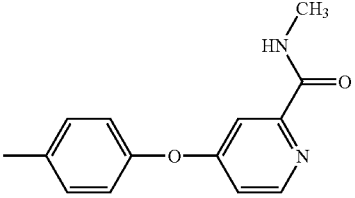 | 2 |
| (357) 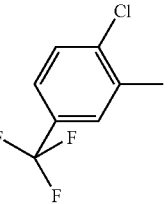 | 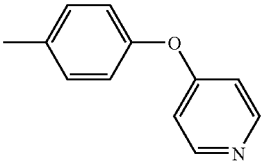 | |
| (358) 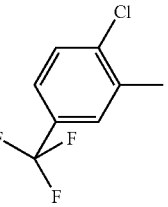 | 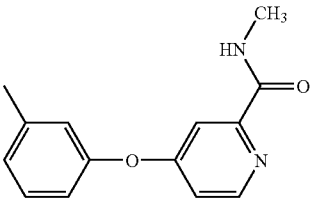 | |

-continued
| | A | B | Rt |
|---|---|---|---|
| (359) | 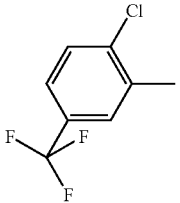 | 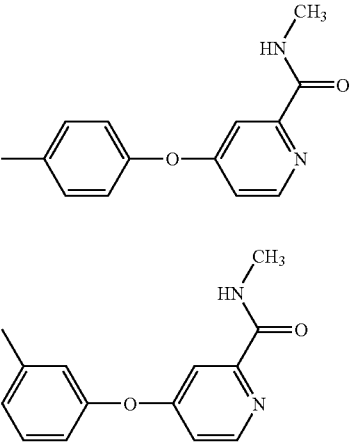 | 2.86 |
| (360) | 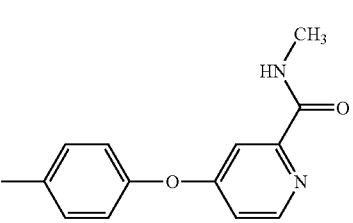 | 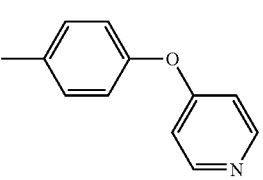 | |
| (361) | 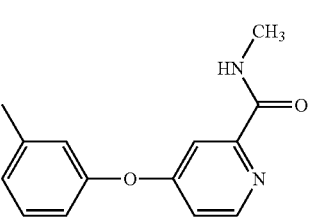 | 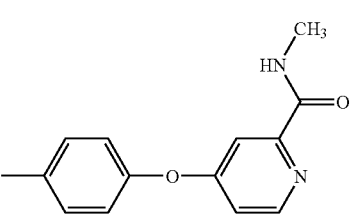 | |
| (362) | 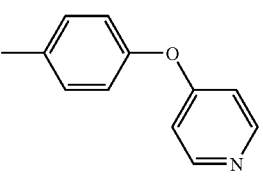 | | |
| (363) | | | |
| (364) | | | |
| (365) | | | |

| A | B | Rt |
|---|---|---|

(366) – A: 3-chloro-4-methyl-1-(trifluoromethyl)benzene; B: N-methyl-4-(3-methylphenoxy)pyridine-2-carboxamide (367) – A: 1-bromo-2,4-dimethylbenzene; B: N-methyl-4-(3-methylphenoxy)pyridine-2-carboxamide (368) – A: 1-bromo-2,4-dimethylbenzene; B: N-methyl-4-(4-methylphenoxy)pyridine-2-carboxamide (369) – A: 2-chloro-1-methoxy-4-methylbenzene; B: N-methyl-4-(3-methylphenoxy)pyridine-2-carboxamide (370) – A: 2-chloro-1-methoxy-4-methylbenzene; B: N-methyl-4-(4-methylphenoxy)pyridine-2-carboxamide (371) – A: 1-bromo-2-methylbenzene; B: 4-(4-methylphenoxy)pyridine (372) – A: 1-bromo-2-methylbenzene; B: 4-(3-methylphenoxy)pyridine -continued
| | A | B | Rt |
|---|---|---|---|
| (373) | 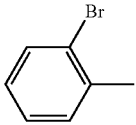 | 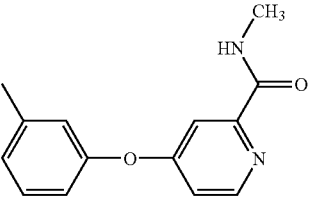 | |
| (374) | 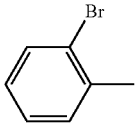 | 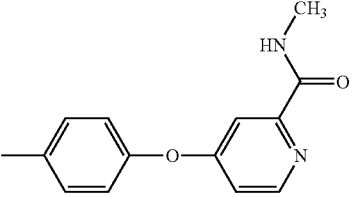 | |
| (375) | 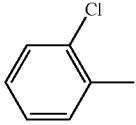 | 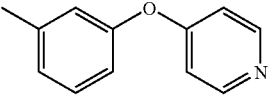 | |
| (376) | 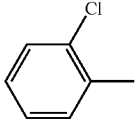 | 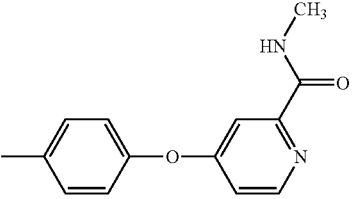 | |
| (377) | 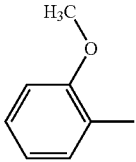 | 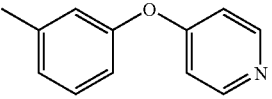 | |
| (378) | 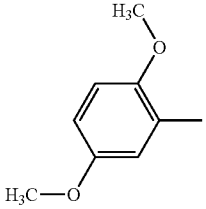 | 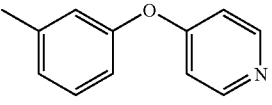 | |
| (379) | 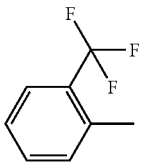 | 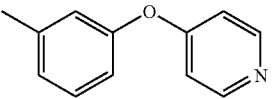 | |
| (380) | 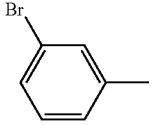 | 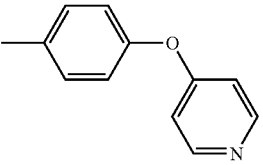 | |

-continued
| | A | B | Rt |
|---|---|---|---|
| (381) | 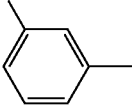 | 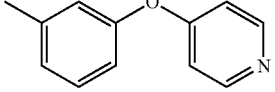 | |
| (382) | 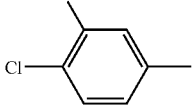 | 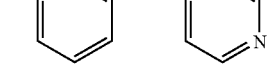 | |
| (383) | 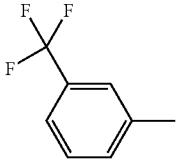 | 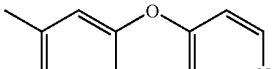 | |
| (384) | 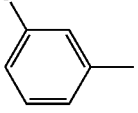 | 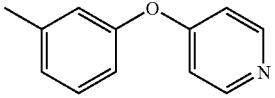 | |
| (385) | 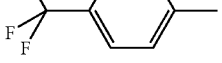 |  | |
| (386) | 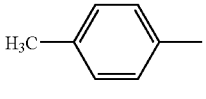 | 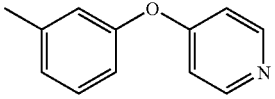 | |
| (387) | 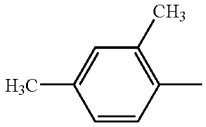 | 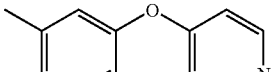 | |
| (388) | 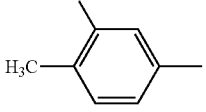 | 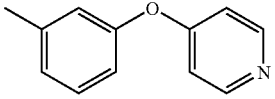 | |
| (389) | 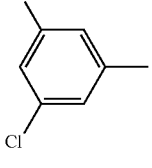 | 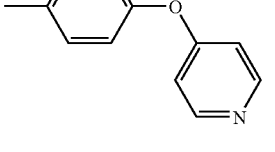 | |
| (390) | 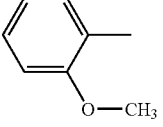 | 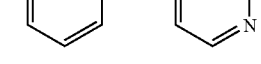 | |

| | A | B | Rt |
|---|---|---|---|
| (391) | H₃C—S-phenyl(3-) | 3-(pyridin-4-yloxy)phenyl | |
| (392) | 3-acetylphenyl | 3-(pyridin-4-yloxy)phenyl | |
| (393) | 2,4-dimethylphenyl | 4-(pyridin-4-yloxy)phenyl | |
| (394) | 2,4-dimethylphenyl | 3-(pyridin-4-yloxy)phenyl | |
| (395) | 3,5-dimethylphenyl | 4-(pyridin-4-yloxy)phenyl | |
| (396) | 3,5-dimethylphenyl | 3-(pyridin-4-yloxy)phenyl | |
| (397) | 3-methylbenzyl | 4-(pyridin-4-yloxy)phenyl | |
| (398) | 3-methylbenzyl | 3-(pyridin-4-yloxy)phenyl | |
| (399) | 3-methylbenzyl | 3-methyl-4-[(2-(N-methylcarbamoyl)pyridin-4-yl)oxy]phenyl | |

-continued
| | A | B | Rt |
|---|---|---|---|
| (400) | 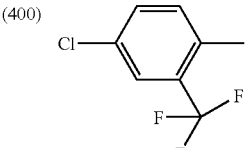 | 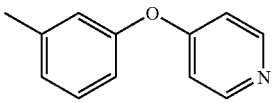 | |
| (401) | 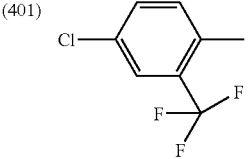 | 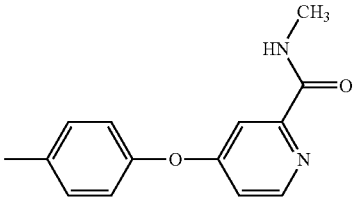 | |
| (402) | 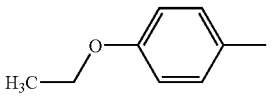 | 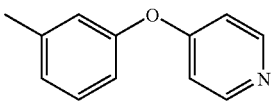 | |
| (403) | 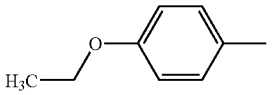 | 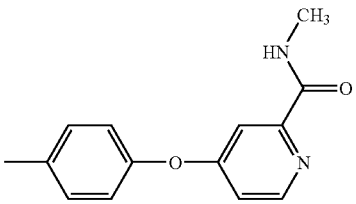 | |
| (404) | 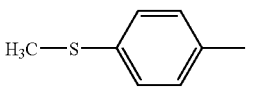 | 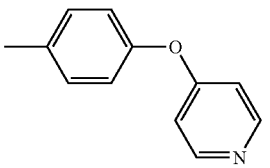 | |
| (405) | 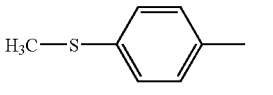 | 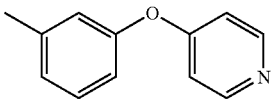 | |
| (406) | 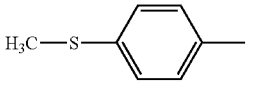 | 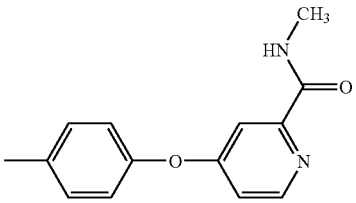 | |
| (407) | 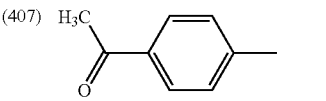 | 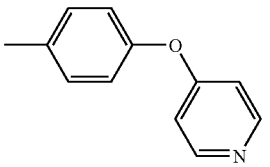 | |
| (408) | 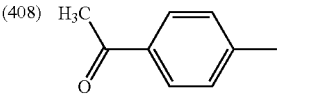 | 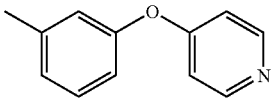 | |

-continued
| | A | B | Rt |
|---|---|---|---|
| (409) | 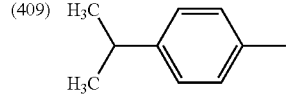 | 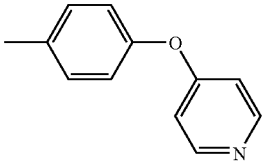 | |
| (410) | 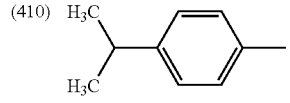 | 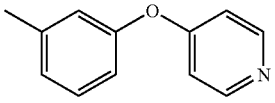 | |
| (411) | 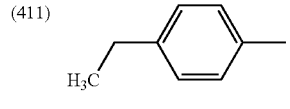 | 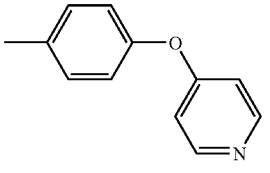 | |
| (412) | 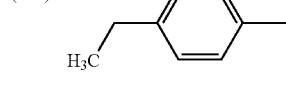 | 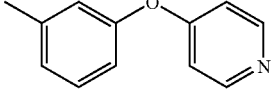 | |
| (413) | 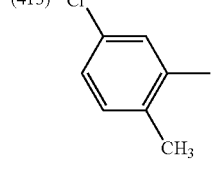 | 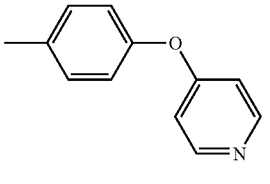 | |
| (414) | 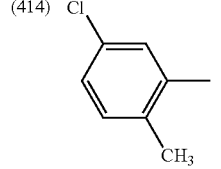 | 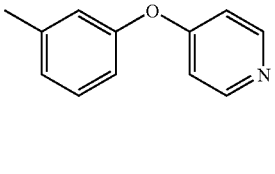 | |
| (415) | 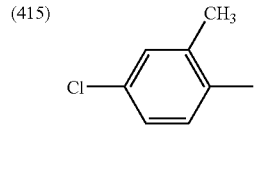 | 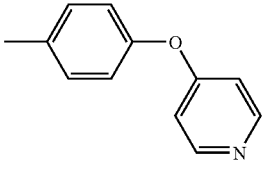 | |
| (416) | 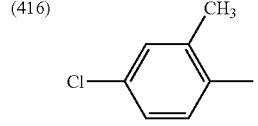 | 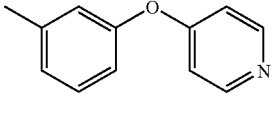 | |
| (417) | 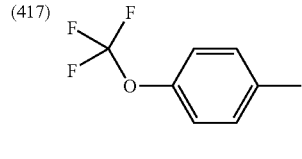 | 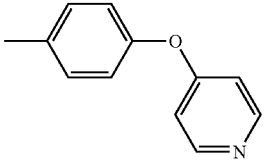 | |

-continued
| | A | B | Rt |
|---|---|---|---|
| (418) | 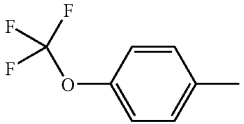 | 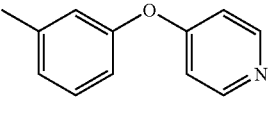 | |
| (419) | 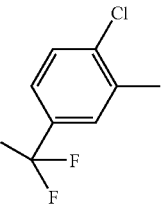 | 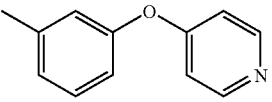 | |
| (420) | 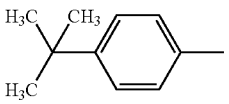 | 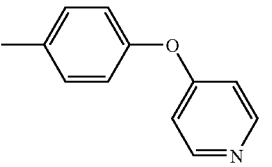 | |
| (421) | 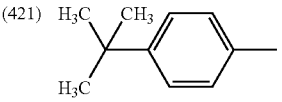 | 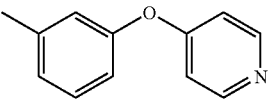 | |
| (422) | 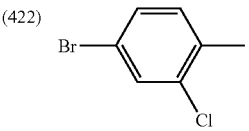 | 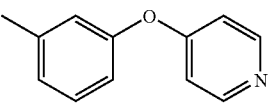 | |
| (423) | 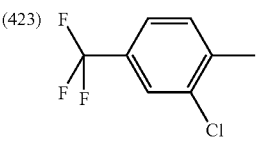 | 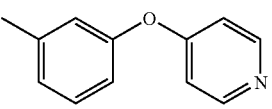 | |
| (424) | 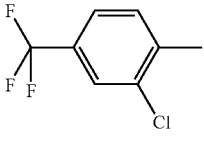 | 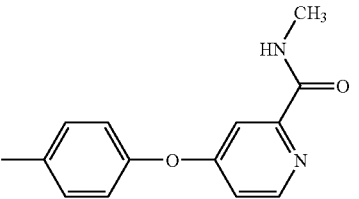 | |
| (425) | 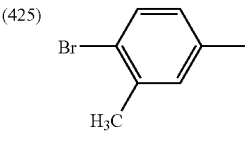 | 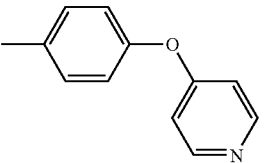 | |
| (426) | 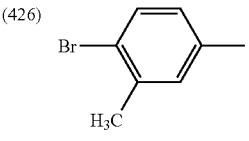 | 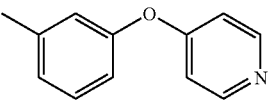 | |

-continued

| A | B | Rt |
|---|---|---|
| (427) 2-chloro-4-methoxyphenyl (Cl, OCH₃) | 4-(pyridin-4-yloxy)phenyl | |
| (428) 2-chloro-4-methoxyphenyl (Cl, OCH₃) | 3-(pyridin-4-yloxy)phenyl | |
| (429) 3-methoxyphenyl (OCH₃) | 4-(pyridin-4-yloxy)phenyl | |
| (430) 3-methoxyphenyl (OCH₃) | 3-(pyridin-4-yloxy)phenyl | |
| (431) 3-methoxyphenyl (OCH₃) | 4-(3-methylphenoxy)-N-methylpyridine-2-carboxamide | |
| (432) 3-methoxyphenyl (OCH₃) | 4-(4-methylphenoxy)-N-methylpyridine-2-carboxamide | |
| (433) 2-fluoro-5-(trifluoromethyl)phenyl | 4-(pyridin-4-yloxy)phenyl | |
| (434) 2-fluoro-5-(trifluoromethyl)phenyl | 3-(pyridin-4-yloxy)phenyl | |

-continued
| | A | B | Rt |
|---|---|---|---|
| (435) | 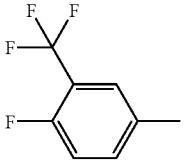 | 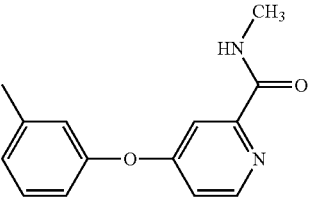 | |
| (436) | 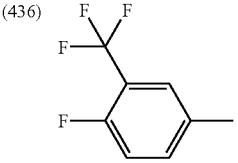 | 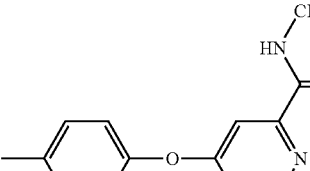 | 2.65 |
| (437) | 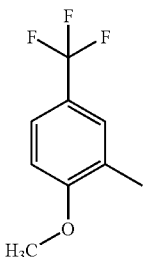 | 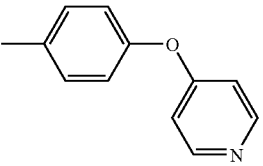 | |
| (438) | 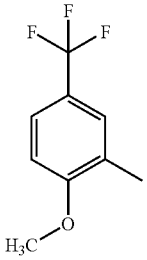 | 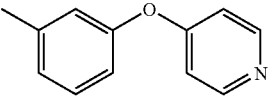 | |
| (439) | 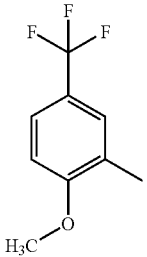 | 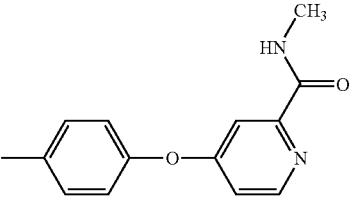 | 2.73 |
| (440) | 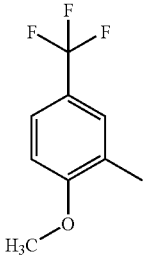 | 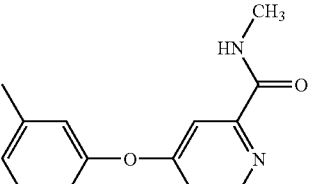 | |

-continued
| | A | B | Rt |
|---|---|---|---|
| (441) | 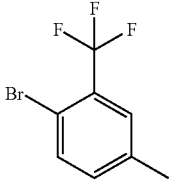 | 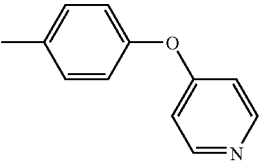 | |
| (442) | 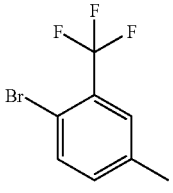 | 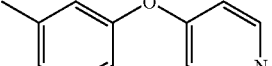 | |
| (443) | 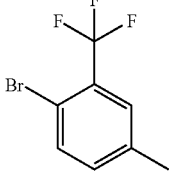 | 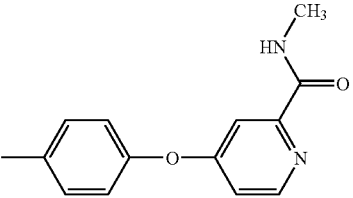 | 2.81 |
| (444) | 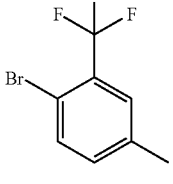 | 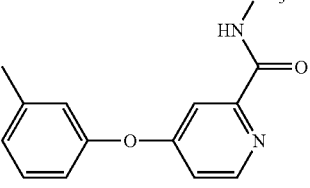 | |
| (445) | 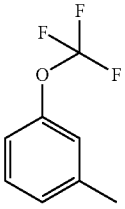 | 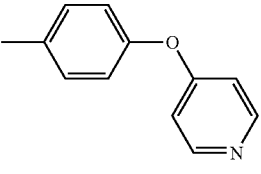 | |
| (446) | 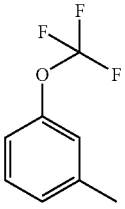 | 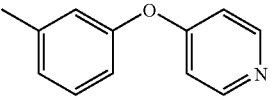 | |
| (447) | 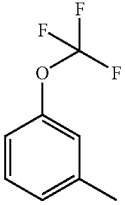 | 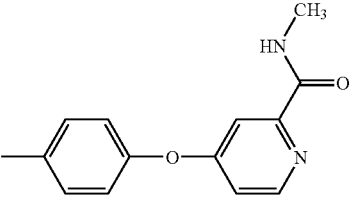 | 2.69 |

-continued
| | A | B | Rt |
|---|---|---|---|
| (448) | 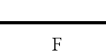 | 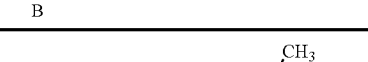 | |
The present invention further relates to compounds (449) to (672) of formula A-NH—CO—CR$^6$R$^7$—NH—B, wherein R$^6$ and R$^7$ form, together with the carbon atom of the methylene moiety they are bound to, a cyclopropane moiety, and wherein A and B are as given in the table below:
| | A | B | Rt |
|---|---|---|---|
| (449) | 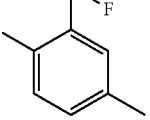 | 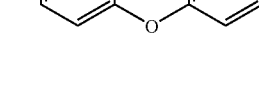 | 2.13 |
| (450) | 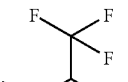 | 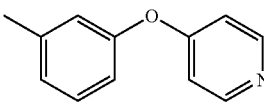 | 2.11 |
| (451) | 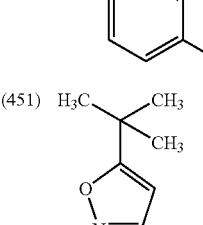 | 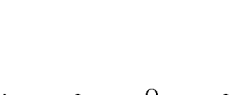 | |
| (452) | 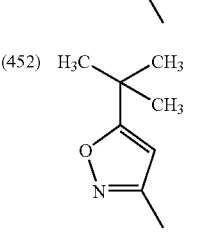 | 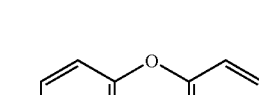 | |
| (453) |  | 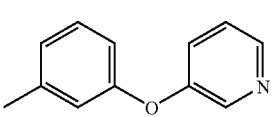 | |
| (454) |  |  | |

-continued
| | A | B | Rt |
|---|---|---|---|
| (455) | 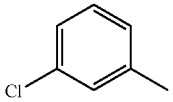 | 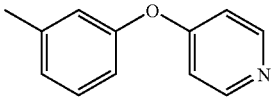 | |
| (456) | 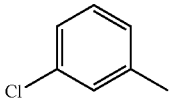 | 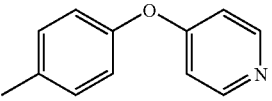 | |
| (457) | 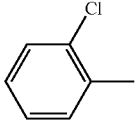 | 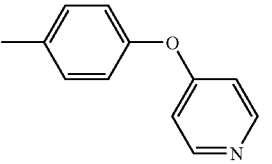 | |
| (458) | 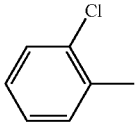 | 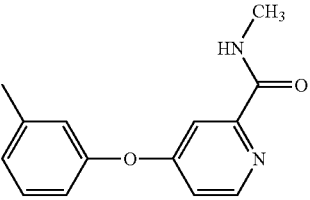 | |
| (459) | 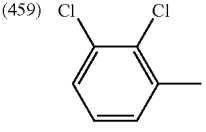 | 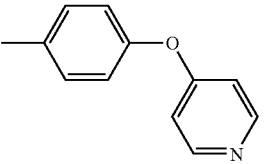 | |
| (460) | 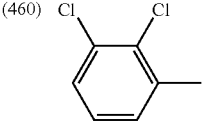 | 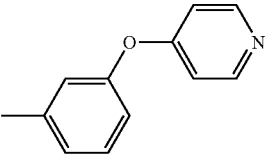 | |
| (461) | 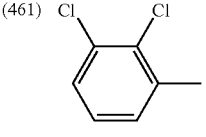 | 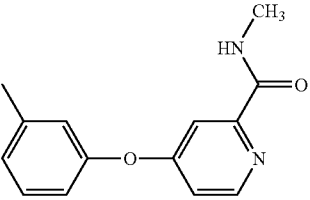 | |
| (462) | 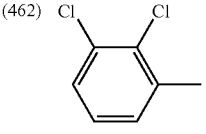 | 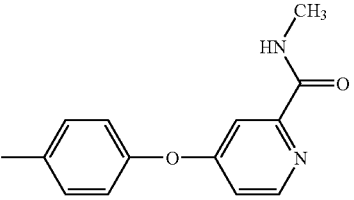 | |
| (463) | 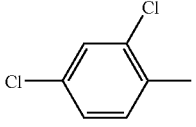 | 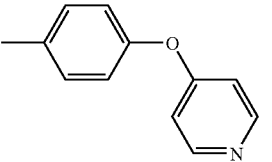 | |

-continued
| A | B | Rt |
|---|---|---|
| (464) 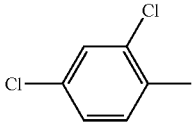 | 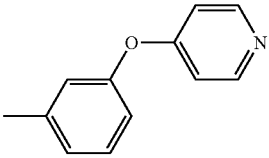 | |
| (465) 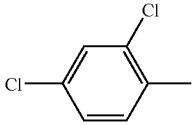 | 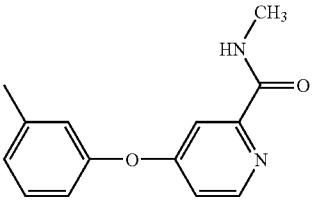 | |
| (466) 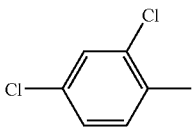 | 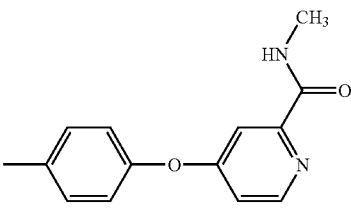 | |
| (467) 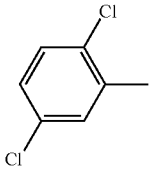 | 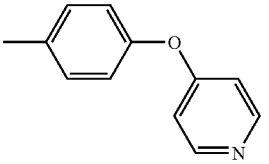 | |
| (468) 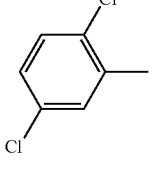 | 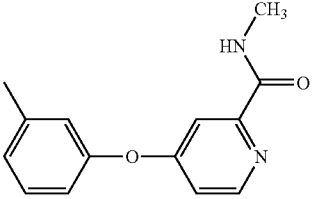 | |
| (469) 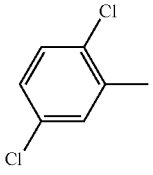 | 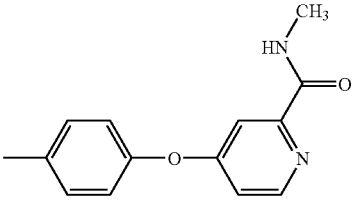 | |
| (470) 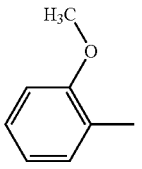 | 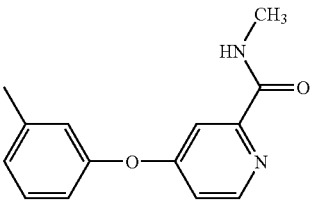 | |

|   | A | B | Rt |
|---|---|---|---|
| (471) | 2-methoxy-6-methylphenyl | 4-[(2-methylaminocarbonyl)pyridin-4-yloxy]phenyl | |
| (472) | 2,5-dimethoxy-4-methylphenyl | 4-(pyridin-4-yloxy)phenyl | |
| (473) | 2,5-dimethoxy-4-methylphenyl | 3-[(2-methylaminocarbonyl)pyridin-4-yloxy]phenyl | |
| (474) | N-methyl-{4-[4-(4-{[2-(methylamino)carbonyl]pyridin-4-yloxy}phenylamino)phenoxy]pyridin-2-yl}carboxamide structure | | |
| (475) | 2-(trifluoromethyl)-6-methylphenyl | 4-(pyridin-4-yloxy)phenyl | |
| (476) | 2-(trifluoromethyl)-6-methylphenyl | 3-[(2-methylaminocarbonyl)pyridin-4-yloxy]phenyl | |
| (477) | 2-(trifluoromethyl)-6-methylphenyl | 4-[(2-methylaminocarbonyl)pyridin-4-yloxy]phenyl | |

-continued
| A | B | Rt |
|---|---|---|
(478)–(484)
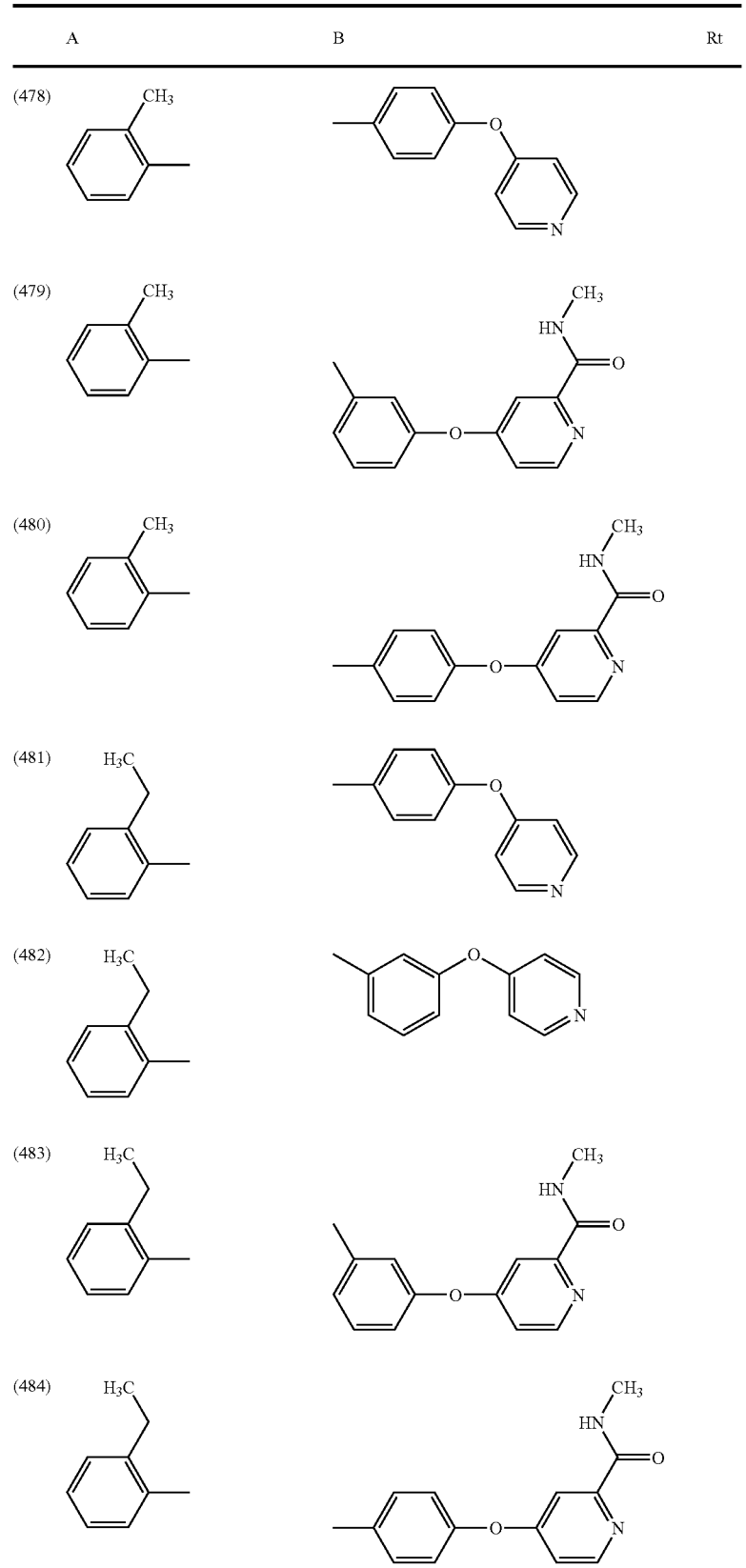

-continued
| | A | B | Rt |
|---|---|---|---|
| (485) | 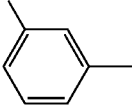 | 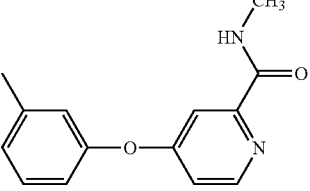 | |
| (486) | 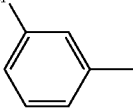 | 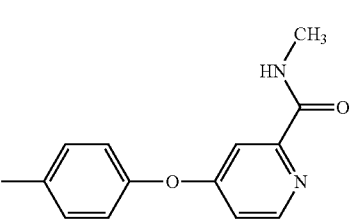 | |
| (487) | 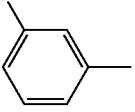 | 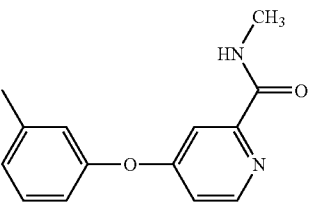 | |
| (488) | 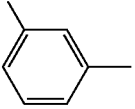 | 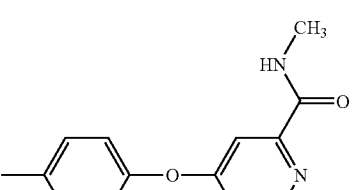 | |
| (489) | 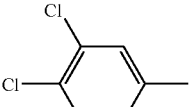 | 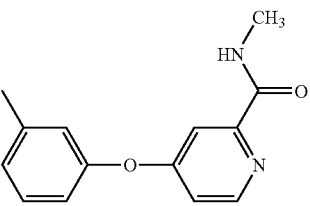 | |
| (490) | 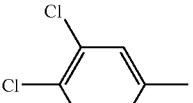 | 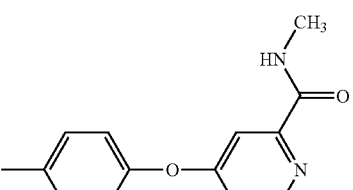 | |
| (491) | 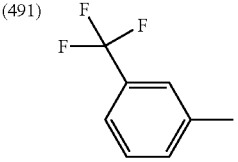 | 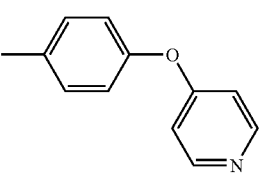 | |

| | -continued | |
|---|---|---|
| A | B | Rt |
| (492) 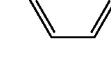 | 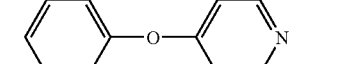 | |
| (493) 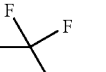 |  | |
| (494) 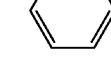 | 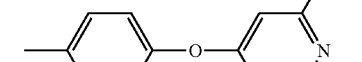 | |
| (495)  | 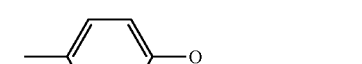 | |
| (496) 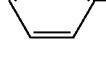 | 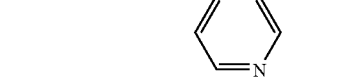 | |
| (497) 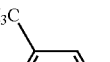 |  | |
| (498) 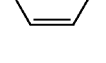 | 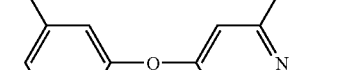 | |
| (499)  |  | |

-continued

| | A | B | Rt |
|---|---|---|---|
| (500) | 4-Br-phenyl- | 4-[(2-(N-methylcarbamoyl)pyridin-4-yl)oxy]phenyl- | |
| (501) | 4-F-phenyl- | 4-(pyridin-4-yloxy)phenyl- | |
| (502) | 4-F-phenyl- | 3-[(2-(N-methylcarbamoyl)pyridin-4-yl)oxy]phenyl- | |
| (503) | 4-F-phenyl- | 4-[(2-(N-methylcarbamoyl)pyridin-4-yl)oxy]phenyl- | |
| (504) | 4-Cl-phenyl- | 4-(pyridin-4-yloxy)phenyl- | |
| (505) | 4-Cl-phenyl- | 3-(pyridin-4-yloxy)phenyl- | |
| (506) | 4-Cl-phenyl- | 3-[(2-(N-methylcarbamoyl)pyridin-4-yl)oxy]phenyl- | |
| (507) | 3-methyl-phenyl- attached to pyridine carboxamide | 4-[(2-(N-methylcarbamoyl)pyridin-4-yl)oxy]phenyl- | |

-continued
| A | B | Rt |
|---|---|---|
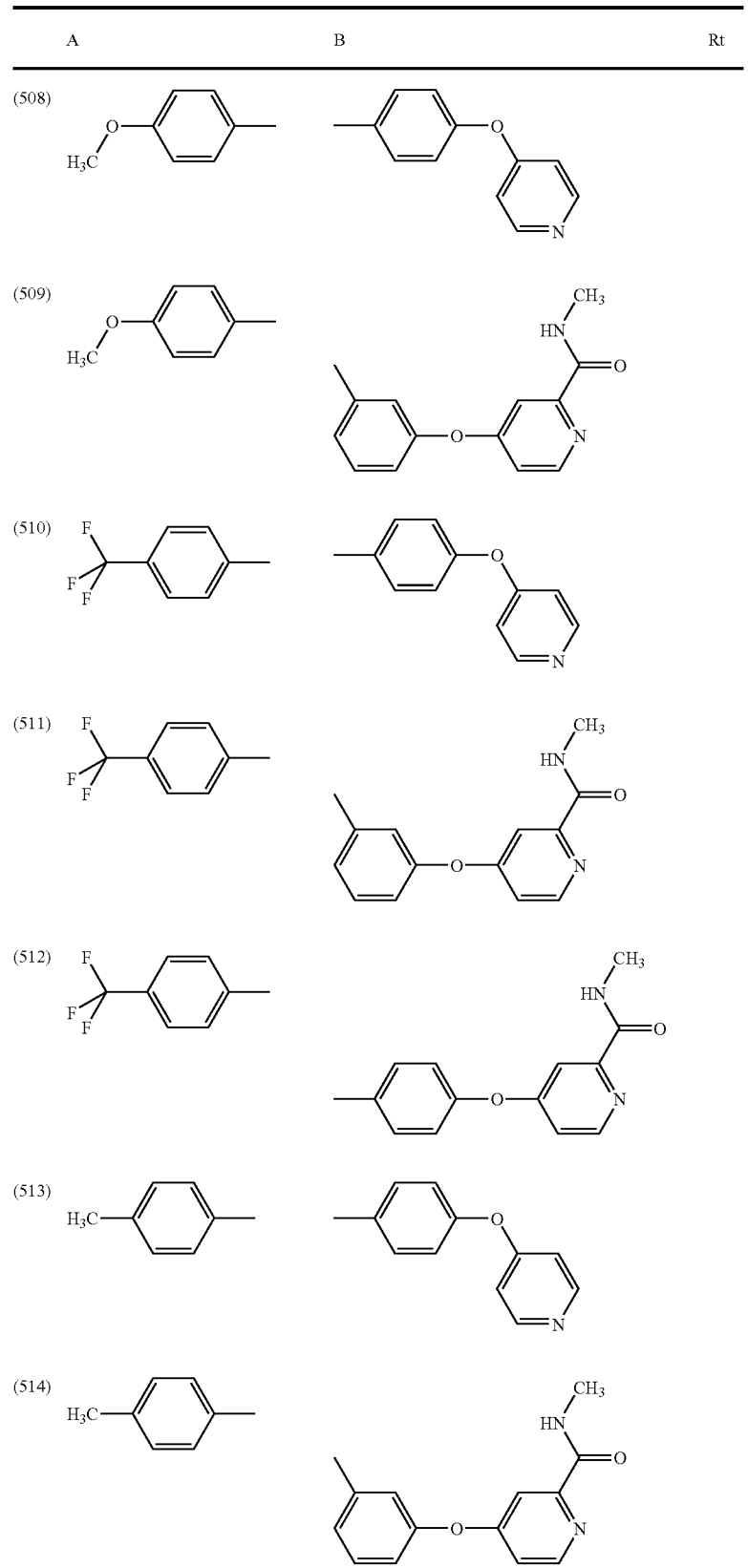

| A | B | Rt |
|---|---|---|
| (515) 4-methylphenyl | N-methyl 4-(4-methylphenoxy)pyridine-2-carboxamide | |
| (516) 3,5-bis(trifluoromethyl)phenyl | 4-(4-methylphenoxy)pyridine | |
| (517) 3,5-bis(trifluoromethyl)phenyl | 4-(3-methylphenoxy)pyridine | |
| (518) 3,5-bis(trifluoromethyl)phenyl | N-methyl 4-(3-methylphenoxy)pyridine-2-carboxamide | |
| (519) 3,5-bis(trifluoromethyl)phenyl | N-methyl 4-(4-methylphenoxy)pyridine-2-carboxamide | |
| (520) 2,4,5-trichlorophenyl | N-methyl 4-(3-methylphenoxy)pyridine-2-carboxamide | |

-continued
| | A | B | Rt |
|---|---|---|---|
| (521) | 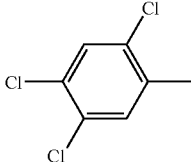 | 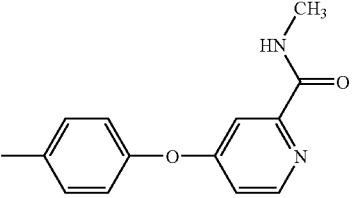 | |
| (522) | 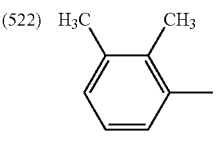 | 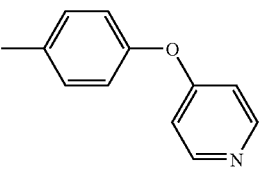 | |
| (523) | 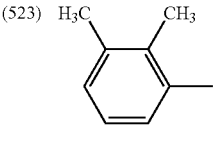 | 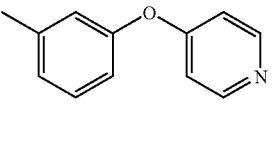 | |
| (524) | 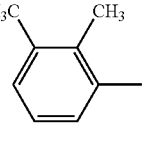 | 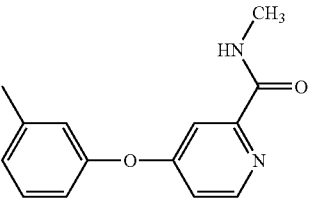 | |
| (525) | 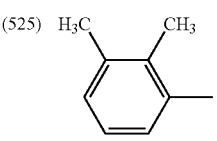 | 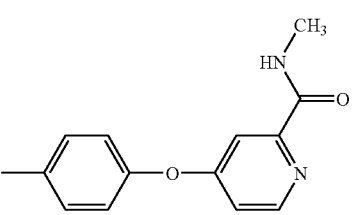 | |
| (526) | 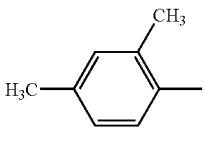 | 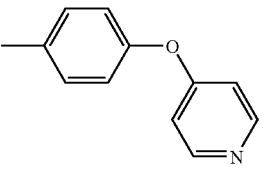 | |
| (527) | 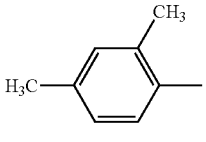 | 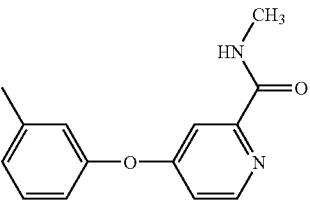 | |
| (528) | 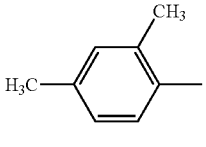 | 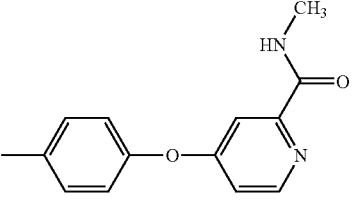 | |

-continued
| A | B | Rt |
|---|---|---|
| (529) 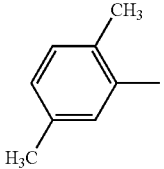 | 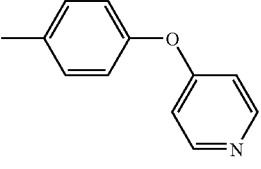 | |
| (530) 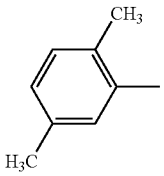 | 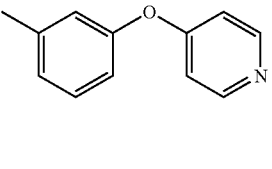 | |
| (531) 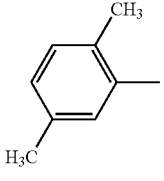 | 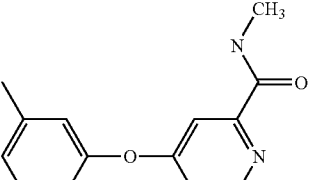 | |
| (532) 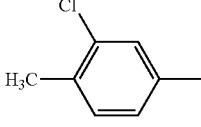 | 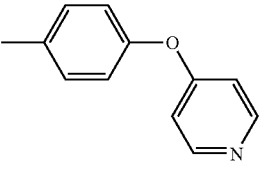 | |
| (533) 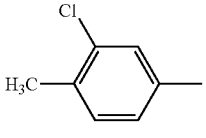 | 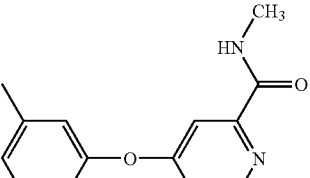 | |
| (534) 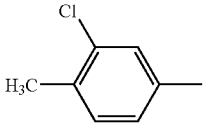 | 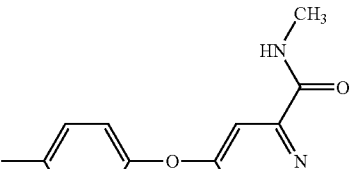 | |
| (535) 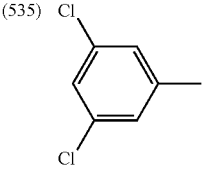 | 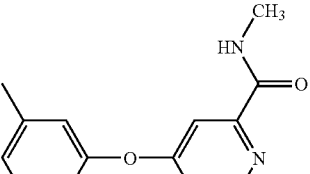 | |

-continued
| | A | B | Rt |
|---|---|---|---|
| (536) | 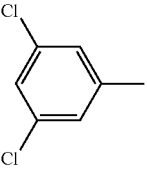 | 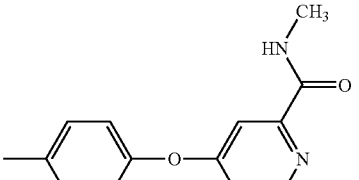 | |
| (537) | 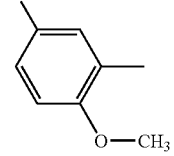 | 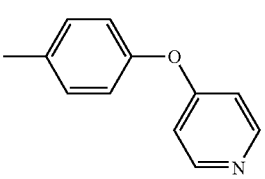 | |
| (538) | 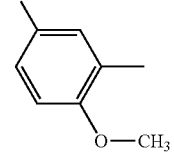 | 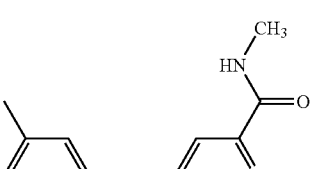 | |
| (539) | 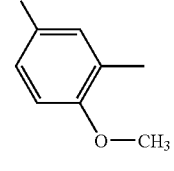 | 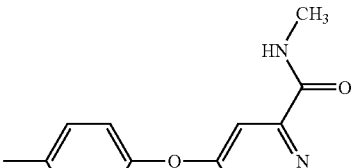 | |
| (540) | 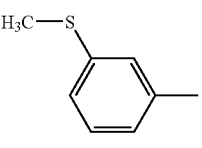 | 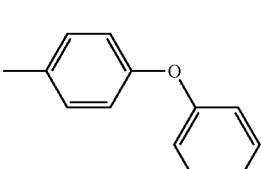 | |
| (541) | 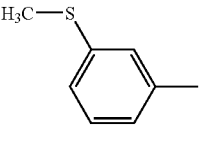 | 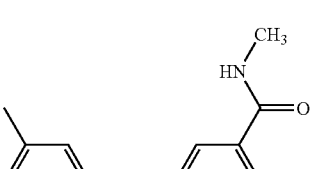 | |
| (542) | 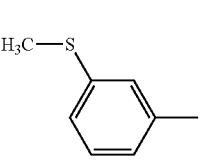 |  | |

-continued

| A | B | Rt |
|---|---|---|
| (543) 3-acetyl-methylbenzene | 4-(pyridin-4-yloxy)phenyl | |
| (544) 3-acetyl-methylbenzene | 3-methylphenyl 4-oxy-pyridine-2-(N-methyl)carboxamide | |
| (545) 3-acetyl-methylbenzene | 4-methylphenyl 4-oxy-pyridine-2-(N-methyl)carboxamide | |
| (546) 2,4-dimethylphenyl | 3-methylphenyl 4-oxy-pyridine-2-(N-methyl)carboxamide | |
| (547) 2,4-dimethylphenyl | 4-methylphenyl 4-oxy-pyridine-2-(N-methyl)carboxamide | |
| (548) 3,5-dimethylphenyl | 3-methylphenyl 4-oxy-pyridine-2-(N-methyl)carboxamide | |
| (549) 3,5-dimethylphenyl | 4-methylphenyl 4-oxy-pyridine-2-(N-methyl)carboxamide | |

-continued
| A | B | Rt |
|---|---|---|
| (550) 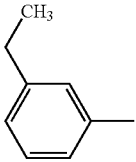 | 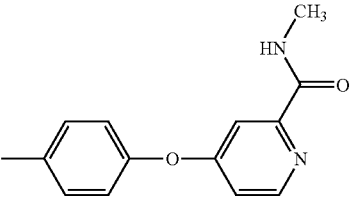 | |
| (551) 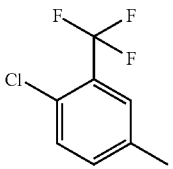 | 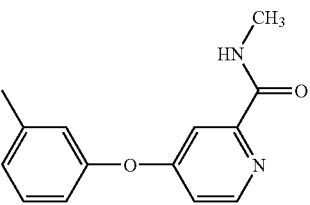 | |
| (552) 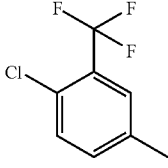 | 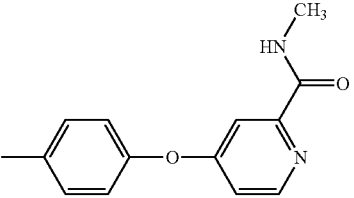 | |
| (553) 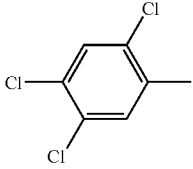 | 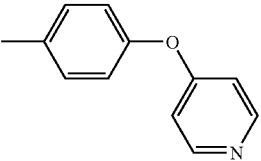 | |
| (554) 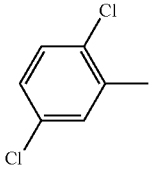 | 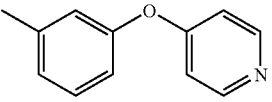 | |
| (555) 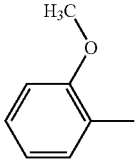 | 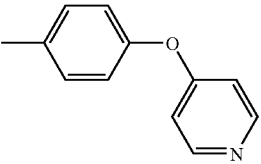 | |
| (556) 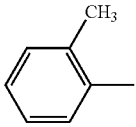 | 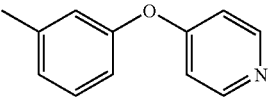 | |
| (557) 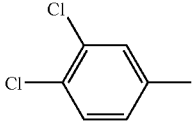 | 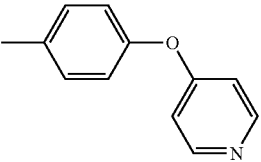 | |

-continued

| | A | B | Rt |
|---|---|---|---|
| (558) | 4-fluorophenyl | 3-methylphenyl 4-pyridyl ether | |
| (559) | 4-methoxy-3-methylphenyl | 3-methylphenyl 4-pyridyl ether | |
| (560) | 4-methoxy-3-methylphenyl | 4-(4-methylphenoxy)-N-methylpyridine-2-carboxamide | |
| (561) | 2,4,5-trichlorophenyl | 3-methylphenyl 4-pyridyl ether | |
| (562) | 2,4-dimethylphenyl | 4-(4-methylphenoxy)-N-methylpyridine-2-carboxamide | |
| (563) | 3,5-dichlorophenyl | 3-methylphenyl 4-pyridyl ether | |
| (564) | 5-chloro-2-methyl-(trifluoromethyl)phenyl | 4-methylphenyl 4-pyridyl ether | |
| (565) | 5-chloro-2-methyl-(trifluoromethyl)phenyl | 4-(3-methylphenoxy)-N-methylpyridine-2-carboxamide | |

-continued
| A | B | Rt |
|---|---|---|
(566)
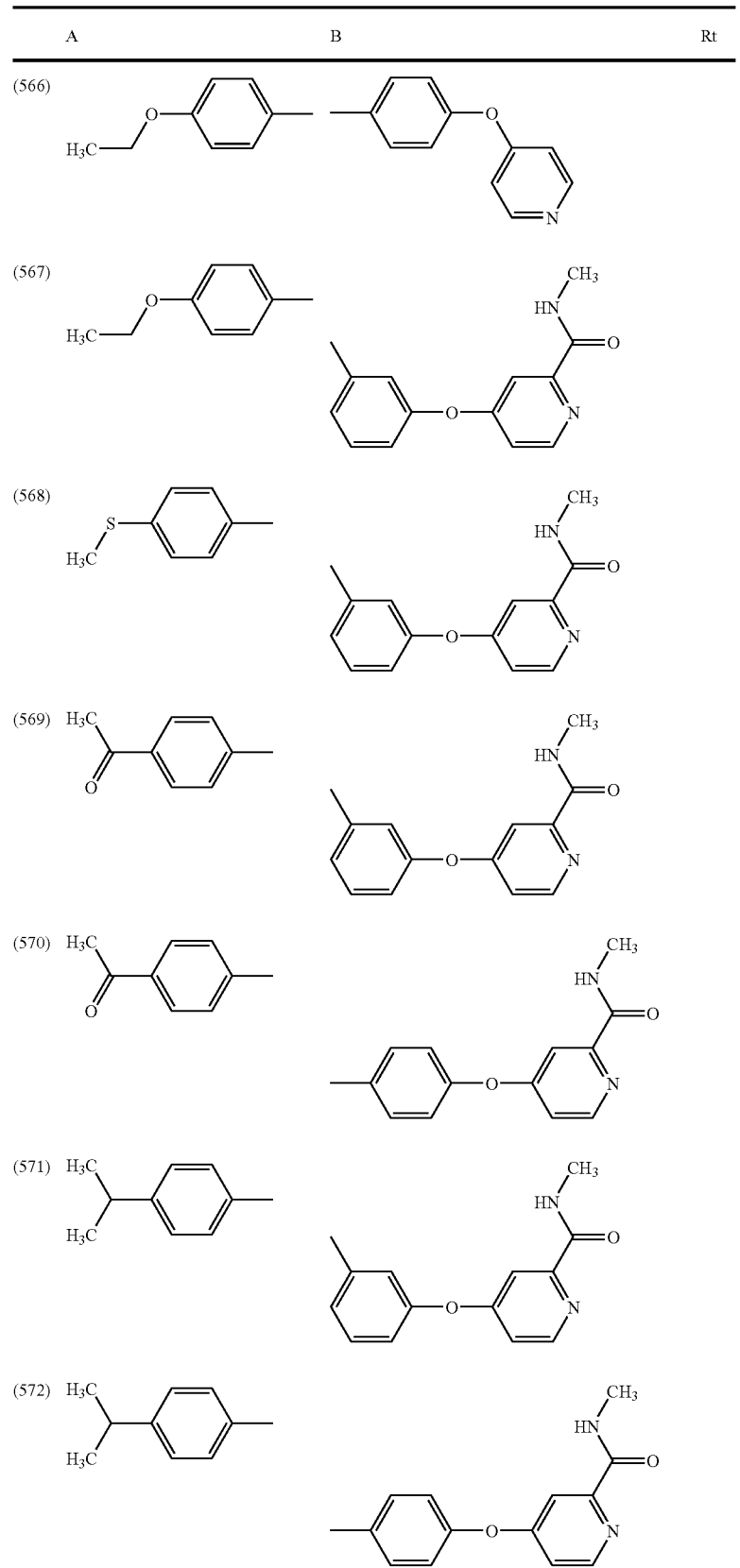
(567)
(568)
(569)
(570)
(571)
(572)

-continued
| | A | B | Rt |
|---|---|---|---|
| (573) | 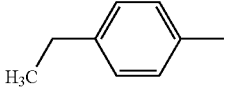 | 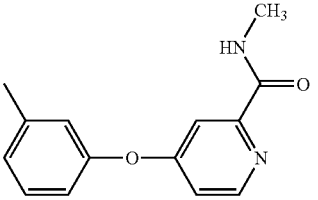 | |
| (574) | 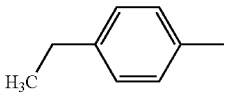 | 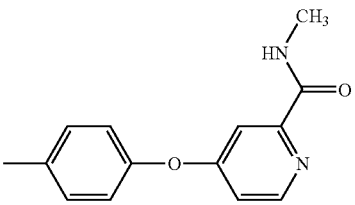 | |
| (575) | 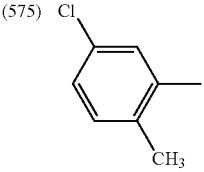 | 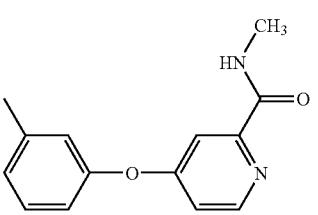 | |
| (576) | 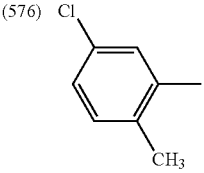 | 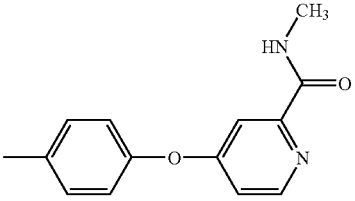 | |
| (577) | 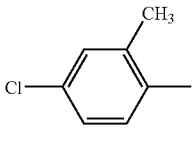 | 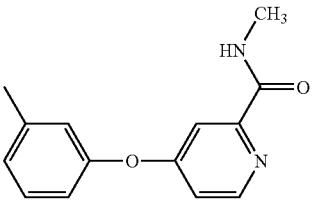 | |
| (578) | 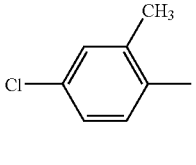 | 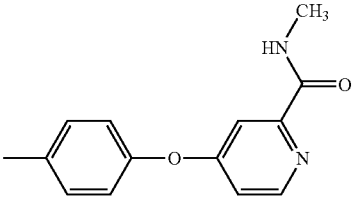 | |
| (579) | 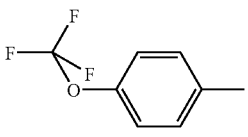 | 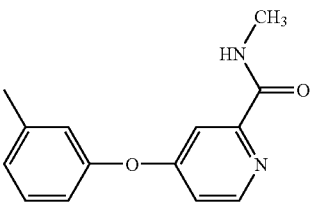 | |

-continued

| A | B | Rt |
|---|---|---|
| (580) 4-(trifluoromethoxy)phenyl, methyl | N-methyl 4-(4-methylphenoxy)pyridine-2-carboxamide | |
| (581) 4-chloro-3-methyl-(trifluoromethyl)phenyl | 4-(4-methylphenoxy)pyridine | |
| (582) 4-chloro-3-methyl-(trifluoromethyl)phenyl | N-methyl 4-(3-methylphenoxy)pyridine-2-carboxamide | |
| (583) 4-chloro-3-methyl-(trifluoromethyl)phenyl | N-methyl 4-(4-methylphenoxy)pyridine-2-carboxamide | |
| (584) 4-tert-butyl-methylphenyl | N-methyl 4-(3-methylphenoxy)pyridine-2-carboxamide | |
| (585) 4-tert-butyl-methylphenyl | N-methyl 4-(4-methylphenoxy)pyridine-2-carboxamide | |
| (586) 4-bromo-3-chloro-methylphenyl | 4-(4-methylphenoxy)pyridine | |

-continued
| A | B | Rt |
|---|---|---|
| (587) 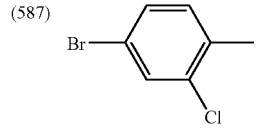 | 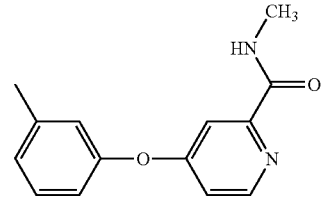 | |
| (588) 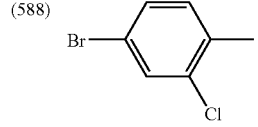 | 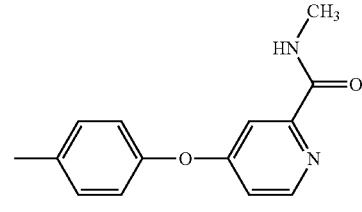 | |
| (589) 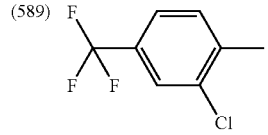 | 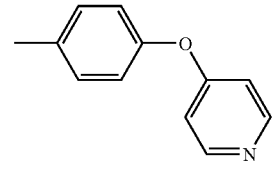 | |
| (590) 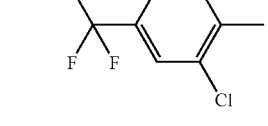 | 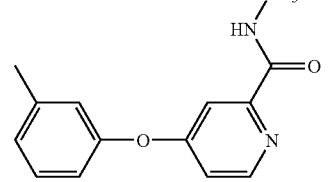 | |
| (591) 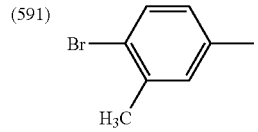 | 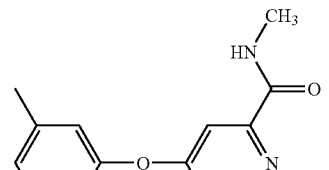 | |
| (592) 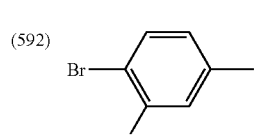 | 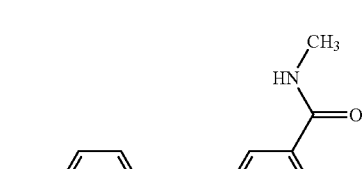 | |
| (593) 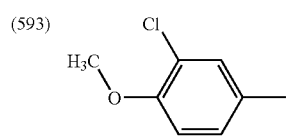 | 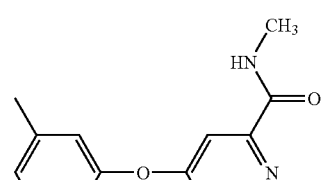 | |

-continued

| | A | B | Rt |
|---|---|---|---|
| (594) | 2-chloro-4-methoxyphenyl (H3C-O, Cl) | 4-(4-methylphenoxy)-N-methylpyridine-2-carboxamide | |
| (595) | 2-bromophenyl | 4-(4-methylphenoxy)pyridine | |
| (596) | 2-bromophenyl | 4-(3-methylphenoxy)pyridine | |
| (597) | 2-bromophenyl | 4-(3-methylphenoxy)-N-methylpyridine-2-carboxamide | |
| (598) | 2-bromophenyl | 4-(4-methylphenoxy)-N-methylpyridine-2-carboxamide | |
| (599) | 2-chlorophenyl | 4-(3-methylphenoxy)pyridine | |
| (600) | 2-chlorophenyl | 4-(4-methylphenoxy)-N-methylpyridine-2-carboxamide | |
| (601) | 2-methoxyphenyl | 4-(3-methylphenoxy)pyridine | |

-continued

| | A | B | Rt |
|---|---|---|---|
| (602) | 2,5-dimethoxy-4-methylphenyl (H₃CO, OCH₃) | 3-(pyridin-4-yloxy)phenyl | |
| (603) | 2-(trifluoromethyl)phenyl-methyl | 3-(pyridin-4-yloxy)phenyl | |
| (604) | 3-bromophenyl | 4-(pyridin-4-yloxy)phenyl | |
| (605) | 3-bromophenyl | 3-(pyridin-4-yloxy)phenyl | |
| (606) | 3,4-dichlorophenyl | 3-(pyridin-4-yloxy)phenyl | |
| (607) | 3-(trifluoromethyl)phenyl | 3-(pyridin-4-yloxy)phenyl | |
| (608) | 3-methylphenyl | 3-(pyridin-4-yloxy)phenyl | |
| (609) | 4-(trifluoromethyl)phenyl | 3-(pyridin-4-yloxy)phenyl | |
| (610) | 4-methylphenyl | 3-(pyridin-4-yloxy)phenyl | |
| (611) | 2,5-dimethylphenyl | 3-(pyridin-4-yloxy)phenyl | |

-continued
| | A | B | Rt |
|---|---|---|---|
| (612) | 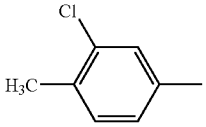 | 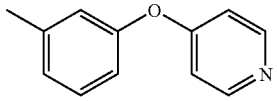 | |
| (613) | 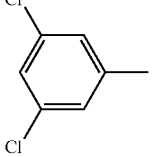 | 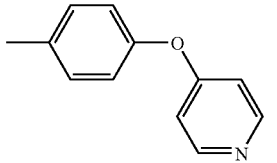 | |
| (614) | 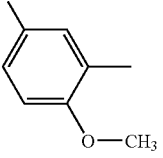 | 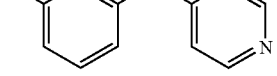 | |
| (615) | 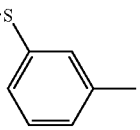 | 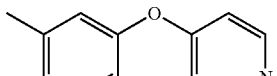 | |
| (616) | 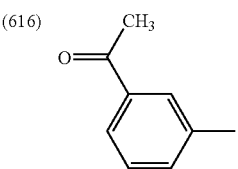 | 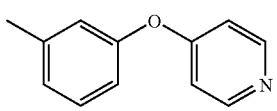 | |
| (617) | 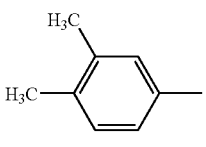 | 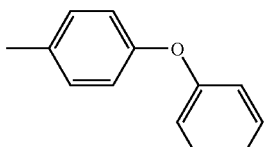 | |
| (618) | 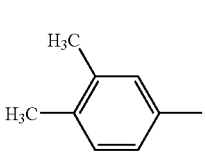 | 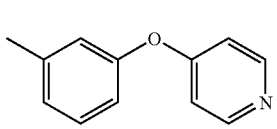 | |
| (619) | 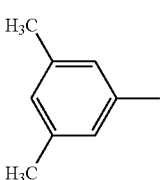 | 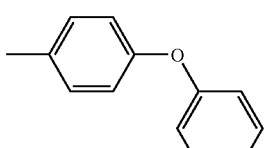 | |
| (620) | 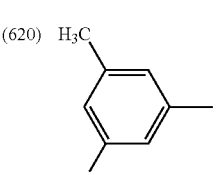 | 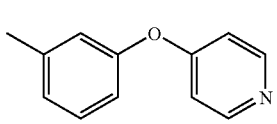 | |

-continued
| A | B | Rt |
|---|---|---|
| (621)  |  | |
| (622)  | 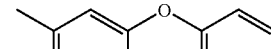 | |
| (623)  |  | |
| (624)  |  | |
| (625)  |  | |
| (625) 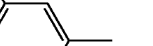 |  | |
| (626)  | 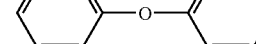 | |
| (627) 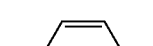 | 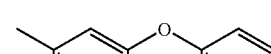 | |

| | -continued | |
|---|---|---|
| A | B | Rt |

(628) 4-(ethylthio)phenyl — 4-(pyridin-4-yloxy)phenyl (629) 4-(ethylthio)phenyl — 3-(pyridin-4-yloxy)phenyl (630) 4-(ethylthio)phenyl — N-methyl-4-(4-methylphenoxy)pyridine-2-carboxamide (631) 4-acetylphenyl — 4-(pyridin-4-yloxy)phenyl (632) 4-acetylphenyl — 3-(pyridin-4-yloxy)phenyl (633) 4-isopropylphenyl — 4-(pyridin-4-yloxy)phenyl (634) 4-isopropylphenyl — 3-(pyridin-4-yloxy)phenyl (635) 4-ethylphenyl — 4-(pyridin-4-yloxy)phenyl (636) 4-ethylphenyl — 3-(pyridin-4-yloxy)phenyl (637) 4-chloro-2,3-dimethylphenyl — 4-(pyridin-4-yloxy)phenyl -continued
| | A | B | Rt |
|---|---|---|---|
| (638) | 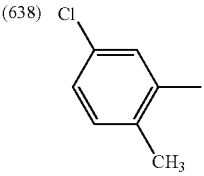 | 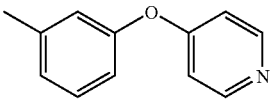 | |
| (639) | 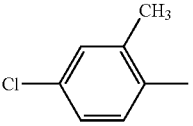 | 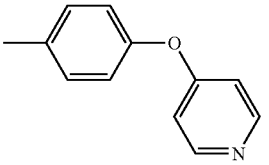 | |
| (640) | 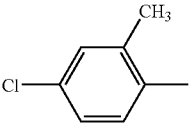 | 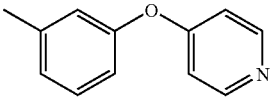 | |
| (641) | 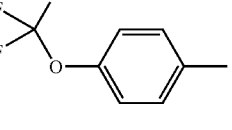 | 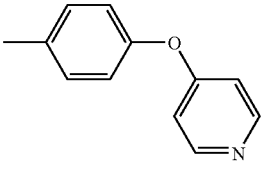 | |
| (642) | 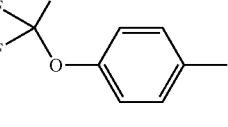 | 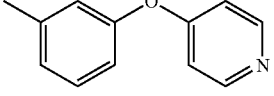 | |
| (643) | 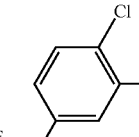 | 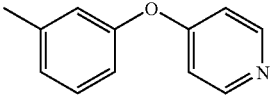 | |
| (644) | 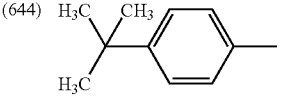 | 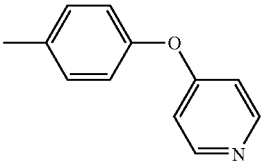 | |
| (645) | 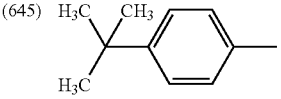 | 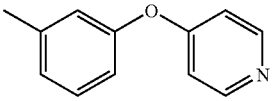 | |
| (646) | 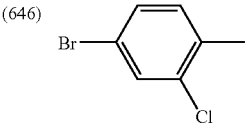 | 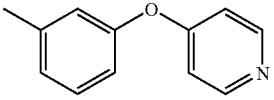 | |

-continued
| | A | B | Rt |
|---|---|---|---|
| (647) | 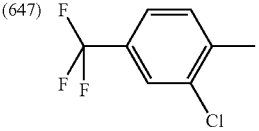 | 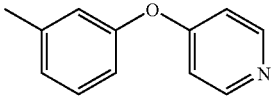 | |
| (648) | 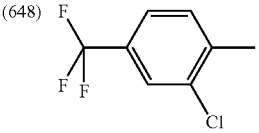 | 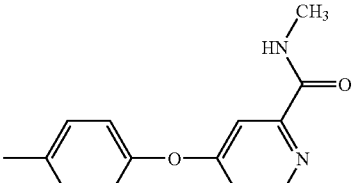 | |
| (649) | 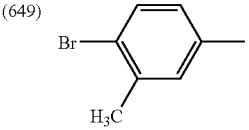 | 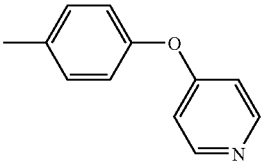 | |
| (650) | 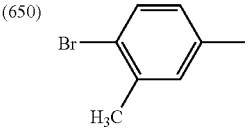 | 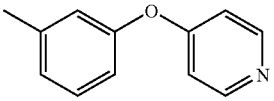 | |
| (651) | 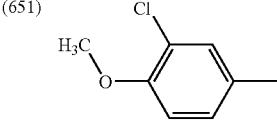 | 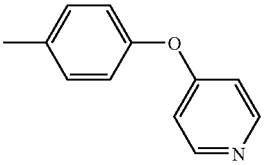 | |
| (652) | 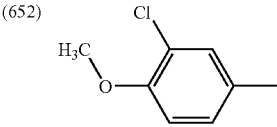 | 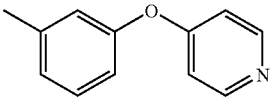 | |
| (653) | 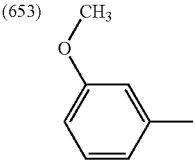 | 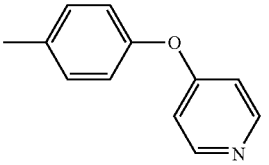 | |
| (654) | 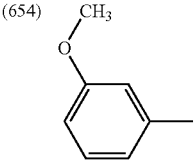 | 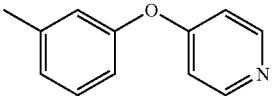 | |
| (655) | 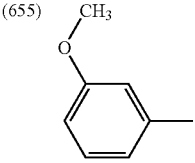 | 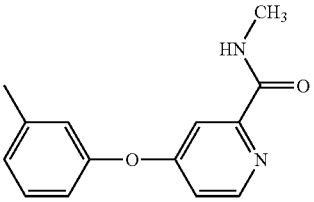 | |

-continued
| | A | B | Rt |
|---|---|---|---|
| (656) | 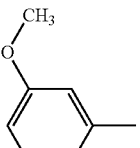 | 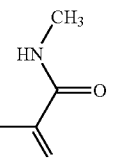 | |
| (657) | 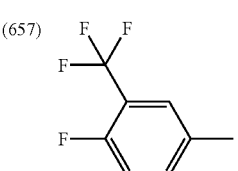 | 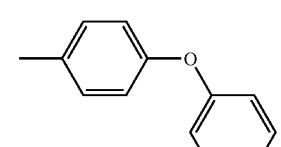 | |
| (658) | 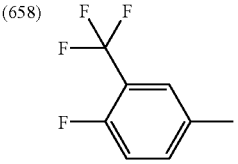 | 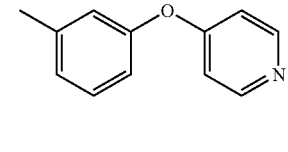 | |
| (659) | 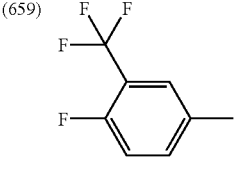 | 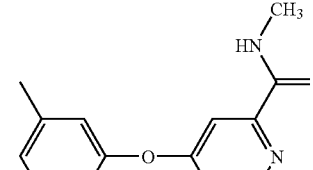 | |
| (660) | 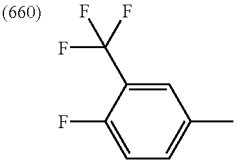 | 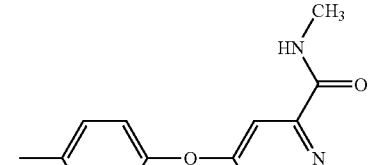 | |
| (661) | 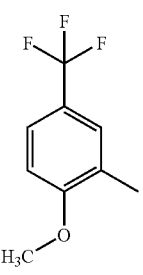 | 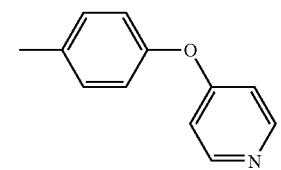 | |
| (662) | 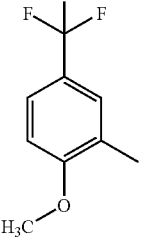 | 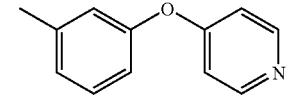 | |

| | -continued | |
|---|---|---|
| A | B | Rt |
| (663) 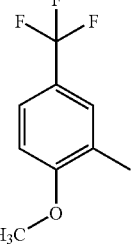 | 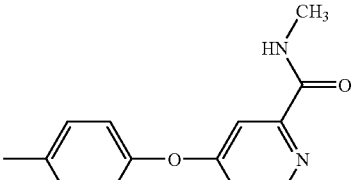 | |
| (664) 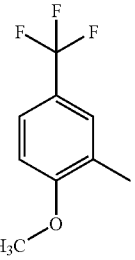 | 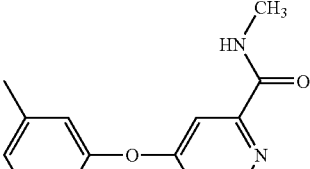 | |
| (665) 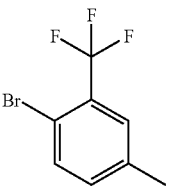 | 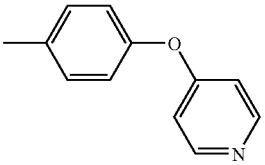 | |
| (666) 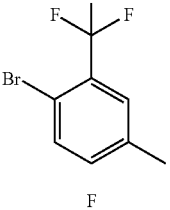 | 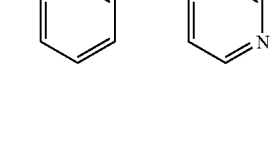 | |
| (667) 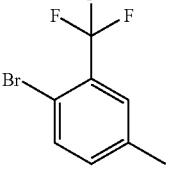 | 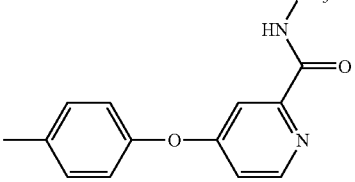 | |
| (668) 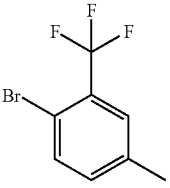 | 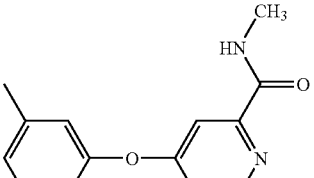 | |
| (669) 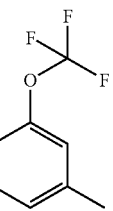 | 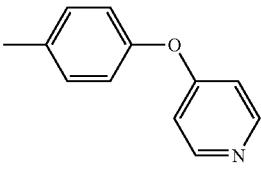 | |

|   | -continued | |
|---|---|---|
| A | B | Rt |
| (670) 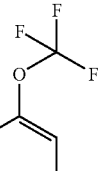 | 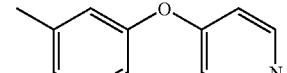 | |
| (671) 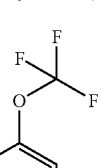 | 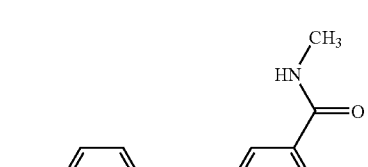 | |
| (672) 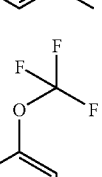 | 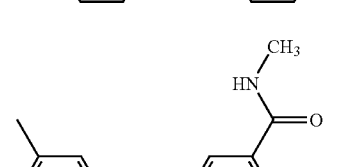 | |
The present invention further relates to compounds (673) to (758) as given in the table below:
| Compound | Rt |
|---|---|
| (673) 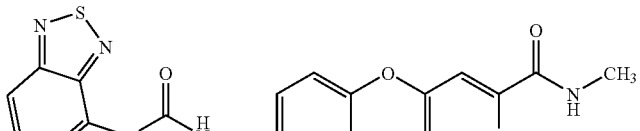 | 2.32 |
| (674) 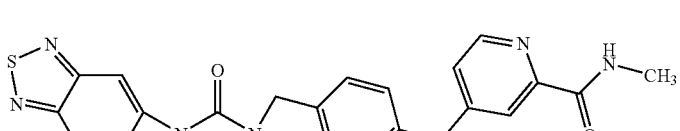 | 2.20 |
| (675) 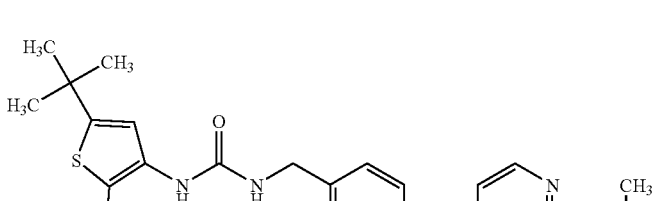 | 2.99 |

-continued
| Compound | Rt |
|---|---|
| (676) 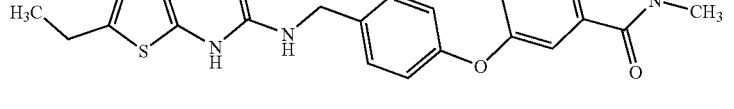 | 2.93 |
| (677) 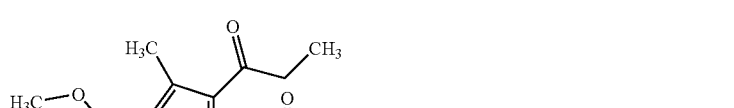 | 2.68 |
| (678) 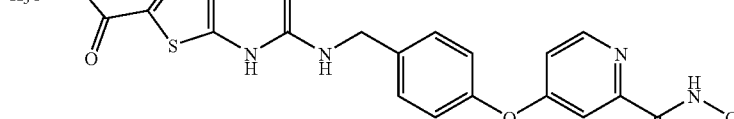 | 2.44 |
| (679)  | 2.40 |
| (680) 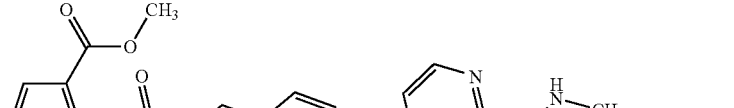 | 2.77 |
| (681) 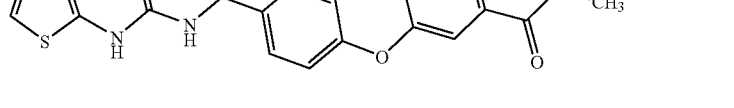 | 2.55 |

| Compound | Rt |
|---|---|
| (682) [structure] | 2.25 |
| (683) [structure] | 2.86 |
| (684) [structure] | 3.20 |
| (685) [structure] | 3.01 |
| (686) [structure] | 2.87 |
| (687) [structure] | 3.19 |
| (688) [structure] | 4.52[a] |

| Compound | Rt |
|---|---|
| (689) | 4.78[a] |
| (690) | 4.41[a] |
| (691) | 4.97[a] |
| (692) | 4.59[a] |
| (693) | 5.28[a] |
| (694) | 4.42[a] |

| Compound | Rt |
|---|---|
| (695) | 3.06[b] |
| (696) | 3.02[b] |
| (697) | 1.30[b] |
| (698) | 2.91 |
| (699) | 3.49[a] |

| Compound | Rt |
|---|---|
| (700) | 3.94[a] |
| (701) | 4.31[a] |
| (702) | 2.44[b] |
| (703) | 5.39[a] |
| (704) | 4.59[a] |

-continued

| Compound | Rt |
|---|---|
| (705) [structure] | 4.61[a] |
| (706) [structure] | 4.71[c] |
| (707) [structure] | 2.31[b] |
| (708) [structure] | 4.85[c] |
| (709) [structure] | 2.33[b] |

-continued

| Compound | Rt |
|---|---|
| (710) | 2.66 |
| (711) | 3.03[b] |
| (712) | 4.68[a] |
| (713) | 4.47[a] |
| (714) | 3.29[a] |
| (715) | 4.03[a] |

-continued

| Compound | Rt |
|---|---|
| (716) | 4.35[a] |
| (717) | 2.41 |
| (718) | 2.13 |
| (719) | 2.51[b] |

-continued
| Compound | Rt |
|---|---|
| (720) 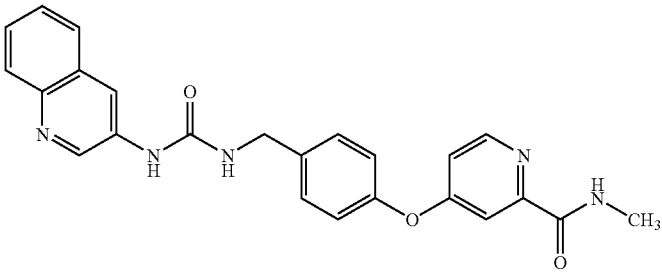 | 2.09[b] |
| (721) 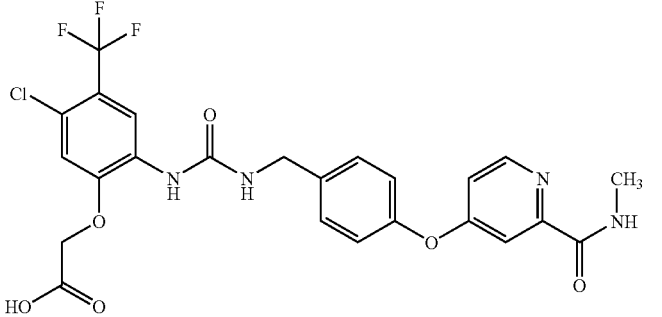 | 2.55 |
| (722) 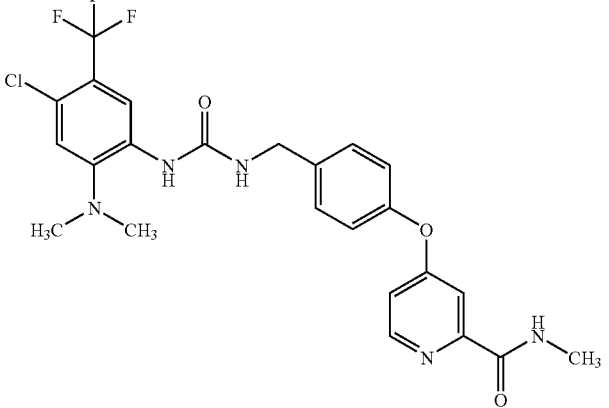 | 2.95 |
| (723) 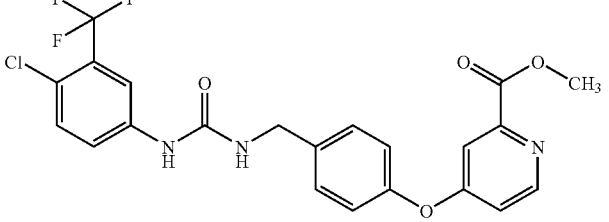 | 2.68 |
| (724) 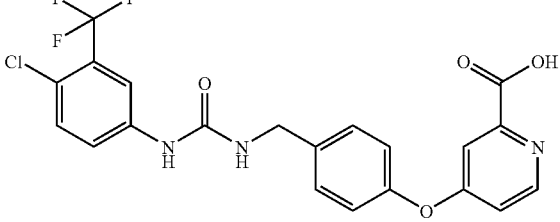 | 2.19 |

-continued

| Compound | Rt |
|---|---|
| (725) | 3.42[b] |
| (726) | 2.83 |
| (727) | 2.61 |
| (728) | 3.19[b] |
| (729) | 3.38[b] |

| Compound | Rt |
|---|---|
| (730) [structure] | 3.59[a] |
| (731) [structure] | 4.91[a] |
| (732) [structure] | 3.59[a] |
| (733) [structure] | 2.17 |
| (734) [structure] | 3.11[b] |
| (735) [structure] | 3.29[b] |

-continued

| Compound | Rt |
|---|---|
| (736) | 3.21[b] |
| (737) | 2.51[b] |
| (738) | 2.79[b] |
| (739) | 2.60 |
| (740) | 2.47 |
| (741) | 2.69 |

-continued

| Compound | Rt |
|---|---|
| (742) | 3.41[b] |
| (743) | 3.23[b] |
| (744) | 3.39[b] |
| (745) | 3.23[b] |
| (746) | 2.64[b] |
| (747) | 3.31[b] |

-continued

| Compound | Rt |
|---|---|
| (748) | 2.05 |
| (749) | 3.13 |
| (750) | 2.06 |
| (751) | 2.03 |
| (752) | 2.65 |

-continued

| Compound | Rt |
|---|---|
| (753) | 3.71[a] |
| (754) | 1.95 |
| (755) | 1.99 |
| (756) | 1.93 |
| (757) | 2.83 |

-continued

| Compound | Rt |
|---|---|
| (758) | 3.04 |

The present invention further relates to compounds (759) to (825) as given in the table below:

| Compound | Rt |
|---|---|
| (759) | 2.03 |
| (760) | 1.99 |
| (761) | 2.55 |

-continued
| Compound | Rt |
|---|---|
| (762) 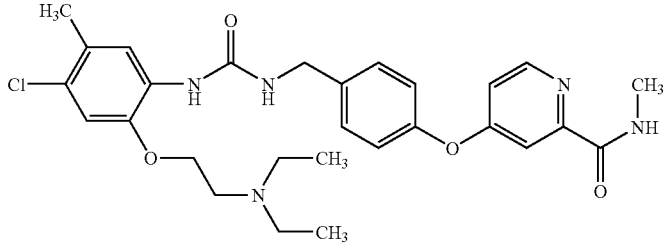 | 2.00 |
| (763) 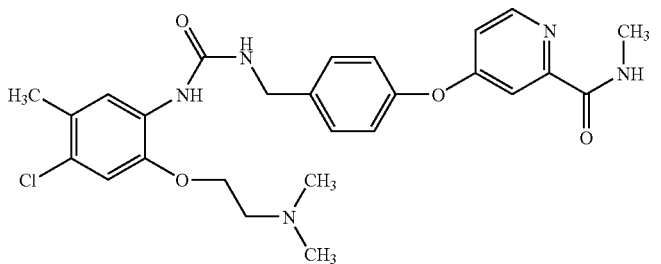 | 1.95 |
| (764) 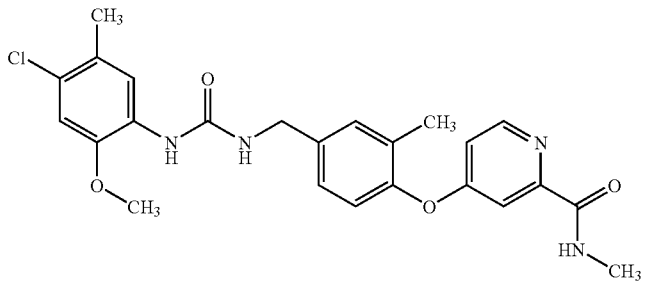 | 3.39[b] |
| (765) 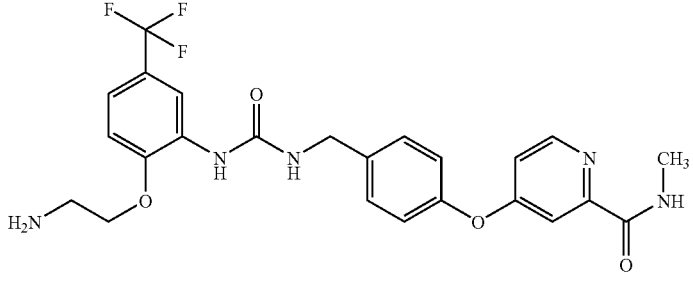 | 1.99 |
| (766) 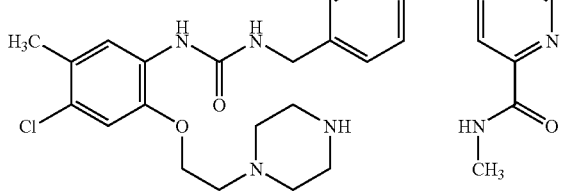 | 1.88 |

-continued

| Compound | Rt |
|---|---|
| (767) [chemical structure] | 2.02 |
| (768) [chemical structure] | 2.11 |
| (769) [chemical structure] | 2.01 |
| (770) [chemical structure] | 2.07 |
| (771) [chemical structure] | 2.01 |

| Compound | | Rt |
|---|---|---|
| (772) | [structure] | 2.23 |
| (773) | [structure] | 2.12 |
| (774) | [structure] | 2.11 |
| (775) | [structure] | 2.2 |
| (776) | [structure] | 2.19 |

| Compound | Rt |
|---|---|
| (777) | 2.18 |
| (778) | 2.23 |
| (779) | 2.66 |
| (780) | 2.09 |
| (781) | 2.13 |

| Compound | Rt |
|---|---|
| (782) | |
| (783) | 3.01[a] |
| (784) | 2.95[a] |
| (785) | 2.07[a] |
| (786) | 3.01[a] |

-continued

| Compound | Rt |
|---|---|
| (787) | 2.11 |
| (788) | 2.03 |
| (789) | 1.93 |
| (790) | 2.08 |
| (791) | 2.05 |

-continued

| Compound | Rt |
|---|---|
| (792) | 1.97 |
| (792b) | 2.89b |
| (793) | 2.93 |
| (794) | 1.93 |
| (795) | 2.03 |

-continued

| Compound | Rt |
|---|---|
| (796) | 2 |
| (797) | 1.97 |
| (798) | 2.91 |
| (799) | 2.91 |

-continued

| Compound | Rt |
|---|---|
| (800) | 2.23 |
| (801) | 2.09 |
| (802) | 2.01 |
| (803) | 2.13 |
| (804) | 2.19 |

| Compound | Rt |
|---|---|
| (805) | 2.2 |
| (806) | 2.13 |
| (807) | 2.73 |
| (808) | 2.79 |
| (809) | 2.21 |

-continued

| Compound | | Rt |
|---|---|---|
| (810) | | 5.11[c] |
| (811) | | 2.81 |
| (812) | | 2.03[b] |
| (813) | | 1.91[b] |
| (814) | | 2.67 |
| (815) | | 2.1 |

| Compound | Rt |
|---|---|
| (816) | 2.11 |
| (817) | 1.65[b] |
| (818) | 2.05[b] |
| (819) | 2.23[b] |
| (820) | 1.85[b] |

| Compound | Rt |
|---|---|
| (821) | 2.41[b] |
| (822) | 2.11 |
| (823) | 5.05[c] |
| (824) | 4.07[c] |
| (825) | 4.18[c] |

The present invention further relates to compounds (826) to (874) as given in the table below:

| Compound | Rt |
|---|---|
| (826) |  |

-continued

| Compound | Rt |
|---|---|
| (827) [structure] | |
| (828) [structure] | |
| (829) [structure] | |
| (830) [structure] | |
| (831) [structure] | |
| (832) [structure] | 2.67 |

| Compound | Rt |
|---|---|
| (833) | |
| (834) | 2.81 |
| (835) | 2.83 |
| (836) | 2.69 |
| (837) | |

| Compound | Rt |
|---|---|
| (838) | 2.61 |
| (839) | 2.84 |
| (840) | 2.88 |
| (841) | 2.09 |

-continued

| Compound | Rt |
|---|---|
| (842) | 2.02 |
| (843) | 2.54 |
| (844) | 2.64 |
| (845) | 3.85[a] |
| (846) | 4.43[a] |

-continued
| Compound | Rt |
|---|---|
| (847) 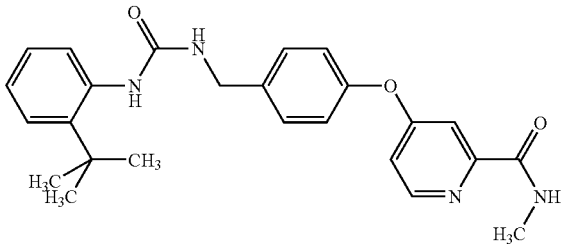 | 4.69[a] |
| (848) 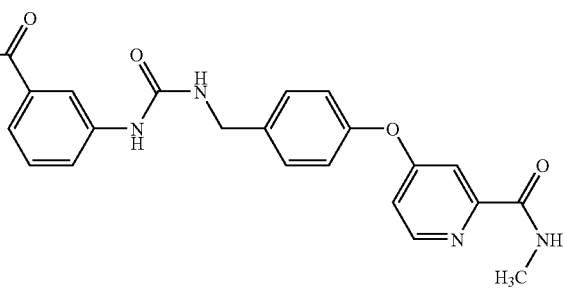 | 4.56[a] |
| (849) 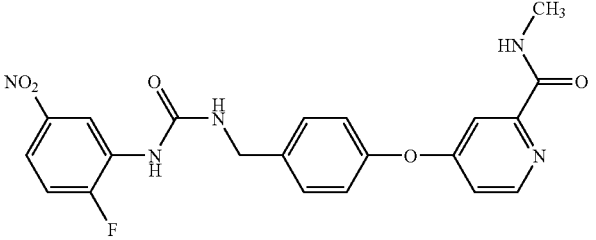 | 4.60[a] |
| (850) 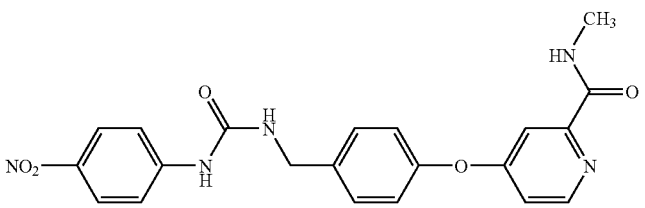 | 4.53 |
| (851) 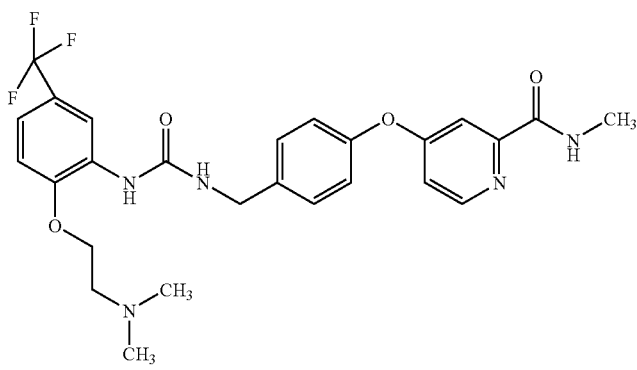 | |

| Compound | Rt |
|---|---|
| (852) | |
| (853) | |
| (854) | |
| (855) | |
| (856) | |

| Compound | Rt |
|---|---|
| (857) | |
| (858) | |
| (859) | |
| (860) | |

| Compound | Rt |
|---|---|
| (861) [chemical structure] | |
| (862) [chemical structure] | |
| (863) [chemical structure] | |
| (864) [chemical structure] | |

| Compound | Rt |
|----------|-----|

(865)

(866)

(867)

(868)

| Compound | Rt |
|---|---|
| (869) | |
| (870) | |
| (871) | |
| (872) | |

| Compound | Rt |
|---|---|
| (873) | |
| (874) | |

The nomenclature as used herein for defining compounds, especially the compounds according to the invention, is in general based on the rues of the IUPAC-organisation for chemical compounds and especially organic compounds.

In a special embodiment, one or more of the methylene urea derivatives according to sub formulae IIa to IIx and/or compounds (1) to (224), compounds (225) to (448), compounds (449) to (672), compounds (673) to (758), compounds (759) to (825) and/or compounds (826) to (874) additionally comprise one or two substituents selected from the group consisting of $O(CH_2)_nNR^{11}R^{12}$, $NR^{11}(CH_2)_nNR^{11}R^{12}$, $O(CH_2)_nOR^{12}$ and $NR^{11}(CH_2)_nOR^{12}$, wherein $R^{11}$, $R^{12}$ are independently selected from a group consisting of H, A, $(CH_2)_mAr^3$ and $(CH_2)_m$Het, or in $NR^{11}R^{12}$, $R^{11}$ and $R^{12}$ form, together with the N-Atom they are bound to, a 5-, 6- or 7-membered heterocyclus which optionally contains 1 or 2 additional hetero atoms, selected from N, O an S, and n is 1, 2, 3, 4, 5 or 6, preferably 2, 3 or 4.

In this special embodiment, the substituents are preferably selected from the group consisting of $HNCH_2CH_2NH_2$, $OCH_2CH_2NH_2$, $NHCH_2CH_2OH$, $OCH_2CH_2NHCH_3$, $N(CH_3)CH_2CH_2NH_2$, $HN(CH_3)CH_2CH_2NH$, $N(CH_3)CH_2CH_2N(CH_3)_2$, $N(CH_3)CH_2CH_2N(CH_3)_2$, $N(CH_3)CH_2CH_2OCH_3$, $OCH_2CH_2N(CH_3)_2$, $OCH_2CH_2N(CH_2CH_3)_2$ and compounds of the formulae

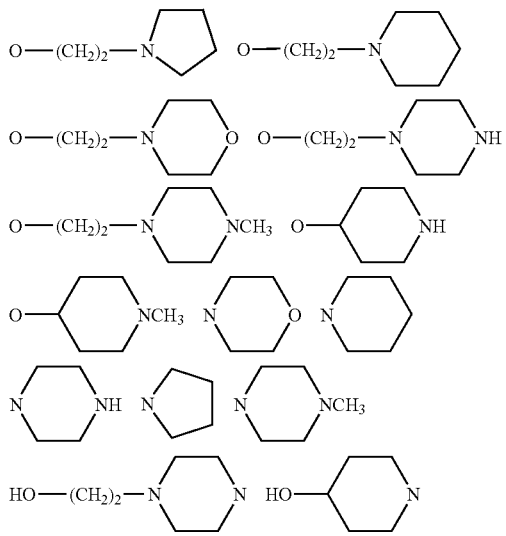

and/or compounds of formulae

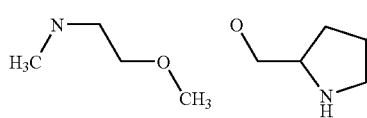

-continued

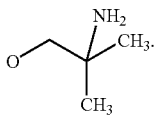

In a further special embodiment, one or more of the methylene urea derivatives according to sub formulae IIa to IIx and/or compounds (1) to (224), compounds (225) to (448), compounds (449) to (672), compounds (673) to (758), compounds (759) to (825) and/or compounds (826) to (874) additionally comprise one or two substituents selected from the group consisting of $(CH_2)_nS(O)_uNR^{11}R^{12}$ and $(CH_2)_nS(O)_uR^{13}$ wherein $R^{11}$, $R^{12}$ and $R^{13}$ are defined as above and n is as defined above, preferably n is 0, 1 or 2 and especially is 0, and u is preferably 2 or 3. In this embodiment, the residues are preferably selected from $SO_2CH_3$, $SO_2CF_3$, $OSO_2CH_3$, $OSO_2CF_3$, $SO_2NH_2$, $SO_2NHCH(CH_3)_2$, $SO_2N(CH_3)_2$, $SO_2N(CH_2CH_3)_2$ and 4-Morpholino-sulfonyl.

In this special embodiments, the additional substituents are preferably bound to one of the aromatic residues directly bound to the methylene urea moiety and/or the pyridinyl residue. More preferably, one or two additional substituents are bound to the residue $Ar^1$ according to formula II. Even more preferably, in one or more of the formulae IIa to IId, one or two additional substituents are bound to the phenyl moiety directly bound to the nitrogen atom of the methylene urea moiety, i.e. the phenyl moiety at the left hand side of the respective formulae. Especially preferred are compounds (1) to (224), compounds (225) to (448) and/or compounds (449) to (672), wherein one or two additional substituents are bound to the moiety A.

Another aspect of the invention relates to a method for producing compounds of formula II, characterised in that
a) A compound of formula III

III wherein
FG is a functional group, selected from —N═C═Y and —NH—(C═Y)-LG,
wherein Y is as defined above and below, LG is a leaving group, preferably a leaving group selected from $OR^{25}$ and $CHal_3$, wherein $R^{25}$ is selected from the group consisting of unsubstituted or substituted aromatic residues, unsubstituted or substituted heteroaromatic residues and $(O)_2—R^{26}$,
wherein $R^{26}$ is selected from unsubstituted or substituted aromatic residues and unsubstituted or substituted alkyl residues residues, and wherein $R^8$, p and $Ar^1$ are as defined above and below,
is reacted
b) with a compound of formula IV,

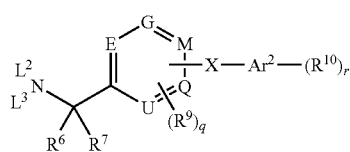

IV wherein
$L^2$, $L^3$ are independently from one another H or a metal ion, and $R^6$, $R^7$, E, G, M, Q, U, $R^9$, q, X, $Ar^2$, $R^{10}$ and r are as defined above and below,
and optionally
c) isolating and/or treating the compound of formula II obtained by said reaction with an acid, to obtain the salt thereof.

The compounds of the formula I and preferably the compounds of the formula II and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in-situ by not isolating them from the reaction mixture, but instead immediately converting them further into the compounds of the formula I or II, respectively. On the other hand, it is possible to carry out the reaction stepwise.

The compounds of the formula I and especially the compounds of formula II can preferably be obtained by reacting compounds of the formula III with compounds of the formula IV.

In compounds of formula II, the group FG is a suitable functional group that this preferably selected from —N═C═Y and —NH—(C═Y)-LG. In the functional groups —N═C═Y and/or —NH—(C═Y)-LG, Y is preferably selected from the group consisting of O, S, $NR^{21}$, $C(R^{22})$—$NO_2$, $C(R^{22})$—CN and $C(CN)_2$, and more preferably selected from O, S and $NR^{21}$, even more preferably selected from O and S and especially is O, wherein $R^{21}$ and $R^{22}$ are as defined above/below.

In the compounds of formula III, wherein FG is —NH—(C═Y)-LG, LG is a suitable leaving group. Suitable leaving groups are known in the art, for example from Houben-Weyl, Methods of Organic chemistry. Preferably, the leaving group is selected from $CHal_3$, wherein Hal is as defined above/below and preferably is chlorine or bromine and especially is chlorine, and $OR^{25}$, wherein $R^{25}$ is selected from the group consisting of unsubstituted or substituted aromatic residues, unsubstituted or substituted heteroaromatic residues and $(O)_2S—R^{26}$, wherein $R^{26}$ is selected from unsubstituted or substituted aromatic residues and unsubstituted or substituted alkyl residues residues, and wherein $R^8$, p and $Ar^1$ are as defined above and below.

In compounds of formula III in which FG is —NH—(C═Y)-LG and LG is $CHal_3$, Hal is preferably selected independently from one another from the group consisting of chlorine, bromine and iodine, even more preferably chlorine and bromine and especially preferred chlorine. Preferably, $CHal_3$ is selected from the group consisting of $CCl_3$ and $CBr_3$ and especially preferred $CHal_3$ is $CCl_3$.

In compounds of formula III in which FG is —NH—(C═Y)-LG and LG is $OR^{25}$, $R^{25}$ is preferably selected from unsubstituted or substituted phenyl moieties, preferably substituted phenyl moieties which comprises one or more nitro groups (—$NO_2$) and/or one or more sulfonic acid groups (—$SO_3H$) or salts thereof as substituents, and $(O)_2S—R^{26}$, wherein $R^{26}$ is selected from unsubstituted or substituted phenyl moieties, preferably alkyl substituted phenyl moieties, and unsubstituted or substituted alkyl residues residues, preferably unsubstituted or substituted $C_1$-$C_4$-alkyl moieties and especially unsubstituted or substituted methyl moieties.

Substituted alkyl moieties preferably comprise one or more halogen substituents up to perhalo. Preferred as halogen substituents are fluorine and chlorine and especially preferred is chlorine. Especially preferred as substituted alkyl moiety is —$CF_3$. Examples of preferred leaving groups $OR^{25}$ are the para-Tosyl- (i.e. p-Me-$C_6H_4$—$SO_3$—) group, the para-Nitrophenolate-group (i.e the p-$O_2N$—$C_6H_4$—O—) group and the triflate- (i.e. the $F_3C$—$SO_3$—) group.

If compounds of formula II are desired wherein Y is other than O, it can be advantageous however to to carry out the reaction of a compound of formula III, wherein Y is O, and a compound of formula IV according to the invention to obtain a compound of formula II, wherein Y is O, and to modify or convert the corresponding C=O group (i.e. the C=Y group, wherein Y is O) in the compound of formula II into a C=$NR^{21}$, C=C($R^{22}$)—$NO_2$, C=C($R^{22}$)—CN or C=C$(CN)_2$ group according to methods known in the art, for example from Houben-Weyl, Methods of Organic Chemistry.

In the compounds of formula IV, $L^2$ and/or $L^3$ is preferably H or a moiety which activates the amino group it is bonded to, for example a metal ion. Suitable metal ions are preferably selected from the group consisting of alkaline metal ions, alkaline-earth metal ions and aluminium ions. Especially preferred metal ions are alkaline metal ions, of which Li, Na K are especially preferred. In case of multi-valent metal ions, the metal ions and the compounds of formula IV form a complex containing one or more compounds of formula IV and one or more metal ions wherein the ratio between compounds of formula IV and metal ions is depending on the valency of the metal ion(s) according to the rules of stoichiometry and/or electroneutrality. Preferably, $L^2$ or $L^3$ and more preferred $L^2$ and $L^3$ are hydrogen.

In detail, the reaction of the compounds of the formula III with the compounds of the formula IV is carried out in the presence or absence of a preferaby inert solvent at temperatures between about −20° C. and about 200° C., preferably between 0° C. and 150° C. and especially between room temperature (25°) and 120°. In many cases, it is advantageous to combine one compound of formula III with one compound of formula IV at the lower end of the given temperature range, preferably between −20° C. and 75° C., more preferred between 0° C. and 60° C. and especially between 10° C. and 40° C., for example at about room temperature, and heat the mixture up to a temperature at the upper end of the given temperature range, preferably between 65° C. and 180° C., more preferred between 75° C. and 150° C. and especially between 80° C. and 120° C., for example at about 80° C., at about 90° C. or at about 100° C. Proceeding in that manner can be advantageous especially in the case that RG is selected from —NH—(C=Y)-LG. If RG is selected from —N=C=Y and preferably is —N=C=O or —N=C=S and especially is —N=C=O, the reaction can be regularly carried out without prolonged heating to higher temperatures. For example it can be carried out at a temperature between 0° C. and 60° C. and preferably at about room temperature.

The reaction between the compounds of formula III, wherein FG is —NH—(C=Y)-LG and especially wherein LG is $CHal_3$, and compounds of formula IV is preferably carried out in the presence of an acid binding means, for example one or more bases. Suitable acid binding means are known in the art. Preferred as acid binding means are inorganic bases and especially organic bases. Examples for inorganic bases are alkaline or alkaline-earth hydroxides, alkaline or alkaline-earth carbonates and alkaline or alkaline-earth bicarbonates or other salts of a weak acid and alkaline or alkaline-earth metals, preferably of potassium, sodium, calcium or cesium. Examples for organic bases are triethyl amine, diisopropyl ethyl amine (DIPEA), diaza bicyclo undecen (DBU), dimethyl aniline, pyridine or chinoline. If an organic base is used, it is advantageous in general to use a base with a boiling point that is higher than the highest reaction temperature employed during the reaction. Especially preferred as organic bases are DBU and DIPEA. DBU is especially preferred in the case that LG is $CHal_3$. DIPEA is especially preferred in the case that LG is $OR^{25}$.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range 10 min and 36 hrs, preferably 30 min and 24 hrs and especially between 45 min and 16 hrs, for example about 1 h, about 2 hrs, about 4 hrs, about 6 or about 16 hrs.

Preferably, the reaction of the compounds of the formula III with the compounds of the formula IV is carried out in the presence of a suitable solvent, that is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO), nitro compounds, such as nitromethane or nitrobenzene; esters, such as ethyl acetate, or mixtures of the said solvents. Polar solvents are in general preferred. Examples for suitable polar solvents are chlorinated hydrocarbons, alcohols, glycol ethers, nitriles, amides and sulfoxides or mixtures thereof. More preferred are chlorinated hydrocarbons, especially dichloromethane, and sulfoxides, especially DMSO.

Preferably, the reaction between a compound of formula III, wherein FG is —N=C=Y and preferably is —N=C=O or —N=C=S and especially is —N=C=O, and a compound of formula IV, especially a compound of formula IV, wherein $L^2$ and $L^3$ is H, is carried out in an inert solvent at the lower end of the given temperature range, for example in a chlorinated hydrocarbon, for example dichloromethane, in a temperature range between 0° C. and 60° C., preferably at about room temperature. Reaction times generally lie in the range of 2 hours to 24 hrs, for example at about 16 hrs. Preferably, no acid binding means is present.

Preferably, the reaction between a compound of formula III, wherein FG is —NH—(C=Y)-LG and especially wherein LG is $CHal_3$, and compounds of formula IV, especially a compound of formula IV, wherein $L^2$ and $L^3$ is H, is carried out in an inert solvent, preferably a solvent boiling at higher temperatures, for example a sulfoxide and especially DMSO, in a temperature range between 60° C. and 120° C., for example at about 80° C. Reaction times generally lie in the range of 1 hrs to 10 hrs, for example between 2 and 6 hrs. Preferably, the reaction is carried out in the presence of an acid binding means, preferably one of the afore mentioned acid binding means, more preferably an organic base and especially in the presence of DBU.

Preferably, the reaction between a compound of formula III, wherein FG is —NH—(C=Y)-LG and especially wherein LG is $OR^{25}$, and compounds of formula IV, especially a compound of formula IV, wherein $L^2$ and $L^3$ is H, is carried out in an inert solvent at the lower end of the given temperature range, for example in a chlorinated hydrocarbon, for example dichloromethane, in a temperature range between 0° C. and 60° C., preferably at about room temperature. Reaction times generally lie in the range of 2 hours to 24 hrs. Preferably, the reaction is carried out in the presence of an acid binding means, preferably one of the afore mentioned acid binding means, more preferably an organic base and especially in the presence of DIPEA.

In general, the compounds of formula III and/or formula IV are new. In any case, they can be prepared according to methods known in the art.

The compounds of formula III can be obtained according to methods known in the art. In an advantageous manner, they can be readily obtained by one or more of the reaction routes given below:

Compounds of formula III, wherein FG is —N=C=Y and Y is O or S can be readily obtained from suitable substituted derivatives of $(R^8)_p$—$Ar^1$ according to known procedures for producing isocyanates and thioisocyanates. When FG is —N=C=O, the compounds of formula III can be readily obtained via Curtius-, Hoffmann or Lossen rearrangement starting from $(R^8)_p$—$Ar^1$—COOH or the respective acid halides, as described in the art. If desired, compounds of formula III, wherein Y is O can be readily derivatized to compounds of formula III, wherein Y is S, according to procedures known in the art.

Compounds of formula III, wherein FG is —NH—(C=Y)-LG and especially wherein LG is $CHal_3$ can be readily obtained from the reaction of suitable amino substituted derivatives of $(R^8)_p$—$Ar^1$ of formula V

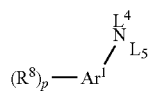

V wherein $R^8$, p, and $Ar^1$ are as defined above/below and $L^4$ and $L^5$ are, selected independently from each other from the meanings given for $L^2$ and $L^3$ and more preferred are hydrogen, with a compound of formula VI

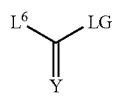

VI wherein Y is as defined above/below and $L^6$ is preferably selected from Cl, Br, I, OH, reactive derivatized OH-moieties, especially reactive esterified OH-moieties, for example alkylsulfonyloxy-moieties comprising 1 to 6 carbon atoms (preferably methylsulfonyloxy) or and arylsulfonyloxy-moiety comprising 6 to 10 carbon atoms (preferably phenyl-oder p-tolylsulfonyloxy), and diazonium moieties, and more preferred selected from Cl, Br or I, and even more preferred is Cl.

Compounds of formula iii, wherein FG is —NH—(C=Y)-LG and especially wherein LG is $CHal_3$ can be readily obtained from the reaction of suitable amino substituted derivatives of $(R^8)_p$—$Ar^1$ of formula V

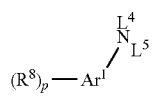

V wherein $R^8$, p, and $Ar^1$ are as defined above/below and $L^4$ and $L^5$ are selected independently from each other from the meanings given for $L^2$ and $L^3$ and more preferred are hydrogen, with a compound of formula VIa

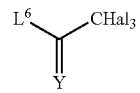

VIa wherein Y and $L^6$ are as defined above/below.

The reaction between compounds of formula V and compounds of formula VI can be carried out in the presence of a suitable solvent, that is preferably inert at the chosen reaction conditions. Suitable solvents are known in the art. Examples of suitable solvents include hydrocarbons, such as hexane, petroleum ether, benzene, toluene or xylene; chlorinated hydrocarbons, such as trichloroethylene, 1,2-dichloroethane, tetrachloromethane, chloroform or dichloromethane; ethers, such as diethyl ether, diisopropyl ether, tetrahydrofuran (THF) or dioxane; nitriles, such as acetonitrile; esters, such as ethyl acetate, or mixtures of said solvents. Non-protic solvents are in general preferred.

The reaction between compounds of formula V and compounds of formula VI can be carried out in the presence of a suitable acid binding means, especially organic or anorganic bases. Examples for inorganic bases are alkaline or alkaline-earth hydroxides, alkaline or alkaline-earth carbonates and alkaline or alkaline-earth bicarbonates or other salts of a weak acid and alkaline or alkaline-earth metals, preferably of potassium, sodium, calcium or cesium. Examples for organic bases are triethyl amine, diisopropyl ethal amine (DIPEA), diaza bicyclo undecan (DBU), dimethyl aniline, pyridine or chinoline. If an organic base is used, it is advantageous in general to use a base with a boiling point that is higher than the highest reaction temperature employed during the reaction.

The reaction between compounds of formula V and compounds of formula VI can be carried out in the presence of a suitable solvent, that is preferably inert at the chosen reaction conditions. Suitable solvents are known in the art. Examples of suitable solvents include hydrocarbons, such as hexane, petroleum ether, benzene, toluene or xylene; chlorinated hydrocarbons, such as trichloroethylene, 1,2-dichloroethane, tetrachloromethane, chloroform or dichloromethane; ethers, such as diethyl ether, diisopropyl ether, tetrahydrofuran (THF) or dioxane; nitriles, such as acetonitrile; esters, such as ethyl acetate, or mixtures of said solvents. Non-protic solvents are in general preferred.

If the reaction between a compound of formula V and a compound of formula VI is carried out in presence of an organic base that is liquid at the chosen reaction conditions, it can be advantagous not to add an additional solvent.

Compounds of formula III, wherein FG is —NH—(C=Y)-LG and preferably wherein LG is $OR^{25}$ and especially wherein $R^{25}$ is an unsubstituted or substituted phenyl moiety, can be readily obtained from the reaction of suitable amino substituted derivatives of $(R^8)_p$—$Ar^1$ of formula V

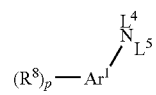

V wherein $R^8$, p, and $Ar^1$ are as defined above/below and $L^4$ and $L^5$ are selected independently from each other from the mean ings given for $L^2$ and $L^3$ and more preferred are hydrogen, with a compound of formula VIb

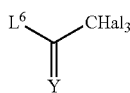

wherein Y and $L^6$ are as defined above/below.

Suitable reaction conditions for carrying out reaction of compounds of formula V with compounds of formula VI, VIa and VIb, respectively, are known in the art. In detail, the reaction of the compounds of the formula V with the compounds of the formula VI is carried out in the presence or absence, preferably in the presence of an inert solvent, preferably one of the afore mentioned inert solvents, more preferably ethers and chlorinated hydrocarbons, and especially in dichloromethane, preferably in a temperature range between 0° C. and 60° C. and more preferably at about room temperature.

The reaction between compounds of formula V and compounds of formula VI is preferably carried out in the presence of an acid binding means, for example one or more bases. Suitable acid binding means are known in the art. Preferred as acid binding means are organic bases, more preferably one of the afore mentioned organic bases and especially pyridine.

In general, the reaction times for the reaction between compounds of formula V and compounds of formula VI lie in the range between 6 hrs and 36 hrs, preferably 12 hrs to 24 hrs, for example at about 16 hrs.

Some of the starting materials of the formula V and/or the formula VI are known and preferably commercially available. If they are not known, they can be prepared by methods known per se.

The compounds of formula IV can be obtained according to methods known in the art.

If the compound of formula IV is a compound according to formula IVa,

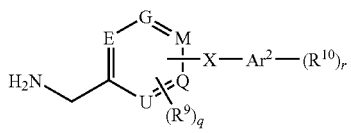

it can be readily obtained in an advantageous manner (reaction route A) by reacting a compound of formula VIIa,

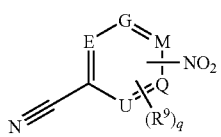

wherein E, G, M, Q, U, $R^9$ and q are as defined above/below, with a compound of formula VIII,

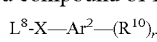

wherein $L^8$ is H or a metal ion, preferably a metal ion selected from the group consisting of alkaline metal ions, alkaline-earth metal ions and aluminum ions, especially preferred alkaline metal ions, of which Li, Na and K are especially preferred, and even more preferred is H; and $Ar^2$, $R^{10}$, r and X are as defined above/below, and preferably wherein X is $(CHR^{11})_h$-Q-$(CHR^{12})_i$, wherein $R^{11}$, h and i and $R^{12}$ are defined above/below, and more preferred wherein h and/or i is 0 and Q is selected from a group consisting of O, S, N—$R^{15}$, (O—$CHR^{18}$O)$_j$, (O—$CHR^{18}CHR^{19}$)$_j$, O—N═CH, N$R^{15}$—N═CH, N$R^{15}$SO$_2$, wherein $R^{15}$, $R^{18}$, $R^{19}$ and j are as defined above/below, and even more preferred wherein h and i is 0 and Q is selected from a group consisting of O, S, N—$R^{15}$;

optionally isolating the reaction product, and transferring the obtained reaction product of formula IX

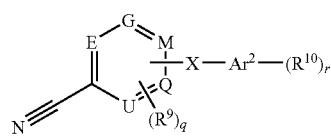

into a compound of formula IVa, preferably by reducing and more preferred by hydrogenating the CN-moiety of the compound of formula IX into a $H_2NCH_2$-moiety. Methods and reaction conditions for hydrogenating said CN-moiety into a $H_2NCH_2$-moiety are known in the art. In general, it is advantageous to carry out the hydrogenation reaction in the presence of a hydrogen delivering means, for example hydrogen gas, in the presence of a suitable catalyst, preferably a Nickel catalyst, for example Raney-Nickel. In general, such hydrogenation reactions are carried out in a suitable solvent. Suitable solvents for hydrogenation reactions are known in the art. Suitable solvents, for example, are alcohols, especially methanol and ethanol and ethers, especially THF, and mixtures thereof. Preferably, the hydrogenation reaction is carried out in a methanol/ammonia mixture, preferably in the presence of Raney nickel. In general, the hydrogenation reactions are carded out at about normal pressure or elevated pressure, for example between normal pressure and 10 bar pressure, preferably at about 5 par pressure (about 500 kPa). The hydrogenation reaction is usually carried out in the temperature range between −20° C. and 150° C., preferably +20° C. and 100° C., for example at about 45° C.

$Ar^2$ is preferably pyridinyl. Accordingly, the compound of formula VIII is preferably selected from the group consisting of formulae VIIIa and VIIIb,

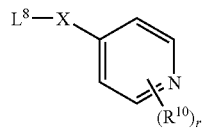

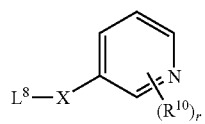

wherein $L^8$, X, $R^{10}$ and r are as defined above, and especially preferred from the group consisting of formulae VIIIc and VIIId, VIIIc

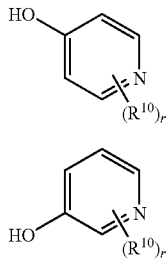

VIIId wherein $R^{10}$ and r are as defined above, or the alkaline metal salts and especially the sodium or potassium salts thereof.

Accordingly, in formulae IVa, VIII, VIIIa, VIIIb and IX, the bridging group X is preferably O, S, $OCH_2$ and $OCH_2CH_2$ and especially is O.

In the formulae VIII, VIIIa and VIII, $L^8$ is preferably H or selected from the group consisting of Na, K and Cs and especially preferred is H.

In general, this reaction is advantageous to produce compounds of formula IVaa,

IVaa

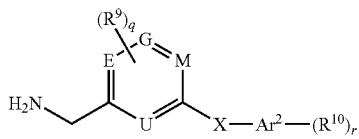

wherein E, G, M, $R^9$, q, X, $Ar^2$, $R^{10}$ and r are as defined above/below.

To obtain compounds of formula IVaa, it is reasonable to employ a compound of formula VII that is selected from the compounds of formula VIIa, VIIa

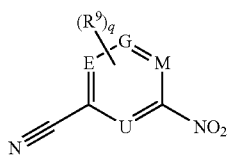

and proceed the reaction as described above/below.

Accordingly, by starting from a compound of formula VIIIa and a compound of formula VIIIa, the reaction preferably leads to compounds of formula IVaaa, IVaaa

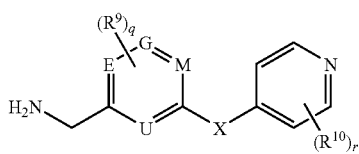

wherein E, G, M, U, $R^9$, q, X, $R^{10}$ and r are as defined above/below.

Accordingly, by starting from a compound of formula VIIa and a compound of formula VIIIb, the reaction preferably leads to compounds of formula IVaab, IVaab

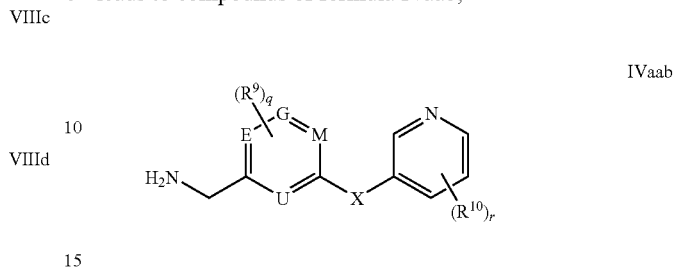

wherein E, G, M, U, $R^9$, q, X, $R^{10}$ and r are as defined above/below.

Accordingly, by starting from a compound of formula VIIIa and a compound of formula VIIIc, the reaction preferably leads to compounds of formula IVaac, IVaac

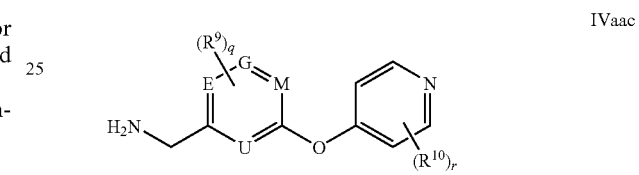

wherein E, G, M, U, $R^9$, q, $R^{10}$ and r are as defined above/below.

Accordingly, by starting from a compound of formula VIIa and a compound of formula VIIId, the reaction preferably leads to compounds of formula IVaad

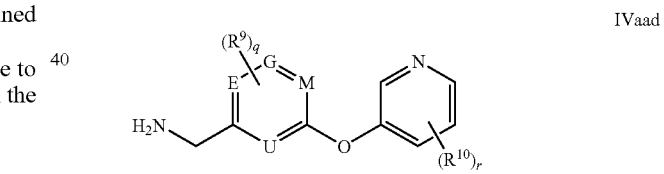

wherein E, G, M, U, $R^9$, q, $R^{10}$ and r are as defined above/below.

Some of the starting materials of the formula VII and/or the formula VIII are known and preferably commercially available. If they are not known, they can be prepared by methods known per se.

The reaction between the compound of formula VII and VIII is preferably carried out in the temperature range between 0° C. and 250° C., more preferred room temperature and 200° C., for example at about 120° C., at about 150° C. or at about 180°. Reaction times depend on the respective reactants and the respective reaction temperature, but generally lie in the range between 30 min and 36 hrs, preferably 3 hrs and 24 hrs, more preferably 8 hrs and 20 hrs for example about 10 hrs, about 16 hrs or about 18 hrs.

The reaction can be carried out in the absence of solvent or preferably in the presence of a solvent, preferable a solvent that is inert under the respective reaction conditions. Suitable inert solvents for carrying out the reaction are known in the art. Examples for suitable solvents are high boiling aliphatic hydrocarbons, high boiling aromatic carbons, for example toluene, xylenes, high boiling chlorinated hydrocarbons, such as trichloroethylene, tetrachloroethanes, pentachloroethanes and hexachloroethanes; high boiling ethers, such as ethylene glycol and propylene glycols; glycol ethers, such as ethylene glycol monomethyl or monoethyl ether or ethylene glycol dimethyl ether (diglyme); amides, such as acetamide, dimethylacetamide, dimethylformamide (DMF) or N-methyl pyrrolidinone (NMP); sulfoxides, such as dimethyl sulfoxide (DMSO); or mixtures of the said solvents. Preferred are amides, especially dimethylformamide (DMF) or N-methylpyrrolidinone (NMP).

Preferably, the reaction is carried out in the presence of a base. Suitable bases are known in the art. Preferred bases are organic bases and especially inorganic bases. Examples for inorganic bases are alkaline or alkaline-earth hydroxides, alkaline or alkaline-earth carbonates and alkaline or alkaline-earth bicarbonates or other salts of a weak acid and alkaline or alkaline-earth metals, preferably of potassium, sodium, calcium or cesium. Preferred inorganic bases are $K_2CO_3$, $Na_2CO_3$, $MgCO_3$, $CaCO_3$, NaOH and KOH, especially preferred is $K_2CO_3$. Examples for organic bases are triethyl amine, diisopropyl ethyl amine (DIPEA), dimethyl aniline, pyridine or chinoline. If an organic base is used, it is advantageous in general to use a base with a boiling point that is higher than the highest reaction temperature employed during the reaction.

Alternatively, if the compound of formula IV is a compound according to formula IVb,

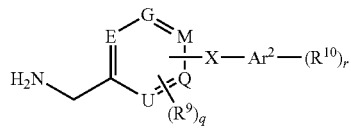

IVb it can be readily obtained in an advantageous manner (reaction route B) by reacting a compound of formula VIIb,

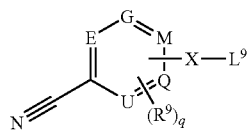

VIIb wherein E, G, M, Q, U, $R^9$ and q are as defined above/below and wherein $L^9$ is selected independently from H or a moiety which activates the group (and preferably a hetero atom such as N, S and especially O which is part of the group) it is bonded to, for example a metal ion. Suitable metal ions are preferably selected from the group consisting of alkaline metal ions, alkaline-earth metal ions and aluminium ions. More preferred, $L^9$ is selected from H, Na and K, and is even more preferred H, especially if X is selected from the group consisting of wherein X is $(CHR^{11})_h$-Q-$(CHR^{12})_i$, wherein $R^{11}$, h and i and $R^{12}$ are defined above/below, and more preferred wherein h and/or i is 0 and Q is selected from a group consisting of O, S, N—$R^{15}$, $(CHR^{18}$—O$)_j$, $(CHR^{18}CHR^{19}$—O$)_j$, CH=N—O, C=N—$NR^{15}$, $SO_2NR^{15}$, wherein $R^{15}$, $R^{18}$, $R^{19}$ and j are as defined above/below, and even more preferred wherein h and i is 0 and Q is selected from a group consisting of O, S, N—$R^{15}$;

with a compound of formula VIIIb,

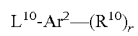

VIIIb wherein $L^{10}$ is preferably Cl, Br, I or diazonium moiety, more preferred Cl, Br or I and even more preferred Br and Cl;

optionally isolating the reaction product, and transferring the obtained reaction product of formula IXb

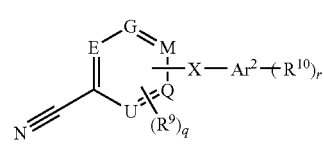

IXb into a compound of formula IVa, preferably by reducing and more preferred by hydrogenating the CN-moiety of the compound of formula IXa into a $H_2NCH_2$-moiety, preferably as described above for the compound IX.

$Ar^2$ is preferably pyridinyl. Accordingly, the compound of formula VIIIb is preferably selected from the group consisting of formulae VIIIe and VIIIf,

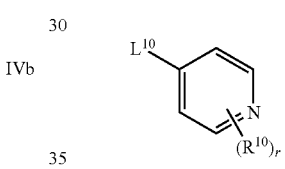

VIIIe

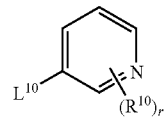

VIIIf wherein $L^{10}$, $R^{10}$ and r are as defined above, and especially preferred from the group consisting of formulae VIIIg and VIIIh,

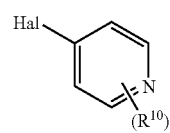

VIIIg

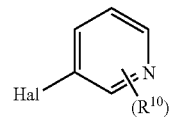

VIIIh wherein Hal, $R^{10}$ and r are as defined above, and wherein Hal is preferably Cl in compounds of formula VIIIg and preferably Br in compounds of formula VIIIh.

Accordingly, in formulae IVb, VIIIb, VIIIe, VIIIf and IXb, the bridging group X is preferably O, S, $OCH_2$ and $OCH_2CH_2$ and especially is O.

In general, this alternative reaction is advantageous to produce compounds of formula IVbb,

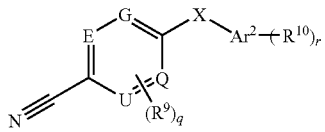

IVbb wherein E, G, Q, U, $R^9$, q, X, $Ar^2$, $R^{10}$ and r areas defined above/below.

To obtain compounds of formula IVbb, it is reasonable to employ a compound of formula VIIIb that is selected from the compounds of formula VIIbb,

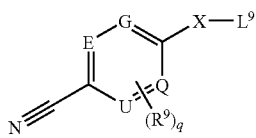

VIIbb wherein E, G, Q, U, X and $L^9$ are as defined above/below, more preferred wherein X-$L^9$ is selected from the group consisting of SH, OH and HN—$R^{17}$ and especially wherein X-$L^9$ is OH, and proceed the alternative reaction as described above/below.

Accordingly, by starting from a compound a formula VIIbb and a compound of formula VIIe, the reaction preferably leads to compounds of formula IVbbe,

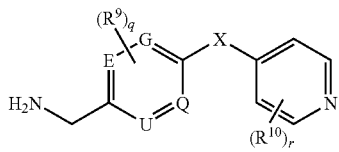

IVbbe wherein E, G, Q, U, $R^9$, q, X, $R^{10}$ and r are as defined above/below.

Accordingly, by starting from a compound of formula VIIbb and a compound of formula VIIIf, the reaction preferably leads to compounds of formula IVbbf,

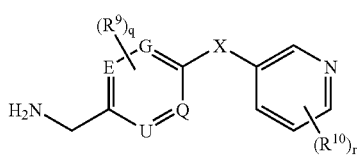

IVbbf wherein E, G, Q, U, $R^9$, q, X, $R^{10}$ and r are as defined above/below.

Accordingly, by starting from a compound of formula VIIbb and a compound of formula VIIIg, the reaction preferably leads to compounds of formula IVbbg,

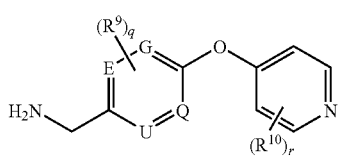

IVbbg wherein E, G, Q, U, $R^9$, q, $R^{10}$ and r are as defined above/below.

Accordingly, by starting from a compound of formula VIIb and a compound of formula VIIIh, the reaction preferably leads to compounds of formula IVbbh,

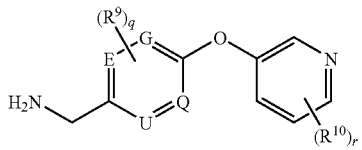

IVbbh wherein E, G, Q, U, $R^9$, q, $R^{10}$ and r are as defined above/below.

Some of the starting materials of the formula VIIIb and/or the formula VIIb are known and preferably commercially available. If they are not known, they can be prepared by methods known per se.

The reaction between the compound of formula VIIb and VIIIb is preferably carried out in the temperature range between 0° C. and 250° C., more preferred 50° C. and 220° C., for example at about 90° C., at about 120° C., at about 160° C., at about 180° C. or at about 200°. Reaction times depend on the respective reactants and the respective reaction temperature, but generally lie in the range between 10 min and 36 hrs, preferably between 60 min and 24 hrs, more preferably 3 h and 20 hrs for example about 6 hrs, about 12 hrs, about 15 hrs or about 18 hrs.

The reaction can be carried out in the absence or the presence of a solvent, preferable a solvent that is inert under the respective reaction conditions. Suitable inert solvents for carrying out the reaction are known in the art. Examples for suitable solvents are high aliphatic hydrocarbons, aromatic carbons, for example toluene and xylenes, high boiling chlorinated hydrocarbons, such as dichlormethane, trichloromethane trichloroethylene, tetrachloroethanes, pentachloroethanes and hexachloroethanes; ethers, such as diethylether, tert.-butyl methyl ether, ethylene glycol and propylene glycols; glycol ethers, such as ethylene glycol monomethyl or monoethyl ether or ethylene glycol dimethyl ether (diglyme); nitriles, such as acetonitrile, amides such as acetamide, diemthyacetamide, dimethylformamide (DMF) or N-methyl pyrrolidinone (NMP); sulfoxides, such as dimethyl sulfoxide (DMSO); or mixtures of the said solvents.

In many cases, it is advantageous to carry out the reaction in the presence of a catalyst. Suitable catalysts are known in the art. Preferred catalysts are compounds comprising catalytically active metals and especially compounds comprising catalytically active copper. A preferred compound comprising catalytically active copper is copper iodide and especially is CuI. Carrying out the reaction in the presence of a catalyst as described above is preferred if a compound of formula VIII is used, wherein $L^{10}$ or Hal is bromine, and is especially preferred if a compound of formula VIIIf or VIIIh is used, wherein $L^{10}$ or Hal is bromine.

In many cases, it is advantageous to carry out the reaction in the presence of an acid binding means, preferably an organic base as described above and more preferred an inorganic base. Preferred inorganic bases are $K_2CO_3$, $Na_2CO_3$, $MgCO_3$, $CaCO_3$, NaOH and KOH, especially preferred is $K_2CO_3$. Carrying out the reaction in the presence of and acid binding means as described above is preferred if a compound of formula VIII is used, wherein $L^{10}$ or Hal is bromine, and is especially preferred if a compound of formula VIIIf or VIIIh is used, wherein $L^{10}$ or Hal is bromine.

Preferably, the reaction is carried out by heating up a reaction mixture comprising one compound of formula VIIb and one compound of formula VIIIb to a suitable reaction temperature, which preferably lies at the upper end of the given temperature ranges and more preferred is in the range between 150° C. and 200° C., for example at about 180° C., preferably in the presence of the suitable catalyst and especially in the presence of copper. Reaction times at this temperature are preferably as given above and especially in the range between 1 h and 5 hrs, for example about 3 hrs. Preferably, the reaction mixture is then allowed to cool down to a temperature in the lower range of the given temperature, more preferred to a temperature in the range between 50° C. and 150° C., for example to about 90°. Preferably, a suitable solvent, especially tert.-butyl methyl ether, is then added and the reaction mixture is preferably kept at about the same temperature for some more time, preferably for 30 min to 2 hrs and more preferred for about one hour.

If the compound IV is a compound according to formula IVc,

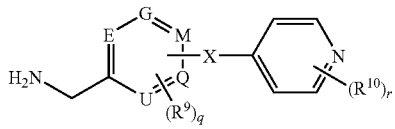

IVc it can be readily obtained in an advantageous manner (reaction route C) by reacting a compound of formula XI

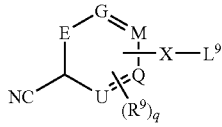

XI wherein $L^9$ is H or a metal ion, preferably a metal ion selected from the group consisting of alkaline metal ions, alkaline-earth metal ions and aluminium ions, especially preferred alkaline metal ions, of which Li, Na, and K are especially preferred, and even more preferred H; and E, G, M, Q, U, $R^9$, q and X are as defined above/below, and especially wherein X is selected from the group consisting of wherein X is $(CHR^{11})_h$-Q-$(CHR^{12})_i$, wherein $R^{11}$, h and i and $R^{12}$ are defined above/below, and more preferred wherein h and/or i is 0 and Q is selected from a group consisting of O, S, N—$R^{15}$, $(CHR^{18}—O)_j$, $(CHR^{18}CHR^{19}—O)_j$, CH=N—O, CH=N—$NR^{15}$, $SO_2NR^{15}$, wherein $R^{15}$, $R^{18}$, $R^{19}$ and j are as defined above/below, and even more preferred wherein h and i is 0 and Q is selected from a group consisting of O, S, N—$R^{15}$;

with a compound of formula XII,

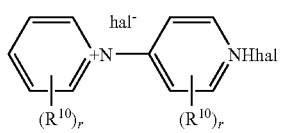

XII wherein hal is independently select selected from the group consisting of Cl, Br and I, the residue $R^{10}$ are the same or different and have the meanings given above/below and preferably have both the same meaning, and the indices r are the same or different and have the meanings given above/below and preferably are the same, optionally isolating the reaction product, and transferring the obtained reaction product of formula XIII

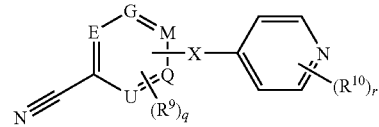

XIII into a compound of formula IVc, preferably by reducing or hydrogenating the CN-moiety of the compound of formula IX into a $H_2NCH_2$-moiety, for example as described above for the compound of formula IX.

In the compounds IVc, XII and XIII, r is preferably in each case identical and even more preferred in each case 0.

In formulae IVc, XI and XIII, the bridging group X is preferably O, S, $OCH_2$ and $OCH_2CH_2$ and especially is O.

In the formula XI, $L^9$ is preferably H or selected from the group consisting of Na, K and Cs and especially preferred is H.

The reaction between the compound of formula XI and XII is preferably carried out in the temperature range between 0° C. and 250° C., more preferred room temperature and 200° C., for example at about 120° C., at about 150° C. or at about 180°. Reaction times depend on the respective reactants and the respective reaction temperature, but generally lie in the range between 30 min and 24 hrs, preferably one hour and 12 hrs, for example about 2 hrs, about 3 hrs or about 6 hrs. The reaction can be carried out in the absence of solvent or in the presence of a solvent, preferable a solvent that is inert under the respective reaction conditions. Suitable inert solvents for carrying out the reaction are known in the art.

In the methods according to the invention for producing compounds, E, G, M, Q, and U are as defined above/below, for example as defined above/below for the compounds according to the invention. More preferably, two or more of E, G, M, Q, and U are carbon atoms. In one embodiment of the method according to the invention for producing compounds, E, G, M, Q, and U all are carbon atoms.

Some of the starting materials of the formula XI and/or the formula XIII are known and preferably commercially available. If they are not known, they can be prepared by methods known per se.

Independently of the chosen reaction route, it is in many cases possible or even feasible to introduce residues $R^8$, $R^9$ and/or $R^{10}$ into one or more of the compounds described above, or, if the compound already comprises one or more residues $R^8$, $R^9$ and/or $R^{10}$, to introduce additional residues $R^8$, $R^9$ and/or $R^{10}$ into said compound. The introduction of additional residues can be readily performed by methods known in the art and especially by aromatic substitution, for example nucleophilic aromatic substitution or electrophilic aromatic substitution. For example, in compounds comprising $Ar^1$, wherein $Ar^1$ comprises one or more halogen and preferably fluorine substituents, one or more of the halogen/fluorine substituents can be easily substituted by hydroxy, thio and/or amino substituted hydrocarbons, preferably selected from the group consisting of $HO(CH_2)_nNR^{11}R^{12}$, $HO(CH_2)_nO(CH_2)_kNR^{11}R^{12}$, $HO(CH_2)_nNR^{11}(CH_2)_kOR^{12}$, $HO(CH_2)_nNR^{11}(CH_2)_kNR^{11}R^{12}$, $HO(CH_2)_nCOOR^{13}$, $HO(CH_2)_nS(O)_uR^{13}HNR^{11}(CH_2)_nNR^{11}R^{12}$, $HNR^{11}(CH_2)_n$ O(CH$_2$)$_k$NR$^{11}$R$^{12}$, HNR$^{11}$(CH$_2$)$_n$NR$^{11}$(CH$_2$)$_k$OR$^{12}$, HNR$^{11}$(CH$_2$)$_n$NR$^{11}$(CH$_2$)$_k$NR$^{11}$R$^{12}$, HNR$^{11}$(CH$_2$)$_n$COOR$^{12}$ and HNR$^{11}$(CH$_2$)$_n$S(O)$_u$R$^{13}$ wherein R$^{11}$, R$^{12}$ and R$^{13}$ are defined as above and n is as defined above, preferably n is 0, 1 or 2 and especially is 0, k is 1 to 4 and preferably 1 or 2, and u is preferably 2. In this embodiment R$^{11}$, R$^{12}$ and R$^{13}$ are more preferably selected independently from each other from the group consisting of H, methyl and ethyl. Even more preferred, the hydroxy, thio and/or amino substituted hydrocarbons are selected from the group consisting of NH$_3$, HN(CH$_3$)$_2$, NH$_2$CH$_3$, HN(C$_2$H$_5$)$_2$, H$_2$NCH$_2$CH$_2$NH$_2$, HOCH$_2$CH$_2$NH$_2$, HOCH$_2$CH$_2$NHCH$_3$, HN(CH$_3$)CH$_2$CH$_2$NH$_2$, HN(CH$_3$)CH$_2$CH$_2$N(CH$_3$)$_2$, HN(CH$_3$)CH$_2$CH$_2$N(CH$_3$)$_2$, HN(CH$_3$)CH$_2$CH$_2$OCH$_3$, HOCH$_2$CH$_2$N(CH$_3$)$_2$, HOCH$_2$CH$_2$N(CH$_2$CH$_3$)$_2$, HSCH$_3$, HSC$_2$H$_5$, and compounds of the formulae

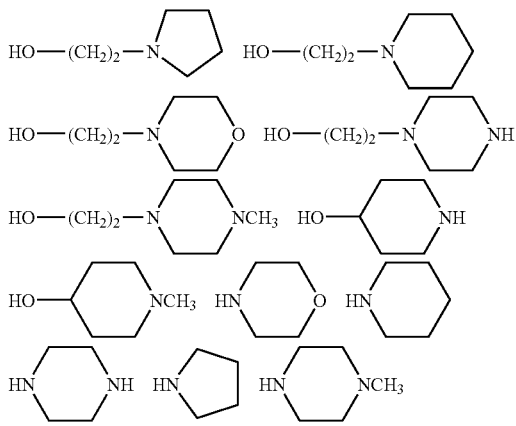

or salts and especially metal salts thereof.

On the other hand, it is in many cases possible or even feasible to modify or derivatize one or more of the residue is R$^8$, R$^9$ and R$^{10}$ into residues R$^8$, R$^9$ and/or R$^{10}$ other than the ones originally present. For example, CH$_3$— groups can be oxidised into aldehyde groups or carbonic acid groups, thio atom containing groups, for example S-alkyl or S-aryl groups, can be oxidised into SO$_2$-alkyl or SO$_2$-aryl groups, respectively, carbonic acid groups can be derivatized to carbonic acid ester groups or carbon amide groups and carbonic acid ester groups or carbon amide groups can be hydrolysed into the corresponding carbonic acid groups. Methods for performing such modifications or derivatizations are known in the art, for example from Houben-Weyl, Methods of Organic Chemistry.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

A base of the formula I or the formula II can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid. Salts with physiologically unacceptable acids, for example picrates, can be used to isolate and/or purify the compounds of the formula I. On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

On the other hand, if desired, the free bases of the formula I or the formula II can be liberated from their salts using bases (for example sodium hydroxide, potassium hydroxide, sodium carbonate or potassium carbonate).

The invention relates to compounds of the formula I and of the formula II and physiologically acceptable salts and solvates thereof as medicaments.

The invention also relates to the compounds for the formula I and of the formula II and physiologically acceptable salts and solvates thereof as kinase inhibitors.

The invention furthermore relates to the use of the compounds of the formula I and/or physiologically acceptable salts and/or solvates thereof for the preparation of pharmaceutical compositions and/or pharmaceutical preparations, in particular by non-chemical methods. The invention furthermore relates to the use of the compounds of the formula II and/or physiologically acceptable salts and/or solvates thereof for the preparation of pharmaceutical compositions and/or pharmaceutical preparations, in particular by non-chemical methods. In this cases, one or more compounds according to the invention can be converted into a suitable dosage form together with at least one solid, liquid and/or semi-liquid excipient or adjuvant and, if desired, in combination with one or more further active ingredients.

The invention further relates to the use of one or more of the compounds according to the invention, selected from the group consisting of compounds of the formula I as free bases, solvates of compounds of the formula I, salts of compounds of formula I, of compounds of the formula II as free bases, solvates of compounds of the formula II and salts of compounds of formula II, for the production of pharmaceutical compositions and/or pharmaceutical preparations, in particular by a non-chemical route. In general, non-chemical routes for the production of pharmaceutical compositions and/or pharmaceutical preparations comprise processing steps on suitable mechanical means known in the art that transfer one or more compounds according to the invention into a dosage form suitable for administration to a patient in need of such a treatment. Usually, the transfer of one or more compounds according to the invention into such a dosage form comprises the addition of one or more compounds, selected from the group consisting of carriers, excipients, auxiliaries and pharmaceutical active ingredients other than the compounds according to the invention. Suitable processing steps include, but are not limited to combining, milling, mixing, granulating, dissolving, dispersing, homogenizing, casting and/or compressing the respective active and non-active ingridients. In this respect, active ingredients are preferably at least one compound according to this invention and one or more additional compounds other than the compounds according to the invention, which show valuable pharmaceutical properties, preferably those pharmaceutical active agents other than the compounds according to invention which are disclosed herein.

The process for preparing pharmaceutical compositions and/or pharmaceutical preparations preferably comprises one or more processing steps, selected from the group consisting of combining, milling, mixing, granulating, dissolving, dispersing, homogenizing and compressing. The one or more processing steps are preferably performed on one or more of the ingredients which are to form the pharmaceutical composition and/or pharmaceutical preparation preferably according to invention. Even more preferred, said processing steps are performed on two or more of the ingredients which are to form the pharmaceutical composition and/or pharmaceutical preparation, said ingredients comprising one or more compounds according to the invention and, additionally, one or more compounds, preferably selected from the group consisting of active ingredients other than the compounds according to the invention, excipients, auxiliaries, adjuvants and carriers. Mechanical means for performing said processing steps are known in the art, for example from Ullmann's Encyclopedia of Industrial Chemistry, 5th Edition.

Preferably, one or more compounds according to the invention are converted into a suitable dosage form together with at least one compound selected from the group consisting of excipients, auxiliaries, adjuvants and carriers, especially solid, liquid and/or semi-liquid excipients, auxiliaries, adjuvants and carriers, and, if desired, in combination with one or more further active ingredients.

Suitable dosage forms include, but are not limited to tablets, capsules, semi-solids, suppositories, aerosols, which can be produced according to methods known in the art, for example as described below:

tablets mixing of active ingredient/s and auxiliaries, compression of said mixture into tablets (direct compression), optionally granulation of part of mixture before compression capsules mixing of active ingredient/s and auxiliaries to obtain a flowable powder, optionally granulating powder, filling powders/granulate into opened capsules, capping of capsules semi-solids (ointments, gels, creams) dissolving/dispersing active ingredient/s in an aqueous or fatty carrier; subsequent mixing of aqueous/fatty phase with complementary fatty resp. aqueous phase, homogenisation (creams only)

suppositories (rectal and vaginal) dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms aerosols: dispersing/dissolving active agent/s in a propellant, bottling said mixture into an atomizer The invention thus relates to pharmaceutical compositions and/or pharmaceutical preparations comprising at least one compound of the formula I and/or one of its physiologically acceptable salts and/or solvates and especially to pharmaceutical compositions and/or pharmaceutical preparations comprising at least one compound of the formula II and/or one of its physiologically acceptable salts and/or solvates.

Preferably, the pharmaceutical compositions and/or pharmaceutical preparations according to the invention contain a therapeutic effective amount of one or more compounds according to the invention. Said therapeutic effective amount of one or more of the compounds according to the invention is known to the skilled artisan or can be easily determined by standard methods known in the art. For example, the compounds according to the invention can be administered to a patient in an analogous manner to other compounds that are effective as raf-kinase inhibitors, especially in an analogous manner to the compounds described in WO 00/42012 (Bayer). Usually, suitable doses that are therapeutically effective lie in the range between 0.0005 mg and 1000 mg, preferably between 0.005 mg and 500 mg and especially between 0.5 and 100 mg per dose unit. The daily dose comprises preferably more than 0.001 mg, more preferred more than 0.01 milligram, even more preferred more than 0.1 mg and especially more than 1.0 mg, for example, more than 2.0 mg, more than 5 mg, more than 10 mg, more than 20 mg, more than 50 mg or more than 100 mg, and preferably less than 1500 mg, more preferred less than 750 mg, even more preferred less than 500 mg, for example less than 400 mg, less than 250 mg, less than 150 mg, less than 100 mg, less than 50 mg or less than 10 mg.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician which advises or attends the therapeutic treatment.

However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular, illness to which the therapy applies. Parenteral administration is preferred. Oral administration is especially preferred.

These compositions and/or preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or vaseline. Examples for suitable dosage forms, which are especially suitable for oral administration are, in particular, tablets, pills, coated tablets, capsulees, powders, granules, syrups, juices or drops. Further examples for suitable dosage forms, which are especially suitable for rectal administration are suppositories, further examples for suitable dosage forms, which are especially suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The compositions and/or preparations indicated may be sterilized and/or comprise assistants, such as lubricants, preservatives, stabilizers and/or wetting agents, emulsifiers, salts for modifying the osmotic pressure, buffer substances, dyes and flavors and/or one or more further active ingredients, for example one or more vitamins.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

The compounds of the formula I and their physiologically acceptable salts and solvates and especially the compounds of formula II and their physiologically acceptable salts and solvates can be employed for combating one or more diseases, for example allergic diseases, psoriasis and other skin diseases, especially melanoma, autoimmune diseases, such as, for example, rheumatoid arthritis, multiple sclerosis, Crohn's disease, diabetes mellitus or ulcerative colitis.

In General, the substances according to the invention are preferably administered in doses corresponding to the compound rolipram of between 1 and 500 mg, in particular between 5 and 100 mg per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular illness to which the therapy applies. Oral administration is preferred.

The compounds of the formula I according to claim 1 and/or their physiologically acceptable salts are also used in pathological processes which are maintained or propagated by angiogenesis, in particular in tumors, restenoses, diabetic retinopathy, macular degenerative disease or rheumatois arthritis.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with pharmaceutically active agents other than the compounds according to the invention, particularly other anti-metastatic, antitumor or anti-angiogenic agents. Angiostatic compounds of interest include angiostatin, enclostatin, carboxy terminal peptides of collagen alpha (XV), etc. Cytotoxic and cytostatic agents of interest include adriamycin, aleran, Ara-C, BICNU, busulfan, CNNU, cisplatinum, cytoxan, daunorubicin, DTIC, 5-FU, hydrea, ifosfamicle, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

The compounds of the invention have been shown to have antiproliferative effect in an in vivo xenograft tumor model. The subject compounds are administered to a subject having a hyperproliferative disorders, e.g., to inhibit tumor growth, to decrease inflammation associated with a lymphoproliferative disorder, to inhibit graft rejection, or neurological damage due to tissue repair, etc. The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g., to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g., primate sp., particularly human; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one hour and one weed. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body.

The compounds according to the invention are preferably administered to human or nonhuman animals, more preferred to mammalian animals and especially to humans.

The compounds also find use in the specific inhibition of a signaling pathway mediated by protein kinases. Protein kinases are involved in signaling pathways for such important cellular activities as responses to extracellular signals and cell cycle checkpoints. Inhibition of specific protein kinases provided a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in the signaling mediated by protein kinases. Such conditions include those associated with defects in cell cycle regulation or in response to extracellular signals, e.g., immunological disorders, autoimmune and immunodeficiency diseases; hyperproliferative disorders, which may include psoriasis, arthritis, inflammation, endometriosis, scarring, cancer, etc. The compounds of the present invention are active in inhibiting purified kinase proteins preferably raf kinases, e.g., there is a decrease in the phosphorylation of a specific substrate in the presence of the compound. The compounds of the invention may also be useful as reagents for studying signal transduction or any of the clinical disorders listed throughout this application.

There are many disorders associated with a dysregulation of cellular proliferation. The conditions of interest include, but are not limited to, the following conditions. The subject compounds are useful in the treatment of a variety of conditions where there is proliferation and/or migration of smooth muscle cells, and/or inflammatory cells into the intimal layer of a vessel, resulting in restricted blood flow through that vessel, e.g., neointimal occlusive lesions. Occlusive vascular conditions of interest include atherosclerosis, graft coronary vascular disease after transplantation, vein graft stenosis, peri-anastomatic prothetic graft stenosis, restenosis after angioplasty or stent placement, and the like.

Diseases where there is hyperproliferation and tissue remodelling or repair or reproductive tissue, e.g., uterine, testicular and ovarian carcinomas, endometriosis, squamous and glandular epithelial carcinomas of the cervix, etc. are reduced in cell number by administration of the subject compounds. The growth and proliferation of neural cells is also of interest.

Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to product a tumor neovasculature.

Tumors of interest for treatment include carcinomas, e.g., colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies; e.g. neuroplastoma, gliomas, etc.; hematological malignancies, e.g., childhood acute leukaemia, non-Hodgkin's lymphomas, chronic lymphocytic leukaemia, malignant cutaneous T-cells, mycosis fungoides, non-MF cutaneous T-cell-lymphoma, lymphomatoid papulosis, T-cell rich cutaneous lymphoid hyperplasia, bullous pemphigoid, discoid lupus erythematosus, lichen planus, etc.; and the like.

Tumors of neural tissue are of particular interest, e.g., gliomas, neuromas, etc. Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltration (or invasive) ductal carcinoma (IDC) has metastasized through the wall of the duct and invaded the fatty tissue of the breast. Infiltrating (or invasive) lobular carcinoma (ILC) is similar to IDC, in that it has the potential to metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamos cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue, remodeling and repair. For example, the chronic skin inflammation of psoriasis is associated with hyperplastic epidermal keratinocyctes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemia's and lymphomas. Symptoms of allergies to environmental and food agents, as well as inflammatory bowel disease, may also be alleviated by the compounds of the invention.

Surprisingly, it has been found that methylene urea derivatives according to invention are able to interact with signaling pathways, especially the signaling pathways described herein and preferably the raf-kinase signaling pathway. Methylene urea derivatives according to the invention preferably show advantageous biological activity which can easily be demonstrated according to methods known in the art, for example by enzyme based assays. Suitable assays are known in the art, for example from the literature cited herein and the references cited in the literature, or can be developed and/or performed in an analogous manner thereof. In such enzyme based assays, methylene urea derivatives according to invention show an effect, preferably a modulating and especially an inhibiting effect which is usually documented by $IC_{50}$ values in a suitable range, preferably in the micromolar range and more preferred in the nanomolar range.

In general, compounds according to the invention are to be regarded as suitable kinase-modulators and especially suitable kinase-inhibitors according to the invention if they show an effect or an activity to one or more kinases, preferably to one or more raf-kinases that preferably lies, determined as $IC_{50}$-value, in the range of 100 µmol or below, preferably 10 µmol or below, more preferably in the range of 3 µmol or below, even more preferably in the range of 1 µmol or below and most preferably in the nanomolar range. Especially preferred for use according to the invention are kinase-inhibitors ast defined above/below, that show an activity, determined as $IC_{50}$-value, to one or more raf-kinases, preferably including A-raf, B-raf and c-raf1 or consisting of A-raf, B-raf and c-raf1 and more preferred including c-raf1 or consisting of c-raf1, in the range of 0.5 µmol or below and especially in the range of 0.1 µmol or below. In many cases an $IC_{50}$-value at the lower end of the given ranges is advantageous and in some cases it is highly desirable that the $IC_{50}$-value is as small as possible or the he $IC_{50}$-values are as small as possible, but in general $IC_{50}$-values that lie between the above given upper limits and a lower limit in the range of 0.0001 µmol, 0.001 µmol, 0.01 µmol or even above 0.1 µmol are sufficient to indicate the desired pharmaceutical activity. However, the activities measured can vary depending on the respective testing system or assay chosen.

Alternatively, the advantageous biological activity of the compounds according to the invention can easily be demonstrated in in vitro assays, such as in vitro proliferation assays or in vitro growth assays. Suitable in vitro assays are known in the art, for example from the literature cited herein and the references cited in the literature or can be performed as described below, or can be developed and/or performed in an analogous manner thereof.

As an example for an in vitro growth assay, human tumor cell lines, for example HCT116, DLD-1 or MiaPaCa, containing mutated K-ras genes can be used in standard proliferation assays, for example for anchorage dependent growth on plastic or anchorage independent growth in soft agar. Human tumor cell lines are commercially available, for example from ATCC (Rockville Md.), and can be cultured according to methods known in the art, for example in RPMI with 10% heat inactivated fetal bovine serum and 200 mM glutamine. Cell culture media, fetal bovine serum and additives are commercially available, for example from Invitrogen/Gibco/BRL (Karlsruhe, Germany) and/or QRH Biosciences (Lenexa, Kans.). In a standard proliferation assay for anchorage dependent growth, $3 \times 10^3$ cells can be seeded into 96-well tissue culture plates and allowed to attach, for example overnight at 37° C. in a 5% $CO_2$ incubator. Compounds can be titrated in media in dilution series and added to 96 well cell cultures. Cells are allowed to grow, for example for 1 to 5 days, typically with a feeding of fresh compound containing media at about half of the time of the growing period, for example on day 3, if the cells are allowed to grow 5 days. Proliferation can be monitored by methods known in the art, such as measuring metabolic activity, for example with standard XTT colorimetric assay (Boehringer Mannheim) measured by standard ELISA plate reader at OD 490/560, by measuring $^3$H-thymidine incorporation into DNA following an 8 h culture with 1 µCu $^3$H-thymidine, harvesting the cells onto glass fiber mats using a cell harvester and measuring $^3$H-thymidine incorporation by liquid scintillation counting, or by staining techniques, such as crystal violet staining. Other suitable cellular assay systems are known in the art.

Alternatively, for anchorage independent cell growth, cells can be plated at $1 \times 10^3$ to $3 \times 10^3$ in 0.4% Seaplaque agarose in RPMI complete media, overlaying a bottom layer containing only 0.64% agar in RPMI complete media, for example in 24-well tissue culture plates. Complete media plus dilution series of compounds can be added to wells and incubated, for example at 37° C. in a 5% $CO_2$ incubator for a sufficient time, for example 10-14 days, preferably with repeated feedings of fresh media containing compound, typically at 3-4 day intervals. Colony formation and total cell mass can be monitored, average colony size and number of colonies can be quantitated according to methods known in the art, for example using image capture technology and image analysis software. Image capture technology and image analysis software, such as Image Pro Plus or media Cybernetics.

As discussed herein, these signaling pathways are relevant for various disorders. Accordingly, by interacting with one or more of said signaling pathways, methylene urea derivatives are useful in the prevention and/or the treatment of disorders that are dependent from said signaling pathways.

The compounds according to the invention are preferably kinase modulators and more preferably kinase inhibitors. According to the invention, kinases include, but are not limited to one or more Raf-kinases, one or more Tie-kinases, one or more VEGFR-kinases, one or more PDGFR-kinases, p38-kinase and/or SAPK2alpha.

Raf-kinases in this respect are respect preferably include or consist of A-Raf, B-Raf and c-Raf1.

Tie-kinases in this respect preferably include or consist of Tie-2 kinase.

VEGFR-kinases in this respect preferably include or consist of VEGFR-2 kinase.

Due to the kinase modulating or inhibiting properties of the compounds according to the invention, the compounds according to the invention preferably interact with one or more signalling pathways which are preferably cell signalling pathways, preferably by downregulating or inhibiting said signaling pathways. Examples for such signalling pathways include, but are not limited to the raf-kinase pathway, the Tie-kinase pathway, the VEGFR-kinase pathway, the PDGFR-kinase pathway, the p38-kinase pathway, the SAPK2alpha pathway and/or the Ras-pathway.

Modulation of the raf-kinase pathway plays an important role in various cancerous and noncancerous disorders, preferably cancerous disorders, such as dermatological tumors, haematological tumors, sarcomas, squamous cell cancer, gastric cancer, head cancer, neck cancer, oesophageal cancer, lymphoma, ovary cancer, uterine cancer and/or prostate cancer. Modulation of the raf-kinase pathway plays a even more important role in various cancer types which show a constitutive activation of the raf-kinase dependent signalling pathway, such as melanoma, colorectal cancer, lung cancer, brain cancer, pancreatic cancer, breast cancer, gynaecological cancer, ovarian cancar, thyroid cancer, chronic leukaemia and acute leukaemia, bladder cancer, hepatic cancer and/or renal cancer. Modulation of the raf-kinase pathway plays also an important role in infection diseases, preferably the infection diseases as mentioned above/below and especially in *Helicobacter pylori* infections, such as *Helicobacter pylori* infection during peptic ulcer disease.

One or more of the signalling pathways mentioned above/below and especially the VEGFR-kinase pathway plays an important role in angiogenesis. Accordingly, due to the kinase modulating or inhibiting properties of the compounds according to the invention, the compounds according to the invention are suitable for the prophylaxis and/or treatment of pathological processes or disorders caused, mediated and/or propagated by angiogenesis, for example by inducing anti-angiogenesis. Pathological processes or disorders caused, mediated and/or propagated by angiogenesis include, but are not limited to tumors, especially solid tumors, arthritis, especially heumatic or rheumatoid arthritis, diabetic retinopathy, psoriasis, restenosis; fibrotic disorders; mesangial cell proliferative disorders, diabetic nephropathy, malignant nephrosclerosis, thrombotic microangiopathy syndromes, organ transplant rejection, glomerulopathies, metabolic disorders, inflammation and neurodegenerative diseases, and especially solid tumors, rheumatic arthritis, diabetic retinopathy and psoriasis.

Modulation of the p38-signalling pathway plays an important role in various cancerous and although in various noncancerous disorders, such as fibrosis, atherosclerosis, restenosis, vascular disease, cardiovascular disease, inflammation, renal disease and/or angiogenesis, and especially noncancerous disorders such as rheumatoid arthritis, inflammation, autoimmune disease, chronic obstructive pulmonary disease, asthma and/or inflammatory bowel disease.

Modulation of the PDGF-signalling pathway plays an important role in various cancerous and although in various noncancerous disorders, such as rheumatoid arthritis, inflammation, autoimmune disease, chronic obstructive pulmonary disease, asthma and/or inflammatory bowel disease, and especially noncancerous disorders such as fibrosis, atherosclerosis, restenosis, vascular disease, cardiovascular disease, inflammation, renal disease and/or angiogenesis.

Subject of the present invention are therefore methylene urea derivatives according to the invention as promoters or inhibitors, preferably as inhibitors, of the signaling pathways described herein. Preferred subject of the invention are therefore methylene urea derivatives according to the invention as promoters or inhibitors, preferably as inhibitors of the raf-kinase pathway. More preferred subject of the invention are therefore methylene urea derivatives according to the invention as promoters or inhibitors, preferably as inhibitors of the raf-kinase. Even more preferred subject of the invention are methylene urea derivatives according to invention as promoters or inhibitors, preferably as inhibitors of one or more raf-kinases, selected from the group consisting of A-raf, B-raf and c-raf1. Especially preferred subject of the invention are methylene urea derivatives according to the invention as promoters or inhibitors, preferably as inhibitors of c-raf1.

Thus, subject of the present invention are methylene urea derivatives according to the invention as medicaments. Subject of the present invention are methylene urea derivatives according to the invention as medicament active ingredients. Further subject of the present invention is the use of one or more methylene urea derivatives according to the invention as a pharmaceutical. Further subject of the present invention is the use of one or more methylene urea derivatives according to the invention in the treatment and/or the prophylaxis of disorders, preferably the disorders described herein, more preferred disorders that are caused, mediated and/or propagated by signalling pathways discussed herein, even more preferred disorders that are caused, mediated and/or propagated by raf-kinases and especially disorders that are caused, mediated and/or propagated by raf-kinases, selected from the group consisting of A-raf, B-raf and c-raf1. Usually, the disorders discussed herein are divided into two groups, hyperproliferative and non hyperproliferative disorders. In this context, psioarsis, arthritis, inflammation, endometriosis, scarring, begnin prostatic hyperplasia, immunological diseases, autoimmune diseases and immunodeficiency diseases are to be regarded as noncancerous disorders, of which arthritis, inflammation, immunological diseases, autoimmune diseases and immunodeficiency diseases are usually regarded as non hyperproliferative disorders. In this context, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia are to be regarded as cancerous disorders, all of which are usually regarded as hyperproliferative disorders. Especially cancerous cell growth and especially cancerous cell growth mediated by raf-kinase is a disorder which is a target of the present invention. Subject of the present invention therefore are methylene urea derivatives according to the invention as medicaments and/or medicament active ingredients in the treatment and/or the prophylaxis of said disorders and the use of methylene urea derivatives according to the invention for the manufacture of a pharmaceutical for the treatment and/or the prophylaxis of said disorders as well as a method of treatment of said disorders, comprising administering one or more methylene urea derivatives according to the invention to a patient in need of such an administration. Subject of the present invention therefore are methylene urea derivatives according to the invention as medicaments and/or medicament active ingredients in the treatment and/or the prophylaxis said disorders and the use of methylene urea derivatives according to the invention for the manufacture of a pharmaceutical for the treatment and/or the prophylaxis of said disorders as well as a method of treatment of said disorders, comprising administering one or more methylene urea derivatives according to the invention to a patient in need of such an administration.

Accordingly, subject of the present invention are pharmaceutical compositions that contain one or more methylene urea derivatives according to the invention. Subject of the present invention are especially pharmaceutical compositions that contain one or more methylene urea derivatives according to the invention and one or more additional compounds (other than the compounds of the instant invention), preferably selected from the group consisting of physiologically acceptable excipients, auxiliaries, adjuvants, carriers and pharmaceutically active ingredients other than the compounds according to the invention.

Accordingly, subject of the present invention is a process for the manufacture of a pharmaceutical composition, wherein one or more methylene urea derivatives according to the invention and one or more compounds (other than the compounds of the instant invention), preferably selected from the group consisting of carriers, excipients, auxiliaries, adjuvants and pharmaceutically active ingredients other than the compounds according to the invention.

Accordingly, the use of the compounds according to the invention in the treatment of Hyperproliferative disorders is a subject of the instant invention.

Accordingly, the use of the compounds according to the invention for producing a medicament for the treatment of hyperproliferative disorders is a subject of the instant invention.

Above and below, all temperatures are given in ° C. In the examples below, "conventional work-up" means that the organic phase is washed with saturated NaHCO$_3$ solution, if desired with water and saturated NaCl solution, the phases are separated, the organic phase is dried over sodium sulfate and evaporated, and the product is purified by chromatography on silica gel, by preparative HPLC and/or by crystallization.

The present invention relates to methylene urea derivatives of formula I, the use of the compounds of formula I as inhibitors of raf-kinase, the use of the compounds of formula I for the manufacture of a pharmaceutical composition and a method of treatment, comprising administering said pharmaceutical composition to a patient.

EXAMPLES

Experimental Part

Synthesis of the Benzylamine Moieties 4-(4-Pyridinyloxy)benzylamine

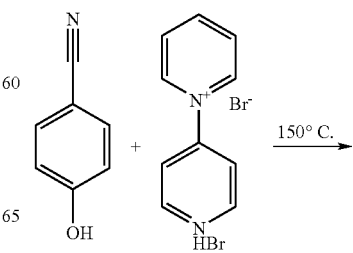

-continued

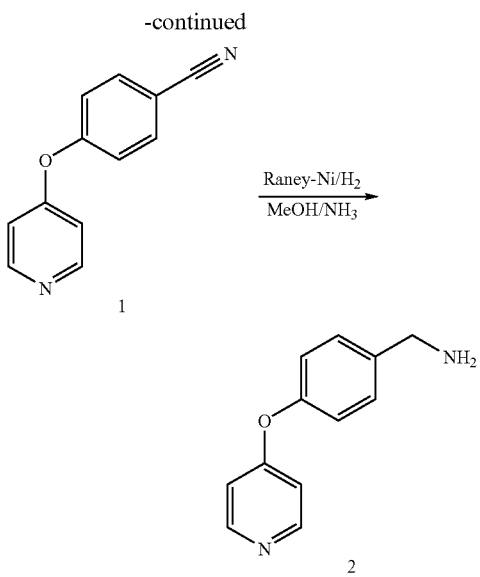

a) 5 g (42 mmol) of 4-hydroxybenzonitrile and 13.36 g (42 mmol) of bipyridine are mixed and heated to 150° C. After the reaction mixture has been stirred at 150° C. for 3 hours, it is cooled, 500 ml of 10% Na$_2$CO$_3$ solution are added, and the mixture is stirred. The resultant precipitate is filtered off with suction, rinsed with 500 ml of water and dried under reduced pressure. Extraction of the aqueous phase with ethyl acetate followed by drying and evaporation gave further product Yield: 3.86 g (47%) of 1, pale-brown solid b) Compound 1 is hydrogenated using Raney nickel in methanolic ammonia solution at 50° C. and 5 bar. The reaction solution is filtered through kieselguhr and rinsed with MeOH, and the filtrate is subsequently evaporated.

Yield: 3.49 g (78%) of 2, brown oil 3-(4-Pyridinyloxy)benzylamine

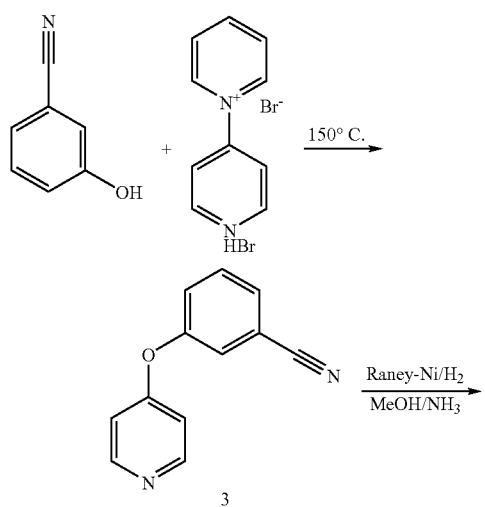

-continued

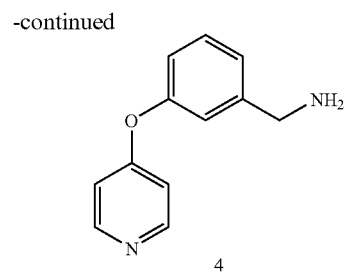

a) 5 g (42 mmol) of 3-hydroxybenzonitrile and 13.36 g (42 mmol) of bipyridine are mixed and heated to 150° C. After the reaction mixture has been stirred at 150° C. for 3 hours, it is cooled, diluted with 600 ml of ethyl acetate and washed with 600 ml of 10% Na$_2$CO$_3$ solution. The organic phase is dried using Na$_2$SO$_4$, filtered and evaporated. The residue is purified by column chromatography (100 g of silica gel; eluent: ethyl acetate:petroleum ether=1:1).

Yield: 2.46 g (35%) of 3, pale-yellow crystals b) Compound 3 is hydrogenated using Raney nickel in methanolic ammonia solution at 50° C. and 5 bar. The reaction solution is filtered through kieselguhr and rinsed with MeOH, and the filtrate is subsequently evaporated.

Yield: 2.33 g (96%) of 4, brown oil 4-(3-Pyridinyloxy)benzylamine

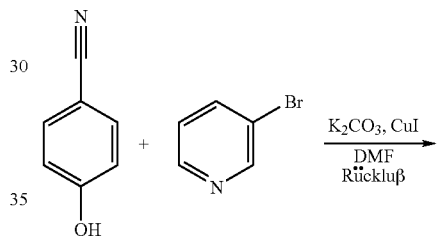

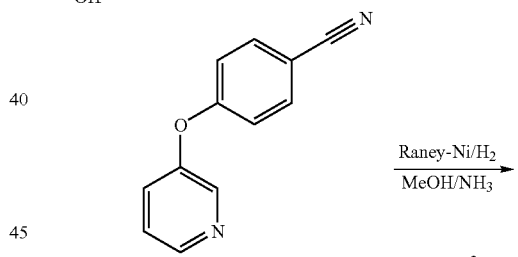

a) 3 g (25 mmol) of 4-hydroxybenzonitrile; 2.44 g (25 mmol) of 3-bromopyridine and 5.71 g (30 mmol) of copper iodide are dissolved in DMF, 6.91 g (50 mmol) of K$_2$CO$_3$ are added, and the mixture is refluxed for 18 hours. The reaction mixture is cooled, 200 ml of dichloromethane are added, and the mixture is stirred for 15 minutes and filtered. The filtrate is washed with water and extracted with 10% HCl solution. The HCl phase is neutralized using NH$_4$OH solution and extracted with dichloromethane. The combined organic phases are washed with NaOH solution (2M), dried using Na$_2$SO$_4$, filtered and evaporated. The residue is purified by column chromatography (25 g of silica gel, eluent: ethyl acetate:petroleum ether=1:2).

Yield: 375 mg (8%) of 5, yellow crystals b) Compound 5 is hydrogenated using Raney nickel in methanolic ammonia solution at 50° C. and 4.8 bar. The reaction solution is filtered through kieselguhr and rinsed with MeOH, and the filtrate is subsequently evaporated.

Yield: 440 mg (97%) of 6, brown oil 3-(3-Pyridinyloxy)benzylamine

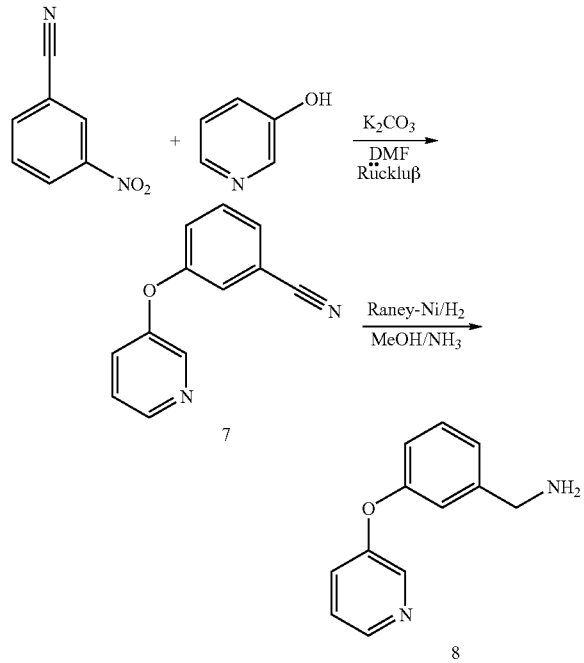

a) 1 g (11 mmol) of 3-hydroxypyridine and 3.26 g (22 mmol) of 3-nitrobenzonitrile are dissolved in DMF, 3.34 g (24 mmol) of potassium carbonate are added, and the mixture is refluxed overnight. The reaction mixture is evaporated, and the residue is taken up in 150 ml of dichloromethane, stirred for 30 minutes and filtered. The filtrate is washed with water and extracted with 10% HCl solution. The HCl phase is neutralized using $NH_4OH$ and extracted with dichloromethane. The combined organic phases are dried using $Na_2SO_4$, filtered and evaporated. The residue is purified by column chromatography (33 g of silica gel, eluent: ethyl acetate:petroleum ether=1:2).

Yield: 956 mg (44%) of 7, yellow oil b) Compound 7 is hydrogenated using Raney nickel in methanolic ammonia solution at 50° C. and 4.8 bar. The reaction solution is filtered through kieselguhr and rinsed with MeOH, and the filtrate is subsequently evaporated.

Yield: 945 mg (97%) of 8, brown oil

Synthesis of the Benzylureas

Variant A 1-(4-Chloro-3-trifluoromethylphenyl)-3-[4-(4-pyridinyloxy)benzyl]urea

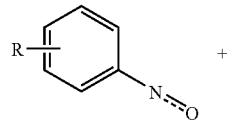

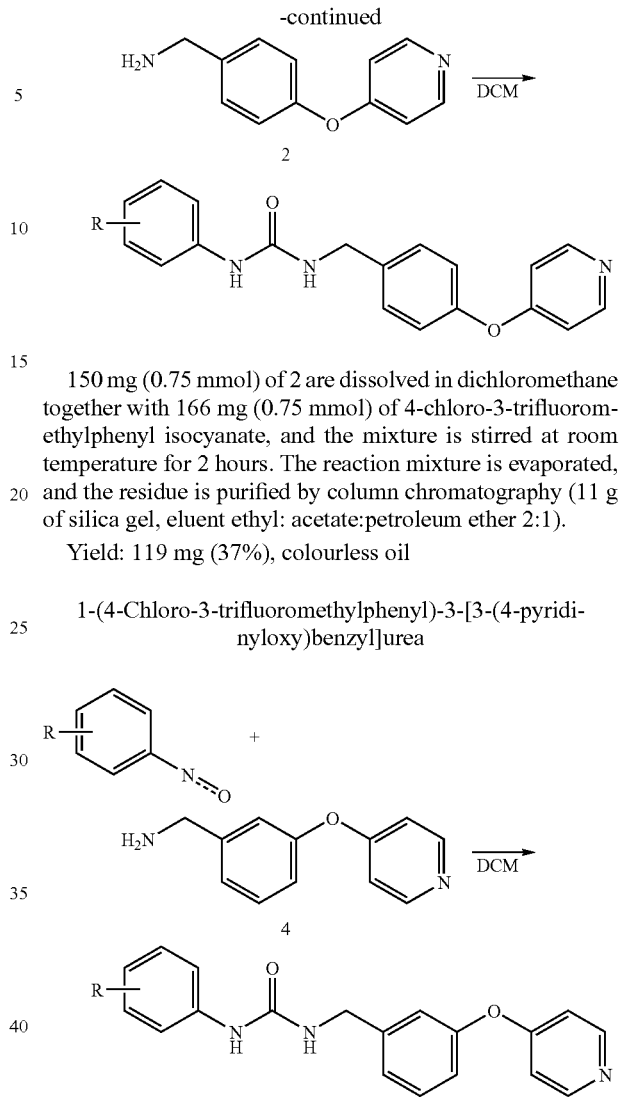

150 mg (0.75 mmol) of 2 are dissolved in dichloromethane together with 166 mg (0.75 mmol) of 4-chloro-3-trifluoromethylphenyl isocyanate, and the mixture is stirred at room temperature for 2 hours. The reaction mixture is evaporated, and the residue is purified by column chromatography (11 g of silica gel, eluent ethyl: acetate:petroleum ether 2:1).

Yield: 119 mg (37%), colourless oil 1-(4-Chloro-3-trifluoromethylphenyl)-3-[3-(4-pyridinyloxy)benzyl]urea 100 mg (0.5 mmol) of 4 are dissolved in dichloromethane together with 133 mg (0.6 mmol) of 4-chloro-3-trifluoromethylphenyl isocyanate and 0.1 ml (0.6 mmol) of N-ethyldiisopropylamine, and the mixture is stirred at room temperature for 2 hours. The resultant precipitate is filtered off with suction, washed with dichloromethane and dried under reduced pressure.

Yield: 201 mg (96%), colourless solid 1-(4-Chloro-3-trifluoromethylphenyl)-3-[4-(3-pyridinyloxy)benzyl]urea

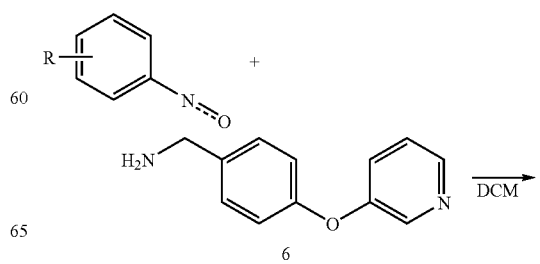

-continued

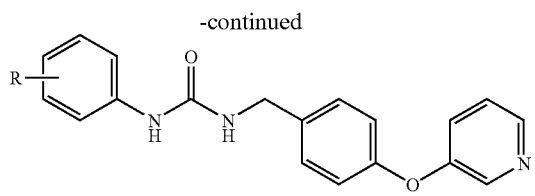

100 mg (0.5 mmol) of 6 are dissolved in dichloromethane together with 111 mg (0.5 mmol) of 4-chloro-3-trifluoromethylphenyl isocyanate. After the reaction mixture has been stirred at room temperature for 4 hours, it is refluxed for 1 hour and subsequently stirred again at room temperature overnight. The reaction mixture is diluted with dichloromethane, extracted with saturated $Na_2HCO_3$ solution, dried using $Na_2SO_4$, filtered and evaporated. The residue is purified by preparative HPLC.

Yield: 40 mg (19%), yellow oil 1-(4-Chloro-3-trifluoromethylphenyl)-3-[3-(3-pyridinyloxy)benzyl]urea

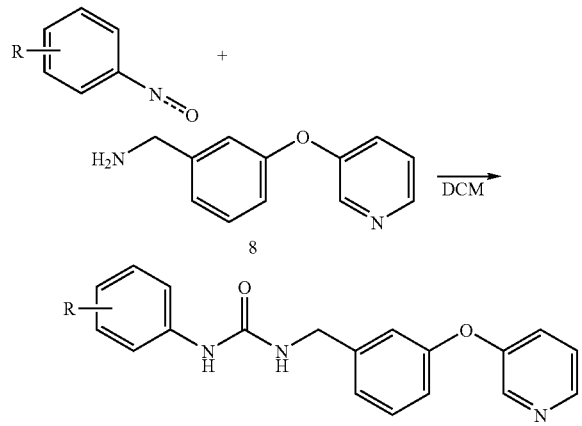

100 mg (0.5 mmol) of 8 are dissolved in dichloromethane together with 111 mg (0.5 mmol) of 4-chloro-3-trifluoromethylphenyl isocyanate. After the reaction mixture has been stirred at room temperature for 4 hours, it is refluxed for 1 hour and subsequently stirred again at room temperature overnight. The reaction mixture is diluted with dichloromethane, extracted with saturated $Na_2HCO_3$ solution, dried using $Na_2SO_4$, filtered and evaporated. The residue is purified by column chromatography (3 g of silica gel, eluent: ethyl acetate:petroleum ether=1:3).

Yield: 34 mg (16%), colourless solid

Variant B 5-t-Butyl-3-isoxazolyl)carbamic acid, 4-nitrophenyl ester

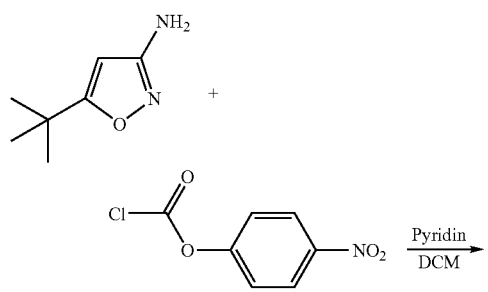

-continued

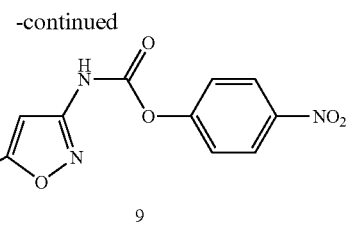

2.91 g (20.76 mmol) of 3-amino-5-tert-butylisoxazole and 1.84 ml (22.83 mmol) of pyridine are dissolved in dichloromethane, and 4.18 g (20.76 mmol) of 4-nitrophenyl chloroformate are added at room temperature. After the reaction mixture has been stirred at room temperature for 2.5 hours, it is evaporated, and the residue is digested with diethyl ether, filtered off with suction and subsequently dried under reduced pressure.

Yield: 5.68 g (90%) of 9, colourless solid.

1-(5-t-Butyl-3-isoxazolyl)-3-[4-(4-pyridinyloxy)benzyl]urea

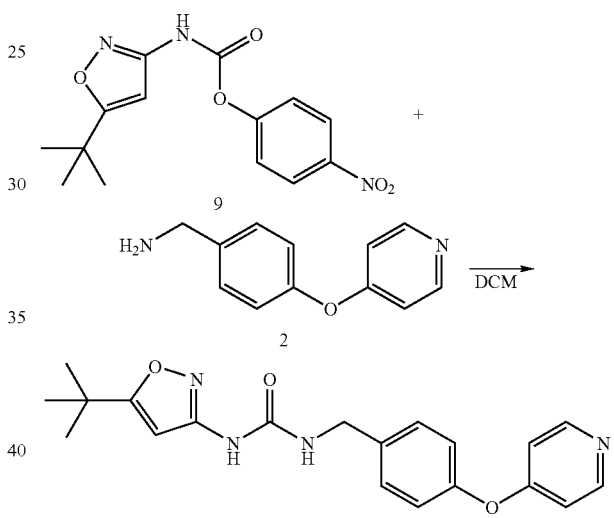

100 mg (0.33 mmol) of 9 and 79 mg (0.39 mmol) of 2 are dissolved in dichloromethane, and the solution is stirred at room temperature for 4 hours. The reaction mixture is evaporated, and the residue is purified by column chromatography (5 g of silica gel, eluent: ethyl acetate).

Yield: 67 mg (56%), colourless solid 1-(5-t-Butyl-3-isoxazolyl)-3-[3-(4-pyridinyloxy)benzyl]urea

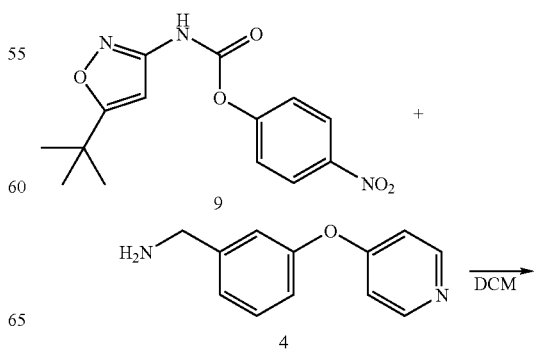

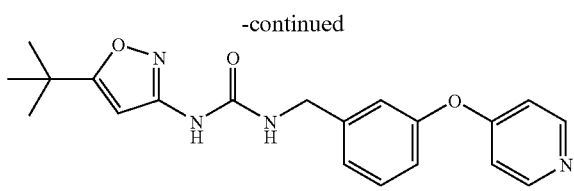

100 mg (0.33 mmol) of 9 and 79 mg (0.39 mmol) of 4 are dissolved in dichloromethane, and the solution is stirred at room temperature for 4 hours. The reaction mixture is evaporated, and the residue is purified by column chromatography (5 g of silica gel, eluent: ethyl acetate).

Yield: 33 mg (27.5%), colourless oil

Synthesis of the Substituted Benzyl Amino Building Blocks

4-[(4-Aminomethyl)phenoxy]-2-pyridine carbonic acid, methylamide

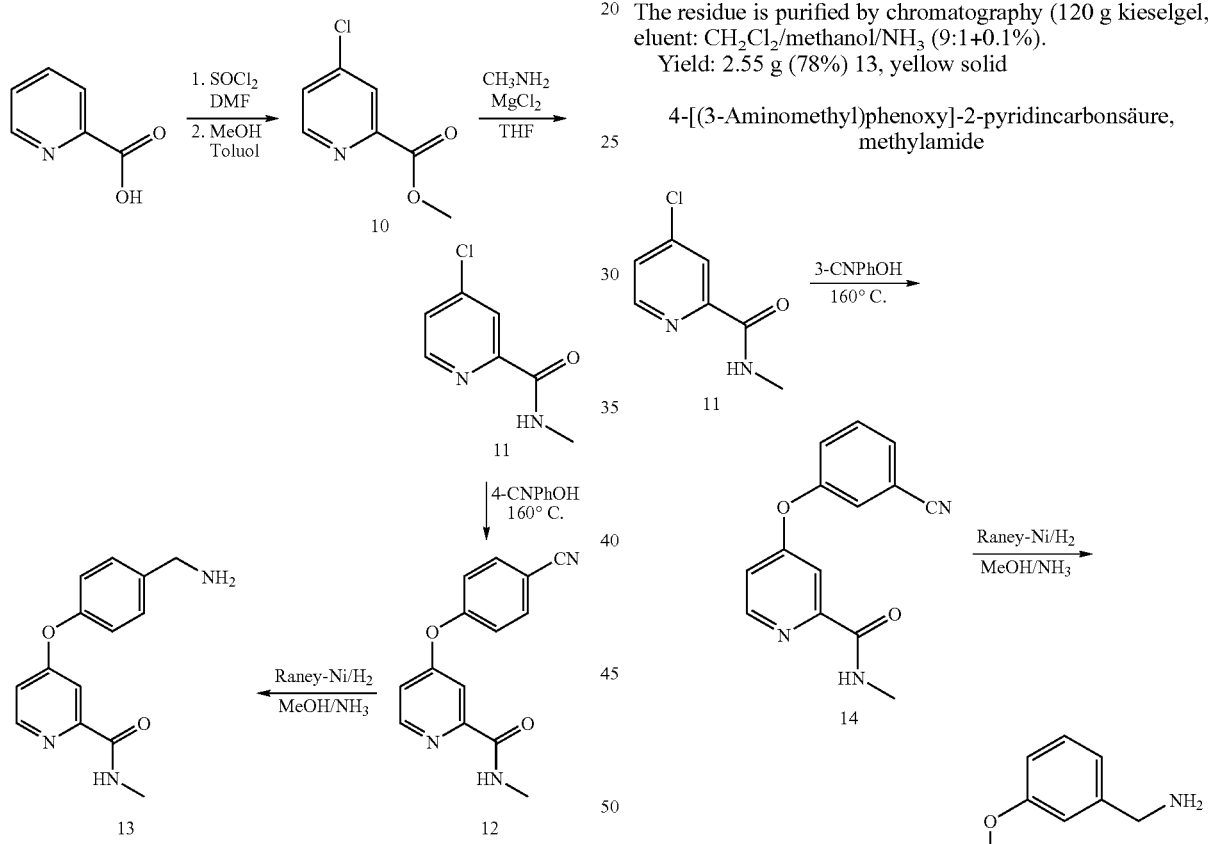

60 ml Thionylchloride are heated to a temperature of 45° C. under a nitrogen atmosphere and 1.83 ml Dimethylformamide is added slowly. 20 g Pyridin-2-carbonic acid is added to the solution in portions, the reaction mixture is stirred another 15 min at 45° C. and then heated to 80° C. for 24 hrs. The reaction mixture is evaporated and the resulting residue treated with dry toluene as a carrier and then evaporated. This procedure is repeated several times. The resulting oil is dissolved in toluene, cooled to 0° C., slowly treated with methanol and stirred for one hour. The resulting precipitate is filtered by suction, washed with toluene and recrystallised from acetone.

Yield: 15 g (44%) 10, colourless crystals 13 g (62.5 mmol) 10 are dissolved together with 2.98 g (31.24 mmol) dry Magnesiumchloride in THF. After 5 min 110 ml methyl amine solution (2M in THF) are added dropwise within 10 min and the suspension stirred for 2 h at room temperature. 120 ml water und 63 mL 1M HCl— solution are added and the mixture is extracted three times with ethyl acetate. The combined organic phases are washed with brine, dried with $Na_2SO_4$, filtered and evaporated.

Yield: 10.5 g (98.5%) 11, colourless oil.

4.15 g (24.32 mmol) 11 are heated to a temperature of 160° C. together with 5.8 g (48.65 mmol) 4-Cyanophenol for 18 hrs in an argon atmosphere. The reaction mixture is cooled down, diluted with ethyl acetate, washed consecutively twice with 30 ml 2N NaOH— solution, twice with 30 ml Wasser and once with 30 ml brine; dried over $Na_2SO_4$, filtered and evaporated. The residue is digested with diethyl ether, filtered by suction, washed with diethyl ether:petrol ether=1:1 and dried in vacuo.

Yield: 3.27 g (52%) 12, brownish solid.

3.27 g (12.65 mmol) 12 are hydrogenated in methanolic ammonia solution in the presence of Raney nickel at 45° C. and 5 bar pressure. The reaction mixture is filtered over kieselguhr, washed with MeOH and the filtrate is evaporated. The residue is purified by chromatography (120 g kieselgel, eluent: $CH_2Cl_2$/methanol/$NH_3$ (9:1+0.1%).

Yield: 2.55 g (78%) 13, yellow solid

4-[(3-Aminomethyl)phenoxy]-2-pyridincarbonsäure, methylamide

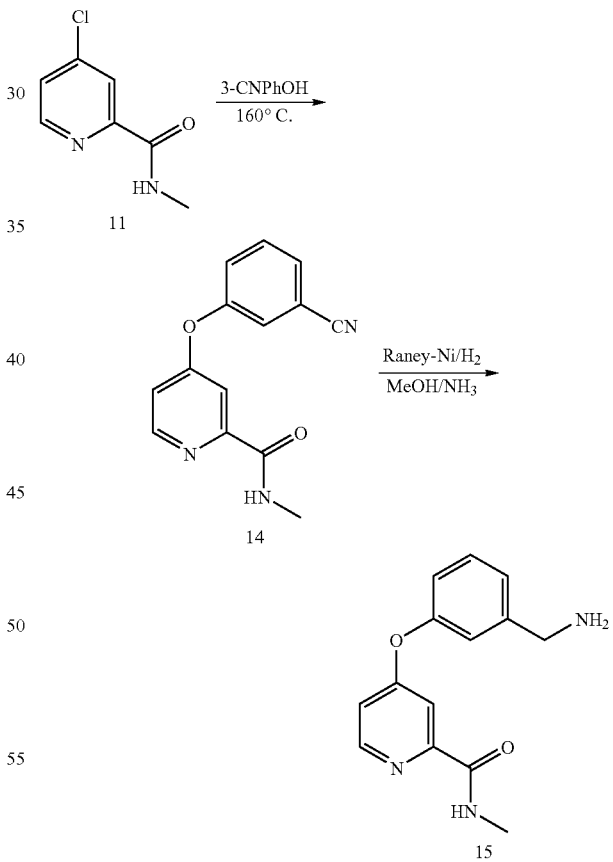

5 g (29.31 mmol) 11 are heated together with 6.98 g (58.62 mmol) 3-Cyanophenol at a temperature of 160° C. in an argon atmosphere. After 18 hrs, further 3.49 g (29.30 mmol) 3-Cyanophenol are added and heating is continued for 6 hrs at 160° C. The reaction mixture is cooled, diluted with ethyl acetate, washed consecutively twice with 40 ml 2N NaOH— solution, twice with 35 ml water and once with 30 ml brine, dried over $Na_2SO_4$, filtered and evaporated. The residue is digested with diethyl ether, filtered by suction, washed with diethyl ether: petrol ether=2:1 and dried in vacuo. Another portion of product is obtained by chromatography of the mother liquor (95 g silica gel, eluent: ethyl acetat:petrol ether=7:3).

Yield: 3.58 g (46%) 14, brownish solid 3.16 g (12.65 mmol) 14 are hydrogenated in methanolic ammonia solution in the presence of Raney nickel at 45° C. and 5 bar pressure. The reaction mixture is filtered over kieselguhr, washed with MeOH and the filtrate is evaporated. The residue is purified by chromatography (120 g silica gel, eluent: $CH_2Cl_2$/methanol/$NH_3$ (9:1+0.1%).

Yield: 2.67 g (86%) 15, light brownish oil

Synthesis of Benzyl Ureas

Variant A

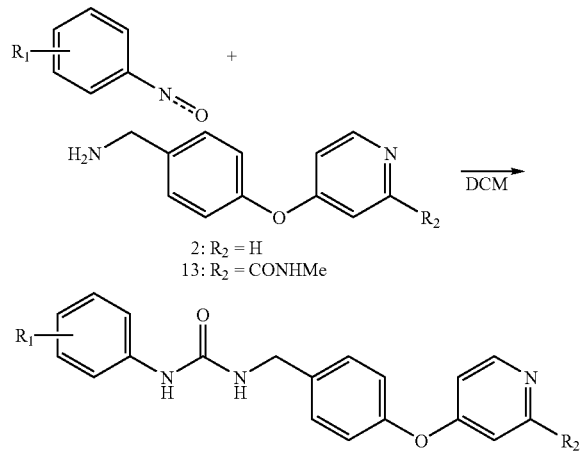

2: $R_2$ = H
13: $R_2$ = CONHMe

A solution of 0.16 mmol isocyanate and 0.16 mmol benzyl amine 2 or 13 in dichlormethane is stirred 16 h at room temperature. Depending to the respective reaction course, the working up of the reaction mixtures is done according to one of the variations given below:

Variant A: The resulting precipitate is filtered by suction, washed consecutively with dichlormethane, ethyl acetate and diethyl ether and dried in vacuo at 40° C.

Variant B: The reaction mixture is evaporated and the residue is treated with 0.5 ml acetonitrile. The resulting precipitate is filtered by suction, washed with acetonitrile and diethyl ether and dried in vacuo at 40° C.

Variant C: The reaction mixture is evaporated, the oily residue taken up in 2 ml acetonitrile:water=1:1, frozen and then freeze dried for 16 hrs.

Variant D: The reaction mixture is evaporated to dryness. The residue is dried in vacuo at 40° C.

Variant E: The reaction mixture is evaporated to dryness. The residue is purified by chromatography (4 g silica gel, eluent: dichlormethane:methanol=98:2 to 95:5). The obtained crude product is taken up in 1.2 ml acetonitrile: water=2:1, frozen and freeze dried for 16 hrs.

Variant F: The reaction mixture is evaporated to dryness, the residue dissolved in 15 ml ethyl acetate and extracted once with 10 ml 25% hydrochloric acid. The water phase is separated, made alkaline with 32% sodium hydroxide solution (pH=9-10) and extracted three times, each time with 10 ml ethyl acetate. The combined organic phases are washed with 15 ml brine, dried over $Na_2SO_4$, filtered and the filtrate evaporated. The residue is dried at 40° C. overnight.

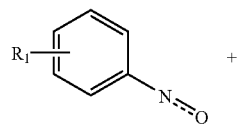

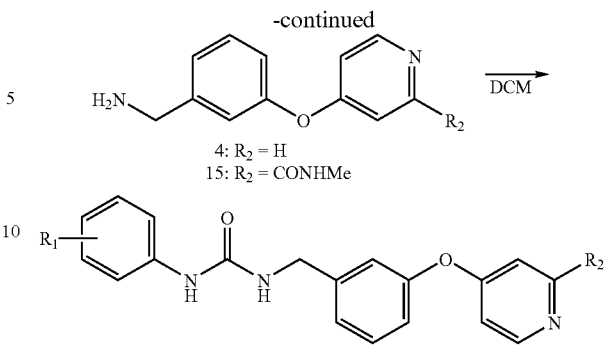

4: $R_2$ = H
15: $R_2$ = CONHMe 0.16 mmol isocyanate and 0.16 mmol benzyl amine 4 or 15 are, dissolved in dichlormethane gelöst and stirred for 16 hrs at room temperature. Depending to the respective reaction course, the working up of the reaction mixtures is done according to one of the variations given below:

Variant A: The resulting precipitate is filtered by suction, washed consecutively with dichlormethane, ethyl acetate and diethyl ether and dried in vacuo at 40° C.

Variant B: The reaction mixture is evaporated. The residue is dried in vacuo at 40° C.

Variant C: The reaction mixture is evaporated to dryness. The residue is purified by chromatography (4 g silica gel, eluent: dichloromethane:methanol=98:2 bis 95:5). The obtained crude product is taken up in 1.2 ml acetonitrile: water=2:1, frozen and freeze dried for 16 hrs.

Variant D: The reaction mixture is evaporated, the oily residue taken up in 2 ml acetonitrile:water=1, frozen and freeze dried for 16 hrs.

Variant E: The reaction mixture is evaporated, the residue digested with 1 ml ethyl acetate:diethyl ether=2:1, filtered by suction, washed with diethyl ether and dried in vacuo at 40° C.

Variant F: The reaction mixture is evaporated and the residue is treated with 0.5 ml acetonitrile. The resulting precipitate is filtered by suction, washed with acetonitrile and diethyl ether and dried in vacuo at 40° C.

Variante G: The reaction mixture is evaporated to dryness, the residue dissolved in 15 ml ethyl acetate and extracted once with 10 ml 25% hydrochloric acid. The water phase is separated, made alkaline with 32% sodium hydroxide solution (pH=9-10) and extracted three times, each time with 10 ml ethyl acetate. The combined organic phases are washed with 15 ml brine, dried over $Na_2SO_4$, filtered and the filtrate evaporated. The residue is dried at 40° C. overnight.

Variant B b) Synthesis of the Trichloro Aceto Anilides

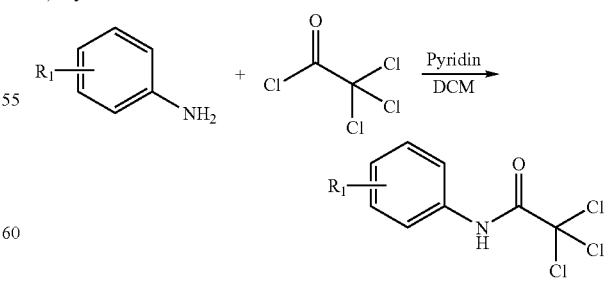

1 g of the substituted aniline and 1.3 eq. pyridine are dissolved in dichloromethane, cooled to 0° C. and 1.1 eq. trichloro acetic acid chloride is slowly added. After the addition is completed, the reaction mixture is allowed warm up to room temperature and stirring is continued for 1 h. Then the reaction mixture is extracted 1N hydrochloric acid and water consecutively and the organic phase is dried over Na$_2$SO$_4$, filtered and evaporated.

R$_1$=2-OMe, 5-CF$_3$; colourless solid, yield: 93%
R$_1$=3-CF$_3$, 4-Br: colourless solid, yield: 100%
R$_1$=3-OCF$_3$; yellow solid, yield: 82%
R$_1$=2-OMe, 4-Me, 5-Cl; beige solid, yield: 84%
R$_1$=2-OMe, 4-Cl, 5-CF$_3$; yellow oil, either: 85%
R$_1$=2-SMe, 5-CF$_3$; yellow solid, yield: 92%
R$_1$=2-OMe, 5-Me; beige solid, yield: 99%
R$_1$=3-Me, 4-Cl; colourless solid, yield: 97% b) Synthesis of the Final Products

2: R$_2$ = H
13: R$_2$ = CONHMe 0.15 mmol of the substituted trichloro aceto anilide and 0.15 mmol benzyl amine 2 or 13 are dissolved in DMSO, 0.15 mmol DBU are added and the mixture heated to 80° C. for 2.5-5.5 hrs. Depending to the respective reaction course, the working up of the reaction mixtures is done according to one of the variations given below.

Variant A: The reaction mixture is cooled, diluted with dichloromethane and extracted with 1N hydrochloric acid. The water phase is made alkaline with 2N sodium hydroxide solution and extracted several times with ethyl acetate. The combined organic phases are dried over Na$_2$SO$_4$, filtered and evaporated.

Variant B: The reaction mixture is cooled, diluted with dichloromethane and extracted with 1N hydrochloric acid. The water phase is made alkaline with 2N sodium hydroxide solution and extracted several times with ethyl acetate. The combined organic phases are dried over Na$_2$SO$_4$, filtered and evaporated. The residue is purified by chromatography (5 g silica gel, eluent: dichloromethane:methanol=98:2 to 95:5).

Variante C: The reaction mixture is cooled, diluted with dichloromethane and washed with water. The organic phases what dried over Na$_2$SO$_4$, filtered and evaporated. The residue is digested with a small amount of water, the resulting precipitate filtered by suction and dried in vacuo at 40° C.

Variante D: The reaction mixture is cooled, diluted with dichloromethane, extracted consecutively twice with 1N hydrochloric acid and with water, dried over Na$_2$SO$_4$, filtered and evaporated.

4: R$_2$ = H
15: R$_2$ = CONHMe 0.15 mmol of the substituted trichloro aceto anilide and 0.15 mmol benzyl amine 4 or 15 are dissolved in DMSO, 0.15 mmol DBU are added and the mixture heated to 80° C. for 2.5-5.5 hrs. Depending to the respective reaction course, the working up of the reaction mixtures is done according to one of the variations given below:

Variant A: The reaction mixture is cooled, diluted with dichloromethane and extracted with 1N hydrochloric acid. The water phase is made alkaline with 2N sodium hydroxide solution and extracted several times with ethyl acetate. The combined organic phases are dried over Na$_2$SO$_4$, filtered and evaporated.

Variant B: The reaction mixture is cooled, diluted with dichloromethane and extracted with 1N hydrochloric acid. The water phase is made alkaline with 2N sodium hydroxide solution and extracted several times with ethyl acetate. The combined organic phases are dried over Na$_2$SO$_4$, filtered and evaporated. The residue is purified by chromatography (5 g silica gel, eluent: dichloromethane:methanol=98:2 to 95:5).

Variant C: The reaction mixture is cooled, diluted with dichloromethane and washed with water. The organic phases whas dried over Na$_2$SO$_4$, filtered and evaporated. The residue is digested with a small amount of water, the resulting precipitate filtered by suction and dried in vacuo at 40° C.

Variante C a) Synthesis of the Anilines 2 mmol 4-Fluoro-3-nitrobenzotrifluoride are dissolved in dimethyl sulfoxide (DMSO), treated with 2-2.4 mmol amine and stirred at 50° C. overnight. The reaction mixture is diluted with dichloromethane and extracted twice with water. The organic phase is dried over Na$_2$SO$_4$, filtered and evaporated in vacuo. The obtained crude product is employed in the next synthesis step without further purification.

R$_1$, R$_2$=Me; orange oil, yield: 96%
R$_1$, R$_2$=Et; orange oil, yield: 97%
R$_1$=Me, R$_2$=(CH$_2$)$_2$OCH$_3$; orange oil, yield: 91.5%
R$_1$=Me, R$_2$=(CH$_{22}$N(CH$_3$)$_2$; orange oil, yield: 85%

The accordingly obtained nitro compounds are hydrogenated in THF in the presence of H$_2$ and Pd/C (5%) at room temperature overnight. Then the catalyst is separated by filtration and the filtrate evaporated to yield the respective aniline.

R$_1$, R$_2$=Me; yellow oil, yield: 92%
R$_1$, R$_2$=Et; yellow oil, yield: 92%

R₁=Me, R₂=(CH₂)OCH₃; red oil, yield: 99%
R₁=Me, R₂=(CH₂)₂N(CH₃)₂; yellow oil, yield 98.5%
R₁=Me, R₂=(CH₂)₂N(CH₃)₂; yellow oil, yield 98.5%

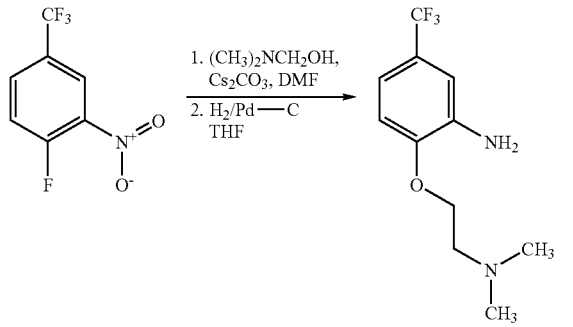

b) Synthesis of the Final Products

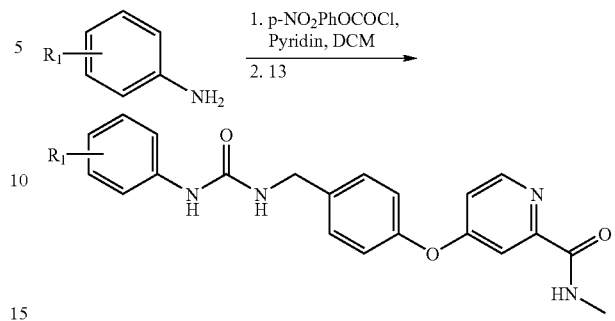

2 mmol 4-Fluor-3-nitrobenzotrifluoride are dissolved in dimethylformamide, treated with 2.2 mmol 2-(Dimethylamino)ethanol and 4.6 mmol cesium carbonate and stirred at room temperature. After 48 h, additional 1 mmol 2-(Dimethylamino)ethanol are added and at the reaction mixture is stirred at 40° C. overnight. The reaction mixture is diluted with ethyl acetate and the resulting solution washed twice with water. The organic phase is dried over Na₂SO₄, filtered, treated with dry toluene as a carrier and then evaporated several times using a Rotavapor and then evaporated for dryness. The obtained residue is purified by chromatography (35 g silica gel, eluent: dichloromethane:acetone=100:0 to 90:10).

Yield: 43%, yellow oil

The accordingly obtained nitro compound is hydrogenated in THF in the presence of H₂ and Pd/C (5%) at room temperature overnight Then the catalyst is separated by filtration and the filtrate evaporated to yield the respective aniline.

Yield: 97%, yellow crystals

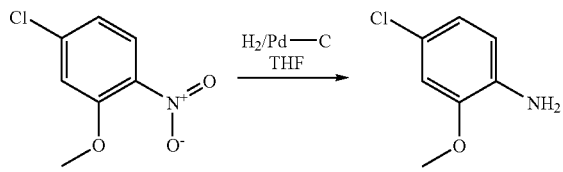

5-Chlor-2-nitroanisol in THF are hydrogenated in the presence of H₂ and Raney nickel at room temperature overnight. The catalyst is separated by filtration and the filtrate evaporated to dryness. The residue is purified by chromatography (35 g silica gel, eluent: dichloromethane:methanol=99:1).

Yield: 69.5%, brown oil 0.3 mmol aniline are dissolved in dichloromethane, consecutively treated with 0.33 mmol pyridine and 0.3 mmol of the p-Nitrophenylester of chloro formic acid and stirred at room temperature. After the reaction is finished, 0.33 mmol 13, suspended in dichloromethane, and 0.3 mmol DIPEA are added und and the resulting solution stirred at room temperature. Depending to the respective reaction course, the working up of the reaction mixtures is done according to one of the variations given below:

Variante A: The reaction mixture is diluted with dichloromethane and washed three times with water. The organic phase is dried over Na₂SO₄, filtered and evaporated. The residue is recrystalized from ethylacetate.

Variant B: The reaction mixture is diluted with dichloromethane and washed three times with water. The organic phase is dried over Na₂SO₄, filtered and evaporated. The residue is purified by chromatography (10 g silica gel, eluent: petrol ether:ethyl acetate=100:0 to 50:50).

Variant C: The reaction mixture is diluted with dichloromethane and washed three times with water. The organic phase is dried over Na₂SO₄, filtered and evaporated. The residue is purified by chromatography (10 g silica gel, eluent: dichlormethane:methanol=100:0 to 95:5).

Variante D: The reaction mixture is treated with water, stirred and then the water phase discarded. The organic phase is washed once with water, once with brine, dried over Na₂SO₄, filtered and evaporated. The residue is taken up in hot acetonitrile. On cooling, a white precipitate is obtained which is filtered by suction and washed with diethylether. After some time, and additional portion of product precipitated from the mother liquor which is washed with diethylether/acetonitril (9:1). The combined products are dried in vaccuo at 40° C.

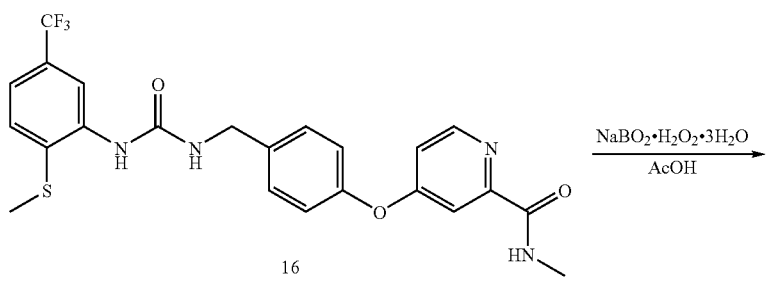

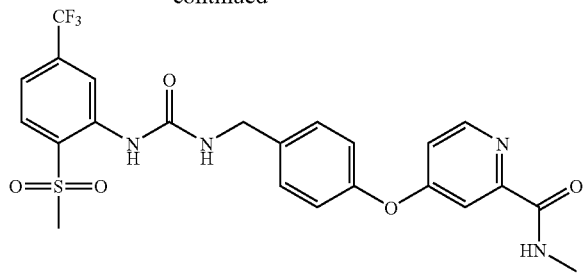

A solution of 16 in acetic acid is treated with 3 eq. sodium perborate trihydrate and heated to 55° C. After stirring for 2 hrs at 55° C. the reaction mixture is allowed to stand overnight. Then, additional 1.5 eq. Sodium perborate trihydrate is added and the reaction mixture is stirred for another 4 hrs at 55° C. Then the reaction mixture is cooled and poured onto ice. After multiple extraction of the reaction mixture with ethyl acetate, the combined organic phases are washed twice with 2 N sodium hydroxide solution, once with water, dried over $Na_2SO_4$, filtered and evaporated. The residue is purified by chromatography (4 g silica gel, eluent: ethyl acetate:n-heptane=4:6 to 8:2).

Yield: 58%, colourless crystals

Synthesis of Methylene Urea Derivatives Substituted on the Methylene Moiety

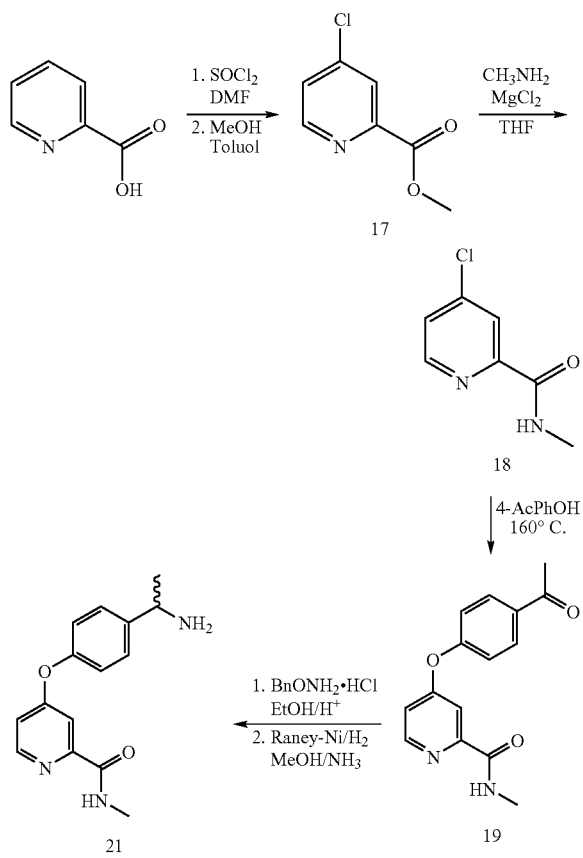

60 ml thionyl chloride are heated to 45° C. under a nitrogen atmosphere and treated slowly with 1.83 ml dimethylformamide. To this solution, 20 g pyridine-to-carbonic acid are added in portions and the reaction mixture stirred another 45 minutes at the same temperature and then heated to 80° C. for 24 hours. The reaction mixture is evaporated and the resulting residue treated with dry toluene as a carrier and then evaporated. This procedure is repeated several times. The resulting oil is dissolved in toluene, cooled to 0° C., slowly treated with methanol and stirred for one hour. The resulting precipitate is filtered by suction, washed with toluene and recrystallised from acetone.

Yield: 15 g (45%) of compound 17, colourless crystals 13 g (62.5 mmol) of compound 17 are dissolved in THF together with 2.98 g (31.24 mmol) dry $MgCl_2$. After five minutes, 110 ml methyl amine-solution (2M THF) are added within ten minutes and the resulting suspension stirred for two hours at room temperature. The reaction mixture is treated with 120 ml water and 63 ml 1N hydrochloric acid and extracted three times with ethyl acetate. The combined organic phases are washed with brine, dried over $Na_2SO_4$, filtered and evaporated.

Yield: 10.5 g (98.5%) of compound 18, colourless oil.

440 mg (2.58 mmol) of compound 18 are heated up together with 1.05 g (7.74 mmol) 4-Hydroxy-acetophenon in an Argon atmosphere for 18 hours. The reaction mixture is cooled, diluted with ethyl acetate, washed three times with 2N sodium hydroxide solution and twice with water, dried over $Na_2SO_4$, filtered and evaporated. The residue is purified by chromatography (10 g silica gel, eluent: ethyl acetate/n-heptane=4:6 to 7:3). Further product is isolated by crystallising the mixed fractions with petrol ether/diethyl ether.

Yield: 344 mg (49%) of compound 19, colourless solid 1 mg (0.37 mmol) of compound 19 is suspended in 2 ml ethanol together with 59 mg (0.37 mmol) O-Benzyl-hydroxylamine and treated with one drop concentrated sulphuric acid. The resulting clear solution, is heated under reflux for 16 hours and then evaporated to dryness. The yellowish residue is treated with water, made alkaline with 1N sodium hydroxide solution (pH=8-9) and extracted twice with ethyl acetate. The combined organic phases are dried over $Na_2SO_4$, filtered and evaporated.

Yield: 151 mg (99%) of compound 20, slightly yellow oil 3.46 g (9.22 mmol) of compound 20 are hydrogenated at room temperature and a pressure of 5 bar in methanolic ammonium solution in the presence of Raney nickel. The reaction mixture is filtered over kieselguhr, washed with methanol and the filtrate is evaporated. The residue is purified by chromatography (120 g silica gel, eluent: $CH_2Cl_2$/methanol/$NH_3$=94:6:0.1).

Yield: 2.29 g (91%) of compound 21, slightly yellow solid

Synthesis of the Methylene Urea Derivatives Substituted on the Methylene Moiety:

Method A

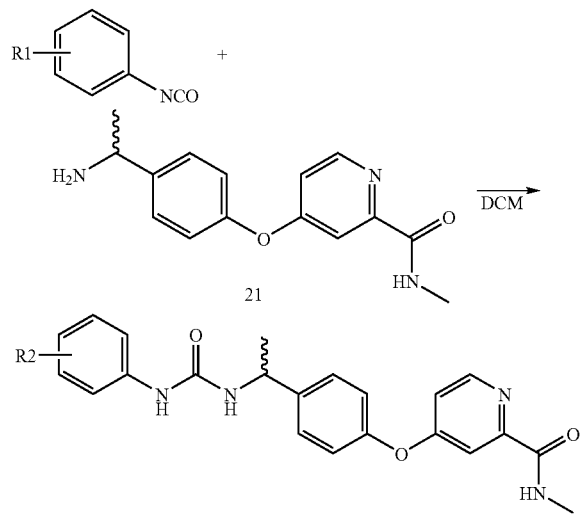

0.16 g isocyanate and 0.16 mmol benzyl amine are diluted in dichloromethane and stirred overnight at room temperature. Depending to the respective reaction course, the working up of the reaction mixtures is done according to one of the variations given below:

Variant A: The resulting precipitate is filtered by suction, washed with little dichloromethane and dried in vacuo at 40° C.

Variant B: The reaction mixture is evaporated and the oily residue taken up in acetonitrile:water=2:1, frozen and freeze dried overnight.

Variant C: The reaction mixture is evaporated to dryness and the residue dried in vacuo at 40° C.

Method B a) Synthesis of the Trichloro Aceto Anilides

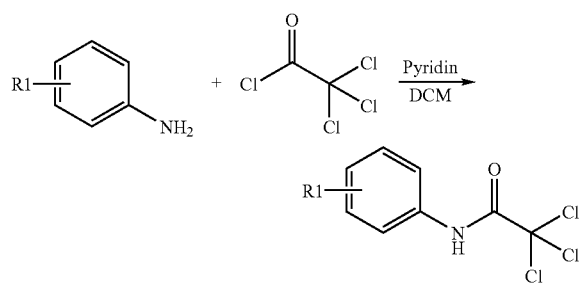

1 g substituted aniline and 1.3 eq. pyridine are dissolved in dichloromethane, cooled to 0° C. and 1.1 eq. trichloro acetic acid chloride is slowly added. After the addition is completed, the reaction mixture is allowed warm up to room temperature and stirring is continued for 1 h. Then the reaction mixture is extracted 1M hydrochloric acid and water consecutively and the organic phase is dried over $Na_2SO_4$, filtered and evaporated.

$R_1$=2-OMe, 5-$CF_3$; colourless solid, yield: 93%

$R_1$=3-$CF_3$, 4-Br; colourless solid, yield: 100%

$R_1$=3-$OCF_3$; yellow solid, yield: 82% b) Synthesis of the Final Products

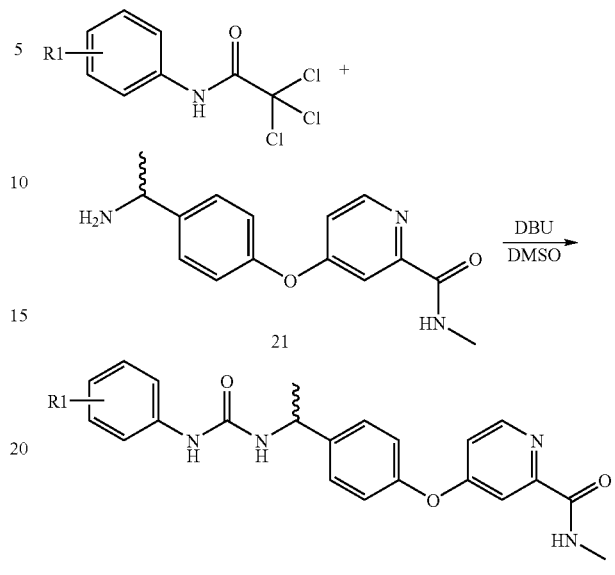

0.15 mmol of the substituted trichloro aceto anilide and 0.15 mmol benzyl amine 5 are dissolved in DMSO, 0.15 mmol DBU are added and the mixture heated to 80° C. for 2.5-34 hrs. Depending to the respective reaction course, the working up of the reaction mixtures is done according to one of the variations given below:

Variante A: The reaction mixture is cooled, diluted with dichloromethane and washed consecutively twice with 1N hydrochloric acid and with water, dried over $Na_2SO_4$, filtered and evaporated. The residue is digested with a small amount of water, the resulting precipitate filtered by suction, washed with diethyl ether and dried in vacuo at 40° C.

Variante B: The reaction mixture is cooled, diluted with dichloromethane, extracted consecutively twice with 1N hydrochloric acid and with water, dried over $Na_2SO_4$, filtered and evaporated. The residue is purified by chromatography (5 g silica gel, eluent: ethyl acetate/n-heptane=4:6 to 6:4, taken up in acetonitrile: water=2:1, frozen and freeze dried overnight.

HPLC Method:
Gradient: 5.5 min; flow rate: 2.75 ml/min from 90:10 to 0:100$H_2O$/ACN
Water+TFA (0.01% by vol.); acetonitrile+TFA (0.01% by vol.)
Column: Chromolith SpeedROD RP 18e 50-4.6
Wavelength: 220 nm, Rt=Retention time.

$^a$HPLC Method:
Gradient: 9 min; flow rate: 1.5 m/min from 80:20 to 0:100$H_2O$/ACN Water+TFA (0.01% by vol.); acetonitrile+TFA (0.01% by vol.)
Column: Lichrospher RP-select-B (5 μm/125 mm)
Wavelength: 220 nm; Rt=Retention time.

The compounds (1) to (224) as described above can preferably be produced according to the procedures described herein or in an analogous manner thereof.

The compounds (225) to (449) as described above can preferably be produced according to the procedures described herein, especially according to the ones for producing methylene urea derivatives being substituted on the methylene moiety, or in an analogous manner thereof.

The compounds (450) to (672) as described above can preferably be produced according to the procedures described herein, especially according to the ones for producing methylene urea derivatives being substituted on the methylene moiety, or in an analogous manner thereof.

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. It is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

Example F

Coated Tablets

Analogously to Example E, tablets are pressed and are then coated in a customary manner using a coating of sucrose, potato starch, talc, tragacanth and colourant.

Example G

Capsules 2 kg of active compound of the formula I are dispensed into hard gelatin capsules in a customary manner such that each capsule contains 20 mg of the active compound.

Example H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

The invention claimed is:
1. A compound of formula II,

II wherein
$Ar^1$ is phenyl,
$Ar^2$ is pyridinyl,
$R^6$, $R^7$ are independently H or A,
$R^8$, $R^9$ and $R^{10}$ are independently selected from the group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOOR^{13}$, $(CH_2)_nCOR^{13}$, $(CH_2)_nCONR^{11}R^{12}$, $(CH_2)_nNR^{11}COR^{13}$, $(CH_2)_nNR^{11}CONR^{11}R^{12}$, $(CH_2)_nNR^{11}SO_2A$, $(CH_2)_nSO_2NR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, CH=N—OA, $CH_2CH=N—OA$, $(CH_2)_nNHOA$, $(CH_2)_nCH=N—R^{11}$, $(CH_2)_nOC(O)NR^{11}R^{12}$, $(CH_2)_nNR^{11}COOR^{13}$, $(CH_2)_nN(R^{11})CH_2CH_2OR^{13}$, $(CH_2)_nN(R^{11})CH_2CH_2OCF_3$, $(CH_2)_nN(R^{11})C(R^{13})HCOOR^{12}$, $(CH_2)_nN(R^{11})C(R^{13})HCOR^{11}$, $(CH_2)_nN(R^{11})CH_2N(R^{12})CH_2COOR^{11}$, $(CH_2)_nN(R^{11})CH_2CH_2NR^{11}R^{12}$, CH=CHCOOR$^{13}$, CH=CHCH$_2$NR$^{11}$R$^{12}$, CH=CHCH$_2$NR$^{11}$R$^{12}$, CH=CHCH$_2$OR$^{13}$, $(CH_2)_nN(COOR^{13})COOR^{14}$, $(CH_2)_nN(CONH_2)COOR^{13}$, $(CH_2)_nN(CONH_2)CONH_2$, $(CH_2)_nN(CH_2COOR^{13})COOR^{14}$, $(CH_2)_nN(CH_2CONH_2)COOR^{13}$, $(CH_2)_nN(CH_2CONH_2)CONH_2$, $(CH_2)_nCHR^{13}COR^{14}$, $(CH_2)_nCHR^{13}COOR^{14}$, $(CH_2)_nCHR^{13}CH_2OR^{14}$, $(CH_2)_nOCN$ and $(CH_2)_nNCO$,
wherein
$R^{11}$ $R^{12}$ are independently selected from the group consisting of H, A and $(CH_2)$,
$R^{13}$, $R^{14}$ are independently selected from the group consisting of H, Hal, A and $(CH_2)_mAr^4$,
A is selected from the group consisting of alkyl, alkenyl, cycloalkyl, alkylenecycloalkyl, alkoxy and alkoxyalkyl,
$Ar^3$, $Ar^4$ are independently aromatic hydrocarbon residues comprising 5 to 12 carbon atoms which are optionally substituted by one or more substituents, selected from the group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2R^{15}R^{16}$, $S(O)_uA$ and $OOCR^{15}$,
$R^{15}$, $R^{16}$ are independently selected from the group consisting of H, A, and $(CH_2)_mAr^6$, wherein
$Ar^6$ is a 5- or 6-membered aromatic hydrocarbon which is optionally substituted by one or more substituents selected from the group consisting of methyl, ethyl, propyl, 2-propyl, tert.-butyl, Hal, CN, OH, $NH_2$ and $CF_3$,
k, n and m are independently of one another 0, 1, 2, 3, 4, or 5;
X is O,
Y is O or S,
p, r are independently 0, 1, 2, 3, 4 or 5,
q is 0, 1, 2, 3 or 4, u is 0, 1, 2 or 3,
and
Hal is selected from the group consisting of F, Cl, Br and I;
and a pharmaceutically acceptable salt thereof.

2. The compound according to claim 1, selected from the compounds of formula IIc, IIe, IIg, IIh, IIi and IIj,

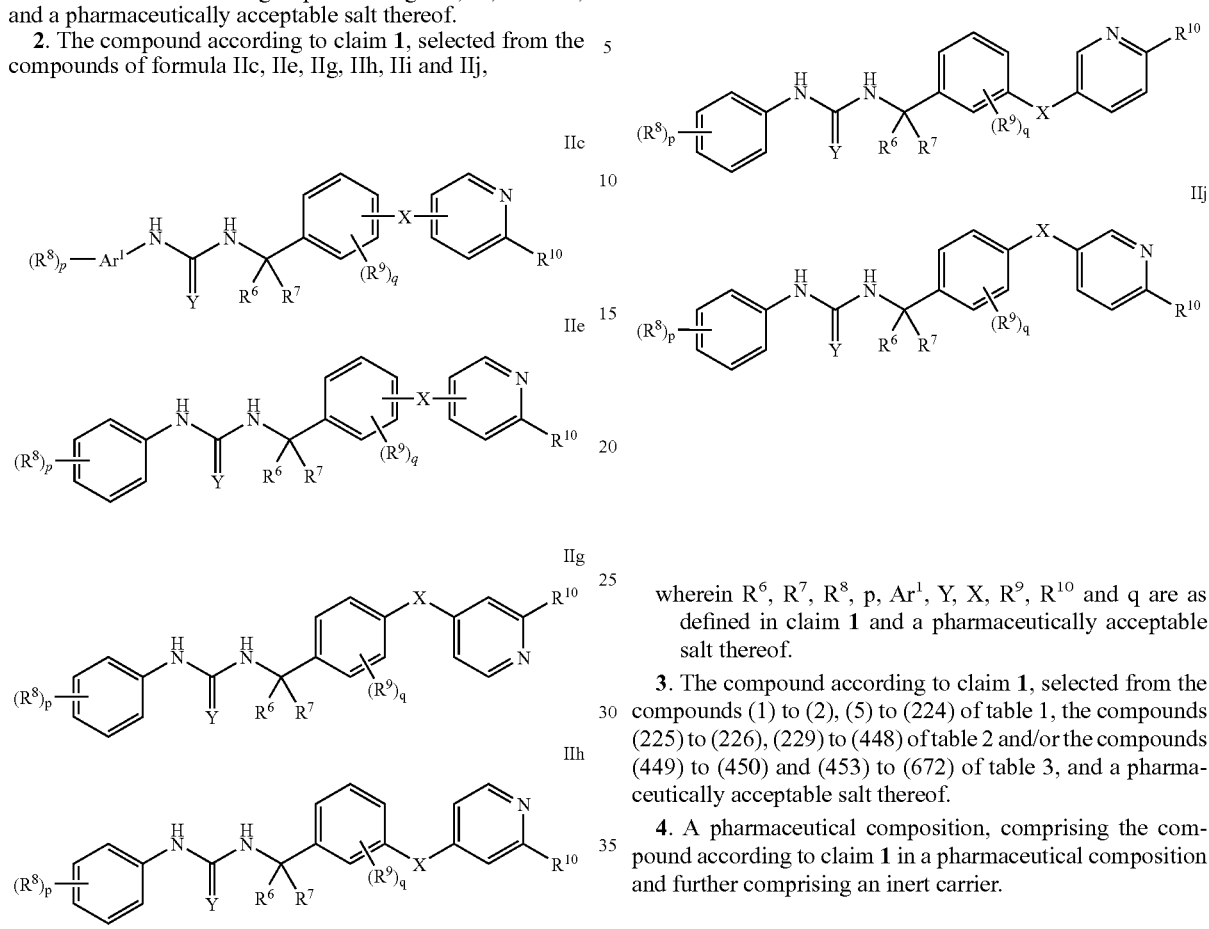

wherein $R^6$, $R^7$, $R^8$, p, $Ar^1$, Y, X, $R^9$, $R^{10}$ and q are as defined in claim 1 and a pharmaceutically acceptable salt thereof.

3. The compound according to claim 1, selected from the compounds (1) to (2), (5) to (224) of table 1, the compounds (225) to (226), (229) to (448) of table 2 and/or the compounds (449) to (450) and (453) to (672) of table 3, and a pharmaceutically acceptable salt thereof.

4. A pharmaceutical composition, comprising the compound according to claim 1 in a pharmaceutical composition and further comprising an inert carrier.

* * * * *

UNITED STATES PATENT AND TRADEMARK OFFICE
CERTIFICATE OF CORRECTION

PATENT NO. : 7,589,112 B2
APPLICATION NO. : 10/532574
DATED : September 15, 2009
INVENTOR(S) : Hans-Peter Buchstaller et al.

Page 1 of 2

It is certified that error appears in the above-identified patent and that said Letters Patent is hereby corrected as shown below:

Please delete Claim 1, at Column 356, line 5, and insert therefor:

--1. A compound of formula II,

wherein
$Ar^1$ is phenyl,
$Ar^2$ is pyridinyl,
$R^6$, $R^7$ are independently H or A,
$R^8$, $R^9$ and $R^{10}$ are independently selected from the group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_nNR^{11}R^{12}$, $(CH_2)_nO(CH_2)_kNR^{11}R^{12}$, $(CH_2)_nNR^{11}(CH_2)_kNR^{11}R^{12}$, $(CH_2)_nO(CH_2)_kOR^{11}$, $(CH_2)_nNR^{11}(CH_2)_kOR^{12}$, $(CH_2)_nCOOR^{13}$, $(CH_2)_nCOR^{13}$, $(CH_2)_nCONR^{11}R^{12}$, $(CH_2)_nNR^{11}COR^{13}$, $(CH_2)_nNR^8CONR^{11}R^{12}$, $(CH_2)_nNR^{11}SO_2A$, $(CH_2)_nSO_2NR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, $CH=N-OA$, $CH_2CH=N-OA$, $(CH_2)_nNHOA$, $(CH_2)_nCH=N-R^{11}$, $(CH_2)_nOC(O)NR^{11}R^{12}$, $(CH_2)_nNR^{11}COOR^{13}$, $(CH_2)_nN(R^{11})CH_2CH_2OR^{13}$, $(CH_2)_nN(R^{11})CH_2CH_2OCF_3$, $(CH_2)_nN(R^{11})C(R^{13})HCOOR^{12}$, $(CH_2)_nN(R^{11})$, $C(R^{13})HCOR^{11}$, $(CH_2)_nN(R^{11})CH_2CH_2N(R^{12})CH_2COOR^{11}$, $(CH_2)_nN(R^{11})CH_2CH_2NR^{11}R^{12}$, $CH=CHCOOR^{13}$, $CH=CHCH_2NR^{11}R^{12}$, $CH=CHCH_2NR^{11}R^{12}$, $CH=CHCH_2OR^{13}$, $(CH_2)_nN(COOR^{13})COOR^{14}$, $(CH_2)_nN(CONH_2)COOR^{13}$, $(CH_2)_nN(CONH_2)CONH_2$, $(CH_2)_nN(CH_2COOR^{13})COOR^{14}$, $(CH_2)_nN(CH_2CONH_2)COOR^{13}$, $(CH_2)_nN(CH_2CONH_2)CONH_2$, $(CH_2)_nCHR^{13}COR^{14}$, $(CH_2)_nCHR^{13}COOR^{14}$, $(CH_2)_nCHR^{13}CH_2OR^{14}$, $(CH_2)_nOCN$ and $(CH_2)_nNCO$,
wherein
$R^{11}$, $R^{12}$ are independently selected from the group consisting of H, A, and $(CH_2)$,
$R^{13}$, $R^{14}$ are independently selected from the group consisting of H, Hal, A, and $(CH_2)_mAr^4$, Signed and Sealed this Tenth Day of August, 2010

David J. Kappos
*Director of the United States Patent and Trademark Office*

A is selected from the group consisting of alkyl, alkenyl, cycloalkyl, alkylenecycloalkyl, alkoxy, and alkoxyalkyl, $Ar^3$, $Ar^4$ are independently aromatic hydrocarbon residues comprising 5 to 12 carbon atoms which are optionally substituted by one or more substituents, selected from the group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2R^{15}R^{16}$, $S(O)_uA$ and $OOCR^{15}$, $R^{15}$, $R^{16}$ are independently selected from the group consisting of H, A, and $(CH_2)_mAr^6$, wherein $Ar^6$ is a 5- or 6-membered aromatic hydrocarbon which is optionally substituted by one or more substituents selected from the group consisting of methyl, ethyl, propyl, 2-propyl, tert.-butyl, Hal, CN, OH, $NH_2$ and $CF_3$, k, n and m are independently of one another 0, 1, 2, 3, 4, or 5;

X is O,

Y is O or S, p, r are independently 0, 1, 2, 3, 4 or 5, q is 0, 1, 2, 3 or 4, u is 0, 1, 2 or 3, and Hal is selected from the group consisting of F, Cl, Br and I;

and a pharmaceutically acceptable salt thereof.--